United States Patent
Wu et al.

(10) Patent No.: US 8,664,411 B2
(45) Date of Patent: *Mar. 4, 2014

(54) TETRAHYDROPYRANOCHROMENE GAMMA SECRETASE INHIBITORS

(75) Inventors: Wen-Lian Wu, Edison, NJ (US); Thomas A. Bara, Scotch Plains, NJ (US); Duane A. Burnett, Bernardsville, NJ (US); John W. Clader, Cranford, NJ (US); Martin S. Domalski, Verona, NJ (US); Yan Jin, Princeton, NJ (US); Hubert B. Josien, Jersey City, NJ (US); Hongmei Li, Warren, NJ (US); Xian Liang, Monmouth Junction, NJ (US); Dmitri A. Pissarnitski, Scotch Plains, NJ (US); Thavalakulamgara K. Sasikumar, Edison, NJ (US); Jesse K. Wong, Monroe Township, NJ (US); Ruo Xu, Watchung, NJ (US); Zhiqiang Zhao, Scotch Plains, NJ (US); Paul McNamara, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 512 days.

This patent is subject to a terminal disclaimer.

(21) Appl. No.: 12/665,580

(22) PCT Filed: Jul. 1, 2008

(86) PCT No.: PCT/US2008/008192
§ 371 (c)(1),
(2), (4) Date: May 19, 2010

(87) PCT Pub. No.: WO2009/008980
PCT Pub. Date: Jan. 15, 2009

(65) Prior Publication Data
US 2011/0236400 A1 Sep. 29, 2011

Related U.S. Application Data

(60) Provisional application No. 60/948,033, filed on Jul. 5, 2007.

(51) Int. Cl.
*C07D 311/80* (2006.01)
*C07D 493/04* (2006.01)
*A61K 31/352* (2006.01)

(52) U.S. Cl.
USPC ............ 549/387; 549/390; 549/391; 549/60; 514/444; 514/455

(58) Field of Classification Search
USPC ............ 549/387, 390, 391, 60; 514/455, 444
See application file for complete search history.

(56) References Cited

U.S. PATENT DOCUMENTS 8,067,621 B2 * 11/2011 Asberom et al. ............. 549/387

FOREIGN PATENT DOCUMENTS

| WO | 0050391 | 8/2000 |
|---|---|---|
| WO | 03/014075 A2 | 2/2003 |
| WO | 2004/031134 A1 | 4/2004 |
| WO | 2004/101539 A1 | 11/2004 |
| WO | 2007/084595 A2 | 7/2007 |
| WO | 2007/143523 A2 | 12/2007 |
| WO | 2010056849 | 5/2010 |

OTHER PUBLICATIONS

Berge, et al., "Pharmaceutical Salts," Journal of Pharmaceutical Sciences, vol. 66, No. 1, pp. 1-19, 1977.
Gould, et al., "Salt Selection for Basic Drugs," International Journal of Pharmaceutics, vol. 33, pp. 301-217, 1986.
McCombie, et al., "A Cyclization-Trapping Route to Carbocyclic and Heterocyclic Benzylic Sylfones," Tetrahedron Letters, vol. 34, No. 50, pp. 8033-8036, 1993.
Posner, et al., α,β-Ethylenic Sylfones from Sulfonornethylphosphonate Carbanions and Aldehydes and Ketones, Journal of Organic Chemistry, vol. 37, pp. 3547-3549, 1972.
Zhang, et al., "Biochemical Characterization for the γ-Secretase Activity That Produces β-Amyloid Peptides," Biochemistry, vol. 40, pp. 5049-5055, 2001.
PCT/US2008/008192 Written Opinion, (2012).

* cited by examiner

*Primary Examiner* — Bernard Dentz
(74) *Attorney, Agent, or Firm* — Susan Hess; John C. Todaro; Henry Jeanette

(57) ABSTRACT

Disclosed are novel gamma secretase inhibitors of the formula. Also disclosed are methods of inhibiting gamma-secretase, methods of treating neurodegenerative diseases, and methods of treating Alzheimer's Disease. Also disclosed are processes for preparing alkenes in one reaction step using a mixture of an aldehyde (or ketone) and an alkyl substituted with two electron withdrawing groups, and reacting the mixture with: (a) a sulfonyl halide (e.g., a sulfonyl chloride) and a basic tertiary amine, or, (b) a sulfonyl anhydride and a basic amine, or (c) an aryl-C(O)-halide and a basic tertiary amine, or (d) an aryl-C(O)—O—C(O)-aryl and a basic tertiary amine, or (e) an heteroaryl-C(O)-halide and a basic tertiary amine, or (f) a heteroaryl-C(O)—O—C(O)-heteroaryl and a basic tertiary amine.

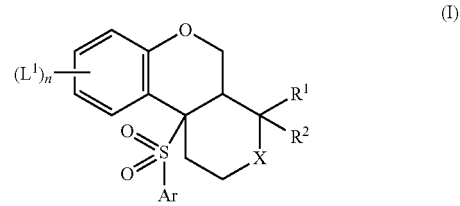

23 Claims, No Drawings

TETRAHYDROPYRANOCHROMENE GAMMA SECRETASE INHIBITORS

REFERENCE TO RELATED APPLICATION

This application claims the benefit of U.S. Provisional Application No. 60/948,033 filed Jul. 5, 2007.

BACKGROUND

WO 00/50391, published Aug. 13, 2000, discloses compounds having a sulfonamide moiety that are useful for the treatment and prevention of Alzheimer's Disease and other diseases relating to the deposition of amyloid protein.

McCombie et al., Tetrahedron Letters, Vol. 34, No. 50, pp. 8033-8036 (1993) describe methods of preparing chromans and thiochromans. However, the chromans and thiochromans described therein are quite different from the compounds of the present invention.

In view of the present interest in the treatment or prevention of neurodegenerative diseases, such as Alzheimer's Disease, a welcome contribution to the art would be compounds for use in such treatment or prevention. This invention provides such a contribution.

SUMMARY OF THE INVENTION

This invention provides compounds that are inhibitors (e.g., antagonists) of gamma-secretase (also termed "γ-secretase") and have the Formula (I)

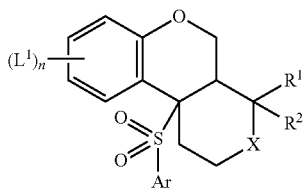

(I)

or a pharmaceutically acceptable salt, solvate, or ester thereof, wherein X, $L^1$, $R^1$, $R^2$ and Ar are independently selected and are as defined below.

This invention also provides compounds of formula (I) that have the formula (I.A1):

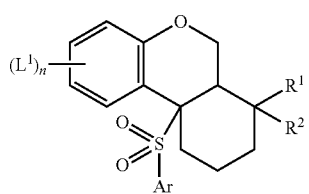

(I.A1)

or a pharmaceutically acceptable salt, solvate, or ester thereof, wherein $L^1$, $R^1$, $R^2$ and Ar are as defined below.

This invention also provides compounds of formula (I) that have the formula (I.A2):

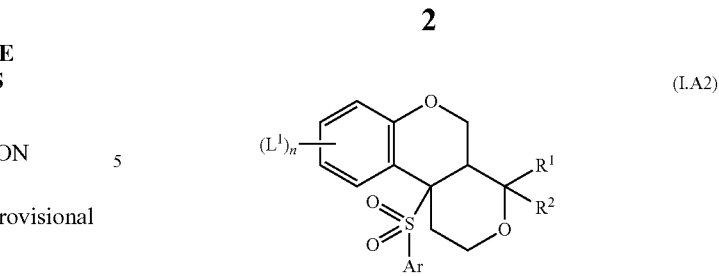

(I.A2)

or a pharmaceutically acceptable salt, solvate, or ester thereof, wherein $L^1$, $R^1$, $R^2$ and Ar are as defined below.

This invention also provides the compounds of formula (I) in pure and isolated form.

This invention also provides the compounds of formula (I) in pure form.

This invention also provides the compounds of formula (I) in isolated form.

This invention also provides the compounds of formula (I.A1) in pure and isolated form.

This invention also provides the compounds of formula (I.A1) in pure form.

This invention also provides the compounds of formula (I.A1) in isolated form.

This invention also provides the compounds of formula (I.A2) in pure and isolated form.

This invention also provides the compounds of formula (I.A2) in pure form.

This invention also provides the compounds of formula (I.A2) in isolated form.

This invention also provides compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), which compounds are identified below.

This invention also provides compounds of 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−) in pure form.

This invention also provides compounds of 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−) in isolated form.

This invention also provides a pharmaceutically acceptable salt of a compound of formula (I).

This invention also provides a solvate of a compound of formula (I).

This invention also provides a pharmaceutically acceptable salt of a compound of formula (I.A1).

This invention also provides a solvate of a compound of formula (I.A1).

This invention also provides a pharmaceutically acceptable salt of a compound of formula (I.A2).

This invention also provides a solvate of a compound of formula (I.A2).

This invention also provides a solvate of a compound selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides a pharmaceutically acceptable ester of a compound of formula (I).

This invention also provides a pharmaceutically acceptable ester of a compound of formula (I.A1).

This invention also provides a pharmaceutically acceptable ester of a compound of formula (I.A2).

This invention also provides a pharmaceutical composition comprising an effective amount of one or more compounds of Formula (I) and at least one pharmaceutically acceptable carrier.

This invention also provides a pharmaceutical composition comprising an effective amount of one or more compounds of Formula (I.A1) and at least one pharmaceutically acceptable carrier.

This invention also provides a pharmaceutical composition comprising an effective amount of one or more compounds of Formula (I.A2) and at least one pharmaceutically acceptable carrier.

This invention also provides a pharmaceutical composition comprising an effective amount of a compound of Formula (I) and at least one pharmaceutically acceptable carrier.

This invention also provides a pharmaceutical composition comprising an effective amount of a compound of Formula (I.A1) and at least one pharmaceutically acceptable carrier.

This invention also provides a pharmaceutical composition comprising an effective amount of a compound of Formula (I.A2) and at least one pharmaceutically acceptable carrier.

This invention also provides a pharmaceutical composition comprising an effective amount of one or more pharmaceutically acceptable salts of the compounds of Formula (I), and at least one pharmaceutically acceptable carrier.

This invention also provides a pharmaceutical composition comprising an effective amount of one or more pharmaceutically acceptable salts of the compounds of Formula (I.A1), and at least one pharmaceutically acceptable carrier.

This invention also provides a pharmaceutical composition comprising an effective amount of one or more pharmaceutically acceptable salts of the compounds of Formula (I.A2), and at least one pharmaceutically acceptable carrier.

This invention also provides a pharmaceutical composition comprising an effective amount of a pharmaceutically acceptable salt of a compound of Formula (I), and at least one pharmaceutically acceptable carrier.

This invention also provides a pharmaceutical composition comprising an effective amount of a pharmaceutically acceptable salt of a compound of Formula (I.A1), and at least one pharmaceutically acceptable carrier.

This invention also provides a pharmaceutical composition comprising an effective amount of a pharmaceutically acceptable salt of a compound of Formula (I.A2), and at least one pharmaceutically acceptable carrier.

This invention also provides a pharmaceutical composition comprising an effective amount of one or more solvates of the compounds of Formula (I), and at least one pharmaceutically acceptable carrier.

This invention also provides a pharmaceutical composition comprising an effective amount of one or more solvates of the compounds of Formula (I.A1), and at least one pharmaceutically acceptable carrier.

This invention also provides a pharmaceutical composition comprising an effective amount of one or more solvates of the compounds of Formula (I.A2), and at least one pharmaceutically acceptable carrier.

This invention also provides a pharmaceutical composition comprising an effective amount of a solvate of a compound of Formula (I), and at least one pharmaceutically acceptable carrier.

This invention also provides a pharmaceutical composition comprising an effective amount of a solvate of a compound of Formula (I.A1), and at least one pharmaceutically acceptable carrier.

This invention also provides a pharmaceutical composition comprising an effective amount of a solvate of a compound of Formula (I.A2), and at least one pharmaceutically acceptable carrier.

This invention also provides a pharmaceutical composition comprising an effective amount of one or more pharmaceutically acceptable esters of the compounds of Formula (I), and at least one pharmaceutically acceptable carrier.

This invention also provides a pharmaceutical composition comprising an effective amount of one or more pharmaceutically acceptable esters of the compounds of Formula (I.A1), and at least one pharmaceutically acceptable carrier.

This invention also provides a pharmaceutical composition comprising an effective amount of one or more pharmaceutically acceptable esters of the compounds of Formula (I.A2), and at least one pharmaceutically acceptable carrier.

This invention also provides a pharmaceutical composition comprising an effective amount of a pharmaceutically acceptable ester of a compound of Formula (I), and at least one pharmaceutically acceptable carrier.

This invention also provides a pharmaceutical composition comprising an effective amount of a pharmaceutically acceptable ester of a compound of Formula (I.A1), and at least one pharmaceutically acceptable carrier.

This invention also provides a pharmaceutical composition comprising an effective amount of a pharmaceutically acceptable ester of a compound of Formula (I.A2), and at least one pharmaceutically acceptable carrier.

This invention also provides a pharmaceutical composition comprising an effective amount of one or more compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides a pharmaceutical composition comprising an effective amount of a compound selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides a pharmaceutical composition comprising an effective amount of one or more (e.g., one) compounds of formula (I) (e.g., compounds of formula (I.A1), or compounds of formula (I.A2)), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

This invention also provides a pharmaceutical composition comprising an effective amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B (−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more (e.g., one) other therapeutically effective pharmaceutical active ingredients (e.g., drugs), and a pharmaceutically acceptable carrier. Examples of the other drugs include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

This invention also provides a pharmaceutical composition comprising an effective amount of one or more (e.g., one) compounds of formula (I) (e.g., compounds of formula (I.A1), or compounds of formula (I.A2)), and effective amount of one or more BACE inhibitors, and a pharmaceutically acceptable carrier.

This invention also provides a pharmaceutical composition comprising an effective amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B (−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more BACE inhibitors, and a pharmaceutically acceptable carrier.

This invention also provides a pharmaceutical composition comprising an effective amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B (−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more cholinesterase inhibitors (e.g., acetyl- and/or butyrylchlolinesterase inhibitors), and a pharmaceutically acceptable carrier.

This invention also provides a pharmaceutical composition comprising an effective amount of one or more (e.g., one) compounds of formula (I) (e.g., compounds of formulas (I.A1), or compounds of formula (I.A2)), and effective amount of one or more muscarinic antagonists (e.g., $m_1$ or $m_2$ antagonists), and a pharmaceutically acceptable carrier.

This invention also provides a pharmaceutical composition comprising an effective amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B (−), 76A(−), 76A(+), 76B(−), 78A(−), 79A(−), 80A(+), 81A-rac, 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more muscarinic antagonists (e.g., $m_1$ or $m_2$ antagonists), and a pharmaceutically acceptable carrier.

This invention also provides a method for inhibiting gamma-secretase comprising administering an effective (i.e., therapeutically effective) amount of one or more compounds of formula (I) to a patient in need of treatment.

This invention also provides a method for inhibiting gamma-secretase comprising administering an effective (i.e., therapeutically effective) amount of one or more compounds of formula (I.A1) to a patient in need of treatment.

This invention also provides a method for inhibiting gamma-secretase comprising administering an effective (i.e., therapeutically effective) amount of one or more compounds of formula (I.A2) to a patient in need of treatment.

This invention also provides a method for inhibiting gamma-secretase comprising administering an effective (i.e., therapeutically effective) amount of a compound of formula (I) to a patient in need of treatment.

This invention also provides a method for inhibiting gamma-secretase comprising administering an effective (i.e., therapeutically effective) amount of a compound of formula (I.A1) to a patient in need of treatment.

This invention also provides a method for inhibiting gamma-secretase comprising administering an effective (i.e., therapeutically effective) amount of a compound of formula (I.A2) to a patient in need of treatment.

This invention also provides a method for inhibiting gamma-secretase comprising administering to a patient in need of treatment an effective (i.e., therapeutically effective) amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides a method of treating one or more neurodegenerative diseases comprising administering an effective (i.e., therapeutically effective) amount of one or more compounds of formula (I) to a patient in need of treatment.

This invention also provides a method of treating one or more neurodegenerative diseases comprising administering an effective (i.e., therapeutically effective) amount of one or more compounds of formula (I.A1) to a patient in need of treatment.

This invention also provides a method of treating one or more neurodegenerative diseases comprising administering an effective (i.e., therapeutically effective) amount of one or more compounds of formula (I.A2) to a patient in need of treatment.

This invention also provides a method of treating one or more neurodegenerative diseases comprising administering an effective (i.e., therapeutically effective) amount of a compound of formula (I) to a patient in need of treatment.

This invention also provides a method of treating one or more neurodegenerative diseases comprising administering an effective (i.e., therapeutically effective) amount of a compound of formula (I.A1) to a patient in need of treatment.

This invention also provides a method of treating one or more neurodegenerative diseases comprising administering an effective (i.e., therapeutically effective) amount of a compound of formula (I.A2) to a patient in need of treatment.

This invention also provides a method for treating one or more neurodegenerative diseases comprising administering to a patient in need of treatment an effective (i.e., therapeutically effective) amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+),106(−), 107(−), 108(−), and 111(−).

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of formula (I) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of formula (I.A1) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of one or more compounds of formula (I.A2) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of a compound of formula (I) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of a compound of formula (I.A1) to a patient in need of treatment.

This invention also provides a method of inhibiting the deposition of amyloid protein (e.g., amyloid beta protein) in, on or around neurological tissue (e.g., the brain) comprising administering an effective (i.e., therapeutically effective) amount of a compound of formula (I.A2) to a patient in need of treatment.

This invention also provides a method of inhibiting the deposition of amyloid protein (e.g., amyloid beta protein) in, on or around neurological tissue (e.g., the brain) comprising administering to a patient in need of treatment an effective (i.e., therapeutically effective) amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+),76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides a method of treating Alzheimer's disease comprising administering an effective (i.e., therapeutically effective) amount of one or more compounds of formula (I) to a patient in need of treatment.

This invention also provides a method of treating Alzheimer's disease comprising administering an effective (i.e., therapeutically effective) amount of one or more compounds of formula (I.A1) to a patient in need of treatment.

This invention also provides a method of treating Alzheimer's disease comprising administering an effective (i.e., therapeutically effective) amount of one or more compounds of formula (I.A2) to a patient in need of treatment.

This invention also provides a method of treating Alzheimer's disease comprising administering an effective (i.e., therapeutically effective) amount of a compound of formula (I) to a patient in need of treatment.

This invention also provides a method of treating Alzheimer's disease comprising administering an effective (i.e., therapeutically effective) amount of a compound of formula (I.A1) to a patient in need of treatment.

This invention also provides a method of treating Alzheimer's disease comprising administering an effective (i.e., therapeutically effective) amount of a compound of formula (I.A2) to a patient in need of treatment.

This invention also provides a method of treating Alzheimer's disease comprising administering to a patient in need of treatment an effective (i.e., therapeutically effective) amount of one or more (e.g., one) compounds selected from the group consisting of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

This invention also provides combination therapies for (1) inhibiting gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) (e.g., compounds of formula (I.A1), or compounds of formula (I.A2)) and the administration of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, this invention also provides any one of the methods of treatment, or methods of inhibiting, described herein, wherein the compound of formula (I) (e.g., the compound of formula (I.A1), or the compound of formula (I.A2)) is used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylcholinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

This invention also provides a method of treating Alzheimer's disease comprising administering an effective (i.e., therapeutically effective) amount of one or more compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease comprising administering an effective (i.e., therapeutically effective) amount of one or more compounds of formula (I.A1), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease comprising administering an effective (i.e., therapeutically effective) amount of one or more compounds of formula (I.A2), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease comprising administering an effective (i.e., therapeutically effective) amount of a compound of formula (I), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease comprising administering an effective (i.e., therapeutically effective) amount of a compound of formula (I.A1), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

This invention also provides a method of treating Alzheimer's disease comprising administering an effective (i.e., therapeutically effective) amount of a compound of formula (I.A2), in combination with an effective (i.e., therapeutically effective) amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

The phrase "any one of the above methods" as used below means that the description below applies to each method described above just as if each method above was separately described with the scope described below.

This invention also provides any one of the above methods wherein a pharmaceutically acceptable salt of a compound of formula (I) is used instead of the compound of formula (I).

This invention also provides any one of the above methods wherein a pharmaceutically acceptable salt of a compound of formula (I.A1) is used instead of the compound of formula (I.A1).

This invention also provides any one of the above methods wherein a pharmaceutically acceptable salt of a compound of formula (I.A2) is used instead of the compound of formula (I.A2).

This invention also provides any one of the above methods wherein a pharmaceutically acceptable ester of a compound of formula (I) is used instead of the compound of formula (I).

This invention also provides any one of the above methods wherein a pharmaceutically acceptable ester of a compound of formula (I.A1) is used instead of the compound of formula (I.A1).

This invention also provides any one of the above methods wherein a pharmaceutically acceptable ester of a compound of formula (I.A2) is used instead of the compound of formula (I.A2).

This invention also provides any one of the above methods wherein a solvate of a compound of formula (I) is used instead of the compound of formula (I).

This invention also provides any one of the above methods wherein a solvate of a compound of formula (I.A1) is used instead of the compound of formula (I.A1).

This invention also provides any one of the above methods wherein a solvate of a compound of formula (I.A2) is used instead of the compound of formula (I.A2).

This invention also provides a kit comprising, in separate containers, in a single package, pharmaceutical compositions for use in combination, wherein one container comprises an effective amount of a compound of formula (I) (e.g., a compound of formula (I.A1), or a compound of formula (I.A2)) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) inhibit gamma-secretase.

This invention also provides a process for preparing alkenes (i.e., diester alkenes), said processing comprising reacting:
(1) a mixture of
(a) an aldehyde or a ketone and
(b) an alkyl substituted with two electron withdrawing groups (i.e., a (EWG)-CH$_2$-(EWG) moiety), such as, for example, a diester of a dicarboxylic acid, (EWG represents an electron withdrawing group), and
(2) either:
(a) a sulfonyl halide (e.g., a sulfonyl chloride) and a basic amine (e.g., a basic tertiary amine), or,
(b) a sulfonyl anhydride and a basic amine (e.g., a basic tertiary amine), or
(c) an aryl-C(O)-halide and a basic amine (e.g., a basic tertiary amine), or
(d) an aryl-C(O)—O—C(O)-aryl and a basic amine (e.g., a basic tertiary amine), or
(e) an heteroaryl-C(O)-halide and a basic amine (e.g., a basic tertiary amine), or
(f) a heteroaryl-C(O)—O—C(O)-heteroaryl and a basic amine (e.g., a basic tertiary amine).

The process (reaction) is conducted in a suitable organic solvent (i.e., an organic solvent wherein moieties in (1) and (2) are in solution in a suitable concentration, i.e., an organic solvent wherein the moieties in (1) and (2) are in admixture). The organic solvent is preferably anhydrous. The process (reaction) is conducted at a suitable temperature (i.e., a temperature that allows the reaction to proceed at a reasonable rate to produce the desired end product without producing undesirable reaction by-products). The reaction can be, and is preferably, carried out under an inert atmosphere (e.g., N$_2$). The desired product can be separated and isolated by techniques well known in the art (e.g., extraction with an organic solvent and concentration of the organic solvent).

This process produces the desired end product in one reaction.

DETAILED DESCRIPTION OF THE INVENTION

This invention provides novel compounds, useful as gamma secretase inhibitors, of the formula:

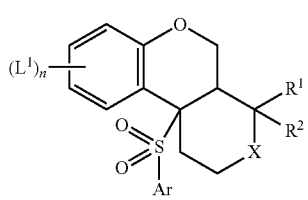

or a pharmaceutically acceptable salt, solvate, or ester thereof, wherein:

X is selected from the group consisting of N and $CH_2$;

$R^1$ is selected from the group consisting of: (1) -alkylene-$S(O)_2$—($C_1$-$C_6$)alkyl, (2) -alkylene-$S(O)_2$—($C_1$-$C_6$)haloalkyl; (3) -alkylene-$S(O)_2$—$R^6$, (4) -alkylene-$S(O)_2$—$R^8$, (5) -alkylene-$S(O)_2$-substituted($C_1$-$C_6$)alkyl, (6) -alkylene-(tetrahydrothiophene 1,1-dioxide), (7) -alkenyl-$S(O)_2$—($C_1$-$C_6$)alkyl, and (8) -cycloalkyl-$S(O)_2$—($C_1$-$C_6$)alkyl;

wherein said -alkylene-$S(O)_2$-substituted($C_1$-$C_6$)alkyl $R^1$ group is substituted with one or more substituents independently selected from the group consisting of: —OH, halo, —CN, —$CF_3$, —O—($C_1$-$C_6$)alkyl (e.g., —$OCH_3$), and —O—(halo($C_1$-$C_6$)alkyl) (e.g., —$OCF_3$), and preferably —OH, and more preferably one —OH, and wherein an example of said -alkylene-$S(O)_2$-substituted($C_1$-$C_6$)alkyl $R^1$ group is -alkylene-$S(O)_2$—($C_1$-$C_6$)hydroxyalkyl;

$R^2$ is selected from the group consisting of: H and alkyl (e.g., $C_1$-$C_6$alkyl or ($C_1$-$C_2$)alkyl), and in one example $R^2$ is H, and in another example $R^2$ is methyl;

$R^6$ is selected from the group consisting of: (1) unsubstituted ($C_6$-$C_{14}$)aryl, (2) ($C_6$-$C_{14}$)aryl substituted with one or more $L^{1A}$ groups, (3) unsubstituted ($C_5$-$C_{14}$)heteroaryl, (4) ($C_5$-$C_{14}$)heteroaryl substituted with one or more $L^{1A}$ groups, (5) unsubstituted ($C_5$-$C_{14}$)heteroarylalkyl-, and (5) ($C_5$-$C_{14}$)heteroarylalkyl-substituted with one or more $L^{1A}$ groups;

$R^8$ is selected from the group consisting of unsubstituted cycloalkyl and cycloalkyl substituted with one or more $L^3$ groups (wherein examples of said cycloalkyl groups (unsubstituted or substituted) include $C_3$-$C_{10}$ cycloalkyl rings);

each $L^3$ is independently selected from the group consisting of: (1) —CN, (2) =O, (3) —$CH_2OH$, (4) amino (i.e., —$NH_2$), (5) halo (e.g., Cl, F, and Br), (6) —$CH_2NH_2$, (7) —$CH_2$NHalkyl (such as, for example, —$CH_2$NH($C_1$-$C_6$ alkyl), (8) —C(O)OH, (9) -alkylene-C(O)NH($C_1$ to $C_6$)alkyl, (10) -alkylene-C(O)N(($C_1$ to $C_6$)alkyl)$_2$ wherein each alkyl is independently selected, (11) -alkylene-C(O)NH($C_1$ to $C_6$)haloalkyl, and (12) -alkylene-C(O)N(($C_1$ to $C_6$)haloalkyl)$_2$ wherein each alkyl is independently selected);

Ar is selected from the group consisting of: (1) unsubstituted aryl (e.g., unsubstituted phenyl), (2) aryl (e.g., phenyl) substituted with one or more $L^{1A}$ groups, (3) unsubstituted heteroaryl (e.g., pyridyl), and (4) substituted heteroaryl (e.g., substituted pyridyl) substituted with one or more $L^{1A}$ groups;

each $L^1$ is independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$ and —$OCH_2CF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), alkoxyalkoxy- (e.g., $CH_3OCH_2CH_2O$—), and —$S(O)_2$($C_1$-$C_6$)alkyl (e.g., —$S(O)_2CH_2CH_3$);

each $L^{1A}$ is independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$ and —$OCH_2CF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), alkoxyalkoxy- (e.g., $CH_3OCH_2CH_2O$—), and —$S(O)_2$($C_1$-$C_6$)alkyl (e.g., —$S(O)_2CH_2CH_3$); and n is 0, 1, 2 or 3.

In the compounds of this invention, the —$S(O)_2$— moiety of the $R^1$ substituents can be bound to any carbon of the alkylene chain. In general the —$S(O)_2$— moiety of the $R^1$ substituents is bound to the terminal carbon of the alkylene chain.

An example of a tetrahydrothiophene 1,1-dioxide moiety is:

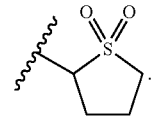

Thus, and example of the -alkylene-(tetrahydrothiophene 1,1-dioxide) $R^1$ moiety is:

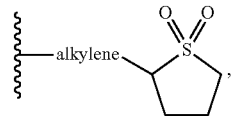

such as, for example,

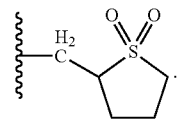

An example of the -alkenyl-$S(O)_2$—($C_1$-$C_6$)alkyl $R^1$ moiety is —($C_2$ to $C_6$)alkenyl-$S(O)_2$—($C_1$-$C_6$)alkyl, such as, for example, —($C_2$ to $C_3$)alkenyl-$S(O)_2$—($C_1$-$C_6$)alkyl, such as, for example, —CH=CH—$S(O)_2$—($C_1$-$C_6$)alkyl.

An example of the -cycloalkyl-$S(O)_2$—($C_1$-$C_6$)alkyl $R^1$ moiety is —($C_3$ to $C_6$)cycloalkyl-$S(O)_2$—($C_1$-$C_6$)alkyl, such as for example, —($C_3$ to $C_5$)cycloalkyl -$S(O)_2$—($C_1$-$C_6$) alkyl, such as, for example, -cyclopropyl-$S(O)_2$—($C_1$-$C_6$) alkyl.

An example of the heteroarylalkyl moiety of the $R^6$ unsubstituted ($C_5$-$C_{14}$)heteroarylalkyl or the substituted ($C_5$-$C_{14}$) heteroarylalkyl substituent is furanyl-alkyl-, such as, for example, furanyl-$CH_2$—, such as, for example,

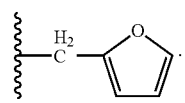

Compounds of formula (I) include compounds of formula (Ii):

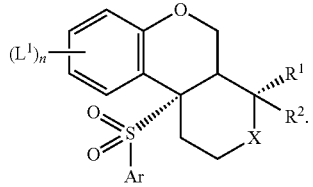

Compounds of formula (I) include compounds of formula (Iii):

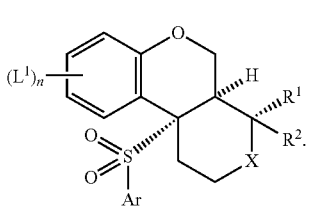

Compounds of formula (I) include compounds of formula (Iiii):

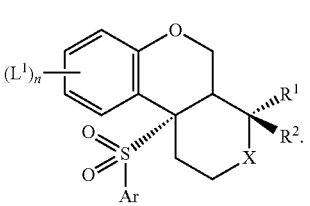

Compounds of formula (I) include compounds of formula (Iiv):

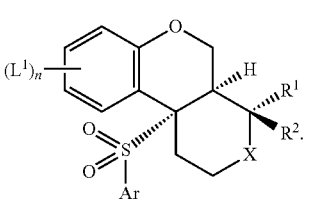

Compounds of formula (I) include compounds of formula (Iv):

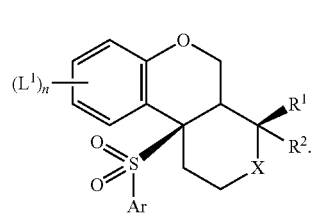

Compounds of formula (I) include compounds of formula (Ivi):

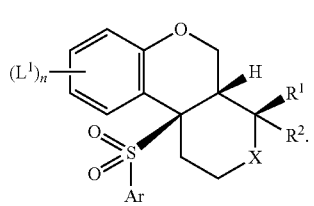

Compounds of formula (I) include compounds of formula (Ivii):

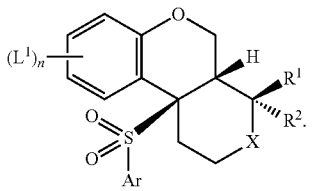

The phrase "any one of the compounds" used below for the compounds of formulas (Ii) to (Ivii), (I.A1a) to (I.A1h), and (I.A2a) to (I.A2h), unless stated otherwise, means that such description applies to each compound mentioned in the description just as if each compound mentioned was separately described. Thus, for example, the description below that the "compounds of formula (I) also include any one of the compounds of formulas (Ii) to (Ivii) wherein n is 2" is intended to describe an embodiment directed to a compound of formula (Ii) wherein n is 2. It is also intended to describe an embodiment directed to a compound of formula (Ii) wherein n is 2. It is also intended to describe an embodiment directed to a compound of formula (Iiii) wherein n is 2. It is also intended to describe an embodiment directed to a compound of formula (Iiv) wherein n is 2. It is also intended to describe an embodiment directed to a compound of formula (Iv) wherein n is 2. It is also intended to describe an embodiment directed to a compound of formula (Ivi) wherein n is 2. It is also intended to describe an embodiment directed to a compound of formula (Ivii) wherein n is 2.

Compounds of formula (I) also include any one of the compounds of formulas (Ii) to (Ivii) above wherein n is 2.

Compounds of formula (I) also include any one of the compounds of formulas (I.A1) or (I.A2) above wherein n is 2, and the $L^1$ groups are bound to the phenyl moiety as as shown in (IIA):

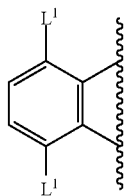

(IIA)

(wherein the squiggly line ~~~ represents the rest of the formula).

Compounds of formula (I) also include any one of the compounds of formulas (Ii) to (Ivii) above wherein n is 2, and the $L^1$ groups are bound to the phenyl moiety as as shown in (IIA):

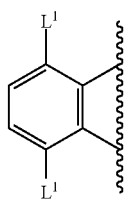

(IIA)

(wherein the squiggly line ~~~ represents the rest of the formula).

Compounds of formula (I) also include any one of the compounds of formulas (Ii) to (Ivii) above wherein n is 2, and the $L^1$ groups are bound to the phenyl moiety as shown in (IIA) and each $L^1$ is the same or different halo.

Compounds of formula (I) also include any one of the compounds of formulas (Ii) to (Ivii) above wherein n is 2, and the $L^1$ groups are bound to the phenyl moiety as shown in (IIA) and each $L^1$ is F.

Compounds of formula (I) also include any one of the compounds of formulas (Ii) to (Ivi) above wherein n is 2, and the $L^1$ groups are bound to the phenyl moiety as shown in (IIA) and Ar is selected from the group consisting of p-Cl-phenyl-, p-CN-phenyl-, p-$CF_3$-phenyl, p-$CH_3CH_2SO_2$phenyl, p-Br-phenyl, m,p-di-F-phenyl, m,p-di-CN-phenyl, p-$CH_3O$-phenyl, p-$CF_3CH_2O$phenyl, pyridyl, and pyridyl substituted with 1 or 2 substituents independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$ and —$OCH_2CF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), and alkoxyalkoxy- (e.g., $CH_3OCH_2CH_2O$—).

Compounds of formula (I) also include any one of the compounds of formulas (Ii) to (Ivii) above wherein n is 2, and the $L^1$ groups are bound to the phenyl moiety as shown in (IIA) and Ar is selected from the group consisting of p-Cl-phenyl-, p-CN-phenyl-, p-$CF_3$-phenyl, p-$CH_3CH_2SO_2$phenyl, p-Br-phenyl, m,p-di-F-phenyl, m,p-di-CN-phenyl, p-$CH_3O$-phenyl, p-$CF_3CH_2O$phenyl, pyridyl, and pyridyl substituted with 1 or 2 substituents independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$ and —$OCH_2CF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), and alkoxyalkoxy- (e.g., $CH_3OCH_2CH_2O$—).

Compounds of formula (I) also include any one of the compounds of formulas (Ii) to (Ivii) above wherein n is 2, and the $L^1$ groups are bound to the phenyl moiety as shown in (IIA) and Ar is selected from the group consisting of p-Cl-phenyl-, p-CN-phenyl-, p-$CF_3$-phenyl, pyridyl, and pyridyl substituted with 1 or 2 substituents independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), and alkoxyalkoxy- (e.g., $CH_3OCH_2CH_2O$—).

Compounds of formula (I) also include any one of the compounds of formulas (Ii) to (Ivii) above wherein n is 2, and the $L^1$ groups are bound to the phenyl moiety as shown in (IIA) and Ar is selected from the group consisting of p-Cl-phenyl-, p-CN-phenyl-, p-$CF_3$-phenyl, pyridyl, and pyridyl substituted with 1 substituent selected from the group consisting of: —Cl, —$CF_3$ and —CN.

Compounds of formula (I) also include any one of the compounds of formulas (Ii) to (Ivii) above wherein n is 2, and the $L^1$ groups are bound to the phenyl moiety as shown in (IIA) and Ar is selected from the group consisting of p-Cl-phenyl-, p-CN-phenyl-, and p-$CF_3$-phenyl.

Compounds of formula (I) also include any one of the compounds of formulas (Ii) to (Ivii) above wherein n is 2, and the $L^1$ groups are bound to the phenyl moiety as shown in (IIA) and Ar is selected from the group consisting of: pyridyl, and pyridyl substituted with 1 substituent selected from the group consisting of: —Cl, —$CF_3$ and —CN.

Compounds of formula (I) also include any one of the compounds of formulas (Ii) to (Ivii) above wherein n is 2, and the $L^1$ groups are bound to the phenyl moiety as shown in (IIA), each $L^1$ is the same or different halo, and Ar is selected from the group consisting of p-Cl-phenyl-, p-CN-phenyl-, p-$CF_3$-phenyl, p-$CH_3CH_2SO_2$phenyl, p-Br-phenyl, m,p-di-F-phenyl, m,p-di-CN-phenyl, p-$CH_3O$-phenyl, p-$CF_3CH_2O$phenyl, pyridyl, and pyridyl substituted with 1 or 2 substituents independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$ and —$OCH_2CF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), and alkoxyalkoxy- (e.g., $CH_3OCH_2CH_2O$—).

Compounds of formula (I) also include any one of the compounds of formulas (Ii) to (Ivii) above wherein n is 2, and the $L^1$ groups are bound to the phenyl moiety as shown in (IIA), each $L^1$ is the same or different halo, and Ar is selected from the group consisting of p-Cl-phenyl-, p-CN-phenyl-, p-$CF_3$-phenyl, pyridyl, and pyridyl substituted with 1 or 2 substituents independently selected from the group consisting of: halogen, alkyl (e.g., $C_1$-$C_6$ alkyl), —CN, —$CF_3$, —O—($C_1$-$C_6$)alkyl (e.g., —$OCH_3$), —O-(halo($C_1$-$C_6$)alkyl) (e.g., —$OCF_3$), —C(O)—O—($C_1$-$C_6$)alkyl (e.g., —C(O)$OCH_3$), -alkylene-OH (e.g., —$CH_2OH$), halo($C_1$-$C_6$)alkyl (e.g., —$CF_3$), hydroxyalkoxy- (e.g., $HOCH_2CH_2O$—), and alkoxyalkoxy - (e.g., $CH_3OCH_2CH_2O$—).

Compounds of formula (I) also include any one of the compounds of formulas (Ii) to (Ivii) above wherein n is 2, and the $L^1$ groups are bound to the phenyl moiety as shown in (IIA), each $L^1$ is the same or different halo, and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (Ii) to (Ivii) above wherein n is 2, and the L$^1$ groups are bound to the phenyl moiety as shown in (IIA), each L$^1$ is the same or different halo, and Ar is selected from the group consisting of p-Cl-phenyl-, p-CN-phenyl-, and p-CF$_3$-phenyl.

Compounds of formula (I) also include any one of the compounds of formulas (Ii) to (Ivii) above wherein n is 2, and the L$^1$ groups are bound to the phenyl moiety as shown in (IIA), each L$^1$ is the same or different halo, and Ar is selected from the group consisting of: pyridyl, and pyridyl substituted with 1 substituent selected from the group consisting of: —Cl, —CF$_3$ and —CN.

Compounds of formula (I) also include any one of the compounds of formulas (Ii) to (Ivii) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$ and —OCH$_2$CF$_3$), —C(O)—O—(C$_1$-C$_6$)alkyl (e.g., —C(O)OCH$_3$), -alkylene-OH (—CH$_2$OH), halo(C$_1$-C$_6$)alkyl (e.g., —CF$_3$), hydroxyalkoxy - (e.g., HOCH$_2$CH$_2$O—), and alkoxyalkoxy- (e.g., CH$_3$OCH$_2$CH$_2$O—).

Compounds of formula (I) also include any one of the compounds of formulas (Ii) to (Ivii) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (Ii) to (Ivii) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (Ii) to (Ivii) above wherein n is 2, and the L$^1$ groups are bound to the phenyl moiety as shown in (IIA), each L$^1$ is F, and Ar is selected from the group consisting of p-Cl-phenyl-, p-CN-phenyl-, and p-CF$_3$-phenyl.

Compounds of formula (I) also include any one of the compounds of formulas (Ii) to (Ivii) above wherein n is 2, and the L$^1$ groups are bound to the phenyl moiety as shown in (IIA), each L$^1$ is F, and Ar is selected from the group consisting of: pyridyl, and pyridyl substituted with substituent selected from the group consisting of: —Cl, —CF$_3$ and —CN.

Compounds of formula (I) include compounds of formula (I.A1a):

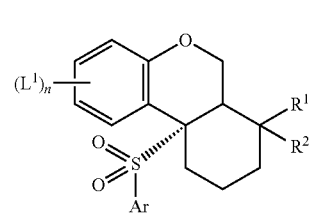

wherein all substituents are as defined for formula (I).

Compounds of formula (I) include compounds of formula (I.A1b):

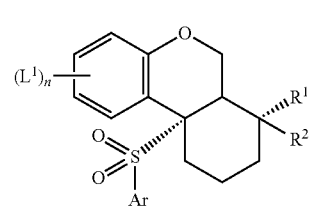

wherein all substituents are as defined for formula (I).

Compounds of formula (I) include compounds of formula (I.A1c):

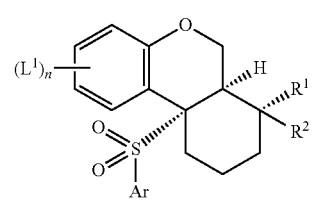

wherein all substituents are as defined for formula (I).

Compounds of formula (I) incluse compounds of formula (I.A1d):

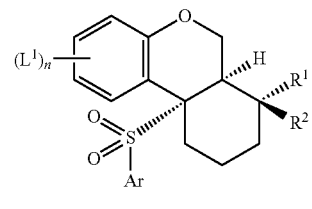

wherein all substituents are as defined for formula (I).

Compounds of formula (I) include compounds of formula (I.A1e):

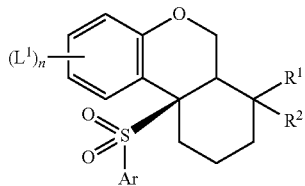

(I.A1e)

wherein all substituents are as defined for formula (I).

Compounds of formula (I) include compounds of formula (I.A1f):

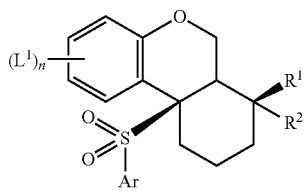

(I.A1f)

wherein all substituents are as defined for formula (I).

Compounds of formula (I) include compounds of formula (I.A1g):

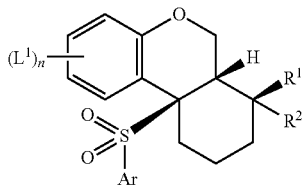

(I.A1g)

wherein all substituents are as defined for formula (I).

Compounds of formula (I) include compounds of formula (I.A1h):

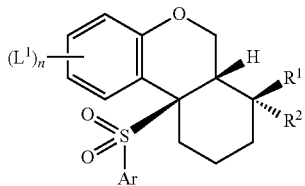

(I.A1h)

wherein all substituents are as defined for formula (I).

Compounds of formula (I) also include any one of the compounds of formulas (I.A1a) to (I.A1h) above wherein n is 2, and the $L^1$ groups are bound to the phenyl moiety as shown in (IIA) and each $L^1$ is the same or different halo.

Compounds of formula (I) also include any one of the compounds of formulas (I.A1a) to (I.A1h) above wherein n is 2, and the $L^1$ groups are bound to the phenyl moiety as shown in (IIA) and each $L^1$ is F.

Compounds of formula (I) also include any one of the compounds of formulas I.A1a to (I.A1h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$ and —OCH$_2$CF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A1a) to (I.A1h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A1a) to (I.A1h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (I.A1a) to (I.A1h) above wherein n is 2, and the $L^1$ groups are bound to the phenyl moiety as shown in (IIA) and Ar is selected from the group consisting of p-Cl-phenyl-, p-CN-phenyl-, and p-CF$_3$-phenyl.

Compounds of formula (I) also include any one of the compounds of formulas (I.A1a) to (I.A1h) above wherein n is 2, and the $L^1$ groups are bound to the phenyl moiety as shown in (IIA) and Ar is selected from the group consisting of: pyridyl, and pyridyl substituted with 1 substituent selected from the group consisting of: —Cl, —CF$_3$ and —CN.

Compounds of formula (I) also include any one of the compounds of formulas (I.A1a) to (I.A1h) above wherein n is 2, and the $L^1$ groups are bound to the phenyl moiety as shown in (IIA), each $L^1$ is the same or different halo, and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$ and —OCH$_2$CF$_3$), —C(O)—O—(C$_1$-C$_6$)alkyl (e.g., —C(O)OCH$_3$), -alkylene-OH (e.g., —CH$_2$OH), halo (C$_1$-C$_6$)alkyl (e.g., —CF$_3$), hydroxyalkoxy- (e.g., HOCH$_2$CH$_2$O—), and alkoxyalkoxy - (e.g., CH$_3$OCH$_2$CH$_2$O—).

Compounds of formula (I) also include any one of the compounds of formulas (I.A1a) to (I.A1h) above wherein n is 2, and the $L^1$ groups are bound to the phenyl moiety as shown in (IIA), each $L^1$ is the same or different halo, and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH₃), -alkylene-OH (e.g., —CH₂OH), halo(C₁-C₆)alkyl (e.g., —CF₃), hydroxyalkoxy- (e.g., HOCH₂CH₂O—), and alkoxyalkoxy- (e.g., CH₃OCH₂CH₂O—).

Compounds of formula (I) also include any one of the compounds of formulas (I.A1a) to (I.A1h) above wherein n is 2, and the L¹ groups are bound to the phenyl moiety as shown in (IIA), each L¹ is the same or different halo, and Ar is selected from the group consisting of p-Cl-phenyl-, p-CN-phenyl-, p-CF₃-phenyl, pyridyl, and pyridyl substituted with 1 substituent selected from the group consisting of: —Cl, —CF₃ and —CN.

Compounds of formula (I) also include any one of the compounds of formulas (I.A1a) to (I.A1h) above wherein n is 2, and the L¹ groups are bound to the phenyl moiety as shown in (IIA), each L¹ is the same or different halo, and Ar is selected from the group consisting of p-Cl-phenyl-, p-CN-phenyl-, and p-CF₃-phenyl.

Compounds of formula (I) also include any one of the compounds of formulas (I.A1a) to (I.A1h) above wherein n is 2, and the L¹ groups are bound to the phenyl moiety as shown in (IIA), each L¹ is the same or different halo, and Ar is selected from the group consisting of: pyridyl, and pyridyl substituted with 1 substituent selected from the group consisting of: —Cl, —CF₃ and —CN.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is selected from the group consisting of p-Cl-phenyl-, p-CN-phenyl-, p-CF₃-phenyl, p-CH₃CH₂SO₂phenyl, p-Br-phenyl, m,p-di-F-phenyl, m,p-di-CN-phenyl, p-CH₃O-phenyl, p-CF₃CH₂Ophenyl, pyridyl, and pyridyl substituted with 1 or 2 substituents independently selected from the group consisting of: halogen, alkyl (e.g., C₁-C₆ alkyl), —CN, —CF₃, —O—(C₁-C₆)alkyl (e.g., —OCH₃), —O-(halo(C₁-C₆)alkyl) (e.g., —OCF₃ and —OCH₂CF₃), —C(O)—O—(C₁-C₆)alkyl (e.g., —C(O)OCH₃), -alkylene-OH (e.g., —CH₂OH), halo(C₁-C₆)alkyl (e.g., —CF₃), hydroxyalkoxy- (e.g., HOCH₂CH₂O—), and alkoxyalkoxy- (e.g., CH₃OCH₂CH₂O—).

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is selected from the group consisting of p-Cl-phenyl-, p-CN-phenyl-, p-CF₃-phenyl, pyridyl, and pyridyl substituted with 1 or 2 substituents independently selected from the group consisting of: halogen, alkyl (e.g., C₁-C₆ alkyl), —CN, —CF₃, —O—(C₁-C₆)alkyl (e.g., —OCH₃), —O-(halo(C₁-C₆)alkyl) (e.g., —OCF₃), —C(O)—O—(C₁-C₆)alkyl (e.g., —C(O)OCH₃), -alkylene-OH (e.g., —CH₂OH), halo(C₁-C₆)alkyl (e.g., —CF₃), hydroxyalkoxy- (e.g., HOCH₂CH₂O—), and alkoxyalkoxy- (e.g., CH₃OCH₂CH₂O—).

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is selected from the group consisting of p-Cl-phenyl-, p-CN-phenyl-, p-CF₃-phenyl, pyridyl, and pyridyl substituted with 1 substituent selected from the group consisting of: —Cl, —CF₃ and —CN.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is selected from the group consisting of p-Cl-phenyl-, p-CN-phenyl-, and p-CF₃-phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is selected from the group consisting of: pyridyl, and pyridyl substituted with 1 substituent selected from the group consisting of: —Cl, —CF₃ and —CN.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-Cl-phenyl-.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-CN-phenyl-.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-CF₃-phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-CH₃CH₂SO₂phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-Br-phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is m,p-di-F-phenyl.

Compounds of formula (I) also include any one of the compounds of formulas, (I.A1a) to (I.A1h) above wherein n is 2, and the L¹ groups are bound to the phenyl moiety as shown in (IIA), each L¹ is F, and Ar is m,p-di-CN-phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-CH₃O-phenyl.

Compounds of formula (I) also include any one of the compounds of formulas (I.A1a) to (I.A1h) above wherein n is 2, and the L¹ groups are bound to the phenyl moiety as shown in (IIA), each L¹ is F, and Ar is p-CF₃CH₂Ophenyl.

Compounds of formula (I) also include any one of the compounds of formulas (I.A1a) to (I.A1h) described above wherein R² is H.

Compounds of formula (I) also include any one of the compounds of formulas (I.A1a) to (I.A1h) described above wherein R² is alkyl.

Compounds of formula (I) also include any one of the compounds of formulas (I.A1a) to (I.A1h) described above wherein R² is methyl.

Compounds of formula (I) include compounds of formula (I.A2a):

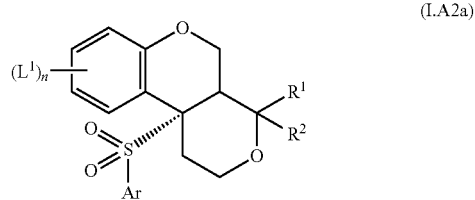

wherein all substituents are as defined for formula (I).

Compounds of formula (I) include compounds of formula (I.A2b):

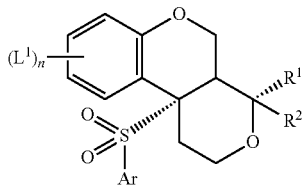
(I.A2b)

wherein all substituents are as defined for formula (I).

Compounds of formula (I) include compounds of formula (I.A2c):

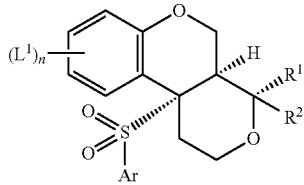
(I.A2c)

wherein all substituents are as defined for formula (I).

Compounds of formula (I) incluse compounds of formula (I.A2d):

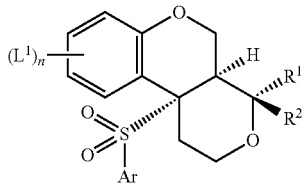
(I.A2d)

wherein all substituents are as defined for formula (I).

Compounds of formula (I) include compounds of formula (I.A2e):

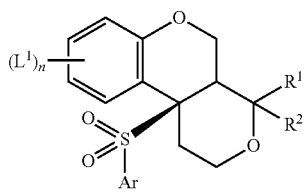
(I.A2e)

wherein all substituents are as defined for formula (I).

Compounds of formula (I) include compounds of formula (I.A2f):

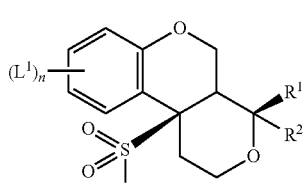
(I.A2f)

wherein all substituents are as defined for formula (I).

Compounds of formula (I) include compounds of formula (I.A2g):

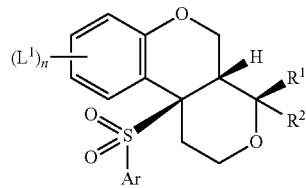
(I.A2g)

wherein all substituents are as defined for formula (I).

Compounds of formula (I) include compounds of formula (I.A2h):

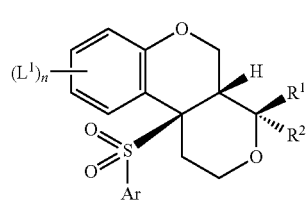
(I.A2h)

wherein all substituents are as defined for formula (I).

Compounds of formula (I) also include any one of the compounds of formulas (I.A2a) to (I.A2h) above wherein n is 2, and the $L^1$ groups are bound to the phenyl moiety as shown in (IIA) and each $L^1$ is the same or different halo.

Compounds of formula (I) also include any one of the compounds of formulas (I.A2a) to (I.A2h) above wherein n is 2, and the $L^1$ groups are bound to the phenyl moiety as shown in (IIA) and each $L^1$ is F.

Compounds of formula (I) also include any one of the compounds of formulas (I.A2a) to (I.A2h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., $C_1$-$C_6$ alkyl), —CN, —CF$_3$, —O—($C_1$-$C_6$)alkyl (e.g., —OCH$_3$), —O-(halo($C_1$-$C_6$)alkyl) (e.g., —OCF$_3$ and —OCH$_2$CF$_3$), —C(O)—O—($C_1$-$C_6$)alkyl (e.g., —C(O)OCH$_3$), -alkylene-OH (e.g., —CH$_2$OH), halo($C_1$-$C_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A2a) to (I.A2h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., $C_1$-$C_6$ alkyl), —CN, —CF$_3$, —O—($C_1$-$C_6$)alkyl (e.g., —OCH$_3$), —O-(halo($C_1$-$C_6$)alkyl) (e.g., —OCF$_3$), —C(O)—O—($C_1$-$C_6$)alkyl (e.g., —C(O)OCH$_3$), -alkylene-OH (e.g., —CH$_2$OH), halo($C_1$-$C_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A2a) to (I.A2h) above wherein n is 2, and the $L^1$ groups are bound to the phenyl moiety as shown in (IIA) and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl moiety as shown in (IIA) and Ar is selected from the group consisting of p-Cl-phenyl-, p-CN-phenyl-, and p-CF$_3$-phenyl.

Compounds of formula (I) also include any one of the compounds of formulas (I.A2a) to (I.A2h) above wherein n is 2, and the L$^1$ groups are bound to the phenyl moiety as shown in (IIA) and Ar is selected from the group consisting of: pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl moiety as shown in (IIA), each L$^1$ is the same or different halo, and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$ and —OCH$_2$CF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A2a) to (I.A2h) above wherein n is 2, and the L$^1$ groups are bound to the phenyl moiety as shown in (IIA), each L$^1$ is the same or different halo, and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$) alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$) alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A2a) to (I.A2h) above wherein n is 2, and the L$^1$ groups are bound to the phenyl moiety as shown in (IIA), each L$^1$ is the same or different halo, and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl moiety as shown in (IIA), each L$^1$ is the same or different halo, and Ar is selected from the group consisting of p-Cl-phenyl-, p-CN-phenyl-, and p-CF$_3$-phenyl.

Compounds of formula (I) also include any one of the compounds of formulas (I.A2a) to (I.A2h) above wherein n is 2, and the L$^1$ groups are bound to the phenyl moiety as shown in (IIA), each L$^1$ is the same or different halo, and Ar is selected from the group consisting of: pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$ and —OCH$_2$CF$_3$), —C(O)—O—(C$_1$-C$_6$)alkyl (e.g., —C(O) OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy- (e.g., CH$_3$OCH$_2$CH$_2$O—).

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, pyridyl, and pyridyl substituted with 1 or 2 substituents independently selected from the group consisting of: halogen, alkyl (e.g., C$_1$-C$_6$ alkyl), —CN, —CF$_3$, —O—(C$_1$-C$_6$)alkyl (e.g., —OCH$_3$), —O-(halo(C$_1$-C$_6$)alkyl) (e.g., —OCF$_3$), —C(O)—O—(C$_1$-C$_6$)alkyl (e.g., —C(O)OCH$_3$), -alkylene-OH (e.g., —CH$_2$OH), halo(C$_1$-C$_6$)alkyl (e.g., —CF$_3$), hydroxyalkoxy- (e.g., HOCH$_2$CH$_2$O—), and alkoxyalkoxy - (e.g., CH$_3$OCH$_2$CH$_2$O—).

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is selected from the group consisting of p-Cl-phenyl-, p-CN-phenyl-, p-CF$_3$-phenyl, pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl, moiety as shown in (IIA), each L$^1$ is F, and Ar is selected from the group consisting of p-Cl-phenyl-, p-CN-phenyl-, and p-CF$_3$-phenyl.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is selected from the group consisting of: pyridyl, and pyridyl substituted with 1 substituent selected from the group consisting of: —Cl, —CF$_3$ and —CN.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is p-Cl-phenyl-.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is p-CN-phenyl-.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is p-CF$_3$-phenyl.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is p-CH$_3$CH$_2$SO$_2$phenyl.

Compounds of formula (I) also include any one of the compounds of formulas (I.A2a) to (I.A2h) above wherein n is 2, and the L$^1$ groups are bound to the phenyl moiety as shown in (IIA), each L$^1$ is F, and Ar is p-Br-phenyl.

Compounds of formula (I) also include any one of the compounds of formulas (I.A2a) to (I.A2h) above wherein n is 2, and the $L^1$ groups are bound to the phenyl moiety as shown in (IIA), each $L^1$ is F, and Ar is m,p-di-F-phenyl.

Compounds of formula (I) also include any one of the compounds of formulas (I.A2a) to (I.A2h) above wherein n is 2, and the $L^1$ groups are bound to the phenyl moiety as shown in (IIA), each $L^1$ is F, and Ar is m,p-di-CN-phenyl.

Compounds of formula (I) also include any one of the compounds of formulas (I.A2a) to (I.A2h) above wherein n is 2, and the $L^1$ groups are bound to the phenyl moiety as shown in (IIA), each $L^1$ is F, and Ar is p-$CH_3O$-phenyl.

Compounds of formula (I) also include any one of the compounds of formulas (I.A2a) to (I.A2h) above wherein n is 2, and the $L^1$ groups are bound to the phenyl moiety as shown in (IIA), each $L^1$ is F, and Ar is p-$CF_3CH_2O$phenyl.

Compounds of formula (I) also include any one of the compounds of formulas (I.A2a) to (I.A2h) described above wherein $R^2$ is H.

Compounds of formula (I) also include any one of the compounds of formulas (I.A2a) to (I.A2h) described above wherein $R^2$ is alkyl.

Compounds of formula (I) also include any one of the compounds of formulas (I.A2a) to (I.A2h) described above wherein $R^2$ is methyl.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is -alkylene-(tetrahydrothiophene 1,1-dioxide).

Compounds of formula (I) also include any one of the compounds of formulas (Ii) to (Ivii), (I.A1), (I.A1a) to (I.A1h), (I.A2), and (I.A2a) to (I.A2h) described above $R^1$ is -alkenyl-$S(O)_2$—$(C_1$-$C_6)$alkyl.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is -cycloalkyl-$S(O)_2$—$(C_1$-$C_6)$alkyl.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is an -alkylene-$S(O)_2$—$(C_1$-$C_6)$alkyl group.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is a —$(C_1$ to $C_2)$ alkylene-$S(O)_2$—$(C_1$-$C_6)$alkyl group.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is a —$(C_1$ to $C_2)$ alkylene-$S(O)_2$—$(C_1$-$C_3)$alkyl group.

Compounds of formula (I) also include any one of the compounds of formulas (Ii) to (Ivii), (I.A1), (I.A1a) to (I.A1h), (I.A2), and (I.A2a) to (I.A2h) described above wherein $R^1$ is a —$(C_2)$ alkylene-$S(O)_2$—$(C_1$-$C_6)$alkyl group.

Compounds of formula (I) also include any one of the compounds of formulas (I.A1), (I.A2), (I.A1a), (I.A1e), (I.A2a) or (I.A2e) wherein $R^1$ is selected from the group consisting of:

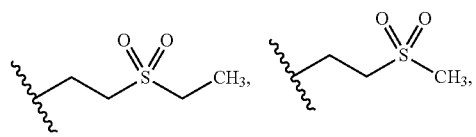

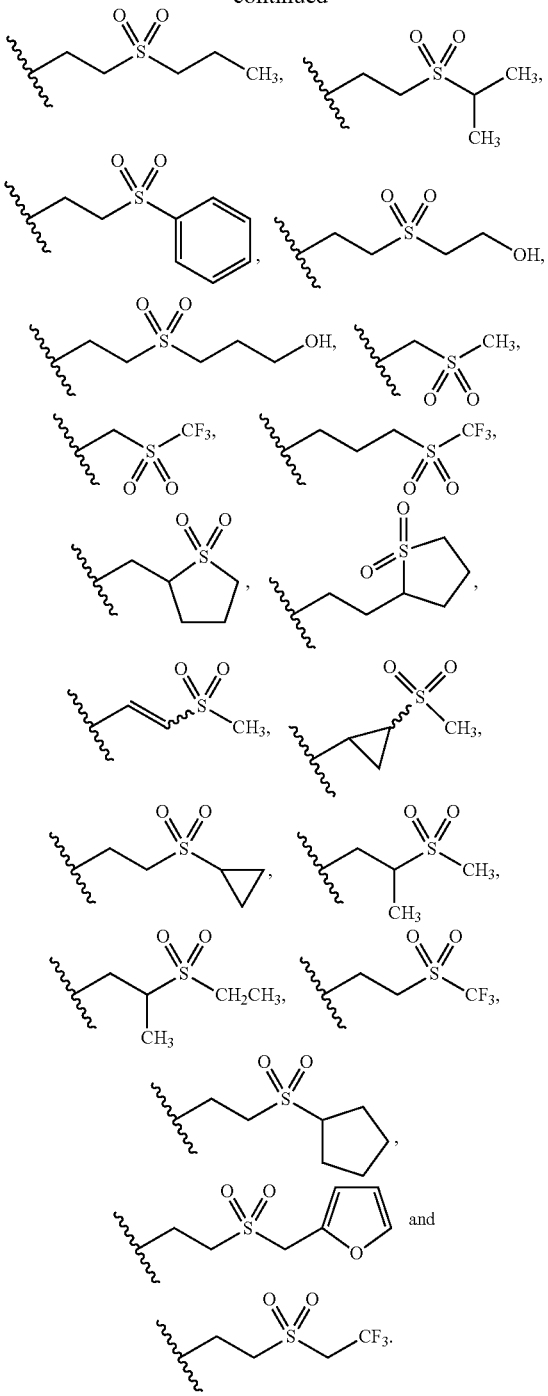

Compounds of formula (I) also include any one of the compounds of formulas (Ii), (Iii), (Iiii), (Iiv), (I.A1b), (I.A1c), (I.A1d), (I.A2b), (I.A2c), or (I.A1d) wherein $R^1$ is selected from the group consisting of:

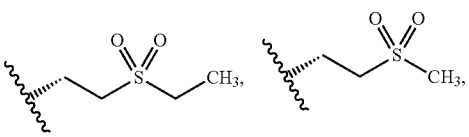

-continued

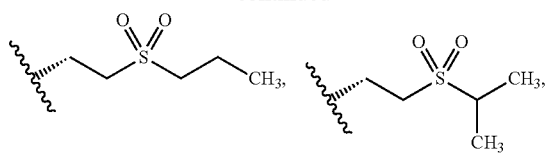

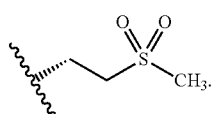

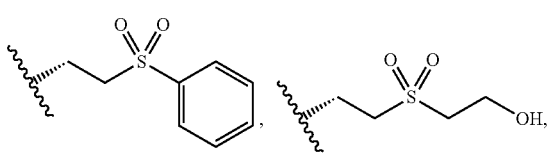

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is

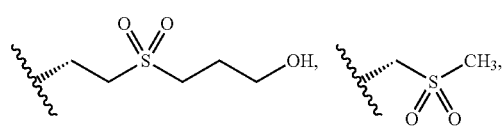

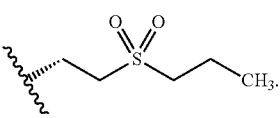

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is

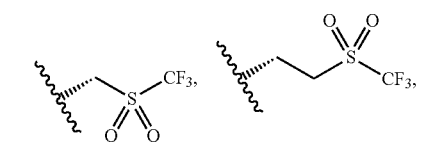

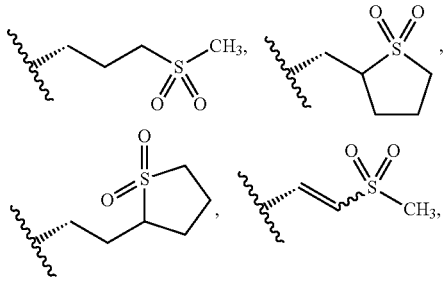

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is

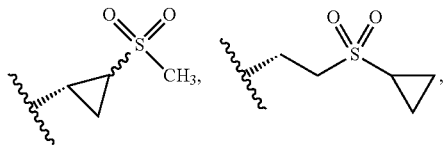

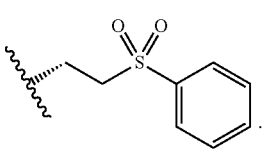

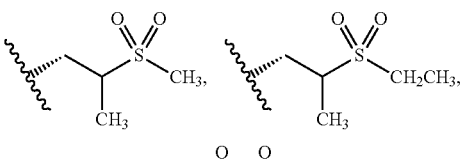

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is and

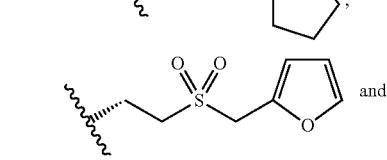

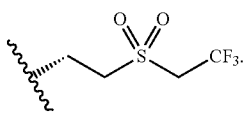

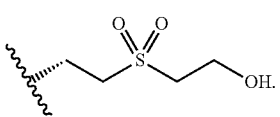

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is Compounds of formula (I) also include any one of the compounds of formulas (Ii), (Iii), (Iiii), (Iiv), (I.A1b), (I.A1c), (I.A1d), (I.A2b), (I.A2c), or (I.A1d), and R¹ is

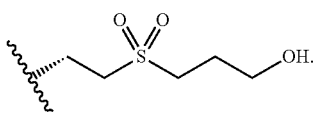

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

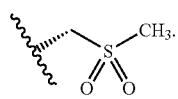

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

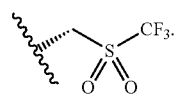

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

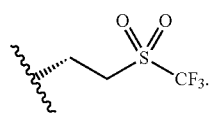

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

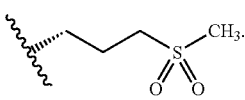

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

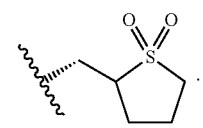

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

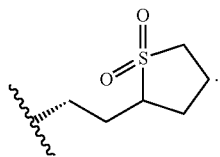

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

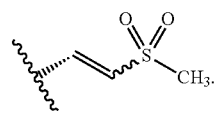

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

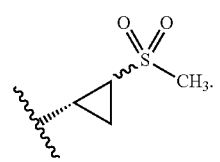

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

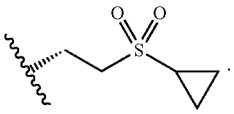

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

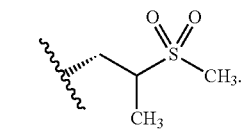

Compounds of formula (I) also include any one of the compounds of formulas (Ii), (Iii), (Iiv), (I.A1b), (I.A1c), (I.A1d), (I.A2b), (I.A2c), or (I.A1d), and $R^1$ is

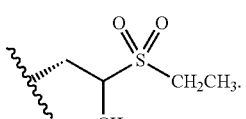

Compounds of formula (I) also include any one of the compounds of formulas (Iii), (Iiii), (Iiv), (I.A1b), (I.A1c), (I.A1d), (I.A2b), (I.A2c), or (I.A1d), and $R^1$ is

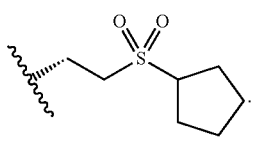

Compounds of formula (I) also include any one of the compounds of formulas (Ii), (Iii), (Iiii), (Iiv), (I.A1b), (I.A1c), (I.A1d), (I.A2b), (I.A2c), or (I.A1d), and $R^1$ is

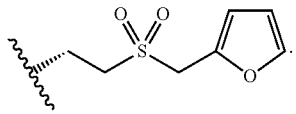

Compounds of formula (I) also include any one of the compounds of formulas (Ii), (Iii), (Iiv), (I.A1b), (I.A1c), (I.A1d), (I.A2b), (I.A2c), or (I.A1d), and $R^1$ is

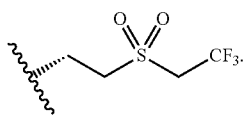

Compounds of formula (I) also include any one of the compounds of formulas (Iv), (Ivi), (Ivii), (I.A1f), (I.A1g), (I.A1h), (I.A2f), (I.A2g), or (I.A2h) wherein $R^1$ is selected from the group consisting of:

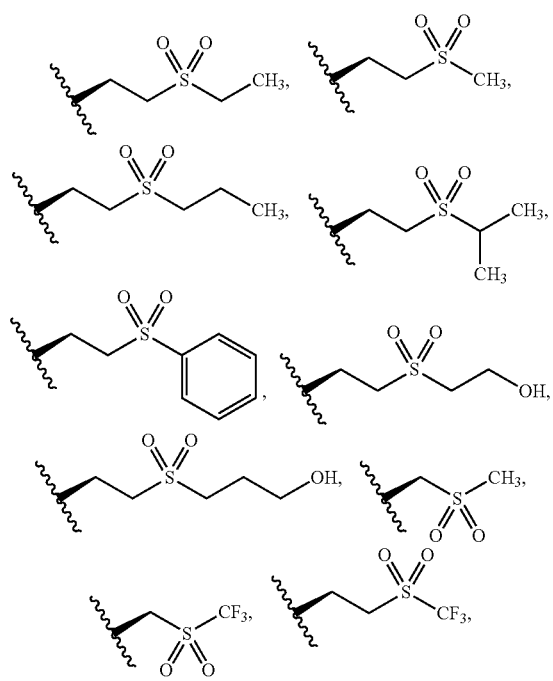

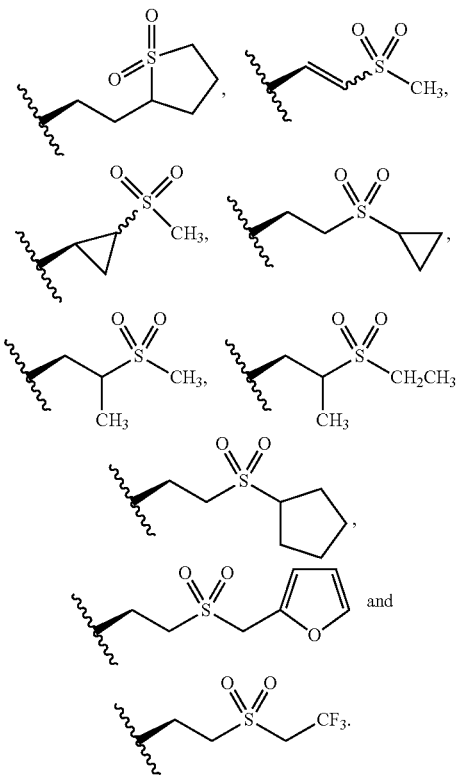

Compounds of formula (I) also include any one of the compounds of formulas (Iv), (Ivi), (Ivii), (I.A1f), (I.A1g), (I.A1h), (I.A2f), (I.A2g), or (I.A2h) wherein $R^1$ is

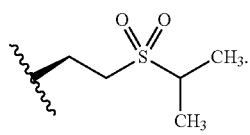

Compounds of formula (I) also include any one of the compounds of formulas (Iv), (Ivi), (Ivii), (I.A1f), (I.A1g), (I.A1h), (I.A2f), (I.A2g), or (I.A2h) wherein $R^1$ is

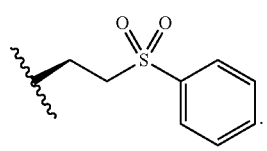

Compounds of formula (I) also include any one of the compounds of formulas (Iv), (Ivi), (Ivii), (I.A1f), (I.A1g), (I.A1h), (I.A2f), (I.A2g), or (I.A2h) wherein $R^1$ is

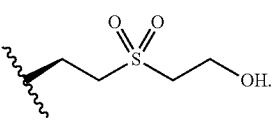

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

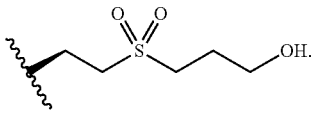

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

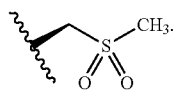

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

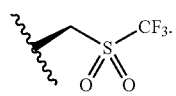

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

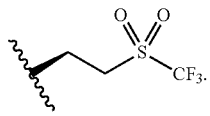

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

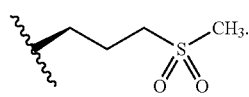

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

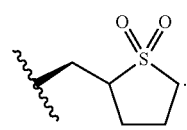

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

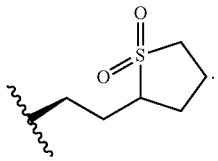

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

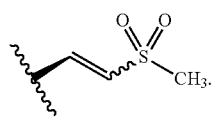

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

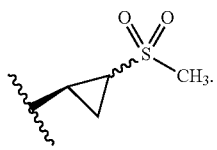 [SMILES: *[C@@H]1CC1S(C)(=O)=O]

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

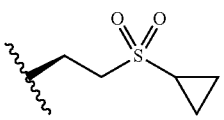

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

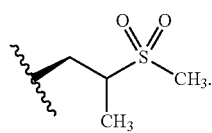

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

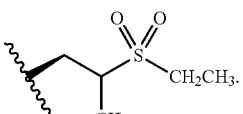

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

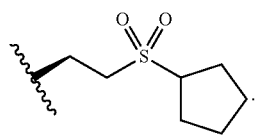

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

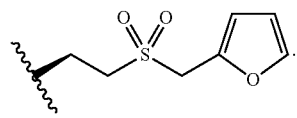

Compounds of formula (I) also include any one of the compounds of formulas (Iv), (Ivi), (Ivii), (I.A1f), (I.A1g), (I.A1h), (I.A2f), (I.A2g), or (I.A2h) wherein R¹ is

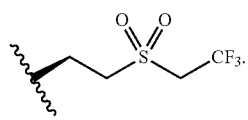

Representative compounds of formula (I) include, but are not limited to:

| Compd No. | STRUCTURE |
|---|---|
| 12 | 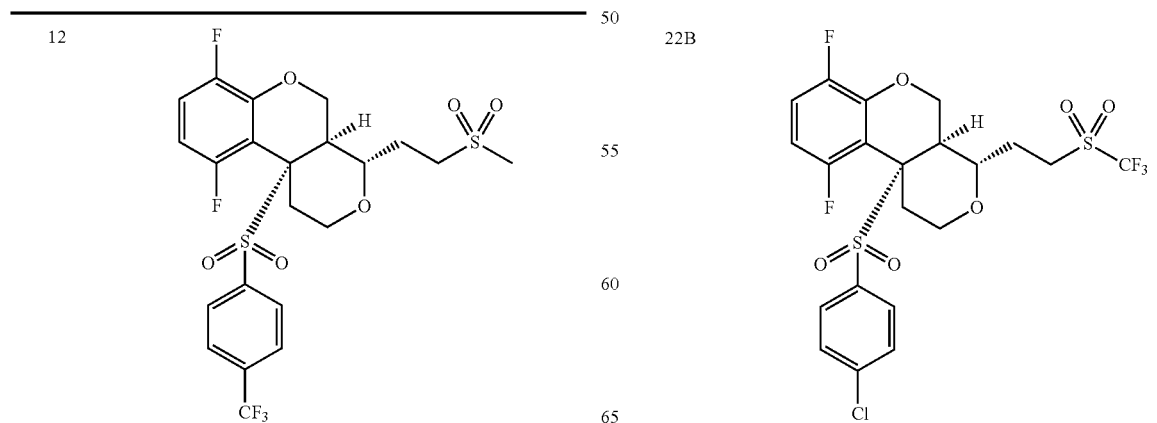 |
| 13 | 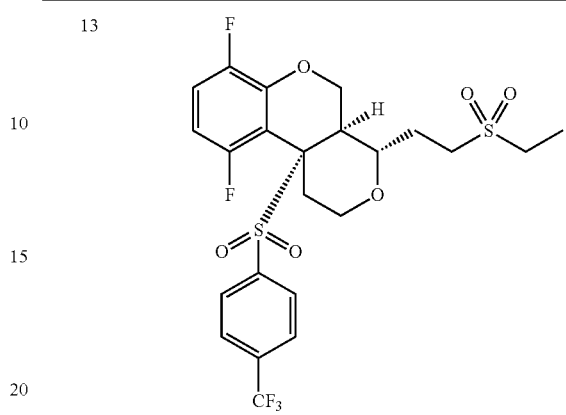 |
| 22A | 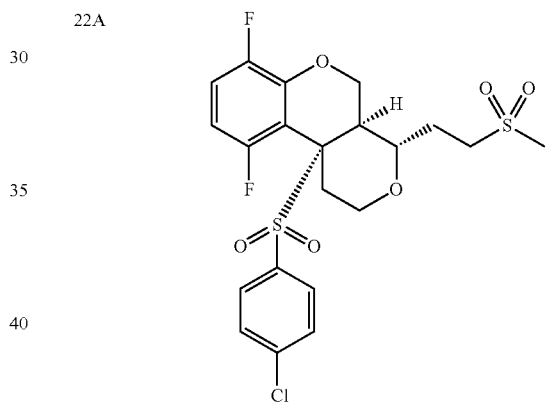 |
| 22B | 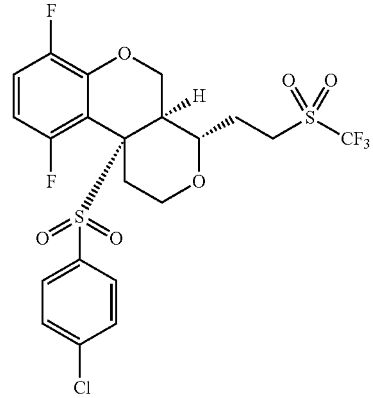 [SMILES: O=S(=O)(CC[C@@H]1OCC[C@@]2(S(=O)(=O)c3ccc(Cl)cc3)c3c(F)ccc(F)c3OC[C@@H]12)C(F)(F)F] |

-continued
| Compd No. | STRUCTURE |
|---|---|
| 22C | 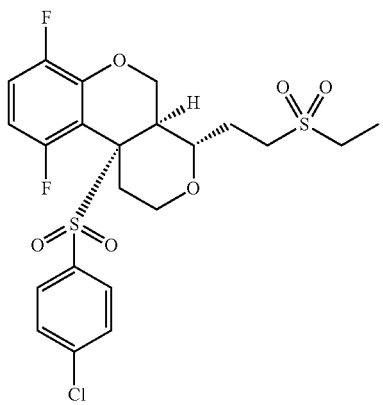 [SMILES: CCS(=O)(=O)CC[C@@H]1OCC[C@@]2(S(=O)(=O)c3ccc(Cl)cc3)c3c(F)ccc(F)c3OC[C@@H]12] |
| 22D | 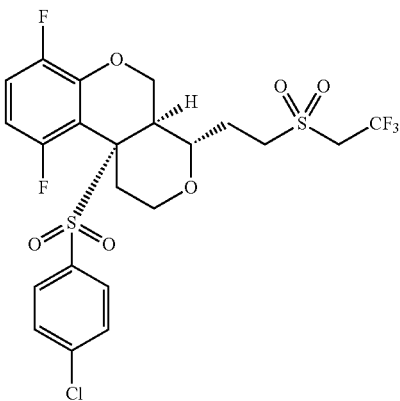 [SMILES: O=S(=O)(CC[C@@H]1OCC[C@@]2(S(=O)(=O)c3ccc(Cl)cc3)c3c(F)ccc(F)c3OC[C@@H]12)CC(F)(F)F] |
| 22E | 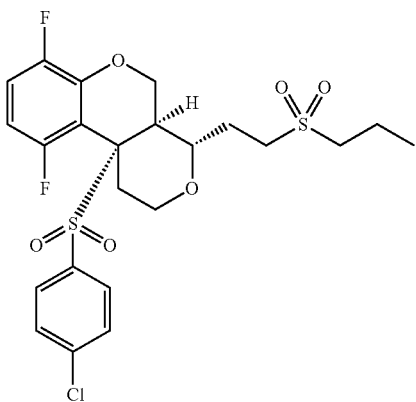 [SMILES: CCCS(=O)(=O)CC[C@@H]1OCC[C@@]2(S(=O)(=O)c3ccc(Cl)cc3)c3c(F)ccc(F)c3OC[C@@H]12] |
-continued
| Compd No. | STRUCTURE |
|---|---|
| 22F | 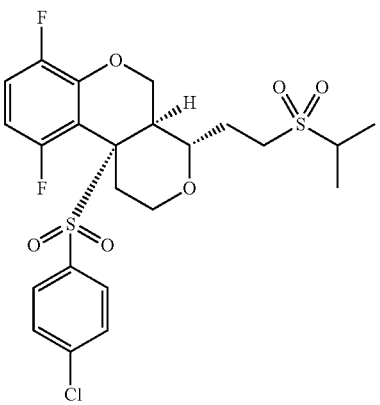 [SMILES: CC(C)S(=O)(=O)CC[C@@H]1OCC[C@@]2(S(=O)(=O)c3ccc(Cl)cc3)c3c(F)ccc(F)c3OC[C@@H]12] |
| 22G | 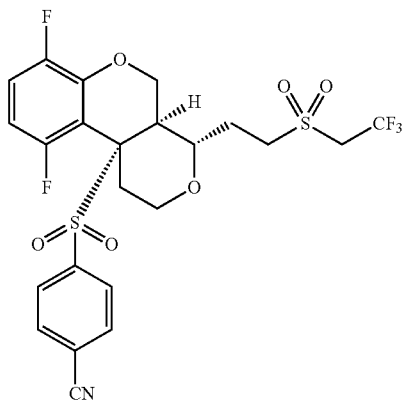 [SMILES: N#Cc1ccc(S(=O)(=O)[C@@]23CCO[C@@H](CCS(=O)(=O)CC(F)(F)F)[C@@H]2COc2c(F)ccc(F)c23)cc1] |
| 22H | 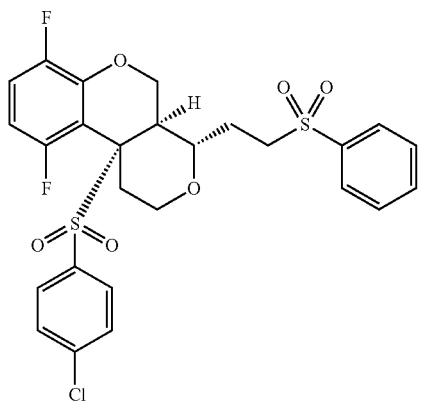 [SMILES: O=S(=O)(CC[C@@H]1OCC[C@@]2(S(=O)(=O)c3ccc(Cl)cc3)c3c(F)ccc(F)c3OC[C@@H]12)c1ccccc1] |

| Compd No. | STRUCTURE |
|---|---|
| 22I | 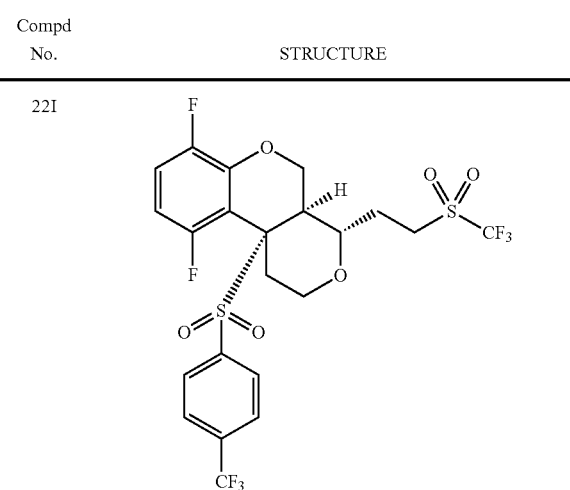 |
| 22J | 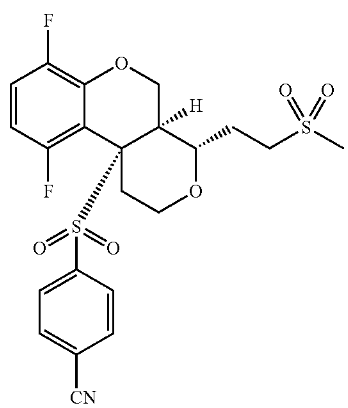 [SMILES: CS(=O)(=O)CC[C@@H]1OCC[C@@]2(S(=O)(=O)c3ccc(C#N)cc3)c3c(F)ccc(F)c3OC[C@@H]12] |
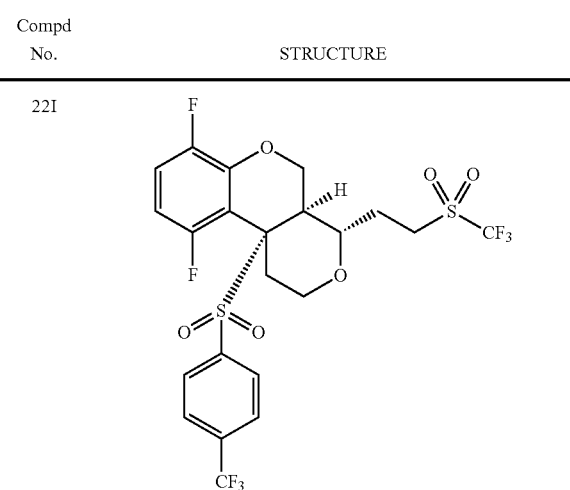
| Compd No. | STRUCTURE |
|---|---|
| 22L | 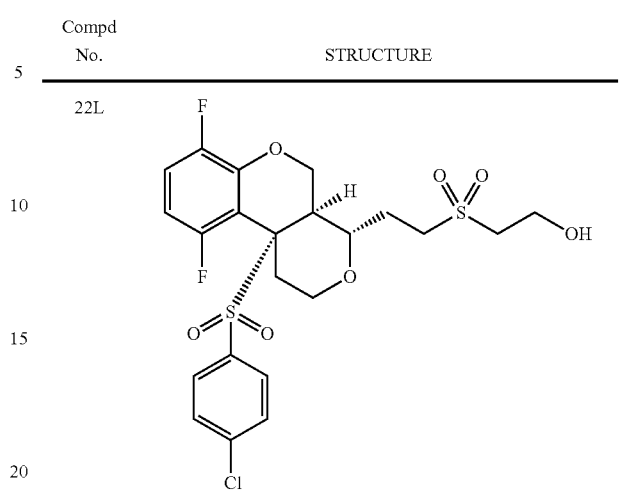 |
| 22M | 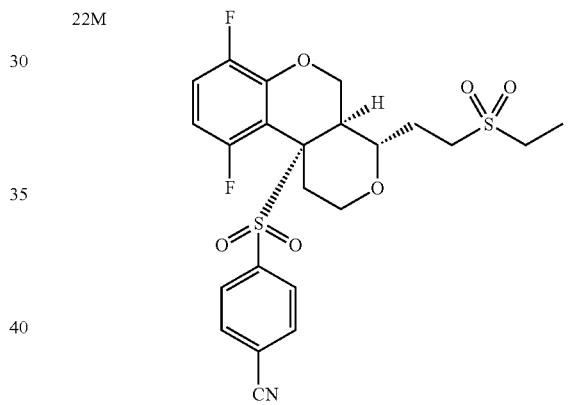 |
| 22N | 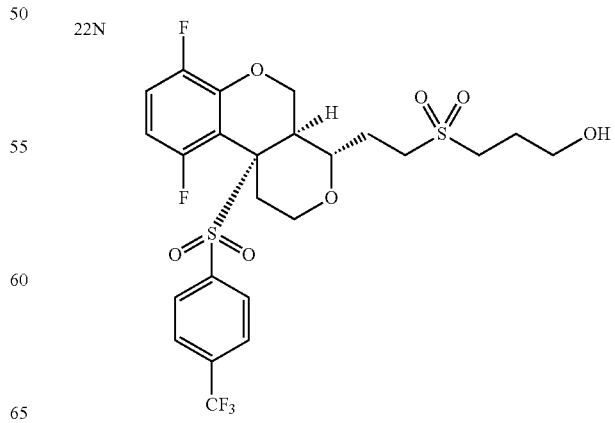 |

-continued
| Compd No. | STRUCTURE |
|---|---|
| 26A | 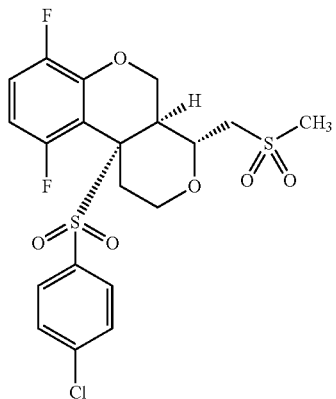 [SMILES: CS(=O)(=O)C[C@@H]1OCC[C@@]2(S(=O)(=O)c3ccc(Cl)cc3)c3c(F)ccc(F)c3OC[C@@H]12] |
| 26B | 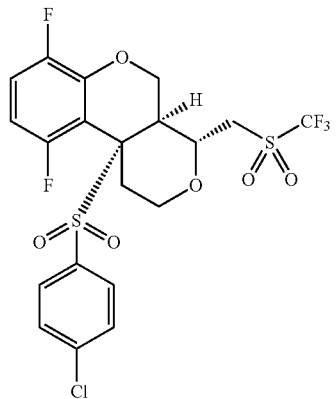 [SMILES: O=S(=O)(C[C@@H]1OCC[C@@]2(S(=O)(=O)c3ccc(Cl)cc3)c3c(F)ccc(F)c3OC[C@@H]12)C(F)(F)F] |
| 27 | 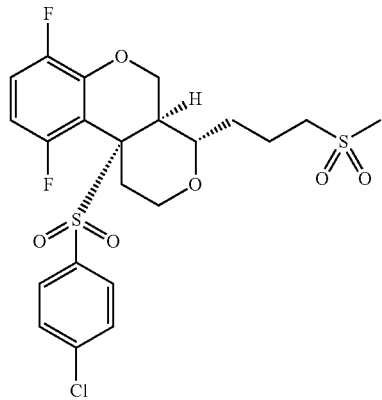 [SMILES: CS(=O)(=O)CCC[C@@H]1OCC[C@@]2(S(=O)(=O)c3ccc(Cl)cc3)c3c(F)ccc(F)c3OC[C@@H]12] |
-continued
| Compd No. | STRUCTURE |
|---|---|
| 28 | 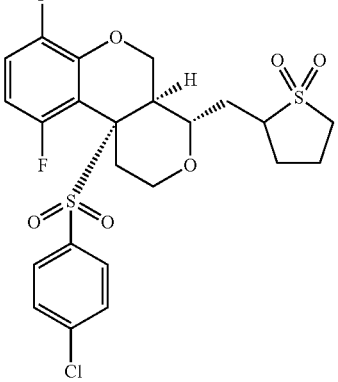 |
| 31 | 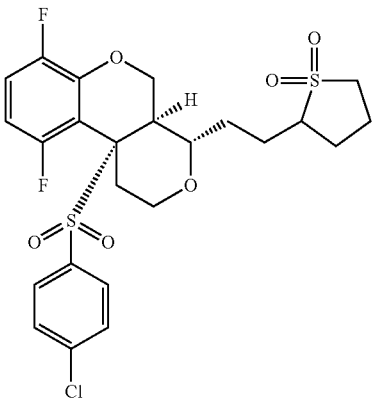 [SMILES: O=S1(=O)CCCC1CC[C@@H]1OCC[C@@]2(S(=O)(=O)c3ccc(Cl)cc3)c3c(F)ccc(F)c3OC[C@@H]12] |
| 33 (−) | 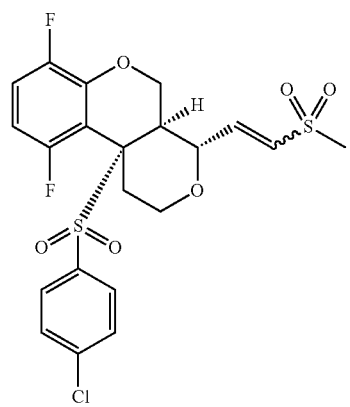 [SMILES: CS(=O)(=O)C=C[C@@H]1OCC[C@@]2(S(=O)(=O)c3ccc(Cl)cc3)c3c(F)ccc(F)c3OC[C@@H]12] |

-continued
| Compd No. | STRUCTURE |
|---|---|
| 36 | 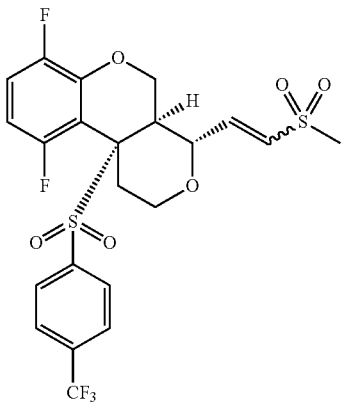 [SMILES: CS(=O)(=O)C=C[C@@H]1OCC[C@@]2(S(=O)(=O)c3ccc(C(F)(F)F)cc3)c3c(F)ccc(F)c3OC[C@@H]12] |
| 37 | 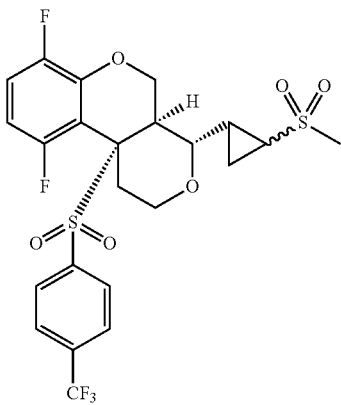 [SMILES: CS(=O)(=O)C1CC1[C@@H]1OCC[C@@]2(S(=O)(=O)c3ccc(C(F)(F)F)cc3)c3c(F)ccc(F)c3OC[C@@H]12] |
| 39 | 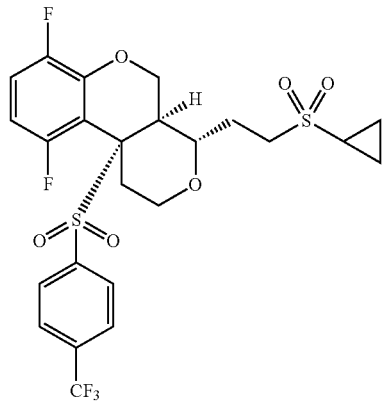 [SMILES: O=S(=O)(CC[C@@H]1OCC[C@@]2(S(=O)(=O)c3ccc(C(F)(F)F)cc3)c3c(F)ccc(F)c3OC[C@@H]12)C1CC1] |
-continued
| Compd No. | STRUCTURE |
|---|---|
| 44A | 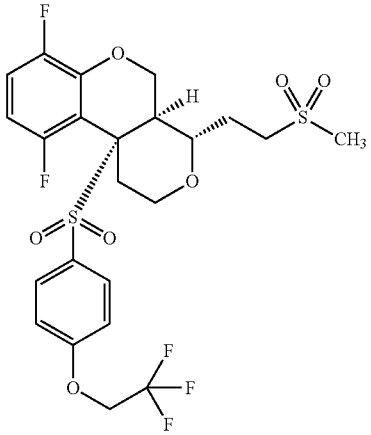 [SMILES: CS(=O)(=O)CC[C@@H]1OCC[C@@]2(S(=O)(=O)c3ccc(OCC(F)(F)F)cc3)c3c(F)ccc(F)c3OC[C@@H]12] |
| 44B | 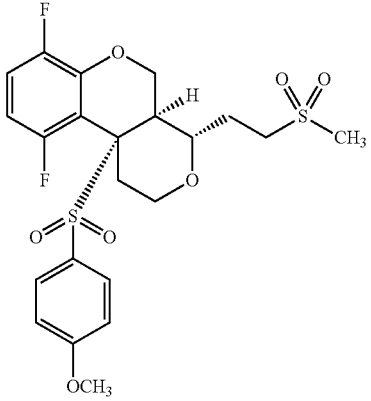 [SMILES: COc1ccc(S(=O)(=O)[C@@]23CCO[C@@H](CCS(C)(=O)=O)[C@@H]2COc2c(F)ccc(F)c23)cc1] |
| 55 | 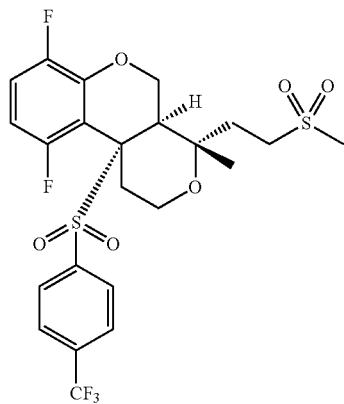 [SMILES: C[C@@]1(CCS(C)(=O)=O)OCC[C@@]2(S(=O)(=O)c3ccc(C(F)(F)F)cc3)c3c(F)ccc(F)c3OC[C@@H]12] |

47
-continued
| Compd No. | STRUCTURE |
|---|---|
| 56 | 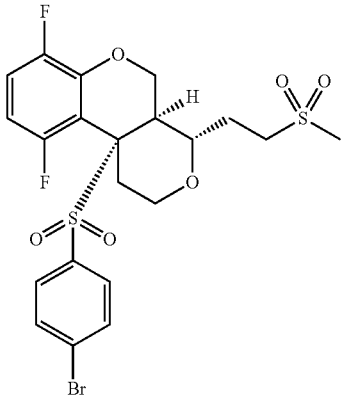 [SMILES: CS(=O)(=O)CC[C@@H]1OCC[C@@]2(S(=O)(=O)c3ccc(Br)cc3)c3c(F)ccc(F)c3OC[C@@H]12] |
| 57 | 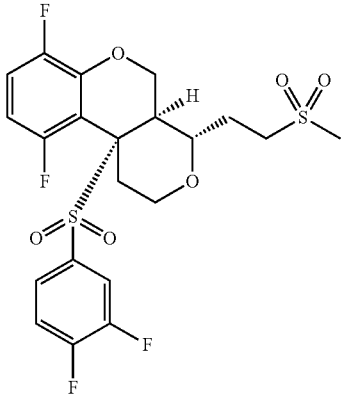 [SMILES: CS(=O)(=O)CC[C@@H]1OCC[C@@]2(S(=O)(=O)c3ccc(F)c(F)c3)c3c(F)ccc(F)c3OC[C@@H]12] |
| 60 | 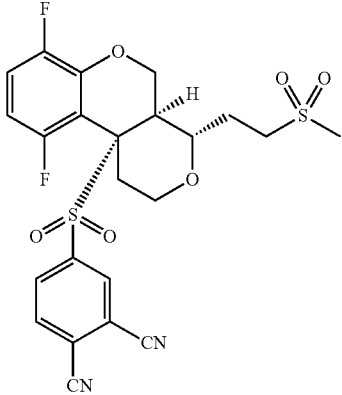 [SMILES: CS(=O)(=O)CC[C@@H]1OCC[C@@]2(S(=O)(=O)c3ccc(C#N)c(C#N)c3)c3c(F)ccc(F)c3OC[C@@H]12] |
48
-continued
| Compd No. | STRUCTURE |
|---|---|
| 70A | 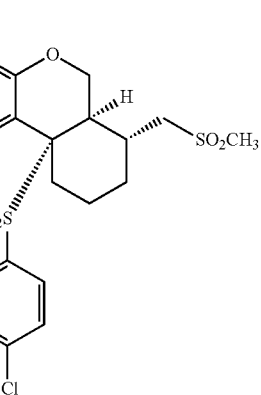 |
| 71A (−) | 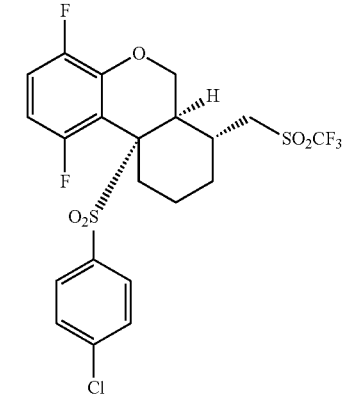 |
| 75A-rac | 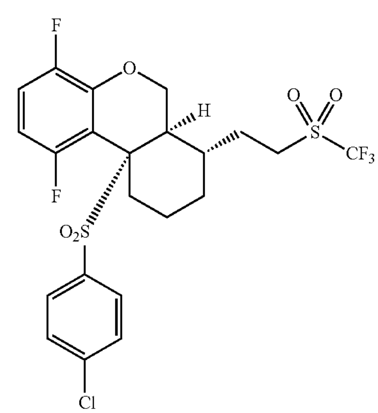 [SMILES: O=S(=O)(CC[C@@H]1CCC[C@@]2(S(=O)(=O)c3ccc(Cl)cc3)c3c(F)ccc(F)c3OC[C@@H]12)C(F)(F)F] |

-continued
| Compd No. | STRUCTURE |
|---|---|
| 75B (−) | 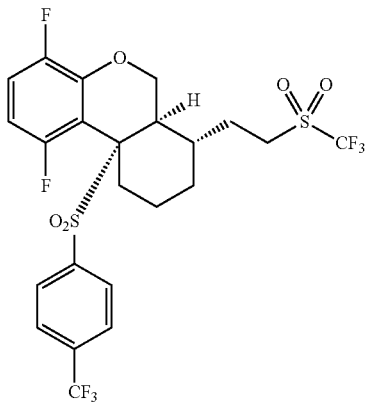 [SMILES: O=S(=O)(CC[C@@H]1CCC[C@@]2(S(=O)(=O)c3ccc(C(F)(F)F)cc3)c3c(F)ccc(F)c3OC[C@@H]12)C(F)(F)F] |
| 76A (−) | 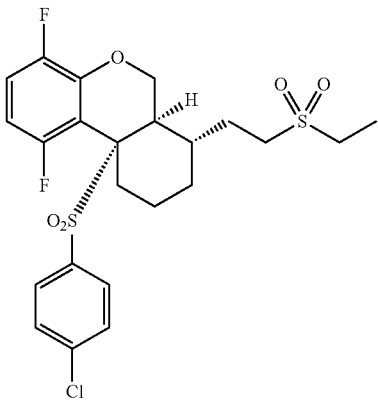 [SMILES: CCS(=O)(=O)CC[C@@H]1CCC[C@@]2(S(=O)(=O)c3ccc(Cl)cc3)c3c(F)ccc(F)c3OC[C@@H]12] |
| 76A (+) | 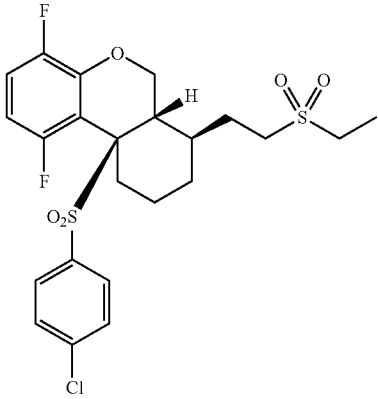 [SMILES: CCS(=O)(=O)CC[C@H]1CCC[C@]2(S(=O)(=O)c3ccc(Cl)cc3)c3c(F)ccc(F)c3OC[C@H]12] |
-continued
| Compd No. | STRUCTURE |
|---|---|
| 76B (−) | 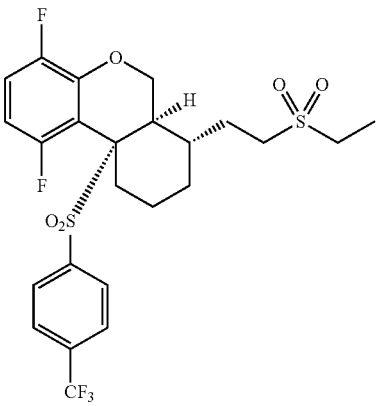 [SMILES: CCS(=O)(=O)CC[C@@H]1CCC[C@@]2(S(=O)(=O)c3ccc(C(F)(F)F)cc3)c3c(F)ccc(F)c3OC[C@@H]12] |
| 78A (−) | 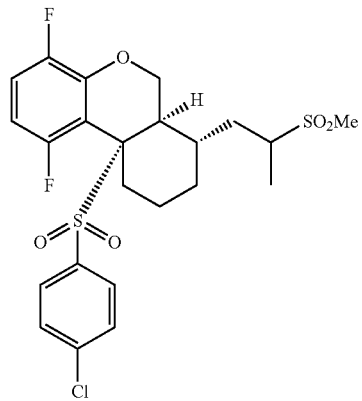 [SMILES: CC(C[C@@H]1CCC[C@@]2(S(=O)(=O)c3ccc(Cl)cc3)c3c(F)ccc(F)c3OC[C@@H]12)S(C)(=O)=O] |
| 79A (−) | 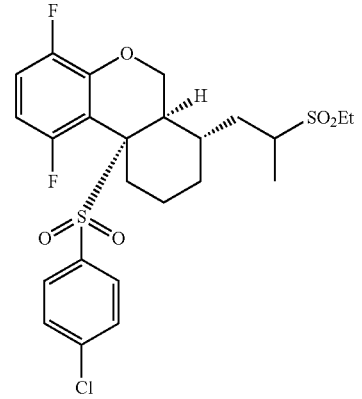 |

| Compd No. | STRUCTURE |
|---|---|
| 80A (−) | 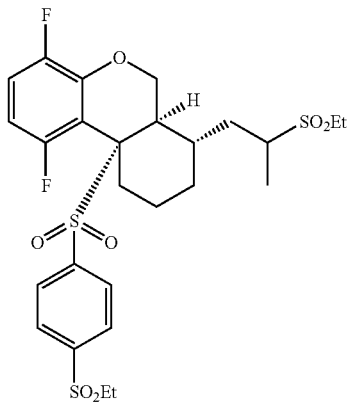 |
| 81A-rac | 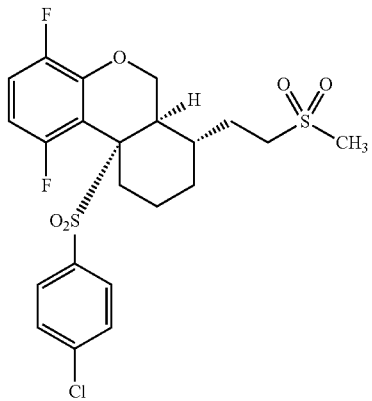 [SMILES: CS(=O)(=O)CC[C@@H]1CCC[C@@]2(S(=O)(=O)c3ccc(Cl)cc3)c3c(F)ccc(F)c3OC[C@@H]12] |
| 81A (−) | 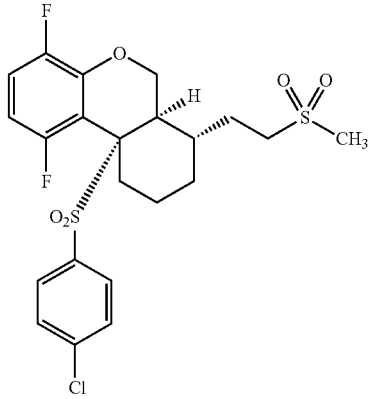 [SMILES: CS(=O)(=O)CC[C@@H]1CCC[C@@]2(S(=O)(=O)c3ccc(Cl)cc3)c3c(F)ccc(F)c3OC[C@@H]12] |
| Compd No. | STRUCTURE |
|---|---|
| 81A (+) | 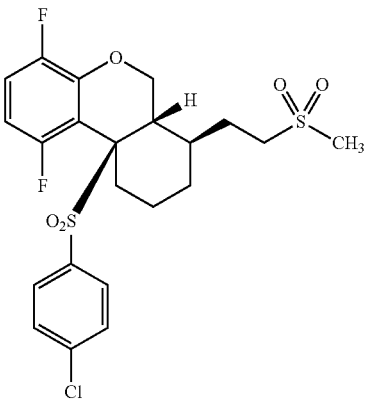 [SMILES: CS(=O)(=O)CC[C@H]1CCC[C@]2(S(=O)(=O)c3ccc(Cl)cc3)c3c(F)ccc(F)c3OC[C@H]12] |
| 81B (−) | 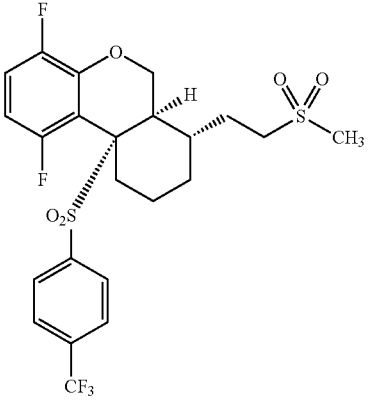 [SMILES: CS(=O)(=O)CC[C@@H]1CCC[C@@]2(S(=O)(=O)c3ccc(C(F)(F)F)cc3)c3c(F)ccc(F)c3OC[C@@H]12] |
| 82A | 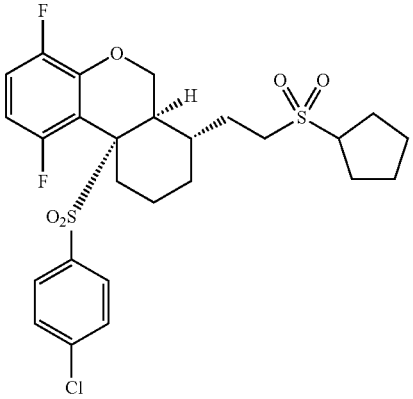 [SMILES: O=S(=O)(CC[C@@H]1CCC[C@@]2(S(=O)(=O)c3ccc(Cl)cc3)c3c(F)ccc(F)c3OC[C@@H]12)C1CCCC1] |

TABLE-continued
| Compd No. | STRUCTURE |
|---|---|
| 83A | 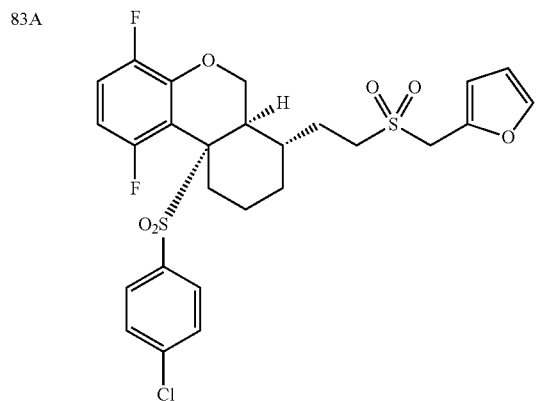 |
| 84A | 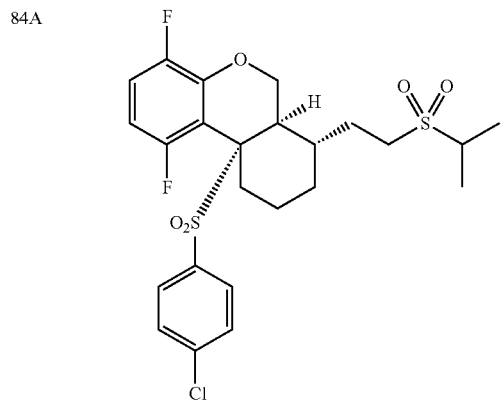 |
| 85A | 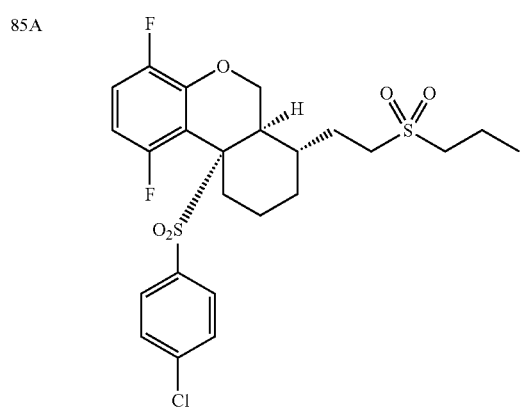 |
| Compd No. | STRUCTURE |
|---|---|
| 85B (−) | 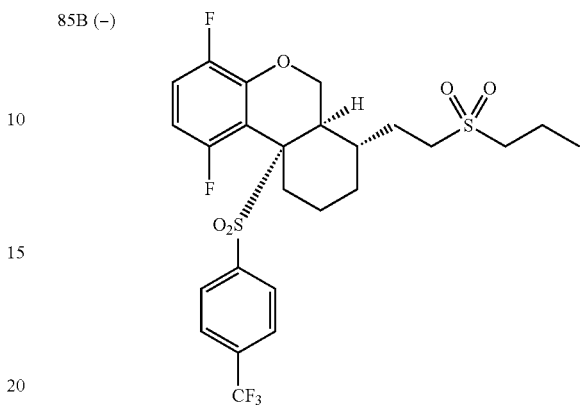 |
| 86A | 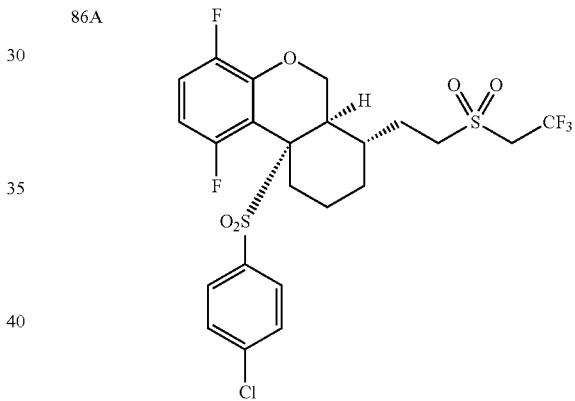 |
| 87B | 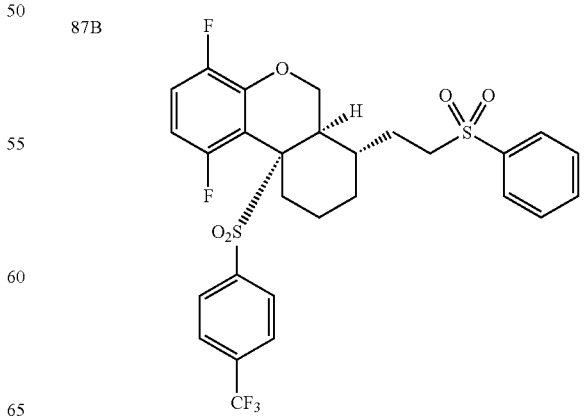 |

| Compd No. | STRUCTURE |
|---|---|
| 95B-rac | (structure) |
| 95B (−) | (structure) |
| 95B (+) | (structure) |
| 106 (−) | (structure) |
| 107 (−) | (structure) |
| 108 (−) | (structure) |
| 111 (−) | (structure) |

One embodiment of the present invention is directed to compounds of Formula (I), or pharmaceutically acceptable salts, solvates or esters thereof.

Another embodiment of this invention is directed to compounds of formula (I).

Another embodiment of this invention is directed to pharmaceutically acceptable salts of the compounds of formula (I).

Another embodiment of this invention is directed to solvates of the compounds of formula (I).

Another embodiment of this invention is directed to pharmaceutically acceptable esters of the compounds of formula (I).

Another embodiment of the present invention is directed to any one of the compounds of formulas (Ii) to (Ivii), or pharmaceutically acceptable salts, solvates or esters thereof.

Another embodiment of this invention is directed to any one of the compounds of formulas (Ii) to (Ivii).

Another embodiment of this invention is directed to pharmaceutically acceptable salts of any one of the compounds of formulas (Ii) to (Ivii).

Another embodiment of this invention is directed to solvates of any one of the compounds of formulas (Ii) to (Ivii).

Another embodiment of this invention is directed to pharmaceutically acceptable esters of any one of the compounds of formulas (Ii) to (Ivii).

Another embodiment of the present invention is directed to any one of the compounds of formulas (I.A1a) to (I.A1h), or pharmaceutically acceptable salts, solvates or esters thereof.

Another embodiment of this invention is directed to any one of the compounds of formulas (I.A1a) to (I.A1h).

Another embodiment of this invention is directed to pharmaceutically acceptable salts of any one of the compounds of formulas (Ii) to (Ivii).

Another embodiment of this invention is directed to solvates of any one of the compounds of formulas (I.A1a) to (I.A1h).

Another embodiment of this invention is directed to pharmaceutically acceptable esters of any one of the compounds of formulas (I.A1a) to (I.A1h).

Another embodiment of the present invention is directed to any one of the compounds of formulas (I.A2a) to (I.A2h), or pharmaceutically acceptable salts, solvates or esters thereof.

Another embodiment of this invention is directed to any one of the compounds of formulas (I.A2a) to (I.A2h).

Another embodiment of this invention is directed to pharmaceutically acceptable salts of any one of the compounds of formulas (Ii) to (Ivii).

Another embodiment of this invention is directed to solvates of any one of the compounds of formulas (I.A2a) to (I.A2h).

Another embodiment of this invention is directed to pharmaceutically acceptable esters of any one of the compounds of formulas (I.A2a) to (I.A2h).

Another embodiment of this invention is directed to any one of the methods of treatment described in the Summary of the invention wherein the compound of formula (I) is any one of the compounds of formulas (Ii) to (Ivii).

Another embodiment of this invention is directed to any one of the methods of treatment described in the Summary of the invention wherein a pharmaceutically acceptable salt of any one of the compounds of (Ii) to (Ivii) is used.

Another embodiment of this invention is directed to any one of the methods of treatment described in the Summary of the invention wherein a solvate of any one of the compounds of formulas (Ii) to (Ivii) is used.

Another embodiment of this invention is directed to any one of the methods of treatment described in the Summary of the invention wherein a pharmaceutically acceptable ester of any one of the compounds of formulas (Ii) to (Ivii) is used.

Another embodiment of this invention is directed to any one of the methods of treatment described in the Summary of the invention wherein any one of the compounds of formulas (I.A1a) to (I.A1h) is used.

Another embodiment of this invention is directed to any one of the methods of treatment described in the Summary of the invention wherein a pharmaceutically acceptable salt of any one of the compounds of formulas (I.A1a) to (I.A1h) is used.

Another embodiment of this invention is directed to any one of the methods of treatment described in the Summary of the invention wherein a solvate of any one of the compounds of formulas (I.A1a) to (I.A1h).

Another embodiment of this invention is directed to any one of the methods of treatment described in the Summary of the invention wherein a pharmaceutically acceptable ester of any one of the compounds of formulas (I.A1a) to (I.A1h) is used.

Another embodiment of this invention is directed to any one of the methods of treatment described in the Summary of the invention wherein any one of the compounds of formulas (I.A2a) to (I.A2h) is used.

Another embodiment of this invention is directed to any one of the methods of treatment described in the Summary of the invention a pharmaceutically acceptable salt of any one of the compounds of formulas (I.A2a) to (I.A2h) is used.

Another embodiment of this invention is directed to any one of the methods of treatment described in the Summary of the invention wherein a solvate of any one of the compounds of formulas (I.A2a) to (I.A2h) is used.

Another embodiment of this invention is directed to any one of the methods of treatment described in the Summary of the invention wherein a pharmaceutically acceptable ester of any one of the compounds of formulas (I.A2a) to (I.A2h) is used.

Another embodiment of this invention is directed to any one of the methods of treatment described in the Summary of the invention wherein the compound used is selected from the group consisting of compounds: 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Another embodiment of this invention is directed to any one of the methods of treatment described in the Summary of the invention wherein the compound used is selected from the group consisting of: the solvates of compounds 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Another embodiment of this invention is directed to any one of the methods of treatment described in the Summary of the invention wherein the compound of formula (I) is compound 12.

Another embodiment of this invention is directed to any one of the methods of treatment described in the Summary of the invention wherein a solvate of a compound of formula (I) is used, and the solvate is a solvate of compound 12.

Another embodiment of this invention is directed to any one of the methods of treatment described in the Summary of the invention wherein the compound of formula (I) is compound 13.

Another embodiment of this invention is directed to any one of the methods of treatment described in the Summary of the invention wherein a solvate of a compound of formula (I) is used, and the solvate is a solvate of compound 13.

Another embodiment of this invention is directed to any one of the methods of treatment described in the Summary of the invention wherein the compound of formula (I) is compound 22A.

Another embodiment of this invention is directed to any one of the methods of treatment described in the Summary of the invention wherein a solvate of a compound of formula (I) is used, and the solvate is a solvate of compound 22A.

Another embodiment of this invention is directed to any one of the methods of treatment described in the Summary of the invention wherein the compound of formula (I) is compound 22B.

Another embodiment of this invention is directed to any one of the methods of treatment described in the Summary of the invention wherein a solvate of a compound of formula (I) is used, and the solvate is a solvate of compound 22B.

Another embodiment of this invention is directed to any one of the methods of treatment described in the Summary of the invention wherein the compound of formula (I) is compound 22B-RAC.

Another embodiment of this invention is directed to any one of the methods of treatment described in the Summary of the invention wherein a solvate of a compound of formula (I) is used, and the solvate is a solvate of compound 22B-RAC.

Another embodiment of this invention is directed to any one of the methods of treatment described in the Summary of the invention wherein the compound of formula (I) is compound 22C.

Another embodiment of this invention is directed to any one of the methods of treatment described in the Summary of the invention wherein a solvate of a compound of formula (I) is used, and the solvate is a solvate of compound 22C.

Another embodiment of this invention is directed to any one of the methods of treatment described in the Summary of the invention wherein the compound of formula (I) is compound 22D.

Another embodiment of this invention is directed to any one of the methods of treatment described in the Summary of the invention wherein a solvate of a compound of formula (I) is used, and the solvate is a solvate of compound 22D.

Another embodiment of this invention is directed to any one of the methods of treatment described in the Summary of the invention wherein the compound of formula (I) is compound 22E.

Another embodiment of this invention is directed to any one of the methods of treatment described in the Summary of the invention wherein a solvate of a compound of formula (I) is used, and the solvate is a solvate of compound 22E.

Another embodiment of this invention is directed to any one of the methods of treatment described in the Summary of the invention wherein the compound of formula (I) is compound 22F.

Another embodiment of this invention is directed to any one of the methods of treatment described in the Summary of the invention wherein a solvate of a compound of formula (I) is used, and the solvate is a solvate of compound 22F.

Another embodiment of this invention is directed to any one of the methods of treatment described in the Summary of the invention wherein the compound of formula (I) is compound 22G.

Another embodiment of this invention is directed to any one of the methods of treatment described in the Summary of the invention wherein a solvate of a compound of formula (I) is used, and the solvate is a solvate of compound 22G.

Another embodiment of this invention is directed to any one of the methods of treatment described in the Summary of the invention wherein the compound of formula (I) is compound 22H.

Another embodiment of this invention is directed to any one of the methods of treatment described in the Summary of the invention wherein a solvate of a compound of formula (I) is used, and the solvate is a solvate of compound 22H.

Another embodiment of this invention is directed to any one of the methods of treatment described in the Summary of the invention wherein the compound of formula (I) is compound 22I.

Another embodiment of this invention is directed to any one of the methods of treatment described in the Summary of the invention wherein a solvate of a compound of formula (I) is used, and the solvate is a solvate of compound 22I.

Another embodiment of this invention is directed to any one of the methods of treatment described in the Summary of the invention wherein the compound of formula (I) is compound 22J.

Another embodiment of this invention is directed to any one of the methods of treatment described in the Summary of the invention wherein a solvate of a compound of formula (1) is used, and the solvate is a solvate of compound 22J.

Another embodiment of this invention is directed to any one of the methods of treatment described in the Summary of the invention wherein the compound of formula (I) is compound 22K.

Another embodiment of this invention is directed to any one of the methods of treatment described in the Summary of the invention wherein a solvate of a compound of formula (I) is used, and the solvate is a solvate of compound 22K.

Another embodiment of this invention is directed to any one of the methods of treatment described in the Summary of the invention wherein the compound of formula (I) is compound 22L.

Another embodiment of this invention is directed to any one of the methods of treatment described in the Summary of the invention wherein a solvate of a compound of formula (I) is used, and the solvate is a solvate of compound 22L.

Another embodiment of this invention is directed to any one of the methods of treatment described in the Summary of the invention wherein the compound of formula (I) is compound 22M.

Another embodiment of this invention is directed to any one of the methods of treatment described in the Summary of the invention wherein a solvate of a compound of formula (I) is used, and the solvate is a solvate of compound 22M.

Another embodiment of this invention is directed to any one of the methods of treatment described in the Summary of the invention wherein the compound of formula (I) is compound 22N.

Another embodiment of this invention is directed to any one of the methods of treatment described in the Summary of the invention wherein a solvate of a compound of formula (I) is used, and the solvate is a solvate of compound 22N.

Another embodiment of this invention is directed to any one of the methods of treatment described in the Summary of the invention wherein the compound of formula (I) is compound 26A.

Another embodiment of this invention is directed to any one of the methods of treatment described in the Summary of the invention wherein a solvate of a compound of formula (I) is used, and the solvate is a solvate of compound 26A.

Another embodiment of this invention is directed to any one of the methods of treatment described in the Summary of the invention wherein the compound of formula (I) is compound 26B.

Another embodiment of this invention is directed to any one of the methods of treatment described in the Summary of the invention wherein a solvate of a compound of formula (I) is used, and the solvate is a solvate of compound 26B.

Another embodiment of this invention is directed to any one of the methods of treatment described in the Summary of the invention wherein the compound of formula (I) is compound 27.

Another embodiment of this invention is directed to any one of the methods of treatment described in the Summary of the invention wherein a solvate of a compound of formula (I) is used, and the solvate is a solvate of compound 27.

Another embodiment of this invention is directed to any one of the methods of treatment described in the Summary of the invention wherein the compound of formula (I) is compound 28.

Another embodiment of this invention is directed to any one of the methods of treatment described in the Summary of the invention wherein a solvate of a compound of formula (I) is used, and the solvate is a solvate of compound 28.

Another embodiment of this invention is directed to any one of the methods of treatment described in the Summary of the invention wherein the compound of formula (I) is compound 31.

Another embodiment of this invention is directed to any one of the methods of treatment described in the Summary of the invention wherein a solvate of a compound of formula (I) is used, and the solvate is a solvate of compound 31.

Another embodiment of this invention is directed to any one of the methods of treatment described in the Summary of the invention wherein the compound of formula (I) is compound 33(−).

Another embodiment of this invention is directed to any one of the methods of treatment described in the Summary of the invention wherein a solvate of a compound of formula (I) is used, and the solvate is a solvate of compound 33(−).

Another embodiment of this invention is directed to any one of the methods of treatment described in the Summary of the invention wherein the compound of formula (I) is compound 36.

Another embodiment of this invention is directed to any one of the methods of treatment described in the Summary of the invention wherein a solvate of a compound of formula (I) is used, and the solvate is a solvate of compound 36.

Another embodiment of this invention is directed to any one of the methods of treatment described in the Summary of the invention wherein the compound of formula (I) is compound 37.

Another embodiment of this invention is directed to any one of the methods of treatment described in the Summary of the invention wherein a solvate of a compound of formula (I) is used, and the solvate is a solvate of compound 37.

Another embodiment of this invention is directed to any one of the methods of treatment described in the Summary of the invention wherein the compound of formula (I) is compound 39.

Another embodiment of this invention is directed to any one of the methods of treatment described in the Summary of the invention wherein a solvate of a compound of formula (I) is used, and the solvate is a solvate of compound 39.

Another embodiment of this invention is directed to any one of the methods of treatment described in the Summary of the invention wherein the compound of formula (I) is compound 44A.

Another embodiment of this invention is directed to any one of the methods of treatment described in the Summary of the invention wherein a solvate of a compound of formula (I) is used, and the solvate is a solvate of compound 44A.

Another embodiment of this invention is directed to any one of the methods of treatment described in the Summary of the invention wherein the compound of formula (I) is compound 44B.

Another embodiment of this invention is directed to any one of the methods of treatment described in the Summary of the invention wherein a solvate of a compound of formula (I) is used, and the solvate is a solvate of compound 44B.

Another embodiment of this invention is directed to any one of the methods of treatment described in the Summary of the invention wherein the compound of formula (I) is compound 55.

Another embodiment of this invention is directed to any one of the methods of treatment described in the Summary of the invention wherein a solvate of a compound of formula (I) is used, and the solvate is a solvate of compound 55.

Another embodiment of this invention is directed to any one of the methods of treatment described in the Summary of the invention wherein the compound of formula (I) is compound 56.

Another embodiment of this invention is directed to any one of the methods of treatment described in the Summary of the invention wherein a solvate of a compound of formula (I) is used, and the solvate is a solvate of compound 56.

Another embodiment of this invention is directed to any one of the methods of treatment described in the Summary of the invention wherein the compound of formula (I) is compound 57.

Another embodiment of this invention is directed to any one of the methods of treatment described in the Summary of the invention wherein a solvate of a compound of formula (I) is used, and the solvate is a solvate of compound 57.

Another embodiment of this invention is directed to any one of the methods of treatment described in the Summary of the invention wherein the compound of formula (I) is compound 60.

Another embodiment of this invention is directed to any one of the methods of treatment described in the Summary of the invention wherein a solvate of a compound of formula (I) is used, and the solvate is a solvate of compound 60.

Another embodiment of this invention is directed to any one of the methods of treatment described in the Summary of the invention wherein the compound of formula (I) is compound 70A.

Another embodiment of this invention is directed to any one of the methods of treatment described in the Summary of the invention wherein a solvate of a compound of formula (I) is used, and the solvate is a solvate of compound 70A.

Another embodiment of this invention is directed to any one of the methods of treatment described in the Summary of the invention wherein the compound of formula (I) is compound 71A(−).

Another embodiment of this invention is directed to any one of the methods of treatment described in the Summary of the invention wherein a solvate of a compound of formula (I) is used, and the solvate is a solvate of compound 71A(−).

Another embodiment of this invention is directed to any one of the methods of treatment described in the Summary of the invention wherein the compound of formula (I) is compound 75A-rac.

Another embodiment of this invention is directed to any one of the methods of treatment described in the Summary of the invention wherein a solvate of a compound of formula (I) is used, and the solvate is a solvate of compound 75A-rac.

Another embodiment of this invention is directed to any one of the methods of treatment described in the Summary of the invention wherein the compound of formula (I) is compound 75B(−).

Another embodiment of this invention is directed to any one of the methods of treatment described in the Summary of the invention wherein a solvate of a compound of formula (I) is used, and the solvate is a solvate of compound 75B(−).

Another embodiment of this invention is directed to any one of the methods of treatment described in the Summary of the invention wherein the compound of formula (I) is compound 76A(−).

Another embodiment of this invention is directed to any one of the methods of treatment described in the Summary of the invention wherein a solvate of a compound of formula (I) is used, and the solvate is a solvate of compound 76A(−).

Another embodiment of this invention is directed to any one of the methods of treatment described in the Summary of the invention wherein the compound of formula (I) is compound 76A(+).

Another embodiment of this invention is directed to any one of the methods of treatment described in the Summary of the invention wherein a solvate of a compound of formula (I) is used, and the solvate is a solvate of compound 76A(+).

Another embodiment of this invention is directed to any one of the methods of treatment described in the Summary of the invention wherein the compound of formula (I) is compound 76B(−).

Another embodiment of this invention is directed to any one of the methods of treatment described in the Summary of the invention wherein a solvate of a compound of formula (I) is used, and the solvate is a solvate of compound 76B(−).

Another embodiment of this invention is directed to any one of the methods of treatment described in the Summary of the invention wherein the compound of formula (I) is compound 78A(−).

Another embodiment of this invention is directed to any one of the methods of treatment described in the Summary of the invention wherein a solvate of a compound of formula (I) is used, and the solvate is a solvate of compound 78A(−).

Another embodiment of this invention is directed to any one of the methods of treatment described in the Summary of the invention wherein the compound of formula (I) is compound 79A(−).

Another embodiment of this invention is directed to any one of the methods of treatment described in the Summary of the invention wherein a solvate of a compound of formula (I) is used, and the solvate is a solvate of compound 79A(−).

Another embodiment of this invention is directed to any one of the methods of treatment described in the Summary of the invention wherein the compound of formula (I) is compound 80A(+).

Another embodiment of this invention is directed to any one of the methods of treatment described in the Summary of the invention wherein a solvate of a compound of formula (I) is used, and the solvate is a solvate of compound 80A(+).

Another embodiment of this invention is directed to any one of the methods of treatment described in the Summary of the invention wherein the compound of formula (I) is compound 81A-rac.

Another embodiment of this invention is directed to any one of the methods of treatment described in the Summary of the invention wherein a solvate of a compound of formula (I) is used, and the solvate is a solvate of compound 81A-rac.

Another embodiment of this invention is directed to any one of the methods of treatment described in the Summary of the invention wherein the compound of formula (I) is compound 81A(−).

Another embodiment of this invention is directed to any one of the methods of treatment described in the Summary of the invention wherein a solvate of a compound of formula (I) is used, and the solvate is a solvate of compound 81A(−).

Another embodiment of this invention is directed to any one of the methods of treatment described in the Summary of the invention wherein the compound of formula (I) is compound 81A(+).

Another embodiment of this invention is directed to any one of the methods of treatment described in the Summary of the invention wherein a solvate of a compound of formula (I) is used, and the solvate is a solvate of compound 81A(+).

Another embodiment of this invention is directed to any one of the methods of treatment described in the Summary of the invention wherein the compound of formula (I) is compound 81B(−).

Another embodiment of this invention is directed to any one of the methods of treatment described in the Summary of the invention wherein a solvate of a compound of formula (I) is used, and the solvate is a solvate of compound 81 B(−).

Another embodiment of this invention is directed to any one of the methods of treatment described in the Summary of the invention wherein the compound of formula (I) is compound 82A.

Another embodiment of this invention is directed to any one of the methods of treatment described in the Summary of the invention wherein a solvate of a compound of formula (I) is used, and the solvate is a solvate of compound 82A.

Another embodiment of this invention is directed to any one of the methods of treatment described in the Summary of the invention wherein the compound of formula (I) is compound 83A.

Another embodiment of this invention is directed to any one of the methods of treatment described in the Summary of the invention wherein a solvate of a compound of formula (I) is used, and the solvate is a solvate of compound 83A.

Another embodiment of this invention is directed to any one of the methods of treatment described in the Summary of the invention wherein the compound of formula (I) is compound 84A.

Another embodiment of this invention is directed to any one of the methods of treatment described in the Summary of the invention wherein a solvate of a compound of formula (I) is used, and the solvate is a solvate of compound 84A.

Another embodiment of this invention is directed to any one of the methods of treatment described in the Summary of the invention wherein the compound of formula (I) is compound 85A.

Another embodiment of this invention is directed to any one of the methods of treatment described in the Summary of the invention wherein a solvate of a compound of formula (I) is used, and the solvate is a solvate of compound 85A.

Another embodiment of this invention is directed to any one of the methods of treatment described in the Summary of the invention wherein the compound of formula (I) is compound 85B(−).

Another embodiment of this invention is directed to any one of the methods of treatment described in the Summary of the invention wherein a solvate of a compound of formula (I) is used, and the solvate is a solvate of compound 85B(−).

Another embodiment of this invention is directed to any one of the methods of treatment described in the Summary of the invention wherein the compound of formula (I) is compound 86A.

Another embodiment of this invention is directed to any one of the methods of treatment described in the Summary of the invention wherein a solvate of a compound of formula (I) is used, and the solvate is a solvate of compound 86A.

Another embodiment of this invention is directed to any one of the methods of treatment described in the Summary of the invention wherein the compound of formula (I) is compound 87B.

Another embodiment of this invention is directed to any one of the methods of treatment described in the Summary of the invention wherein a solvate of a compound of formula (I) is used, and the solvate is a solvate of compound 87B.

Another embodiment of this invention is directed to any one of the methods of treatment described in the Summary of the invention wherein the compound of formula (I) is compound 95B-rac.

Another embodiment of this invention is directed to any one of the methods of treatment described in the Summary of the invention wherein a solvate of a compound of formula (I) is used, and the solvate is a solvate of compound 95B-rac.

Another embodiment of this invention is directed to any one of the methods of treatment described in the Summary of the invention wherein the compound of formula (I) is compound 95B(−).

Another embodiment of this invention is directed to any one of the methods of treatment described in the Summary of the invention wherein a solvate of a compound of formula (I) is used, and the solvate is a solvate of compound 95B(−).

Another embodiment of this invention is directed to any one of the methods of treatment described in the Summary of the invention wherein the compound of formula (I) is compound 95B(+).

Another embodiment of this invention is directed to any one of the methods of treatment described in the Summary of the invention wherein a solvate of a compound of formula (I) is used, and the solvate is a solvate of compound 95B(+).

Another embodiment of this invention is directed to any one of the methods of treatment described in the Summary of the invention wherein the compound of formula (I) is compound 106(−).

Another embodiment of this invention is directed to any one of the methods of treatment described in the Summary of the invention wherein a solvate of a compound of formula (I) is used, and the solvate is a solvate of compound 106(−).

Another embodiment of this invention is directed to any one of the methods of treatment described in the Summary of the invention wherein the compound of formula (I) is compound 107(−).

Another embodiment of this invention is directed to any one of the methods of treatment described in the Summary of the invention wherein a solvate of a compound of formula (I) is used, and the solvate is a solvate of compound 107(−).

Another embodiment of this invention is directed to any one of the methods of treatment described in the Summary of the invention wherein the compound of formula (I) is compound 108(−).

Another embodiment of this invention is directed to any one of the methods of treatment described in the Summary of the invention wherein a solvate of a compound of formula (I) is used, and the solvate is a solvate of compound 108(−).

Another embodiment of this invention is directed to any one of the methods of treatment described in the Summary of the invention wherein the compound of formula (I) is compound 111(−).

Another embodiment of this invention is directed to any one of the methods of treatment described in the Summary of the invention wherein a solvate of a compound of formula (I) is used, and the solvate is a solvate of compound 111(−).

Another embodiment of this invention is directed to any one of the pharmaceutical compositions described above wherein a compound of any one of formulas (Ii) to (Ivii) is used.

Another embodiment of this invention is directed to any one of the pharmaceutical compositions described above wherein a pharmaceutically acceptable salt of any one of the compounds of formulas (Ii) to (Ivii) is used.

Another embodiment of this invention is directed to any one of the pharmaceutical compositions described above wherein a solvate of any one of the compounds of formulas (Ii) to (Ivii) is used.

Another embodiment of this invention is directed to any one of the pharmaceutical compositions described above wherein a pharmaceutically acceptable ester of the compounds of formulas (Ii) to (Ivii) is used.

Another embodiment of this invention is directed to any one of the pharmaceutical compositions described above wherein a compound of any one of formulas (I.A1a) to (I.A1h) is used.

Another embodiment of this invention is directed to any one of the pharmaceutical compositions described above wherein a pharmaceutically acceptable salt of any one of the compounds of formulas (I.A1a) to (I.A1h) is used.

Another embodiment of this invention is directed to any one of the pharmaceutical compositions described above wherein a solvate of any one of the compounds of formulas (I.A1a) to (I.A1h) is used.

Another embodiment of this invention is directed to any one of the pharmaceutical compositions described above wherein a pharmaceutically acceptable ester of the compounds of formulas (I.A1a) to (I.A1h) is used.

Another embodiment of this invention is directed to any one of the pharmaceutical compositions described above wherein a compound of any one of formulas (I.A2a) to (I.A2h) is used.

Another embodiment of this invention is directed to any one of the pharmaceutical compositions described above wherein a pharmaceutically acceptable salt of any one of the compounds of formulas (I.A2a) to (I.A2h) is used.

Another embodiment of this invention is directed to any one of the pharmaceutical compositions described above wherein a solvate of any one of the compounds of formulas (I.A2a) to (I.A2h) is used.

Another embodiment of this invention is directed to any one of the pharmaceutical compositions described above wherein a pharmaceutically acceptable ester of the compounds of formulas (I.A2a) to (I.A2h) is used.

Another embodiment of this invention is directed to compound 12.

Another embodiment of this invention is directed to compound 12 in pure form.

Another embodiment of this invention is directed to compound 12 in isolated form.

Another embodiment of this invention is directed to a solvate of compound 12.

Another embodiment of this invention is directed to compound 13.

Another embodiment of this invention is directed to compound 13 in pure form.

Another embodiment of this invention is directed to compound 13 in isolated form.

Another embodiment of this invention is directed to a solvate of compound 13.

Another embodiment of this invention is directed to compound 22A.

Another embodiment of this invention is directed to compound 22A in pure form.

Another embodiment of this invention is directed to compound 22A in isolated form.

Another embodiment of this invention is directed to a solvate of compound 22A.

Another embodiment of this invention is directed to compound 22B.

Another embodiment of this invention is directed to compound 22B in pure form.

Another embodiment of this invention is directed to compound 22B in isolated form.

Another embodiment of this invention is directed to a solvate of compound 22B.

Another embodiment of this invention is directed to compound 22B-RAC.

Another embodiment of this invention is directed to compound 22B-RAC in pure form.

Another embodiment of this invention is directed to compound 22B-RAC in isolated form.

Another embodiment of this invention is directed to a solvate of compound 22B-RAC.

Another embodiment of this invention is directed to compound 22C.

Another embodiment of this invention is directed to compound 22C in pure form.

Another embodiment of this invention is directed to compound 22C in isolated form.

Another embodiment of this invention is directed to a solvate of compound 22C.

Another embodiment of this invention is directed to compound 22D.

Another embodiment of this invention is directed to compound 22D in pure form.

Another embodiment of this invention is directed to compound 22D in isolated form.

Another embodiment of this invention is directed to a solvate of compound 22D.

Another embodiment of this invention is directed to compound 22E.

Another embodiment of this invention is directed to compound 22E in pure form.

Another embodiment of this invention is directed to compound 22E in isolated form.

Another embodiment of this invention is directed to a solvate of compound 22E.

Another embodiment of this invention is directed to compound 22F.

Another embodiment of this invention is directed to compound 22F in pure form.

Another embodiment of this invention is directed to compound 22F in isolated form.

Another embodiment of this invention is directed to a solvate of compound 22F.

Another embodiment of this invention is directed to compound 22G.

Another embodiment of this invention is directed to compound 22G in pure form.

Another embodiment of this invention is directed to compound 22G in isolated form.

Another embodiment of this invention is directed to a solvate of compound 22G.

Another embodiment of this invention is directed to compound 22H.

Another embodiment of this invention is directed to compound 22H in pure form.

Another embodiment of this invention is directed to compound 22H in isolated form.

Another embodiment of this invention is directed to a solvate of compound 22H.

Another embodiment of this invention is directed to compound 22I.

Another embodiment of this invention is directed to compound 22I in pure form.

Another embodiment of this invention is directed to compound 22I in isolated form.

Another embodiment of this invention is directed to a solvate of compound 22I.

Another embodiment of this invention is directed to compound 22J.

Another embodiment of this invention is directed to compound 22J in pure form.

Another embodiment of this invention is directed to compound 22J in isolated form.

Another embodiment of this invention is directed to a solvate of compound 22J.

Another embodiment of this invention is directed to compound 22K.

Another embodiment of this invention is directed to compound 22K in pure form.

Another embodiment of this invention is directed to compound 22K in isolated form.

Another embodiment of this invention is directed to a solvate of compound 22K.

Another embodiment of this invention is directed to compound 22L.

Another embodiment of this invention is directed to compound 22L in pure form.

Another embodiment of this invention is directed to compound 22L in isolated form.

Another embodiment of this invention is directed to a solvate of compound 22L.

Another embodiment of this invention is directed to compound 22M.

Another embodiment of this invention is directed to compound 22M in pure form.

Another embodiment of this invention is directed to compound 22M in isolated form.

Another embodiment of this invention is directed to a solvate of compound 22M.

Another embodiment of this invention is directed to compound 22N.

Another embodiment of this invention is directed to compound 22N in pure form.

Another embodiment of this invention is directed to compound 22N in isolated form.

Another embodiment of this invention is directed to a solvate of compound 22N.

Another embodiment of this invention is directed to compound 26A.

Another embodiment of this invention is directed to compound 26A in pure form.

Another embodiment of this invention is directed to compound 26A in isolated form.

Another embodiment of this invention is directed to a solvate of compound 26A.

Another embodiment of this invention is directed to compound 26B.

Another embodiment of this invention is directed to compound 26B in pure form.

Another embodiment of this invention is directed to compound 26B in isolated form.

Another embodiment of this invention is directed to a solvate of compound 26B.

Another embodiment of this invention is directed to compound 27.

Another embodiment of this invention is directed to compound 27 in pure form.

Another embodiment of this invention is directed to compound 27 in isolated form.

Another embodiment of this invention is directed to a solvate of compound 27.

Another embodiment of this invention is directed to compound 28.

Another embodiment of this invention is directed to compound 28 in pure form.

Another embodiment of this invention is directed to compound 28 in isolated form.

Another embodiment of this invention is directed to a solvate of compound 28.

Another embodiment of this invention is directed to compound 31.

Another embodiment of this invention is directed to compound 31 in pure form.

Another embodiment of this invention is directed to compound 31 in isolated form.

Another embodiment of this invention is directed to a solvate of compound 31.

Another embodiment of this invention is directed to compound 33(−).

Another embodiment of this invention is directed to compound 33(−) in pure form.

Another embodiment of this invention is directed to compound 33(−) in isolated form.

Another embodiment of this invention is directed to a solvate of compound 33(−).

Another embodiment of this invention is directed to compound 36.

Another embodiment of this invention is directed to compound 36 in pure form.

Another embodiment of this invention is directed to compound 36 in isolated form.

Another embodiment of this invention is directed to a solvate of compound 36.

Another embodiment of this invention is directed to compound 37.

Another embodiment of this invention is directed to compound 37 in pure form.

Another embodiment of this invention is directed to compound 37 in isolated form.

Another embodiment of this invention is directed to a solvate of compound 37.

Another embodiment of this invention is directed to compound 39.

Another embodiment of this invention is directed to compound 39 in pure form.

Another embodiment of this invention is directed to compound 39 in isolated form.

Another embodiment of this invention is directed to a solvate of compound 39.

Another embodiment of this invention is directed to compound 44A.

Another embodiment of this invention is directed to compound 44A in pure form.

Another embodiment of this invention is directed to compound 44A in isolated form.

Another embodiment of this invention is directed to a solvate of compound 44A.

Another embodiment of this invention is directed to compound 44B.

Another embodiment of this invention is directed to compound 44B in pure form.

Another embodiment of this invention is directed to compound 44B in isolated form.

Another embodiment of this invention is directed to a solvate of compound 44B.

Another embodiment of this invention is directed to compound 55.

Another embodiment of this invention is directed to compound 55 in pure form.

Another embodiment of this invention is directed to compound 55 in isolated form.

Another embodiment of this invention is directed to a solvate of compound 55.

Another embodiment of this invention is directed to compound 56.

Another embodiment of this invention is directed to compound 56 in pure form.

Another embodiment of this invention is directed to compound 56 in isolated form.

Another embodiment of this invention is directed to a solvate of compound 56.

Another embodiment of this invention is directed to compound 57.

Another embodiment of this invention is directed to compound 57 in pure form.

Another embodiment of this invention is directed to compound 57 in isolated form.

Another embodiment of this invention is directed to a solvate of compound 57.

Another embodiment of this invention is directed to compound 60.

Another embodiment of this invention is directed to compound 60 in pure form.

Another embodiment of this invention is directed to compound 60 in isolated form.

Another embodiment of this invention is directed to a solvate of compound 60.

Another embodiment of this invention is directed to compound 70A.

Another embodiment of this invention is directed to compound 70A in pure form.

Another embodiment of this invention is directed to compound 70A in isolated form.

Another embodiment of this invention is directed to a solvate of compound 70A.

Another embodiment of this invention is directed to compound 71A(−).

Another embodiment of this invention is directed to compound 71A(−) in pure form.

Another embodiment of this invention is directed to compound 71A(−) in isolated form.

Another embodiment of this invention is directed to a solvate of compound 71A(−).

Another embodiment of this invention is directed to compound 75A-rac.

Another embodiment of this invention is directed to compound 75A-rac in pure form.

Another embodiment of this invention is directed to compound 75A-rac in isolated form.

Another embodiment of this invention is directed to a solvate of compound 75A-rac.

Another embodiment of this invention is directed to compound 75B(−).

Another embodiment of this invention is directed to compound 75B(−) in pure form.

Another embodiment of this invention is directed to compound 75B(−) in isolated form.

Another embodiment of this invention is directed to a solvate of compound 75B(−).

Another embodiment of this invention is directed to compound 76A(−).

Another embodiment of this invention is directed to compound 76A(−) in pure form.

Another embodiment of this invention is directed to compound 76A(−) in isolated form.

Another embodiment of this invention is directed to a solvate of compound 76A(−).

Another embodiment of this invention is directed to compound 76A(+).

Another embodiment of this invention is directed to compound 76A(+) in pure form.

Another embodiment of this invention is directed to compound 76A(+) in isolated form.

Another embodiment of this invention is directed to a solvate of compound 76A(+).

Another embodiment of this invention is directed to compound 76B(−).

Another embodiment of this invention is directed to compound 76B(−) in pure form.

Another embodiment of this invention is directed to compound 76B(−) in isolated form.

Another embodiment of this invention is directed to a solvate of compound 76B(−).

Another embodiment of this invention is directed to compound 78A(−).

Another embodiment of this invention is directed to compound 78A(−) in pure form.

Another embodiment of this invention is directed to compound 78A(−) in isolated form.

Another embodiment of this invention is directed to a solvate of compound 78A(−).

Another embodiment of this invention is directed to compound 79A(−).

Another embodiment of this invention is directed to compound 79A(−) in pure form.

Another embodiment of this invention is directed to compound 79A(−) in isolated form.

Another embodiment of this invention is directed to a solvate of compound 79A(−).

Another embodiment of this invention is directed to compound 80A(+).

Another embodiment of this invention is directed to compound 80A(+) in pure form.

Another embodiment of this invention is directed to compound 80A(+) in isolated form.

Another embodiment of this invention is directed to a solvate of compound 80A(+).

Another embodiment of this invention is directed to compound 81A-rac.

Another embodiment of this invention is directed to compound 81A-rac in pure form.

Another embodiment of this invention is directed to compound 81A-rac in isolated form.

Another embodiment of this invention is directed to a solvate of compound 81A-rac.

Another embodiment of this invention is directed to compound 81A(−).

Another embodiment of this invention is directed to compound 81A(−) in pure form.

Another embodiment of this invention is directed to compound 81A(−) in isolated form.

Another embodiment of this invention is directed to a solvate of compound 81A(−).

Another embodiment of this invention is directed to compound 81A(+).

Another embodiment of this invention is directed to compound 81A(+) in pure form.

Another embodiment of this invention is directed to compound 81A(+) in isolated form.

Another embodiment of this invention is directed to a solvate of compound 81A(+).

Another embodiment of this invention is directed to compound 81 B(−).

Another embodiment of this invention is directed to compound 81 B(−) in pure form.

Another embodiment of this invention is directed to compound 81 B(−) in isolated form.

Another embodiment of this invention is directed to a solvate of compound 81B(−).

Another embodiment of this invention is directed to compound 82A.

Another embodiment of this invention is directed to compound 82A in pure form.

Another embodiment of this invention is directed to compound 82A in isolated form.

Another embodiment of this invention is directed to a solvate of compound 82A.

Another embodiment of this invention is directed to compound 83A.

Another embodiment of this invention is directed to compound 83A in pure form.

Another embodiment of this invention is directed to compound 83A in isolated form.

Another embodiment of this invention is directed to a solvate of compound 83A.

Another embodiment of this invention is directed to compound 84A.

Another embodiment of this invention is directed to compound 84A in pure form.

Another embodiment of this invention is directed to compound 84A in isolated form.

Another embodiment of this invention is directed to a solvate of compound 84A.

Another embodiment of this invention is directed to compound 85A.

Another embodiment of this invention is directed to compound 85A in pure form.

Another embodiment of this invention is directed to compound 85A in isolated form.

Another embodiment of this invention is directed to a solvate of compound 85A.

Another embodiment of this invention is directed to compound 85B(−).

Another embodiment of this invention is directed to compound 85B(−) in pure form.

Another embodiment of this invention is directed to compound 85B(−) in isolated form.

Another embodiment of this invention is directed to a solvate of compound 85B(−).

Another embodiment of this invention is directed to compound 86A.

Another embodiment of this invention is directed to compound 86A in pure form.

Another embodiment of this invention is directed to compound 86A in isolated form.

Another embodiment of this invention is directed to a solvate of compound 86A.

Another embodiment of this invention is directed to compound 87B.

Another embodiment of this invention is directed to compound 87B in pure form.

Another embodiment of this invention is directed to compound 87B in isolated form.

Another embodiment of this invention is directed to a solvate of compound 87B.

Another embodiment of this invention is directed to compound 95B-rac.

Another embodiment of this invention is directed to compound 95B-rac in pure form.

Another embodiment of this invention is directed to compound 95B-rac in isolated form.

Another embodiment of this invention is directed to a solvate of compound 95B-rac.

Another embodiment of this invention is directed to compound 95B(−).

Another embodiment of this invention is directed to compound 95B(−) in pure form.

Another embodiment of this invention is directed to compound 95B(−) in isolated form.

Another embodiment of this invention is directed to a solvate of compound 95B(−).

Another embodiment of this invention is directed to compound 95B(+).

Another embodiment of this invention is directed to compound 95B(+) in pure form.

Another embodiment of this invention is directed to compound 95B(+) in isolated form.

Another embodiment of this invention is directed to a solvate of compound 95B(+).

Another embodiment of this invention is directed to compound 106(−).

Another embodiment of this invention is directed to compound 106(−) in pure form.

Another embodiment of this invention is directed to compound 106(−) in isolated form.

Another embodiment of this invention is directed to a solvate of compound 106(−).

Another embodiment of this invention is directed to compound 107(−).

Another embodiment of this invention is directed to compound 107(−) in pure form.

Another embodiment of this invention is directed to compound 107(−) in isolated form.

Another embodiment of this invention is directed to a solvate of compound 107(−).

Another embodiment of this invention is directed to compound 108(−).

Another embodiment of this invention is directed to compound 108(−) in pure form.

Another embodiment of this invention is directed to compound 108(−) in isolated form.

Another embodiment of this invention is directed to a solvate of compound 108(−).

Another embodiment of this invention is directed to compound 111(−).

Another embodiment of this invention is directed to compound 111(−) in pure form.

Another embodiment of this invention is directed to compound 111(−) in isolated form.

Another embodiment of this invention is directed to a solvate of compound 111(−).

Another embodiment of this invention is directed to a pharmaceutical composition comprising an effective amount of one or more compounds selected from the group consisting of: 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and at least one pharmaceutically acceptable carrier.

Another embodiment of this invention is directed to a pharmaceutical composition comprising an effective amount of a compound selected from the group consisting of: 12, 13, 22A to 22N, 22B-rac, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85A, 85B(−), 86A, 87B, 95B-rac, 95B(−), 95B(+), 106(−), 107(−), 108(−), and 111(−), and at least one pharmaceutically acceptable carrier.

Another embodiment of this invention is directed to a pharmaceutical composition comprising an effective amount of compound 12, and at least one pharmaceutically acceptable carrier.

Another embodiment of this invention is directed to a pharmaceutical composition comprising an effective amount of compound 13, and at least one pharmaceutically acceptable carrier.

Another embodiment of this invention is directed to a pharmaceutical composition comprising an effective amount of compound 22A, and at least one pharmaceutically acceptable carrier.

Another embodiment of this invention is directed to a pharmaceutical composition comprising an effective amount of compound 22B, and at least one pharmaceutically acceptable carrier.

Another embodiment of this invention is directed to a pharmaceutical composition comprising an effective amount of compound 22B-RAC, and at least one pharmaceutically acceptable carrier.

Another embodiment of this invention is directed to a pharmaceutical composition comprising an effective amount of compound 22C, and at least one pharmaceutically acceptable carrier.

Another embodiment of this invention is directed to a pharmaceutical composition comprising an effective amount of compound 22D, and at least one pharmaceutically acceptable carrier.

Another embodiment of this invention is directed to a pharmaceutical composition comprising an effective amount of compound 22E, and at least one pharmaceutically acceptable carrier.

Another embodiment of this invention is directed to a pharmaceutical composition comprising an effective amount of compound 22F, and at least one pharmaceutically acceptable carrier.

Another embodiment of this invention is directed to a pharmaceutical composition comprising an effective amount of compound 22G, and at least one pharmaceutically acceptable carrier.

Another embodiment of this invention is directed to a pharmaceutical composition comprising an effective amount of compound 22H, and at least one pharmaceutically acceptable carrier.

Another embodiment of this invention is directed to a pharmaceutical composition comprising an effective amount of compound 22I, and at least one pharmaceutically acceptable carrier.

Another embodiment of this invention is directed to a pharmaceutical composition comprising an effective amount of compound 22J, and at least one pharmaceutically acceptable carrier.

Another embodiment of this invention is directed to a pharmaceutical composition comprising an effective amount of compound 22K, and at least one pharmaceutically acceptable carrier.

Another embodiment of this invention is directed to a pharmaceutical composition comprising an effective amount of compound 22L, and at least one pharmaceutically acceptable carrier.

Another embodiment of this invention is directed to a pharmaceutical composition comprising an effective amount of compound 22M, and at least one pharmaceutically acceptable carrier.

Another embodiment of this invention is directed to a pharmaceutical composition comprising an effective amount of compound 22N, and at least one pharmaceutically acceptable carrier.

Another embodiment of this invention is directed to a pharmaceutical composition comprising an effective amount of compound 26A, and at least one pharmaceutically acceptable carrier.

Another embodiment of this invention is directed to a pharmaceutical composition comprising an effective amount of compound 26B, and at least one pharmaceutically acceptable carrier.

Another embodiment of this invention is directed to a pharmaceutical composition comprising an effective amount of compound 27, and at least one pharmaceutically acceptable carrier.

Another embodiment of this invention is directed to a pharmaceutical composition comprising an effective amount of compound 28, and at least one pharmaceutically acceptable carrier.

Another embodiment of this invention is directed to a pharmaceutical composition comprising an effective amount of compound 31, and at least one pharmaceutically acceptable carrier.

Another embodiment of this invention is directed to a pharmaceutical composition comprising an effective amount of compound 33(−), and at least one pharmaceutically acceptable carrier.

Another embodiment of this invention is directed to a pharmaceutical composition comprising an effective amount of compound 36, and at least one pharmaceutically acceptable carrier.

Another embodiment of this invention is directed to a pharmaceutical composition comprising an effective amount of compound 37, and at least one pharmaceutically acceptable carrier.

Another embodiment of this invention is directed to a pharmaceutical composition comprising an effective amount of compound 39, and at least one pharmaceutically acceptable carrier.

Another embodiment of this invention is directed to a pharmaceutical composition comprising an effective amount of compound 44A, and at least one pharmaceutically acceptable carrier.

Another embodiment of this invention is directed to a pharmaceutical composition comprising an effective amount of compound 44B, and at least one pharmaceutically acceptable carrier.

Another embodiment of this invention is directed to a pharmaceutical composition comprising an effective amount of compound 55, and at least one pharmaceutically acceptable carrier.

Another embodiment of this invention is directed to a pharmaceutical composition comprising an effective amount of compound 56, and at least one pharmaceutically acceptable carrier.

Another embodiment of this invention is directed to a pharmaceutical composition comprising an effective amount of compound 57, and at least one pharmaceutically acceptable carrier.

Another embodiment of this invention is directed to a pharmaceutical composition comprising an effective amount of compound 60, and at least one pharmaceutically acceptable carrier.

Another embodiment of this invention is directed to a pharmaceutical composition comprising an effective amount of compound 70A, and at least one pharmaceutically acceptable carrier.

Another embodiment of this invention is directed to a pharmaceutical composition comprising an effective amount of compound 71IA(−), and at least one pharmaceutically acceptable carrier.

Another embodiment of this invention is directed to a pharmaceutical composition comprising an effective amount of compound 75A-rac, and at least one pharmaceutically acceptable carrier.

Another embodiment of this invention is directed to a pharmaceutical composition comprising an effective amount of compound 75B(−), and at least one pharmaceutically acceptable carrier.

Another embodiment of this invention is directed to a pharmaceutical composition comprising an effective amount of compound 76A(−), and at least one pharmaceutically acceptable carrier.

Another embodiment of this invention is directed to a pharmaceutical composition comprising an effective amount of compound 76A(+), and at least one pharmaceutically acceptable carrier.

Another embodiment of this invention is directed to a pharmaceutical composition comprising an effective amount of compound 76B(−), and at least one pharmaceutically acceptable carrier.

Another embodiment of this invention is directed to a pharmaceutical composition comprising an effective amount of compound 78A(−), and at least one pharmaceutically acceptable carrier.

Another embodiment of this invention is directed to a pharmaceutical composition comprising an effective amount of compound 79A(−), and at least one pharmaceutically acceptable carrier.

Another embodiment of this invention is directed to a pharmaceutical composition comprising an effective amount of compound 80A(+), and at least one pharmaceutically acceptable carrier.

Another embodiment of this invention is directed to a pharmaceutical composition comprising an effective amount of compound 81A-rac, and at least one pharmaceutically acceptable carrier.

Another embodiment of this invention is directed to a pharmaceutical composition comprising an effective amount of compound 81A(−), and at least one pharmaceutically acceptable carrier.

Another embodiment of this invention is directed to a pharmaceutical composition comprising an effective amount of compound 81A(+), and at least one pharmaceutically acceptable carrier.

Another embodiment of this invention is directed to a pharmaceutical composition comprising an effective amount of compound 81 B(−), and at least one pharmaceutically acceptable carrier.

Another embodiment of this invention is directed to a pharmaceutical composition comprising an effective amount of compound 82A, and at least one pharmaceutically acceptable carrier.

Another embodiment of this invention is directed to a pharmaceutical composition comprising an effective amount of compound 83A, and at least one pharmaceutically acceptable carrier.

Another embodiment of this invention is directed to a pharmaceutical composition comprising an effective amount of compound 84A, and at least one pharmaceutically acceptable carrier.

Another embodiment of this invention is directed to a pharmaceutical composition comprising an effective amount of compound 85A, and at least one pharmaceutically acceptable carrier.

Another embodiment of this invention is directed to a pharmaceutical composition comprising an effective amount of compound 85B(−), and at least one pharmaceutically acceptable carrier.

Another embodiment of this invention is directed to a pharmaceutical composition comprising an effective amount of compound 86A, and at least one pharmaceutically acceptable carrier.

Another embodiment of this invention is directed to a pharmaceutical composition comprising an effective amount of compound 87B, and at least one pharmaceutically acceptable carrier.

Another embodiment of this invention is directed to a pharmaceutical composition comprising an effective amount of compound 95B-rac, and at least one pharmaceutically acceptable carrier.

Another embodiment of this invention is directed to a pharmaceutical composition comprising an effective amount of compound 95B(−), and at least one pharmaceutically acceptable carrier.

Another embodiment of this invention is directed to a pharmaceutical composition comprising an effective amount of compound 95B(+), and at least one pharmaceutically acceptable carrier.

Another embodiment of this invention is directed to a pharmaceutical composition comprising an effective amount of compound 106(−), and at least one pharmaceutically acceptable carrier.

Another embodiment of this invention is directed to a pharmaceutical composition comprising an effective amount of compound 107(−), and at least one pharmaceutically acceptable carrier.

Another embodiment of this invention is directed to a pharmaceutical composition comprising an effective amount of compound 108(−), and at least one pharmaceutically acceptable carrier.

Another embodiment of this invention is directed to a pharmaceutical composition comprising an effective amount of compound 111(−), and at least one pharmaceutically acceptable carrier.

Another embodiment of this invention is directed to a pharmaceutical composition comprising an effective amount of one or more solvates selected from the group consisting of: the solvates of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and at least one pharmaceutically acceptable carrier.

Another embodiment of this invention is directed to a pharmaceutical composition comprising an effective amount of a solvate selected from the group consisting of: the solvates of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and at least one pharmaceutically acceptable carrier.

Another embodiment of this invention is directed to a pharmaceutical composition comprising an effective amount of a solvate of compound 12, and at least one pharmaceutically acceptable carrier.

Another embodiment of this invention is directed to a pharmaceutical composition comprising an effective amount of a solvate of compound 13, and at least one pharmaceutically acceptable carrier.

Another embodiment of this invention is directed to a pharmaceutical composition comprising an effective amount of a solvate of compound 22A, and at least one pharmaceutically acceptable carrier.

Another embodiment of this invention is directed to a pharmaceutical composition comprising an effective amount of a solvate of compound 22B, and at least one pharmaceutically acceptable carrier.

Another embodiment of this invention is directed to a pharmaceutical composition comprising an effective amount of a solvate of compound 22B-RAC, and at least one pharmaceutically acceptable carrier.

Another embodiment of this invention is directed to a pharmaceutical composition comprising an effective amount of a solvate of compound 22C, and at least one pharmaceutically acceptable carrier.

Another embodiment of this invention is directed to a pharmaceutical composition comprising an effective amount of a solvate of compound 22D, and at least one pharmaceutically acceptable carrier.

Another embodiment of this invention is directed to a pharmaceutical composition comprising an effective amount of a solvate of compound 22E, and at least one pharmaceutically acceptable carrier.

Another embodiment of this invention is directed to a pharmaceutical composition comprising an effective amount of a solvate of compound 22F, and at least one pharmaceutically acceptable carrier.

Another embodiment of this invention is directed to a pharmaceutical composition comprising an effective amount of a solvate of compound 22G, and at least one pharmaceutically acceptable carrier.

Another embodiment of this invention is directed to a pharmaceutical composition comprising an effective amount of a solvate of compound 22H, and at least one pharmaceutically acceptable carrier.

Another embodiment of this invention is directed to a pharmaceutical composition comprising an effective amount of a solvate of compound 22I, and at least one pharmaceutically acceptable carrier.

Another embodiment of this invention is directed to a pharmaceutical composition comprising an effective amount of a solvate of compound 22J, and at least one pharmaceutically acceptable carrier.

Another embodiment of this invention is directed to a pharmaceutical composition comprising an effective amount of a solvate of compound 22K, and at least one pharmaceutically acceptable carrier.

Another embodiment of this invention is directed to a pharmaceutical composition comprising an effective amount of a solvate of compound 22L, and at least one pharmaceutically acceptable carrier.

Another embodiment of this invention is directed to a pharmaceutical composition comprising an effective amount of a solvate of compound 22M, and at least one pharmaceutically acceptable carrier.

Another embodiment of this invention is directed to a pharmaceutical composition comprising an effective amount of a solvate of compound 22N, and at least one pharmaceutically acceptable carrier.

Another embodiment of this invention is directed to a pharmaceutical composition comprising an effective amount of a solvate of compound 26A, and at least one pharmaceutically acceptable carrier.

Another embodiment of this invention is directed to a pharmaceutical composition comprising an effective amount of a solvate of compound 26B, and at least one pharmaceutically acceptable carrier.

Another embodiment of this invention is directed to a pharmaceutical composition comprising an effective amount of a solvate of compound 27, and at least one pharmaceutically acceptable carrier.

Another embodiment of this invention is directed to a pharmaceutical composition comprising an effective amount of a solvate of compound 28, and at least one pharmaceutically acceptable carrier.

Another embodiment of this invention is directed to a pharmaceutical composition comprising an effective amount of a solvate of compound 31, and at least one pharmaceutically acceptable carrier.

Another embodiment of this invention is directed to a pharmaceutical composition comprising an effective amount of a solvate of compound 33(−), and at least one pharmaceutically acceptable carrier.

Another embodiment of this invention is directed to a pharmaceutical composition comprising an effective amount of a solvate of compound 36, and at least one pharmaceutically acceptable carrier.

Another embodiment of this invention is directed to a pharmaceutical composition comprising an effective amount of a solvate of compound 37, and at least one pharmaceutically acceptable carrier.

Another embodiment of this invention is directed to a pharmaceutical composition comprising an effective amount of a solvate of compound 39, and at least one pharmaceutically acceptable carrier.

Another embodiment of this invention is directed to a pharmaceutical composition comprising an effective amount of a solvate of compound 44A, and at least one pharmaceutically acceptable carrier.

Another embodiment of this invention is directed to a pharmaceutical composition comprising an effective amount of a solvate of compound 44B, and at least one pharmaceutically acceptable carrier.

Another embodiment of this invention is directed to a pharmaceutical composition comprising an effective amount of a solvate of compound 55, and at least one pharmaceutically acceptable carrier.

Another embodiment of this invention is directed to a pharmaceutical composition comprising an effective amount of a solvate of compound 56, and at least one pharmaceutically acceptable carrier.

Another embodiment of this invention is directed to a pharmaceutical composition comprising an effective amount of a solvate of compound 57, and at least one pharmaceutically acceptable carrier.

Another embodiment of this invention is directed to a pharmaceutical composition comprising an effective amount of a solvate of compound 60, and at least one pharmaceutically acceptable carrier.

Another embodiment of this invention is directed to a pharmaceutical composition comprising an effective amount of a solvate of compound 70A, and at least one pharmaceutically acceptable carrier.

Another embodiment of this invention is directed to a pharmaceutical composition comprising an effective amount of a solvate of compound 71IA(−), and at least one pharmaceutically acceptable carrier.

Another embodiment of this invention is directed to a pharmaceutical composition comprising an effective amount of a solvate of compound 75A-rac, and at least one pharmaceutically acceptable carrier.

Another embodiment of this invention is directed to a pharmaceutical composition comprising an effective amount of a solvate of compound 75B(−), and at least one pharmaceutically acceptable carrier.

Another embodiment of this invention is directed to a pharmaceutical composition comprising an effective amount of a solvate of compound 76A(−), and at least one pharmaceutically acceptable carrier.

Another embodiment of this invention is directed to a pharmaceutical composition comprising an effective amount of a solvate of compound 76A(+), and at least one pharmaceutically acceptable carrier.

Another embodiment of this invention is directed to a pharmaceutical composition comprising an effective amount of a solvate of compound 76B(−), and at least one pharmaceutically acceptable carrier.

Another embodiment of this invention is directed to a pharmaceutical composition comprising an effective amount of a solvate of compound 78A(−), and at least one pharmaceutically acceptable carrier.

Another embodiment of this invention is directed to a pharmaceutical composition comprising an effective amount of a solvate of compound 79A(−), and at least one pharmaceutically acceptable carrier.

Another embodiment of this invention is directed to a pharmaceutical composition comprising an effective amount of a solvate of compound 80A(+), and at least one pharmaceutically acceptable carrier.

Another embodiment of this invention is directed to a pharmaceutical composition comprising an effective amount of a solvate of compound 81A-rac, and at least one pharmaceutically acceptable carrier.

Another embodiment of this invention is directed to a pharmaceutical composition comprising an effective amount of a solvate of compound 81A(−), and at least one pharmaceutically acceptable carrier.

Another embodiment of this invention is directed to a pharmaceutical composition comprising an effective amount of a solvate of compound 81A(+), and at least one pharmaceutically acceptable carrier.

Another embodiment of this invention is directed to a pharmaceutical composition comprising an effective amount of a solvate of compound 81 B(−), and at least one pharmaceutically acceptable carrier.

Another embodiment of this invention is directed to a pharmaceutical composition comprising an effective amount of a solvate of compound 82A, and at least one pharmaceutically acceptable carrier.

Another embodiment of this invention is directed to a pharmaceutical composition comprising an effective amount of a solvate of compound 83A, and at least one pharmaceutically acceptable carrier.

Another embodiment of this invention is directed to a pharmaceutical composition comprising an effective amount of a solvate of compound 84A, and at least one pharmaceutically acceptable carrier.

Another embodiment of this invention is directed to a pharmaceutical composition comprising an effective amount of a solvate of compound 85A, and at least one pharmaceutically acceptable carrier.

Another embodiment of this invention is directed to a pharmaceutical composition comprising an effective amount of a solvate of compound 85B(−), and at least one pharmaceutically acceptable carrier.

Another embodiment of this invention is directed to a pharmaceutical composition comprising an effective amount of a solvate of compound 86A, and at least one pharmaceutically acceptable carrier.

Another embodiment of this invention is directed to a pharmaceutical composition comprising an effective amount of a solvate of compound 87B, and at least one pharmaceutically acceptable carrier.

Another embodiment of this invention is directed to a pharmaceutical composition comprising an effective amount of a solvate of compound 95B-rac, and at least one pharmaceutically acceptable carrier.

Another embodiment of this invention is directed to a pharmaceutical composition comprising an effective amount of a solvate of compound 95B(−), and at least one pharmaceutically acceptable carrier.

Another embodiment of this invention is directed to a pharmaceutical composition comprising an effective amount of a solvate of compound 95B(+), and at least one pharmaceutically acceptable carrier.

Another embodiment of this invention is directed to a pharmaceutical composition comprising an effective amount of a solvate of compound 106(−), and at least one pharmaceutically acceptable carrier.

Another embodiment of this invention is directed to a pharmaceutical composition comprising an effective amount of a solvate of compound 107(−), and at least one pharmaceutically acceptable carrier.

Another embodiment of this invention is directed to a pharmaceutical composition comprising an effective amount of a solvate of compound 108(−), and at least one pharmaceutically acceptable carrier.

Another embodiment of this invention is directed to a pharmaceutical composition comprising an effective amount of a solvate of compound 111(−), and at least one pharmaceutically acceptable carrier.

Another embodiment of this invention is directed to a pharmaceutical composition comprising an effective amount of one or more (e.g., one) compounds of formula (I) (e.g., compounds of formula (I.A1), or compounds of formula (I.A2)), and an effective amount of one or more (e.g., one) other pharmaceutically active ingredients (e.g.,) drugs, and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention also provides a pharmaceutical composition comprising an effective amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more (e.g., one) other therapeutically effective pharmaceutical active ingredients (e.g., drugs), and a pharmaceutically acceptable carrier. Examples of the other drugs include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

The other pharmaceutically active ingredients (e.g., drugs), used in the pharmaceutical compositions with the compounds of formula (I), as well as being used in the methods of treatment with the compounds of formula (I) (i.e., the combination therapies described herein) include, but are not limited to: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators, HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase, PDE-10 inhibitors, and cholesterol absorption inhibitors (e.g., ezetimibe).

Thus, another embodiment of this invention is directed to pharmaceutical compositions comprising an effective amount of one or more (e.g., one) compounds of formula (I) (e.g., compounds of formula (I.A1), or compounds of formula (I.A2)), and an effective amount of one or more (e.g., one) other pharmaceutically active ingredients (e.g., drugs), and a pharmaceutically acceptable carrier, wherein said other pharmaceutically active ingredients are selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators, HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists;

AMPA agonists; PDE4 inhibitors; GABA$_A$ inverse agonists; inhibitors of amyloid aggregation; glycogen synthase kinase beta inhibitors; promoters of alpha secretase activity, PDE-10 inhibitors and cholesterol absorption inhibitors (e.g., ezetimibe).

Another embodiment of this invention is directed to a pharmaceutical composition comprising an effective amount of one or more (e.g., one) compounds of formula (I) (e.g., compounds of formula (I.A1), or compounds of formula (I.A2)), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more BACE inhibitors, and a pharmaceutically acceptable carrier.

Another embodiment of this invention is directed to a pharmaceutical composition comprising an effective amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I) (e.g., compounds of formulas (I.A1), or compounds of formula (I.A2)), and effective amount of one or more muscarinic antagonists (e.g., $m_1$ or $m_2$ antagonists), and a pharmaceutically acceptable carrier.

Another embodiment of this invention is directed to a pharmaceutical composition comprising an effective amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−), and effective amount of one or more muscarinic antagonists (e.g., $m_1$ or $m_2$ antagonists), and a pharmaceutically acceptable carrier.

Another embodiment of this invention is directed to a method for inhibiting gamma-secretase comprising administering to a patient in need of treatment an effective (i.e., therapeutically effective) amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+),76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Another embodiment of this invention is directed to a method for treating one or more neurodegenerative diseases comprising administering to a patient in need of treatment an effective (i.e., therapeutically effective) amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Another embodiment of this invention is directed to a method of inhibiting the deposition of amyloid protein (e.g., amyloid beta protein) in, on or around neurological tissue (e.g., the brain) comprising administering to a patient in need of treatment an effective (i.e., therapeutically effective) amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Another embodiment of this invention is directed to a method of treating Alzheimer's disease comprising administering to a patient in need of treatment an effective (i.e., therapeutically effective) amount of one or more (e.g., one) compounds selected from the group consisting of compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+),76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−).

Other embodiments of this invention are directed to combination therapies for (1) inhibiting gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of one or more (e.g. one) compounds of formula (I) (e.g., compounds of formula (I.A1), or compounds of formula (I.A2)) and the administration of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein the compound of formula (I) (e.g., the compound of formula (I.A1), or the compound of formula (I.A2)) is used in combination with an effective amount of one or more other pharmaceutically active ingredients selected from the group consisting of: BACE inhibitors (beta secretase inhibitors), muscarinic antagonists (e.g., $m_1$ or $m_2$ antagonists), cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABA$_A$ inverse agonists; inhibitors of amyloid aggregation; glycogen synthase kinase beta inhibitors; promoters of alpha secretase activity; PDE-10 inhibitors and cholesterol absorption inhibitors (e.g., ezetimibe).

Examples of cholinesterase inhibitors are tacrine, donepezil, rivastigmine, galantamine, pyridostigmine and neostigmine, with tacrine, donepezil, rivastigmine and galantamine being preferred. Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759336 filed Jun. 7, 2007, U.S. Application Ser. No. 60/874362 filed Dec. 12, 2006, and U.S. Application Ser. No. 60/874419 filed Dec. 12, 2006, the disclosures of each being incorporated incorporated herein by reference thereto.

Other embodiments of this invention are described below. The embodiments have been numbered for ease of reference. When an Embodiment refers to "any one of" that Embodiment describes a separate embodiment to each group or embodiment listed. For example, Embodiment No. 1 is meant to describe: (1) an embodiment directed to compounds of formula (I) wherein Ar is unsubstituted aryl (e.g., unsubstituted phenyl), (2) an embodiment directed to any one of compounds (iI) to (Ivii) wherein Ar is unsubstituted aryl (e.g., unsubstituted phenyl), (3) an embodiment directed to compounds of formula (I.A1) wherein Ar is unsubstituted aryl (e.g., unsubstituted phenyl), (4) an embodiment directed to any one of compounds (I.A1a) to (I.A1h) wherein Ar is unsubstituted aryl (e.g., unsubstituted phenyl), (5) an embodiment directed to compounds of formula (I.A2) wherein Ar is unsubstituted aryl (e.g., unsubstituted phenyl), and (6) an embodiment directed to any one of compounds (I.A2a) to (I.A2h) wherein Ar is unsubstituted aryl (e.g., unsubstituted phenyl).

Embodiment No. 1 is directed to any one of the compounds of formulas (I), (iI) to (Ivii), (I.A1), (I.A1a) to (I.A1h), (I.A2), and (I.A2a) to (I.A2h) wherein Ar is unsubstituted aryl (e.g., unsubstituted phenyl).

Embodiment No. 2 is directed to any one of the compounds of formulas (I), (iI) to (Ivii), (I.A1), (I.A1a) to (I.A1h), (I.A2), and (I.A2a) to (I.A2h) wherein Ar is substituted aryl (e.g., substituted phenyl). Examples of substituted phenyls include, for example, (1) halo substituted phenyl (such as, for example chloro substituted phenyl, such as, for example, p-Cl-phenyl-), (2) haloalkyl substituted phenyl (such as, for example, —$CF_3$ substituted phenyl, such as, for example, p-$CF_3$-phenyl-), and (3) cyano substituted phenyl (such as, for example, p-CN-phenyl-).

Embodiment No. 3 is directed to any one of the compounds of formulas (I), (iI) to (Ivii), (I.A1), (I.A1a) to (I.A1h), (I.A2), and (I.A2a) to (I.A2h) wherein Ar is unsubstituted heteroaryl (e.g., unsubstituted pyridyl).

Embodiment No. 4 is directed to any one of the compounds of formulas (I), (iI) to (Ivii), (I.A1), (I.A1a) to (I.A1h), (I.A2), and (I.A2a) to (I.A2h) wherein Ar is substituted heteroaryl (e.g., substituted pyridyl). Examples of substituted pyridyls include, for example, (1) halo substituted pyridyl (such as, for example chloro substituted pyridyl), (2) haloalkyl substituted pyridyl (such as, for example, —$CF_3$ substituted pyridyl), and (3) cyano substituted pyridyl.

Embodiment No. 5 is directed to any one of the compounds of formulas (I), (iI) to (Ivii), (I.A1), (I.A1a) to (I.A1h), (I.A2), and (I.A2a) to (I.A2h) wherein each $L^1$ is the same or different halo.

Embodiment No. 6 is directed to any one of the compounds of formulas (I), (iI) to (Ivii), (I.A1), (I.A1a) to (I.A1h), (I.A2), and (I.A2a) to (I.A2h) wherein n is 2 and each $L^1$ is the same or different halo.

Embodiment No. 7 is directed to any one of the compounds of formulas (I), (iI) to (Ivii), (I.A1), (I.A1a) to (I.A1h), (I.A2), and (I.A2a) to (I.A2h) wherein n is 2 and each $L^1$ is the same halo.

Embodiment No. 8 is directed to any one of the compounds of formulas (I), (iI) to (Ivii), (I.A1), (I.A1a) to (I.A1h), (I.A2), and (I.A2a) to (I.A2h) wherein n is 2 and each $L^1$ is F.

Embodiment No. 9 is directed to any one of the compounds of formulas (I), (iI) to (Ivii), (I.A1), (I.A1a) to (I.A1h), (I.A2), and (I.A2a) to (I.A2h), wherein each $L^1$ is the same or different halo, and Ar is unsubstituted aryl (e.g., unsubstituted phenyl).

Embodiment No. 10 is directed to any one of the compounds of formulas (I), (iI) to (Ivii), (I.A1), (I.A1a) to (I.A1h), (I.A2), and (I.A2a) to (I.A2h), wherein n is 2, each $L^1$ is the same or different halo, and Ar is unsubstituted aryl (e.g., unsubstituted phenyl).

Embodiment No. 11 is directed to any one of the compounds of formulas (I), (iI) to (Ivii), (I.A1), (I.A1a) to (I.A1h), (I.A2), and (I.A2a) to (I.A2h), wherein n is 2, each $L^1$ is the same halo, and Ar is unsubstituted aryl (e.g., unsubstituted phenyl).

Embodiment No. 12 is directed to any one of the compounds of formulas (I), (iI) to (Ivii), (I.A1), (I.A1a) to (I.A1h), (I.A2), and (I.A2a) to (I.A2h), wherein n is 2, each $L^1$ is F, and Ar is unsubstituted aryl (e.g., unsubstituted phenyl).

Embodiment No. 13 is directed to any one of the compounds of formulas (I), (iI) to (Ivii), (I.A1), (I.A1a) to (I.A1h), (I.A2), and (I.A2a) to (I.A2h), wherein each $L^1$ is the same or different halo, and Ar is substituted aryl (e.g., substituted phenyl). Examples of substituted phenyls include, for example, (1) halo substituted phenyl (such as, for example chloro substituted phenyl, such as, for example, p-Cl-phenyl-), (2) haloalkyl substituted phenyl (such as, for example, —$CF_3$ substituted phenyl, such as, for example, p-$CF_3$-phenyl-), and (3) cyano substituted phenyl (such as, for example, p-CN-phenyl-).

Embodiment No. 14 is directed to any one of the compounds of formulas (I), (iI) to (Ivii), (I.A1), (I.A1a) to (I.A1h), (I.A2), and (I.A2a) to (I.A2h), wherein n is 2, each $L^1$ is the same or different halo, and Ar is substituted aryl (e.g., substituted phenyl).

Examples of substituted phenyls include, for example, (1) halo substituted phenyl (such as, for example chloro substituted phenyl, such as, for example, p-Cl-phenyl-), (2) haloalkyl substituted phenyl (such as, for example, —CF$_3$ substituted phenyl, such as, for example, p-CF$_3$-phenyl-), and (3) cyano substituted phenyl (such as, for example, p-CN-phenyl-).

Embodiment No. 15 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same halo, and Ar is substituted aryl (e.g., substituted phenyl). Examples of substituted phenyls include, for example, (1) halo substituted phenyl (such as, for example chloro substituted phenyl, such as, for example, p-Cl-phenyl-), (2) haloalkyl substituted phenyl (such as, for example, —CF$_3$ substituted phenyl, such as, for example, p-CF$_3$-phenyl-), and (3) cyano substituted phenyl (such as, for example, p-CN-phenyl-).

Embodiment No. 16 is directed to any one of the compounds of formulas (I), (iI) to (Ivii), (I.A1), (I.A1a) to (I.A1h), (I.A2), and (I.A2a) to (I.A2h), wherein n is 2, each L$^1$ is F, and Ar is substituted aryl (e.g., substituted phenyl). Examples of substituted phenyls include, for example, (1) halo substituted phenyl (such as, for example chloro substituted phenyl, such as, for example, p-Cl-phenyl-), (2) haloalkyl substituted phenyl (such as, for example, —CF$_3$ substituted phenyl, such as, for example, p-CF$_3$-phenyl-), and (3) cyano substituted phenyl (such as, for example, p-CN-phenyl-).

Embodiment No. 17 is directed to any one of the compounds of formulas (I), (iI) to (Ivii), (I.A1), (I.A1a) to (I.A1h), (I.A2), and (I.A2a) to (I.A2h), wherein each L$^1$ is the same or different halo, and Ar is unsubstituted heteroaryl (e.g., unsubstituted pyridyl).

Embodiment No. 18 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same or different halo, and Ar is unsubstituted heteroaryl (e.g., unsubstituted pyridyl).

Embodiment No. 19 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same halo, and Ar is unsubstituted heteroaryl (e.g., unsubstituted pyridyl).

Embodiment No. 20 is directed to any one of the compounds of formulas (I), (iI) to (Ivii), (I.A1), (I.A1a) to (I.A1h), (I.A2), and (I.A2a) to (I.A2h), wherein n is 2, each L$^1$ is F, and Ar is unsubstituted heteroaryl (e.g., unsubstituted pyridyl).

Embodiment No. 21 is directed to any one of the compounds of formulas (I), (iI) to (Ivii), (I.A1), (I.A1a) to (I.A1h), (I.A2), and (I.A2a) to (I.A2h), wherein each L$^1$ is the same or different halo, and Ar is substituted heteroaryl (e.g., substituted pyridyl). Examples of substituted pyridyls include, for example, (1) halo substituted pyridyl (such as, for example chloro substituted pyridyl), (2) haloalkyl substituted pyridyl (such as, for example, —CF$_3$ substituted pyridyl), and (3) cyano substituted pyridyl.

Embodiment No. 22 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same or different halo, and Ar is substituted heteroaryl (e.g., substituted pyridyl). Examples of substituted pyridyls include, for example, (1) halo substituted pyridyl (such as, for example chloro substituted pyridyl), (2) haloalkyl substituted pyridyl (such as, for example, —CF$_3$ substituted pyridyl), and (3) cyano substituted pyridyl.

Embodiment No. 23 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same halo, and Ar is substituted heteroaryl (e.g., substituted pyridyl). Examples of substituted pyridyls include, for example, (1) halo substituted pyridyl (such as, for example chloro substituted pyridyl), (2) haloalkyl substituted pyridyl (such as, for example, —CF$_3$ substituted pyridyl), and (3) cyano substituted pyridyl.

Embodiment No. 24 is directed to any one of the compounds of formulas (I), (iI) to (Ivii), (I.A1), (I.A1a) to (I.A1h), (I.A2), and (I.A2a) to (I.A2h), wherein n is 2, each L$^1$ is F, and Ar is substituted heteroaryl (e.g., substituted pyridyl). Examples of substituted pyridyls include, for example, (1) halo substituted pyridyl (such as, for example chloro substituted pyridyl), (2) haloalkyl substituted pyridyl (such as, for example, —CF$_3$ substituted pyridyl), and (3) cyano substituted pyridyl.

Embodiment No. 25 is directed to any one of the compounds of formulas (I), (iI) to (Ivii), (I.A1), (I.A1a) to (I.A1h), (I.A2), and (I.A2a) to (I.A2h), wherein n is 2, each L$^1$ is the same halo, and Ar is substituted aryl selected from the group consisting p-CH$_3$CH$_2$SO$_2$phenyl, p-Br-phenyl, m,p-di-F-phenyl, m,p-di-CN-phenyl, p-CH$_3$O-phenyl, and p-CF$_3$CH$_2$Ophenyl.

Embodiment No. 26 is directed to any one of the compounds of formulas (I), (iI) to (Ivii), (I.A1), (I.A1a) to (I.A1h), (I.A2), and (I.A2a) to (I.A2h), wherein n is 2, each L$^1$ is F, and Ar is substituted aryl selected from the group consisting p-CH$_3$CH$_2$SO$_2$phenyl, p-Br-phenyl, m,p-di-F-phenyl, m,p-di-CN-phenyl, p-CH$_3$O-phenyl, and p-CF$_3$CH$_2$Ophenyl.

Embodiment No. 27 is directed to any one of Embodiment Nos. 1 to 26 wherein R$^2$ is H.

Embodiment No. 28 is directed to any one of Embodiment Nos. 1 to 26 wherein R$^2$ is alkyl.

Embodiment No. 29 is directed to any one of Embodiment Nos. 1 to 26 wherein R$^2$ is methyl.

Embodiment No. 30 is directed to any one of Embodiment Nos. 1 to 26 wherein R$^1$ is -alkylene-(tetrahydrothiophene 1,1-dioxide).

Embodiment No. 31 is directed to any one of Embodiment Nos. 1 to 26 wherein R$^1$ is -alkenyl-S(O)$_2$—(C$_1$-C$_6$)alkyl.

Embodiment No. 32 is directed to any one of Embodiment Nos. 1 to 26 wherein R$^1$ is -cycloalkyl-S(O)$_2$—(C$_1$-C$_6$)alkyl.

Embodiment No. 33 is directed to any one of Embodiment Nos. 1 to 26 wherein R$^1$ is an -alkylene-S(O)$_2$—(C$_1$-C$_6$)alkyl group.

Embodiment No. 34 is directed to any one of Embodiment Nos. 1 to 26 wherein R$^1$ is a —(C$_1$ to C$_2$) alkylene-S(O)$_2$—(C$_1$-C$_6$)alkyl group.

Embodiment No. 35 is directed to any one of Embodiment Nos. 1 to 26 wherein R$^1$ is a —(C$_1$ to C$_2$) alkylene-S(O)$_2$—(C$_1$-C$_3$)alkyl group.

Embodiment No. 36 is directed to any one of Embodiment Nos. 1 to 26 wherein R$^1$ is a —(C$_2$) alkylene-S(O)$_2$—(C$_1$-C$_6$) alkyl group.

Embodiment No. 37 is directed to any one of Embodiment Nos. 1 to 26, wherein the compound is a compound of the formula (I), (I.A1), (I.A2), (I.A1a), (I.A1e), (I.A2a) or (I.A2e) wherein R$^1$ is selected from the group consisting of:

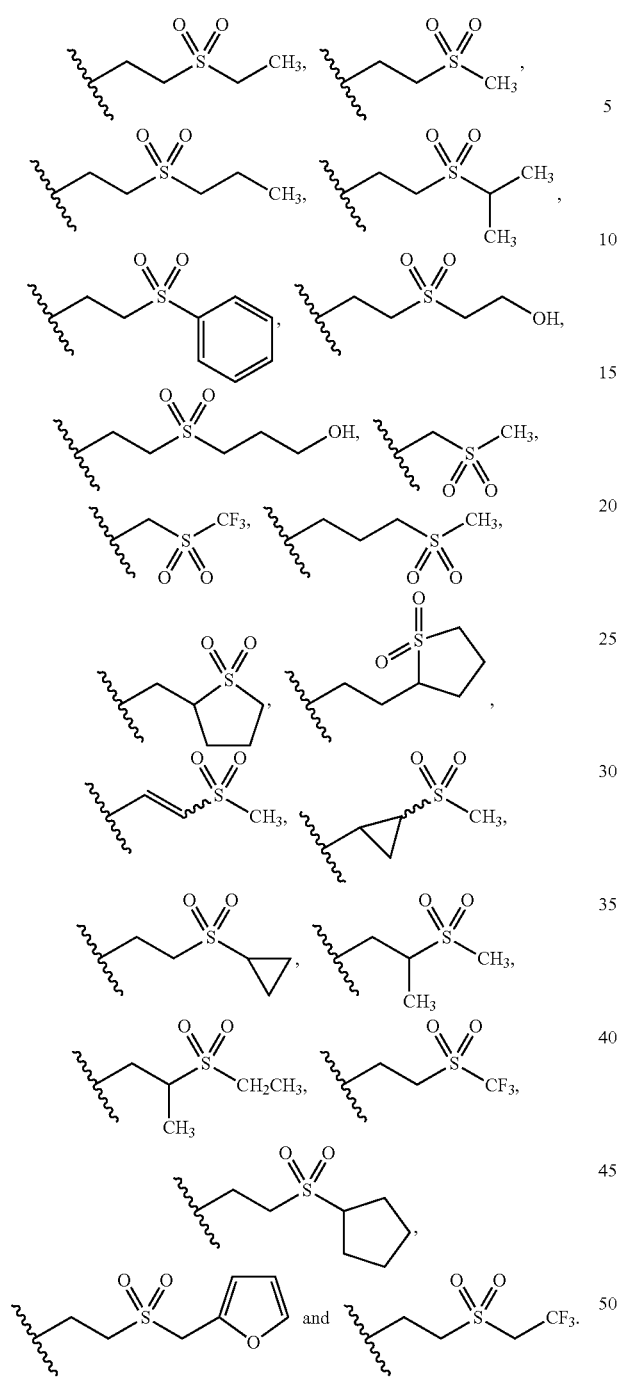

Embodiment No. 38 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is selected from the group consisting of:

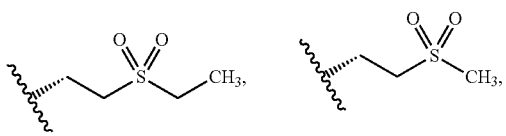

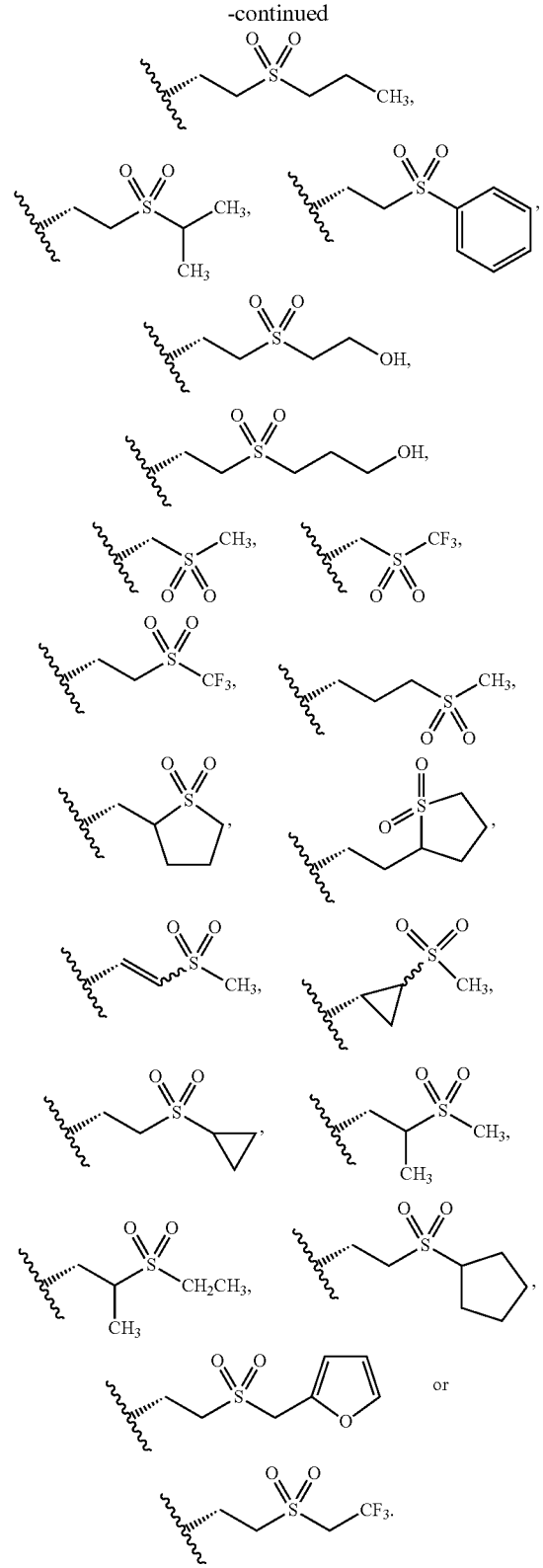

Embodiment No. 39 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is selected from the group consisting of:

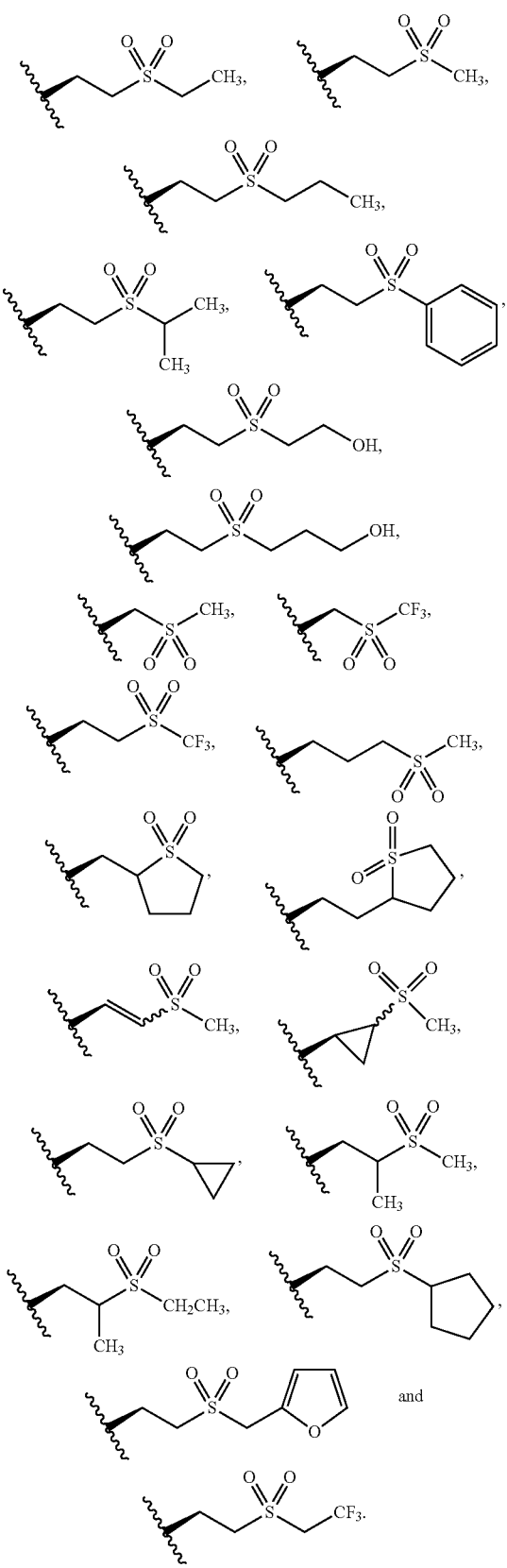

Embodiment No. 40 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is

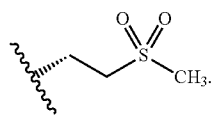

Embodiment No. 41 is directed to any one of Embodiment Nos. 1 to 26, wherein the compound is a compound of the formula (Ii), (Iii), (Iiv), (I.A1b), (I.A1c), (I.A1d), (I.A2b), (I.A2c), or (I.A1d), and $R^1$ is

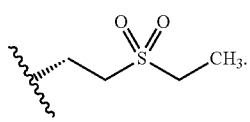

Embodiment No. 42 is directed to any one of Embodiment Nos. 1 to 26, wherein the compound is a compound of the formula (Ii), (Iiii), (Iiv), (I.A1b), (I.A1c), (I.A1d), (I.A2b), (I.A2c), or (I.A1d). and $R^1$ is

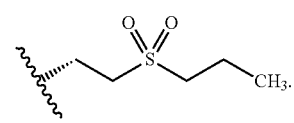

Embodiment No. 43 is directed to any one of Embodiment Nos. 1 to 26, wherein the compound is a compound of the formula (Ii), (Iiii), (Iiv), (I.A1 b), (I.A1c), (I.A1d), (I.A2b), (I.A2c), or (I.A1d), and $R^1$ is

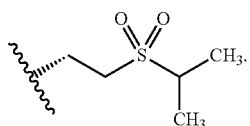

Embodiment No. 44 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is

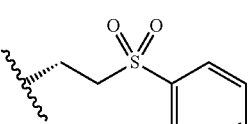

Embodiment No. 45 is directed to any one of Embodiment Nos. 1 to 26, wherein the compound is a compound of the formula (Ii), (Iiii), (Iiv), (I.A1b), (I.A1c), (I.A1d), (I.A2b), (I.A2c), or (I.A1d), and $R^1$ is

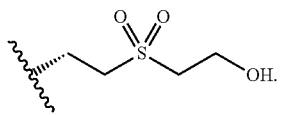

Embodiment No. 46 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

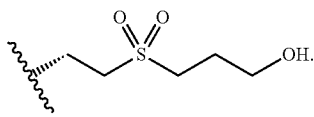

Embodiment No. 47 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

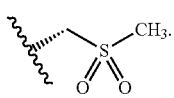

Embodiment No. 48 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

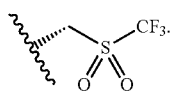

Embodiment No. 49 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

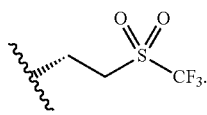

Embodiment No. 50 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

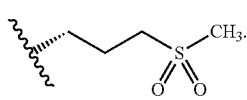

Embodiment No. 51 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d1_ and R¹ is Embodiment No. 52 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

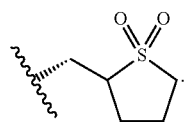

Embodiment No. 53 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

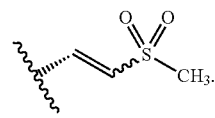

Embodiment No. 54 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

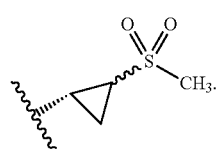 [SMILES: *[C@H]1CC1S(C)(=O)=O]

Embodiment No. 55 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

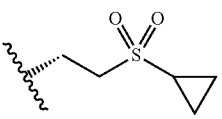

Embodiment No. 56 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and R¹ is

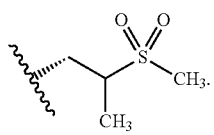

Embodiment No. 57 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is

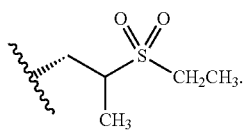

Embodiment No. 58 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is

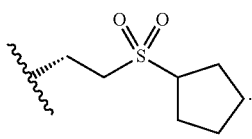

Embodiment No. 59 is directed to any one of Embodiment Nos. 1 to 26, wherein the compound is a compound of the formula (Ii), (Iii), (Iiii), (Iiv), (I.A1b), (I.A1c), (I.A1d), (I.A2b), (I.A2c), or (I.A1d), and $R^1$ is

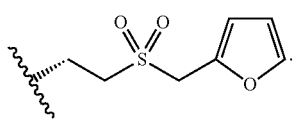

Embodiment No. 60 is directed to any one of Embodiment Nos. 1 to 26, wherein the compound is a compound of the formula (Ii), (Iii), (Iiv), (I.A1b), (I.A1c), (I.A1d), (I.A2b), (I.A2c), or (I.A1d), and $R^1$ is

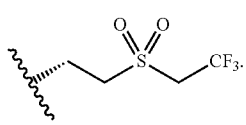

Embodiment No. 61 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

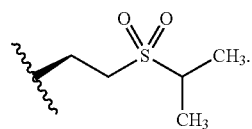

Embodiment No. 62 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

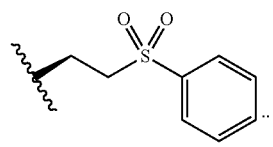

Embodiment No. 63 is directed to any one of Embodiment Nos. 1 to 26, wherein the compound is a compound of the formula (Iv), (Ivi), (I.A1f), (I.A1g), (I.A1h), (I.A2f), (I.A2g), or (I.A2h) wherein $R^1$ is

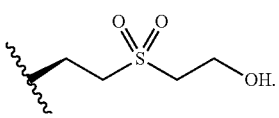

Embodiment No. 64 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

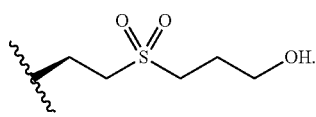

Embodiment No. 65 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

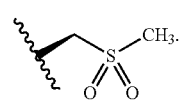

Embodiment No. 66 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

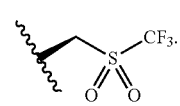

Embodiment No. 67 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

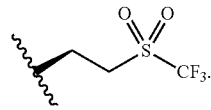

Embodiment No. 68 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

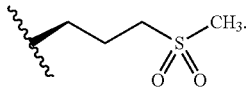

Embodiment No. 69 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

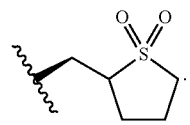

Embodiment No. 70 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

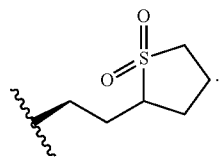

Embodiment No. 71 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

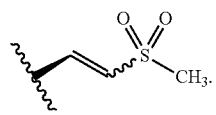

Embodiment No. 72 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

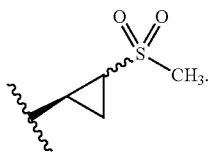 [SMILES: *[C@@H]1CC1S(C)(=O)=O]

Embodiment No. 73 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

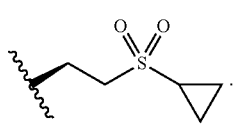

Embodiment No. 74 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is Embodiment No. 75 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

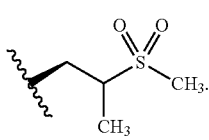

Embodiment No. 76 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

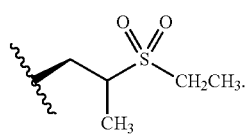

Embodiment No. 77 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

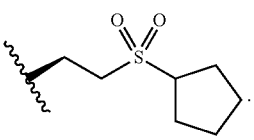

Embodiment No. 78 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein R¹ is

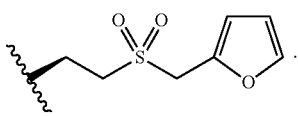

Embodiment No. 79 is directed to any one of Embodiment Nos. 1 to 26, wherein the compound is a compound of the formula (Iv), (Ivi), (Ivii), (I.A1f), (I.A1g), (I.A1h), (I.A2f), (I.A2g), or (I.A2h) wherein $R^1$ is

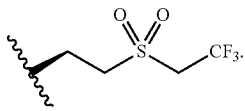

Embodiment No. 80 is directed to any one of Embodiment Nos. 37 to 79 wherein $R^2$ is H.

Embodiment No. 81 is directed to any one of Embodiment Nos. 37 to 79 wherein $R^2$ is alkyl.

Embodiment No. 82 is directed to any one of Embodiment Nos. 37 to 79 wherein $R^2$ is methyl.

Embodiment No. 83 is directed to any one of Embodiment Nos. 1 to 26 wherein $R^1$ is a -alkylene-S(O)$_2$—(C$_1$-C$_6$)haloalkyl group.

Embodiment No. 84 is directed to any one of Embodiment Nos. 1 to 26 wherein $R^1$ is a —(C$_1$ to C$_2$) alkylene-S(O)$_2$—(C$_1$-C$_3$)haloalkyl group.

Embodiment No. 85 is directed to any one of Embodiment Nos. 1 to 26 wherein $R^1$ is a —(C$_1$ to C$_2$) alkylene-S(O)$_2$—(C$_1$-C$_2$)haloalkyl group.

Embodiment No. 86 is directed to any one of Embodiment Nos. 1 to 26 wherein $R^1$ is a —(C$_2$) alkylene-S(O)$_2$—(C$_1$-C$_2$) haloalkyl group.

Embodiment No. 87 is directed to any one of Embodiment Nos. 1 to 26 wherein $R^1$ is a -alkylene-(tetrahydrothiophene 1,1-dioxide) group.

Embodiment No. 88 is directed to any one of Embodiment Nos. 1 to 26 wherein $R^1$ is a -alkenyl-S(O)$_2$—(C$_1$-C$_6$)alkyl group.

Embodiment No. 89 is directed to any one of Embodiment Nos. 1 to 26 wherein $R^1$ is a -cycloalkyl-S(O)$_2$—(C$_1$-C$_6$)alkyl group.

Embodiment No. 90 is directed to any one of Embodiment Nos. 1 to 26 wherein $R^1$ is a -alkylene-S(O)$_2$—(C$_1$-C$_6$)haloalkyl group, wherein the terminal carbon of said haloalkyl group is substituted with 1 to 3 of the same or different halo atoms.

Examples of said haloalkyl groups include groups wherein the terminal carbon is substituted with 1 to 3 F atoms, or 2 to 3 F atoms, or 3 F atoms (with 3 F atoms being preferred).

Embodiment No. 91 is directed to any one of Embodiment Nos. 1 to 26 wherein $R^1$ is a —(C$_1$ to C$_2$) alkylene-S(O)$_2$—(C$_1$-C$_3$)haloalkyl group, wherein the terminal carbon of said haloalkyl group is substituted with 1 to 3 of the same or different halo atoms. Examples of said haloalkyl groups include groups wherein the terminal carbon is substituted with 1 to 3 F atoms, or 2 to 3 F atoms, or 3 F atoms (with 3 F atoms being preferred).

Embodiment No. 92 is directed to any one of Embodiment Nos. 1 to 26 wherein $R^1$ is a —(C$_1$ to C$_2$) alkylene-S(O)$_2$—(C$_1$-C$_2$)haloalkyl group, wherein the terminal carbon of said haloalkyl group is substituted with 1 to 3 of the same or different halo atoms. Examples of said haloalkyl groups include groups wherein the terminal carbon is substituted with 1 to 3 F atoms, or 2 to 3 F atoms, or 3 F atoms (with 3 F atoms being preferred).

Embodiment No. 93 is directed to any one of Embodiment Nos. 1 to 26 wherein $R^1$ is a —(C$_2$) alkylene-S(O)$_2$—(C$_1$-C$_2$) haloalkyl group, wherein the terminal carbon of said haloalkyl group is substituted with 1 to 3 of the same or different halo atoms. Examples of said haloalkyl groups include groups wherein the terminal carbon is substituted with 1 to 3 F atoms, or 2 to 3 F atoms, or 3 F atoms (with 3 F atoms being preferred).

Embodiment No. 94 is directed to any one of Embodiment Nos. 83 to 93 wherein the compound is a compound of formula (Ii), (Iii), (Iiv), (I.A1b), (I.A1c), (I.A1d), (I.A2b), (I.A2c), or (I.A1d), and $R^1$ is any one of the $R^1$ groups described in any one of Embodiment Nos. 40 to 60.

Embodiment No. 95 is directed to any one of Embodiment Nos. 1 to 26 wherein $R^1$ is an -alkylene-S(O)$_2$-substituted(C$_1$-C$_6$)alkyl group, such as, for example, an -alkylene-S(O)$_2$—(C$_1$-C$_6$)hydroxyalkyl group.

Embodiment No. 96 is directed to any one of Embodiment Nos. 1 to 26 wherein $R^1$ is a —(C$_1$ to C$_2$) alkylene-S(O)$_2$-substituted(C$_1$-C$_3$)alkyl group, such as, for example, a —(C$_1$ to C$_2$) alkylene-S(O)$_2$—(C$_1$-C$_3$)hydroxyalkyl group.

Embodiment No. 97 is directed to any one of Embodiment Nos. 1 to 26 wherein $R^1$ is a —(C$_1$ to C$_2$) alkylene-S(O)$_2$-substituted(C$_1$-C$_2$) alkyl group, such as, for example, a —(C$_1$ to C$_2$) alkylene-S(O)$_2$—(C$_1$-C$_2$)hydroxyalkyl group.

Embodiment No. 98 is directed to any one of Embodiment Nos. 1 to 26 wherein $R^1$ is a —(C$_2$) alkylene-S(O)$_2$-substituted(C$_1$-C$_2$)alkyl group, such as, for example, a —(C$_2$) alkylene-S(O)$_2$-substituted(C$_1$-C$_2$)hydroxyalkyl group.

Embodiment No. 99 is directed to any one of Embodiment Nos. 1 to 26 wherein $R^1$ is an -alkylene-S(O)$_2$-substituted(C$_1$-C$_6$)alkyl group, such as, for example, an -alkylene-S(O)$_2$—(C$_1$-C$_6$)hydroxyalkykl group, wherein the terminal carbon of said substituted alkyl group is substituted.

Embodiment No. 100 is directed to any one of Embodiment Nos. 1 to 26 wherein $R^1$ is a —(C$_1$ to C$_2$) alkylene-S(O)$_2$-substituted(C$_1$-C$_3$) alkyl group, such as, for example, a —(C$_1$ to C$_2$) alkylene-S(O)$_2$—(C$_1$-C$_3$)hydroxyalkyl group, wherein the terminal carbon of said alkyl group is substituted.

Embodiment No. 101 is directed to any one of Embodiment Nos. 1 to 26 wherein $R^1$ is a —(C$_1$ to C$_2$) alkylene-S(O)$_2$-substituted(C$_1$-C$_2$)alkyl group, such as, for example, a —(C$_1$ to C$_2$) alkylene-S(O)$_2$—(C$_1$-C$_2$)hydroxyalkyl group, wherein the terminal carbon of said alkyl group is substituted.

Embodiment No. 102 is directed to any one of Embodiment Nos. 1 to 26 wherein $R^1$ is a —(C$_2$) alkylene-S(O)$_2$-substituted(C$_1$-C$_2$)alkyl group, such as, for example, a —(C$_1$ to C$_2$) alkylene-S(O)$_2$—(C$_1$-C$_2$)hydroxyalkyl group, wherein the terminal carbon of said alkyl group is substituted.

Embodiment No. 103 is directed to any one of Embodiment Nos. 83 to 102 wherein $R^2$ is H.

Embodiment No. 104 is directed to any one of Embodiment Nos. 83 to 102 wherein $R^2$ is alkyl.

Embodiment No. 105 is directed to any one of Embodiment Nos. 83 to 102 wherein $R^2$ is methyl.

As used above, and throughout this disclosure, the following terms, unless otherwise indicated, shall be understood to have the following meanings:

"RAC" (or "rac") means racemate.

"Patient" includes both human and animals.

"Mammal" means humans and other mammalian animals.

"One or more" means at least one, for example, 1, 2 or 3, or 1 or 2, or 1, thus, for example, "one or more $L^3$ groups" means at least one L³ group, and examples include 1-3 L³ groups, 1 or 2 L³ groups, and one L³ group.

"At least one" means there is at least one, and examples include 1, 2 or 3, or 1 or 2, or 1.

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain, which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH (alkyl), —NH(cycloalkyl), —N(alkyl)$_2$, carboxy and —C(O)O-alkyl (unless expressly defined otherwise). Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Alkylene" means a divalent aliphatic hydrocarbon radical derived from an alkyl group, as defined above. Both "open" valences may be on the same carbon atom, or on different carbon atoms. Examples of alkylene groups include $C_1$-$C_6$ alkylene groups, for example, $C_1$ to $C_4$ alkylene groups, and in another example, $C_1$-$C_3$ alkylene groups, and in another example $C_1$ to $C_2$ alkylene groups. Non-limiting examples of alkylene groups include —CH$_2$—, —CH$_2$—CH$_2$—, —CH(CH$_3$)—, etc.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain, which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable saturated monocyclic cycloalkyls include cyclopropyl, cyclopentyl, cyclohexyl, cycloheptyl and the like, and non-limiting examples of non-aromatic, unsaturated monocyclic cycloalkyls include cyclopentenyl, cyclohexenyl, etc. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Fluorine, chlorine and bromine are preferred.

"Heteroalkyl" means an alkyl group (as defined herein) wherein one or more carbon atoms have been replaced with heteroatoms, such as, for example, heteroatoms each independently selected from the group consisting of: N, —(NR$^{13A}$)—, O, S(O), and S(O)$_2$.

"Ring system substituent" means a substituent attached to an aromatic or non-aromatic ring system, which, for example, replaces an available hydrogen on the ring system. Ring system substituents may be the same or different, each being independently selected from the group consisting of alkyl, alkenyl, alkynyl, aryl (substituted or unsubstituted, heteroaryl (substituted or unsubstituted, alkylene-aryl, heteroarylalkenyl, heteroarylalkynyl, hydroxy, hydroxyalkyl, alkoxy, aryloxy, aryl substituted alkoxy, acyl, aroyl, halo, nitro, cyano, carboxy, alkoxycarbonyl, aryloxycarbonyl, arylalkoxycarbonyl, alkylsulfonyl, arylsulfonyl, heteroarylsulfonyl, alkylthio, arylthio, heteroarylthio, arylalkylthio, heteroarylalkylthio, cycloalkyl, heterocycloalkyl, —C(=N—CN)—NH$_2$, —C(═NH)—NH₂, —C(═NH)—NH(alkyl), Y₁Y₂N—, Y₁Y₂N-alkyl-, Y₁Y₂NC(O)—, Y₁Y₂NSO₂— and —SO₂NY₁Y₂, wherein Y₁ and Y₂ can be the same or different and are independently selected from the group consisting of hydrogen, alkyl, aryl, cycloalkyl, and -alkylene-aryl (unless expressly defined otherwise). The term "ring system substituent" may also mean a single moiety in which two available hydrogens on two adjacent carbon atoms are simultaneously replaced (e.g., one H on each carbon) on a ring system. Examples of such moiety are methylenedioxy, ethylenedioxy, —C(CH₃)₂— and the like which form moieties such as, for example:

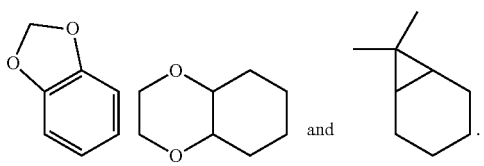

"Heterocycloalkyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. Any —NH in a heterocycloalkyl ring may exist in protected form, for example, as an —N(Boc), —N(CBz), —N(Tos) group and the like; such protected forms are also considered part of this invention. The heterocycloalkyl can be optionally substituted by one or more "ring system substituents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of non-aromatic, unsaturated monocyclic heterocycloalkyl rings include thiazolinyl, 2,3-dihydrofuranyl, 2,3-dihydrothiophenyl, etc.

It should be noted that in the hetero-atom containing ring systems of this invention, there are no hydroxyl groups on carbon atoms adjacent to a N, O or S, as well as there are no N or S groups on carbon atoms adjacent to another heteroatom. Thus, for example, in the ring:

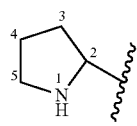

there is no —OH attached directly to carbons marked 2 and 5.

It should also be noted that tautomeric forms such as, for example, the moieties:

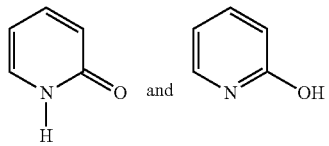 [SMILES: O=c1cccc[nH]1 ; Oc1ccccn1]

are considered equivalent in this invention.

"Hydroxyalkyl" means an alkyl group substituted with a hydroxyl (—OH) group in which alkyl is as previously defined. Preferred hydroxyalkyls contain lower alkyl. Non-limiting examples of suitable hydroxyalkyl groups include hydroxymethyl and 2-hydroxyethyl.

"Haloalkyl" means an alkyl group substituted with one or more independently selected halo atoms (e.g., F, Cl and Br, and in one example, one or more F atoms), and wherein one example is —CF₃.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an —O-alkyl; group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl" means an -alkyl-O-alkyl group wherein alkyl is as previously described.

"Aryloxy" means an —O-aryl group in which the aryl group is as previously described. Non-limiting examples of suitable aryloxy groups include phenoxy and naphthoxy. The bond to the parent moiety is through the ether oxygen.

"Alkylthio" means an —S-alkyl group in which the alkyl group is as previously described. Non-limiting examples of suitable alkylthio groups include methylthio and ethylthio. The bond to the parent moiety is through the sulfur.

"Arylthio" means an —S-aryl group in which the aryl group is as previously described. Non-limiting examples of suitable arylthio groups include phenylthio and naphthylthio. The bond to the parent moiety is through the sulfur.

"Arylalkylthio" means an —S-alkylene-aryl group in which the alkylene and aryl groups are as previously described. A non-limiting example of a suitable arylalkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an —C(O)—O-alkylene-aryl group. A non-limiting example of a suitable arylalkoxycarbonyl group is benzyloxycarbonyl. The bond to the parent moiety is through the carbonyl.

"Alkylsulfonyl" means an alkyl-S(O₂)—group. Preferred groups are those in which the alkyl group is a lower alkyl. The bond to the parent moiety is through the sulfonyl.

"Arylsulfonyl" means an aryl-S(O$_2$)—group. The bond to the parent moiety is through the sulfonyl.

"Alkanoyl" means an alkyl-C(O)— group.

"Carbamoyl" means an NH$_2$-C(O)— group.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

By "stable compound' or "stable structure" is meant a compound that is sufficiently robust to survive isolation to a useful degree of purity from a reaction mixture, and formulation into an efficacious therapeutic agent.

When a group is substituted with "one or more" substituents, the indicated group may be substituted with one substituent, two substituents, etc., provided that the resulting substituted group forms a stable structure, as described above.

The term "optionally substituted" means optional substitution with the specified groups, radicals or moieties. For example, an aryl optionally substituted with an indicated group of substituents includes unsubstituted aryl as well as aryl substituted with any of the indicated substituents.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon atom as well as any heteroatom with unsatisfied valences in the text, schemes, examples, Tables, etc. herein is assumed to have the sufficient number of hydrogen atom(s) to satisfy the valences.

When a functional group in a compound is termed "protected", this means that the group is present in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York, herein incorporated by reference in its entirety.

When any variable (e.g., aryl, heterocycloalkyl, L$^1$, etc.) occurs more than one time in any constituent or in Formula (I), its definition on each occurrence is independent of its definition at every other occurrence (unless otherwise expressly indicated).

As used herein, the term "composition" is intended to encompass a product comprising the specified ingredients in the specified amounts, as well as any product which results, directly or indirectly, from combination of the specified ingredients in the specified amounts.

An "electron withdrawing group" (abbreviated as EWG), as used herein is a group that will draw electrons to itself more than a hydrogen atom would if it occupied the same position in the molecule (see, for example, Jerry March, "Advanced Organic Chemistry", 4$^{th}$ Edition, page 18, John Wiley & Sons, 1992)

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are H$_2$O.

"Effective amount" or "therapeutically effective amount" is meant to describe an amount of compound or a composition of the present invention effective in preventing the formation and/or deposition of amyloid protein, and thus producing the desired therapeutic, ameliorative, inhibitory or preventative effect.

The compounds of Formula (I) can form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines)

such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The compounds according to the invention have pharmacological properties; in particular, the compounds of Formula (I) can inhibit gamma-secretase, and are therefore useful in the treatment or prevention of neurodegenerative diseases, e.g., Alzheimer's Disease.

Representative compounds of the invention include but are not limited to the compounds and Examples described herein.

Pharmaceutical compositions can comprise one or more of the compounds of Formula (I). For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

This invention is also directed to a process (Process 1) for preparing a compound of the formula:

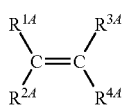

said process comprising reacting:
(1) a mixture comprising:
 (a) a compound of the formula:

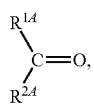

and
 (b) a compound of the formula:

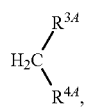

and
 (c) a suitable organic solvent (preferably anhydrous); with
(2) either:
 (a) a basic amine, and a compound of the formula

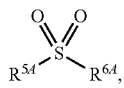

or
 (b) a basic amine, and a compound of the formula

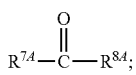

wherein:
$R^{1A}$ and $R^{2A}$ are each independently selected from the group consisting of: H, alkyl, alkenyl, alkynyl, cycloalkyl, heterocycloalkyl, heteroalkyl, aryl, heteroaryl, substituted alkyl, substituted alkenyl, substituted alkynyl, substituted cycloalkyl, substituted heterocycloalkyl, substituted heteroalkyl, substituted aryl, and substituted heteroaryl; wherein said substituted groups are substituted with one or more (e.g., 1 to 5, 1 to 4, 1 to 3, 1 to 2, or 1) substituents each independently selected from the group consisting of: —$NO_2$, —NO, —$SO_2R^{7B}$, —$SO_2$-aryl (e.g., —$SO_2$-phenyl), —$SO_2$—heteroaryl (e.g., —$SO_2$-pyridyl), —$SO_{2OR}{}^{7B}$, —CN, —COOH, halo (e.g., F, Cl, Br, and I), —$CF_3$, —Oaryl (e.g., —O-phenyl), —Oheteroaryl (e.g., —O-pyridyl), —$COOR^{7B}$, —$CONH_2$, —$CONHR^{7B}$, $CON(R^{7B})_2$, —CHO, —$OR^{7B}$, —$COR^{7B}$, —SH, —$SR^{7B}$, —OH, aryl (e.g., phenyl), and heteroaryl (e.g., pyridyl); and wherein in one example said substituted groups are substituted with one or more (e.g., 1 to 5, 1 to 4, 1 to 3, 1 to 2, or 1) substituents each independently selected from the group consisting of: halo (e.g., Cl, F, and Br), -$NO_2$, —CN, —$C(O)OR^{12A}$, —$C(O)R^{12A}$, —$CF_3$, —S(O), and —$S(O)_2$; wherein:

(1) examples of the heterocycloalkyl ring of said $R^{1A}$ or $R^{2A}$ heterocycloalkyl ring, or of said $R^{1A}$ or $R^{2A}$ substituted heterocycloalkyl ring, include, but are not limited to: heterocycloalkyl rings comprising a total of 3 to 7 ring members (e.g., 3 to 6, or 3 to 5, or 3 to 4 total ring members) wherein 1 to 4 (e.g., 1 to 4, 1 to 3, 1 to 2, 1, or 2) ring members are hetero atoms independently selected from the group consisting of: N, —($NR^{13A}$)—, —O—, —S—, —S(O)—, and —$S(O)_2$—; and examples of said heterocycloalkyl rings also include, but are not limited to: piperidine, piperazine, pyrrolidine, azetidine, homopiperazine, tetrahydropyran, tetrahydropyran and oxetane; and examples of said substituted heterocycloalkyl rings include, but are not limited to: substituted piperidine, substituted piperazine, substituted pyrrolidine, substituted azetidine, substituted homopiperazine, substituted tetrahydropyran, substituted tetrahydrofuran and substituted oxetane, wherein the substituents are as defined above for said $R^{1A}$ and $R^{2A}$ substituted heterocycloalkyl groups;

(2) examples of the heteroaryl ring of said $R^{1A}$ or $R^{2A}$ heteroaryl ring, or of said $R^{1A}$ or $R^{2A}$ substituted heteroaryl ring, include, but are not limited to: heteroaryl rings comprising a total of 5 to 6 ring members (e.g., 5 total ring members, or 6 total ring members) wherein 1 to 4 (e.g., 1 to 4, 1 to 3, 1 to 2, 1, or 2) ring members are hetero atoms independently selected from the group consisting of: N, —($NR^{13A}$)—, —O—, —S—, —S(O)—, and —$S(O)_2$—; and examples of said heteroaryl rings also include, but are not limited to:

pyridine, pyrimidine, pyrazine, thiophene, and furan; and examples of said substituted heteroaryl rings include, but are not limited to: substituted pyridine, substituted pyrimidine, substituted pyrazine, substituted thiophene, and substituted furan, wherein the substituents are as defined above for said $R^{1A}$ and $R^{2A}$ substituted heteroaryl groups; and (3) examples of the heteroalkyl group of said $R^{1A}$ or $R^{2A}$ heteroalkyl group, or of said $R^{1A}$ or $R^{2A}$ substituted heteroalkyl group, include, but are not limited to: hetero($C_3$ to $C_{20}$)alkyl groups comprising at least one (e.g., 1 to 3, or 1 to 2, or 1 or 2) heteroatoms each independently selected from the group consisting of: N, —($NR^{13A}$)—, O, S(O), and $S(O)_2$;

$R^{3A}$ and $R^{4A}$ are each independently selected from the group consisting of: —$NO_2$, —NO, —$SO_2R^{7B}$, —$SO_2$-aryl (e.g., —$SO_2$-phenyl), —$SO_2$-heteroaryl (e.g., —$SO_2$—pyridyl), —$SO_2OR^{7B}$, —CN, —COOH, halo (e.g., F, Cl, Br, and I), —$CF_3$, —Oaryl (e.g., —O-phenyl), —Oheteroaryl (e.g., —O-pyridyl), —$COOR^{7B}$, —$CONH_2$, —$CONHR^{7B}$, $CON(R^{7B})_2$, —CHO, —$OR^{7B}$, —$COR^{7B}$, —SH, —$SR^{7B}$, —OH, aryl (e.g., phenyl), and heteroaryl (e.g., pyridyl); and in one example $R^{3A}$ and $R^{4A}$ are each independently selected from the group consisting of: —$C(O)OR^{12A}$, —CN, —$NO_2$, —$CF_3$, —$C(O)R^{12A}$, —S(O), and —$S(O)_2$;

$R^{5A}$ is selected from the group consisting of: H, alkyl, alkenyl, alkynyl, cycloalkyl, heterocycloalkyl, heteroalkyl, aryl, heteroaryl, substituted alkyl, substituted alkenyl, substituted alkynyl, substituted cycloalkyl, substituted heterocycloalkyl, substituted heteroalkyl, substituted aryl, and substituted heteroaryl; and wherein:

said substituted alkyl groups are substituted with one or more (e.g., 1 to 5, 1 to 4, 1 to 3, 1 to 2, or 1) substituents each independently selected from the group consisting of: halo (e.g., Cl, F, and Br), —$NO_2$, —CN, and —$OR^{12}$; and said substituted alkenyl, substituted alkynyl, substituted cycloalkyl, substituted heterocycloalkyl, substituted heteroalkyl, substituted aryl, and substituted heteroaryl groups are substituted with one or more (e.g., 1 to 5, 1 to 4, 1 to 3, 1 to 2, or 1) substituents each independently selected from the group consisting of: halo (e.g., Cl, F, and Br), —NO$_2$, —CN, and —OR$^{12A}$, alkyl and halo substituted alkyl (e.g., F substituted alkyl, such as, for example, —CF$_3$); and wherein:

(1) examples of the heterocycloalkyl ring of said R$^{5A}$ heterocycloalkyl ring, or of said R$^{5A}$ substituted heterocycloalkyl ring, include, but are not limited to: heterocycloalkyl rings comprising a total of 3 to 7 ring members (e.g., 3 to 6, or 3 to 5, or 3 to 4 total ring members) wherein 1 to 4 (e.g., 1 to 4, 1 to 3, 1 to 2, 1, or 2) ring members are hetero atoms independently selected from the group consisting of: N, —(NR$^{13A}$)—, —O—, —S—, —S(O)—, and —S(O)$_2$—; and examples of said heterocycloalkyl rings also include, but are not limited to: piperidine, piperazine, pyrrolidine, azetidine, homopiperazine, tetrahydropyran, tetrahydropyran and oxetane; and examples of said substituted heterocycloalkyl rings also include, but are not limited to: substituted piperidine, substituted piperazine, substituted pyrrolidine, substituted azetidine, substituted homopiperazine, substituted tetrahydropyran, substituted tetrahydrofuran and substituted oxetane, wherein the substituents are as defined above for said R$^{5A}$ substituted heterocycloalkyl groups;

(2) examples of the heteroaryl ring of said R$^{5A}$ heteroaryl ring, or of said R$^{5A}$ substituted heteroaryl ring, include, but are not limited to: heteroaryl rings comprising a total of 5 to 6 ring members (e.g., 5 total ring members, or 6 total ring members) wherein 1 to 4 (e.g., 1 to 4, 1 to 3, 1 to 2, 1, or 2) ring members are hetero atoms independently selected from the group consisting of: N, —(NR$^{13A}$)—, —O—, —S—, —S(O)—, and —S(O)$_2$—; and examples of said heteroaryl rings also include, but are not limited to: pyridine, pyrimidine, pyrazine, thiophene, and furan; and examples of said substituted heteroaryl rings also include, but are not limited to: substituted pyridine, substituted pyrimidine, substituted pyrazine, substituted thiophene, and substituted furan, wherein the substituents are as defined above for said R$^{5A}$ substituted heteroaryl groups; and (3) examples of the heteroalkyl group of said R$^{5A}$ heteroalkyl group, or of said R$^{5A}$ substituted heteroalkyl group, include, but are not limited to: hetero(C$_3$ to C$_{20}$) alkyl groups comprising at least one (e.g., 1 to 3, or 1 to 2, or 1 or 2) heteroatoms each independently selected from the group consisting of: N, —(NR$^{13A}$)—, O, S(O), and S(O)$_2$;

R$^{6A}$ is selected from the group consisting of: halo (e.g., Cl, F, and Br, and preferably Cl), and —OSO$_2$R$^{5A}$ (and preferably R$^{6A}$ is halo);

R$^{7A}$ is selected from the group consisting of: unsubstituted aryl, aryl substituted with at least one (e.g., 1 to 3, or 1 to 2, or 1) electron withdrawing group, heteroaryl, and heteroaryl substituted with at least one electron withdrawing group (e.g., 1 to 3, or 1 to 2, or 1); and wherein an example of said aryl moiety (of said R$^{7A}$ aryl, or said R$^{7A}$ substituted aryl groups) is phenyl; and wherein an example of said heteroaryl moiety (of said R$^{7A}$ heteroaryl, or said R$^{7A}$ substituted heteroaryl groups) is pyridyl; and wherein:

(1) in one example each electron withdrawing group is independently selected from the group consisting of: —NO$_2$, —NO, —SO$_2$R$^{7B}$, —SO$_2$-aryl (e.g., —SO$_2$-phenyl), —SO$_2$-heteroaryl (e.g., —SO$_2$-pyridyl), —SO$_2$OR$^{7B}$, —CN, —COOH, halo (e.g., F, Cl, Br, and I), —CF$_3$, —Oaryl (e.g., —O-phenyl), —Oheteroaryl (e.g., —O-pyridyl), —COOR$^{7B}$, —CONH$_2$, —CONHR$^{7B}$, CON(R$^{7B}$)$_2$, —CHO, —OR$^{7B}$, —COR$^{7B}$, —SH, —SR$^{7B}$, —OH, aryl (e.g., phenyl), and heteroaryl (e.g., pyridyl); and (2) in another example, each electron withdrawing group is independently selected from the group consisting of: —NO$_2$, —CN, —CF$_3$, —C(O)R$^{12A}$, —S(O), —SO$_2$, and halo (e.g., Cl, F, and Br); and (3) in another example, said heteroaryl moiety of said R$^{7A}$ substituted heteroaryl group comprises 1 to 4 ring hetero atoms (e.g., 1 to 4, 1 to 3, 1 to 2, 1, or 2 hetero atoms) wherein each heteroatom is independently selected from the group consisting of: —O—, —S—, —S(O)—, and —S(O)$_2$—, and said heteroaryl ring comprises a total of 5 or 6 ring members;

(4) in another example, said heteroaryl moiety of said R$^{7A}$ substituted heteroaryl group comprises 1 to 4 ring hetero atoms (e.g., 1 to 4, 1 to 3, 1 to 2, 1, or 2 hetero atoms) wherein each heteroatom is independently selected from the group consisting of: —O—, —S—, —S(O)—, and —S(O)$_2$—, and said heteroaryl ring comprises a total of 5 or 6 ring members, and each electron withdrawing group is independently selected from the group consisting of: —NO$_2$, —NO, —SO$_2$R$^{7B}$, —SO$_2$-aryl (e.g., —SO$_2$-phenyl), —SO$_2$-heteroaryl (e.g., —SO$_2$-pyridyl), —SO$_2$OR$^{7B}$, —CN, —COOH, halo (e.g., F, Cl, Br, and I), —CF$_3$, —Oaryl (e.g., —O-phenyl), —Oheteroaryl (e.g., —O-pyridyl), —COOR$^{7B}$, —CONH$_2$, —CONHR$^{7B}$, CON(R$^{7B}$)$_2$, —CHO, —OR$^{7B}$, —COR$^{7B}$, —SH, —SR$^{7B}$, —OH, aryl (e.g., phenyl), and heteroaryl (e.g., phenyl); and (5) in another example, said heteroaryl moiety of said R$^{7A}$ substituted heteroaryl group comprises 1 to 4 ring hetero atoms (e.g., 1 to 4, 1 to 3, 1 to 2, 1, or 2 hetero atoms) wherein each heteroatom is independently selected from the group consisting of: —O—, —S—, —S(O)—, and —S(O)$_2$—, and said heteroaryl ring comprises a total of 5 or 6 ring members, and each electron withdrawing group is independently selected from the group consisting of: —NO$_2$, —CN, —CF$_3$, —C(O)R$^{12A}$, —S(O), —SO$_2$, and halo (e.g., Cl, F, and Br);

Each R$^{7B}$ is independently selected from the group consisting of: alkyl (e.g., C$_1$ to C$_6$, or C$_1$ to C$_4$, or C$_1$ to C$_2$, or methyl, or ethyl), cycloalkyl and heteroalkyl;

R$^{8A}$ is selected from the group consisting of: halo (e.g., Cl, F, and Br), and —OC(O)R$^{7A}$;

R$^{12A}$ is alkyl (e.g., C$_1$ to C$_6$, or C$_1$ to C$_4$, or C$_1$ to C$_2$, or methyl, or ethyl); and R$^{13A}$ is selected from the the group consisting of: alkyl, alkoxyalkyl, hydroxyalkyl, alkanoyl, aryl, heteroaryl, aroyl, and carbamoyl, and preferably alkyl.

Examples of the basic amine used in the processes of this invention (see, for example, steps (2)(a) and (2)(b)), include, but are not limited to: (1) nitrogen based heteroaryls (i.e., the only hetero atom is N), and (2) amines of the formula:

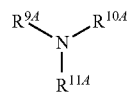

(wherein R$^{9A}$, R$^{10A}$ and R$^{11A}$ are defined below).

Examples of the nitrogen based heteroaryl basic amine include, but are not limited to: imidazolyl and pyridyl.

Examples of the basic amine of the formula:

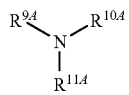

include, but are not limited to trialkylamines (i.e., $R^{9A}$, $R^{10A}$ and $R^{11A}$ are each alkyl and are each independently selected), such as, for example, triethylamine (TEA) and diisopropyl ethyl amine (i.e., two of $R^{9A}$, $R^{10A}$, and $R^{11A}$ groups are diisopropyl groups, and the remaining group is an ethyl group), with TEA being preferred.

Each $R^{9A}$, $R^{10A}$, and $R^{11A}$ is independently selected from the group consisting of: alkyl, alkenyl, alkynyl, cycloalkyl, heterocycloalkyl, heteroalkyl, aryl, heteroaryl, substituted alkyl, substituted alkenyl, substituted alkynyl, substituted cycloalkyl, substituted heterocycloalkyl, substituted heteroalkyl, substituted aryl, and substituted heteroaryl; wherein said substituted groups are substituted with one or more (e.g., 1 to 5, 1 to 4, 1 to 3, 1 to 2, or 1) substituents each independently selected from the group consisting of: halo (e.g., Cl, F, and Br), alkyl and alkoxy; wherein:

(1) examples of the heterocycloalkyl ring of said $R^{9A}$, $R^{10A}$ or $R^{11A}$ heterocycloalkyl ring, or of said $R^{9A}$, $R^{10A}$, or $R^{11A}$ substituted heterocycloalkyl ring, include, but are not limited to: heterocycloalkyl rings comprising a total of 3 to 7 ring members (e.g., 3 to 6, or 3 to 5, or 3 to 4 total ring members) wherein 1 to 4 (e.g., 1 to 4, 1 to 3, 1 to 2, 1, or 2) ring members are hetero atoms independently selected from the group consisting of: N, —($NR^{13A}$)—, —O—, —S—, —S(O)—, and —$S(O)_2$—; examples of said heterocycloalkyl rings also include, but are not limited to: piperidine, piperazine, pyrrolidine, azetidine, homopiperazine, tetrahydropyran, tetrahydropyran and oxetane; examples of said substituted heterocycloalkyl rings include, but are not limited to: substituted piperidine, substituted piperazine, substituted pyrrolidine, substituted azetidine, substituted homopiperazine, substituted tetrahydropyran, substituted tetrahydrofuran and substituted oxetane, wherein the substituents are as defined above for said $R^{9A}$, $R^{10A}$, and $R^{11A}$ substituted heterocycloalkyl groups;

(2) examples of the heteroaryl ring of said $R^{9A}$, $R^{10A}$, or $R^{11A}$ heteroaryl ring, or of said $R^{9A}$, $R^{10A}$, or $R^{11A}$ substituted heteroaryl ring, include, but are not limited to: heteroaryl rings comprising a total of 5 to 6 ring members (e.g., 5 total ring members, or 6 total ring members) wherein 1 to 4 (e.g., 1 to 4, 1 to 3, 1 to 2, 1, or 2) ring members are hetero atoms independently selected from the group consisting of: N, —($NR^{13A}$)—, —O—, —S—, —S(O)—, and —$S(O)_2$—; examples of said heteroaryl rings also include, but are not limited to: pyridine, pyrimidine, pyrazine, thiophene, and furan; examples of said substituted heteroaryl rings include, but are not limited to: substituted pyridine, substituted pyrimidine, substituted pyrazine, substituted thiophene, and substituted furan, wherein the substituents are as defined above for said $R^{9A}$, $R^{10A}$, and $R^{11A}$ substituted heteroaryl groups; and (3) examples of the heteroalkyl group of said $R^{9A}$, $R^{10A}$, or $R^{11A}$ heteroalkyl group, or of said $R^{9A}$, $R^{10A}$, or $R^{11A}$ substituted heteroalkyl group, include, but are not limited to: hetero($C_3$ to $C_{20}$)alkyl groups comprising at least one (e.g., 1 to 3, or 1 to 2, or 1 or 2) heteroatoms each independently selected from the group consisting of: N, —($NR^{13A}$)—, O, S(O), and $S(O)_2$.

Examples of the alkyl groups in the processes of this invention include, but are not limited to: $C_1$ to $C_6$ alkyl, $C_1$ to $C_4$ alkyl, $C_1$ to $C_2$ alkyl, ethyl and methyl);

The processes of this invention are carried out in suitable organic solvents (preferably anhydrous). Examples of such solvents include, but are not limited to: (1) haloalkanes (such as, for example, dichloromethane, dichloroethane (e.g., $CH_2Cl$—$CH_2Cl$), trichloromethane, and tetrachloromethane), (2) arylhalides (such as, for example, chlorobenzene), (3) DMSO, (4) DMF, (5) THF, (6) ethers (such as, for example, diethyl ether), and (7) mixtures thereof.

In one embodiment the organic solvent (preferably anhydrous) is selected from the group consisting of: dichloromethane, dichloroethane, chlorobenzene, DMSO, DMF, THF, and diethylether.

In one embodiment the solvent is a haloalkane.

In another embodiment the solvent is dichloromethane.

Examples of the (—$NR^9R^{10}R^{11}$) basic tertiary amine used in the processes of this invention include, but are not limited to: triethylamine (i.e., TEA), and diisopropyl ethyl amine (i.e., $C_2H_5N(CH_2CH_3)_2$).

In one embodiment of the processes of this invention the basic tertiary amine (—$NR^9R^{10}R^{11}$) is triethylamine (i.e., TEA).

Examples of the $R^{7A}C(O)R^{8A}$ moiety include, but are not limited to:

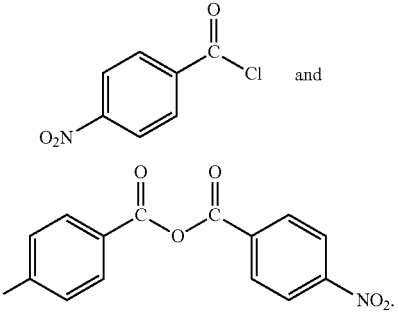

Examples of the $R^{5A}S(O)_2R^{6A}$ moiety include, but are not limited to:

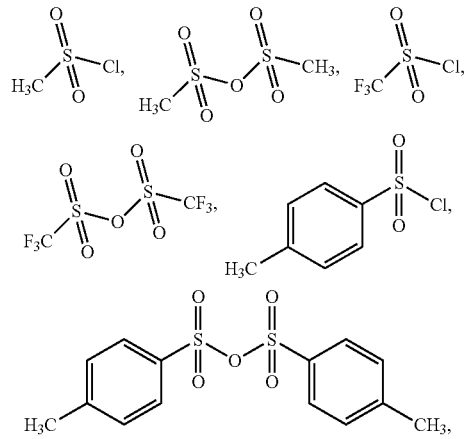

-continued

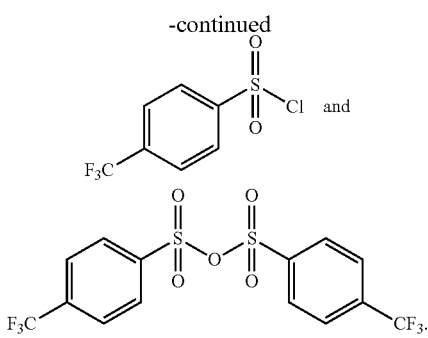

In one example the $R^{54}S(O)_2R^{64}$ moiety is

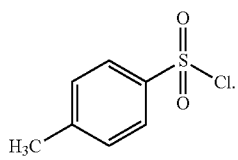

Preferably, the $R^{54}S(O)_2R^{64}$ moiety is mesyl chloride:

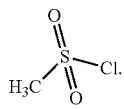

The processes of this invention are carried at a suitable temperature. A suitable temperature is one wherein the reaction proceeds at a reasonable rate, and one wherein the production of unwanted by-products or degradation products are minimized.

In one embodiment of this invention, Process 1 is carried out at a temperature within the range of about −40° C. to about 40° C.

In another embodiment of this invention, Process 1 is carried out at a temperature within the range of about 0° C. to about 30° C.

In another embodiment of this invention, Process 1 is carried out at a temperature within the range of about 0° C. to about 10° C.

In another embodiment of Process 1 the basic amine is a trialkylamine.

In another embodiment of Process 1 the basic amine is TEA.

In another embodiment of Process 1 the basic amine is diisopropyl ethyl amine.

In another embodiment of this invention, Process 1 is carried out at a temperature within the range of about −40° C. to about 40° C., and the basic amine is a trialkylamine.

In another embodiment of this invention, Process 1 is carried out at a temperature within the range of about 0° C. to about 30° C., and the basic amine is a trialkylamine.

In another embodiment of this invention, Process 1 is carried out at a temperature within the range of about 0° C. to about 10° C., and the basic amine is a trialkylamine.

In another embodiment of this invention, Process 1 is carried out at a temperature within the range of about −40° C. to about 40° C., and the basic amine is TEA.

In another embodiment of this invention, Process 1 is carried out at a temperature within the range of about 0° C. to about 30° C., and the basic amine is TEA.

In another embodiment of this invention, Process 1 is carried out at a temperature within the range of about 0° C. to about 10° C., and the basic amine is TEA.

In another embodiment of this invention, Process 1 is carried out at a temperature within the range of about −40° C. to about 40° C., and the basic amine is diisopropyl ethyl amine.

In another embodiment of this invention, Process 1 is carried out at a temperature within the range of about 0° C. to about 30° C., and the basic amine is diisopropyl ethyl amine.

In another embodiment of this invention, Process 1 is carried out at a temperature within the range of about 0° C. to about 10° C., and the basic amine is diisopropyl ethyl amine.

In another embodiment of this invention, Process 1 is carried out at a temperature within the range of about −40° C. to about 40° C., and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 30° C., and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 10° C., and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about −40° C. to about 40° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 30° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 10° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about −40° C. to about 40° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 30° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 10° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about −40° C. to about 40° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 30° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of this invention, Process 1 is carried out at a temperature within the range of about 0° C. to about 10° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

Another embodiment of the processes of this invention is directed to any one of the above process embodiments wherein the mixture of (1)(a) and (1)(b) is reacted with (2)(a).

Thus, in another embodiment of Process 1, the mixture of (1)(a) and (1)(b) is reacted with (2)(a), the reaction is carried out at a temperature within the range of about −40° C. to about 40° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about 0° C. to about 30° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about 0° C. to about 10° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about −40° C. to about 40°

C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane. In another embodiment of Process 1, the mixture of (1)(a) and (1)(b) is reacted with (2)(a), the reaction is carried out at a temperature within the range of about 0° C. to about 30° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about 0° C. to about 10° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane.

Another embodiment of Process 1 is directed to any of the above process embodiments wherein the $R^{54}S(O)_2R^{64}$ moiety is selected from the group consisting of:

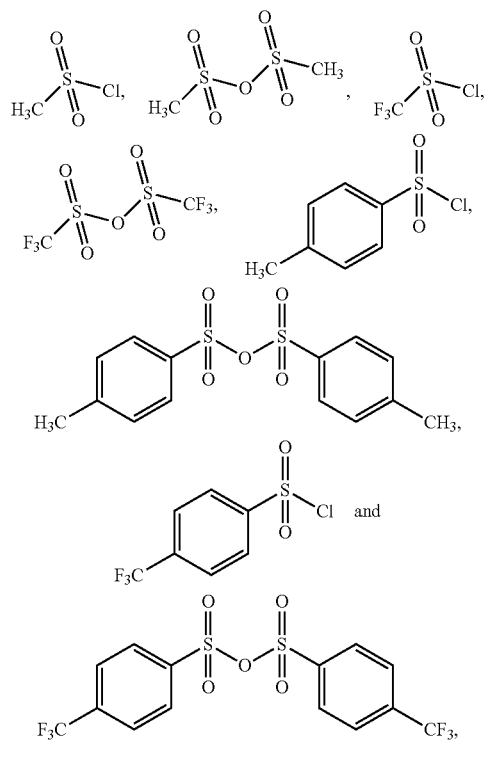

and preferably, the $R^{54}S(O)_2R^{64}$ moiety is mesyl chloride:

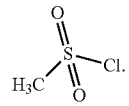

Another embodiment of Process 1 is directed to any of the above process embodiments wherein the $R^{54}S(O)_2R^{64}$ moiety is mesyl chloride:

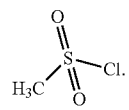

Thus, in another embodiment of Process 1, the mixture of (1)(a) and (1)(b) is reacted with (2)(a), the reaction is carried out at a temperature within the range of about −40° C. to about 40° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

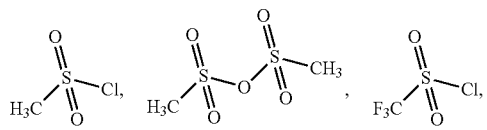

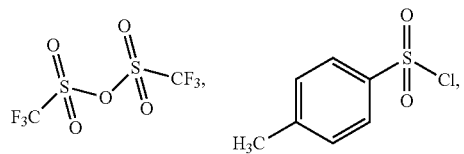

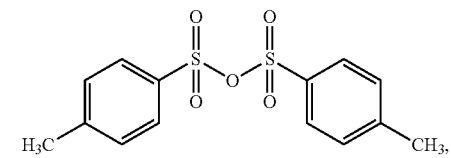

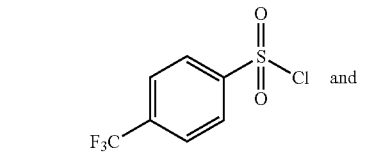

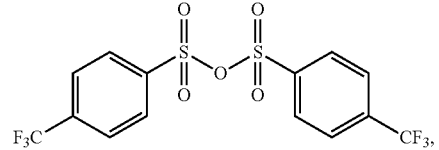

and preferably, the $R^{5A}S(O)_2R^{6A}$ moiety is mesyl chloride:

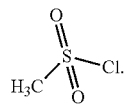

In another embodiment of Process 1, the mixture of (1)(a) and (1)(b) is reacted with (2)(a), the reaction is carried out at a temperature within the range of about 0° C. to about 30° C., the basic amine is a trialkylamine, and the organic solvent (step (1)(c) (preferably anhydrous) is selected from the group consisting of (i) haloalkanes (such as, for example, dichloromethane, dichloroethane (e.g., CH$_2$Cl—CH$_2$Cl), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

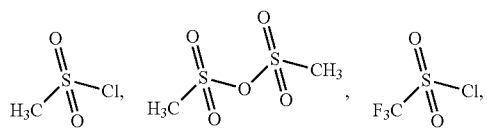

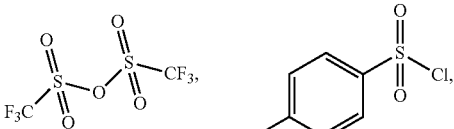

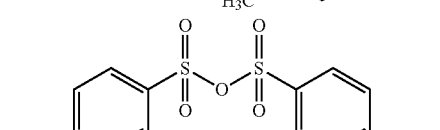

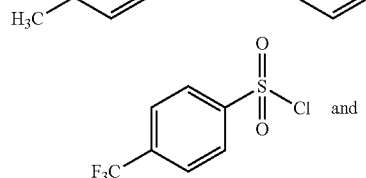

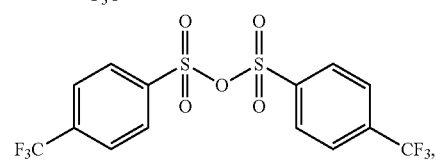

and preferably, the $R^{5A}S(O)_2R^{6A}$ moiety is mesyl chloride:

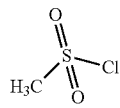

In another embodiment of Process 1, the mixture of (1)(a) and (1)(b) is reacted with (2)(a), the reaction is carried out at a temperature within the range of about 0° C. to about 10° C., the basic amine is a trialkylamine, and the organic solvent (step (1)(c) (preferably anhydrous) is selected from the group consisting of (i) haloalkanes (such as, for example, dichloromethane, dichloroethane (e.g., CH$_2$Cl—CH$_2$Cl), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

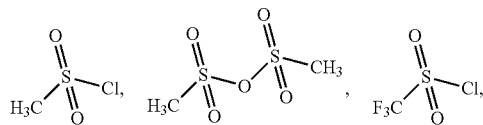

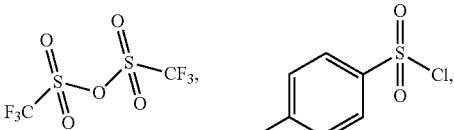

-continued

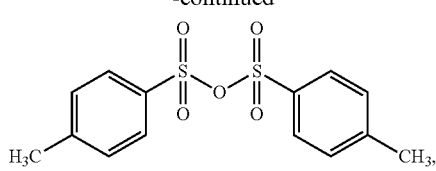

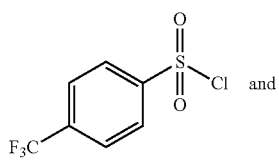 and

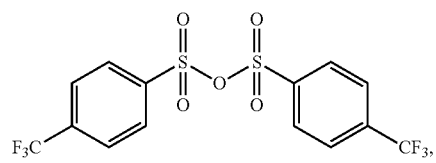

and preferably, the $R^{5A}S(O)_2R^{6A}$ moiety is mesyl chloride:

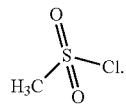

In another embodiment of Process 1, the mixture of (1)(a) and (1)(b) is reacted with (2)(a), the reaction is carried out at a temperature within the range of about −40° C. to about 40° C., the basic amine is TEA, and the organic solvent (step (1)(c) (preferably anhydrous) is selected from the group consisting of (i) haloalkanes (such as, for example, dichloromethane, dichloroethane (e.g., CH$_2$Cl—CH$_2$Cl), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

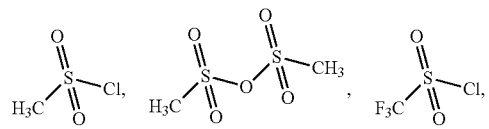

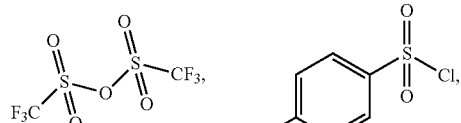

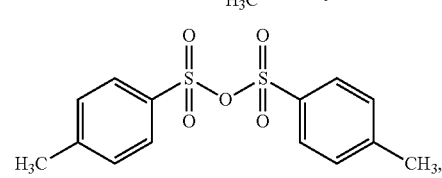

-continued

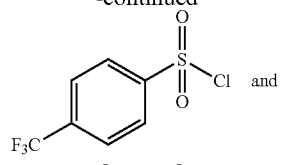 and

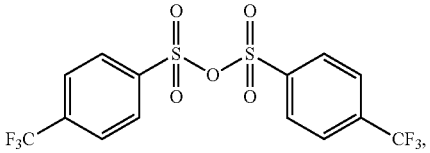

and preferably, the $R^{5A}S(O)_2R^{6A}$ moiety is mesyl chloride:

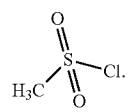

In another embodiment of Process 1, the mixture of (1)(a) and (1)(b) is reacted with (2)(a), the reaction is carried out at a temperature within the range of about 0° C. to about 30° C., the basic amine is TEA, and the organic solvent (step (1)(c) (preferably anhydrous) is selected from the group consisting of (i) haloalkanes (such as, for example, dichloromethane, dichloroethane (e.g., CH$_2$Cl—CH$_2$Cl), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

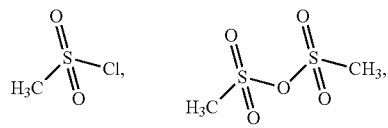

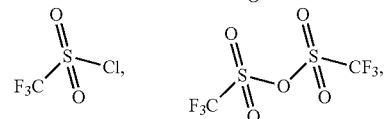

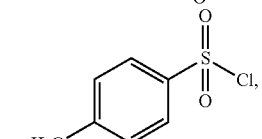

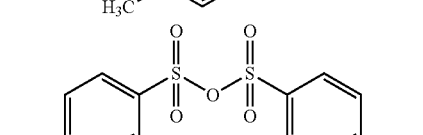

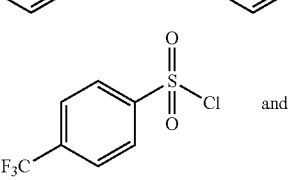 and

-continued

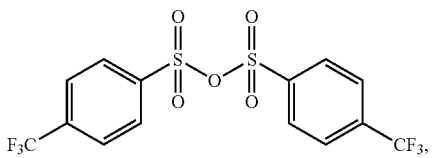

and preferably, the $R^{5A}S(O)_2R^{6A}$ moiety is mesyl chloride:

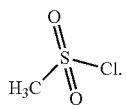

In another embodiment of Process 1, the mixture of (1)(a) and (1)(b) is reacted with (2)(a), the reaction is carried out at a temperature within the range of about 0° C. to about 10° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

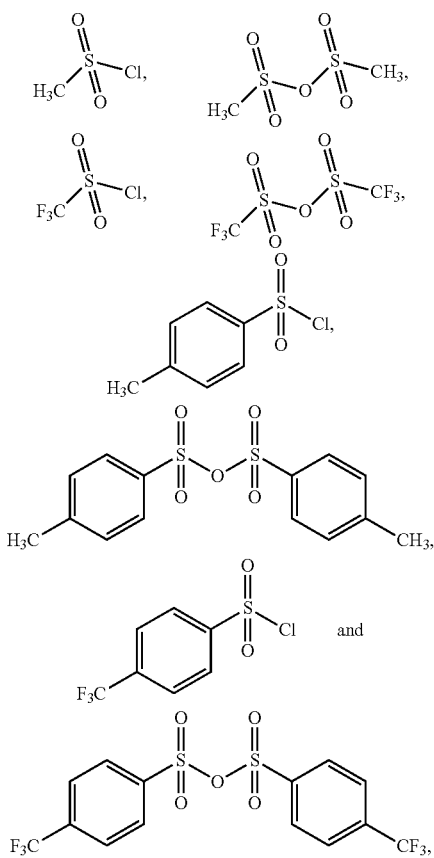

and preferably, the $R^{5A}S(O)_2R^{6A}$ moiety is mesyl chloride:

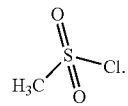

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

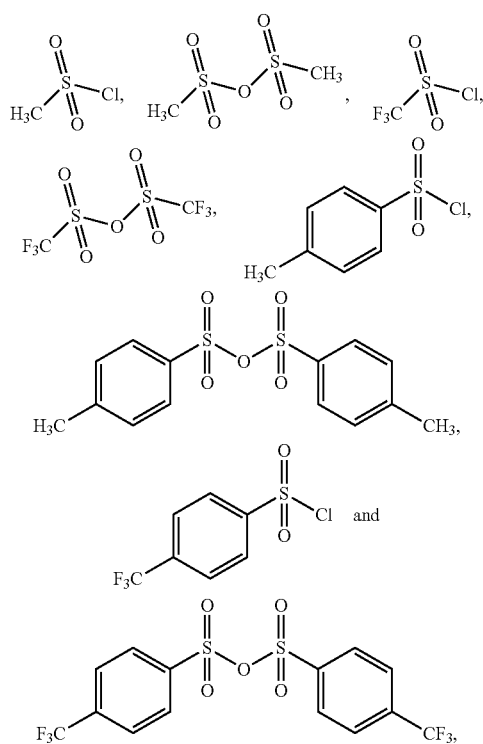

and preferably, the $R^{5A}S(O)_2R^{6A}$ moiety is mesyl chloride:

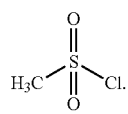

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl-CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

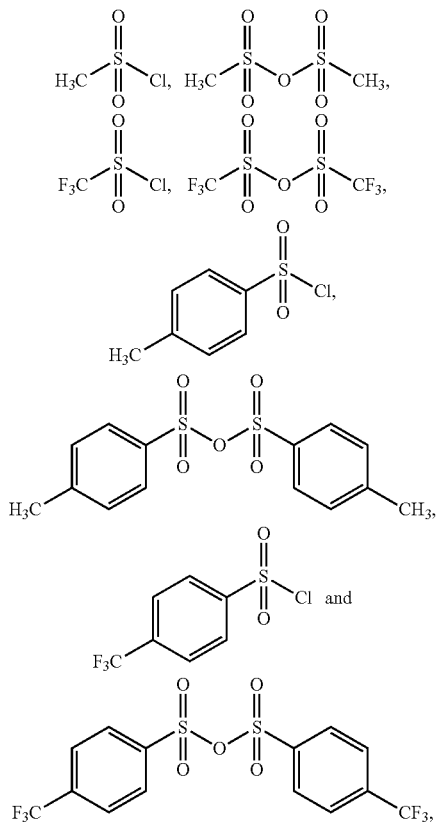

and preferably, the $R^{5A}S(O)_2R^{6A}$ moiety is mesyl chloride:

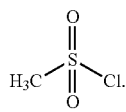

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl-CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is selected from the group consisting of:

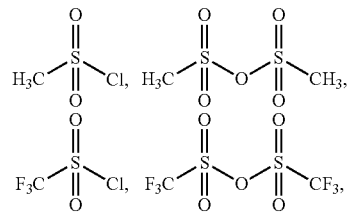

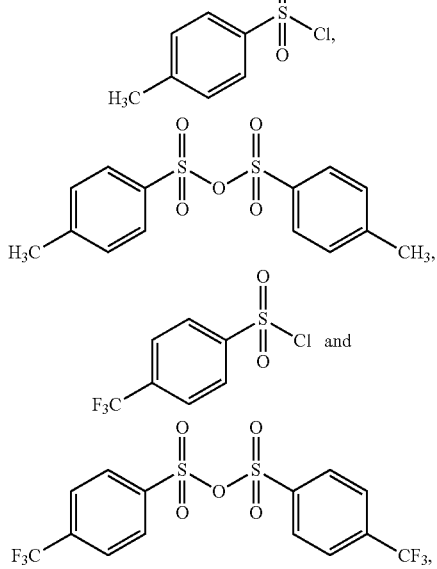

and preferably, the $R^{5A}S(O)_2R^{6A}$ moiety is mesyl chloride:

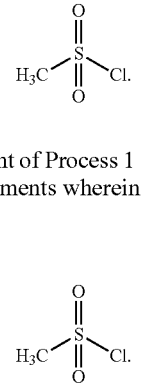

Another embodiment of Process 1 is directed to any of the above process embodiments wherein the $R^{5A}S(O)_2R^{6A}$ moiety is mesyl chloride:

Thus, in another embodiment of Process 1, the mixture of (1)(a) and (1)(b) is reacted with (2)(a), the reaction is carried out at a temperature within the range of about -40° C. to about 40° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl-CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is

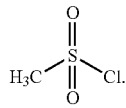

In another embodiment of Process 1, the mixture of (1)(a) and (1)(b) is reacted with (2)(a), the reaction is carried out at a temperature within the range of about 0° C. to about 30° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is

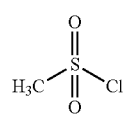

In another embodiment of Process 1, the mixture of (1)(a) and (1)(b) is reacted with (2)(a), the reaction is carried out at a temperature within the range of about 0° C. to about 10° C., the basic amine is a trialkylamine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is

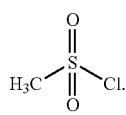

In another embodiment of Process 1, the mixture of (1)(a) and (1)(b) is reacted with (2)(a), the reaction is carried out at a temperature within the range of about −40° C. to about 40° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is

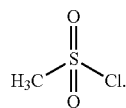

In another embodiment of Process 1, the mixture of (1)(a) and (1)(b) is reacted with (2)(a), the reaction is carried out at a temperature within the range of about 0° C. to about 30° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is

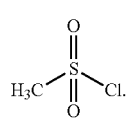

In another embodiment of Process 1, the mixture of (1)(a) and (1)(b) is reacted with (2)(a), the reaction is carried out at a temperature within the range of about 0° C. to about 10° C., the basic amine is TEA, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is:

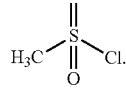

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{54}S(O)_2R^{64}$ moiety is

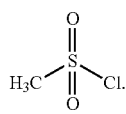

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl$—$CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is

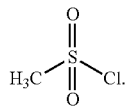

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, and the organic solvent (step (1)(c) (preferably anhydrous) is selected from the group consisting of (i) haloalkanes (such as, for example, dichloromethane, dichloroethane (e.g., $CH_2Cl$—$CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably the organic solvent is a haloalkane, and more preferably the organic solvent is anhydrous dichloromethane, and the $R^{5A}S(O)_2R^{6A}$ moiety is

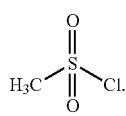

In another embodiment of Process 1, the mixture of (1)(a) and (1)(b) is reacted with (2)(a), the reaction is carried out at a temperature within the range of about −40° C. to about 40° C., the basic amine is a trialkylamine, and the organic solvent (step (1)(c) is anhydrous dichloromethane, and the $R^{5A}S(O)_2R^{6A}$ moiety is

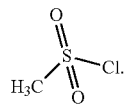

In another embodiment of Process 1, the mixture of (1)(a) and (1)(b) is reacted with (2)(a), the reaction is carried out at a temperature within the range of about 0° C. to about 30° C., the basic amine is a trialkylamine, and the organic solvent (step (1)(c) is anhydrous dichloromethane, and the $R^{5A}S(O)_2R^{6A}$ moiety is

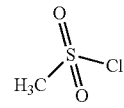

In another embodiment of Process 1, the mixture of (1)(a) and (1)(b) is reacted with (2)(a), the reaction is carried out at a temperature within the range of about 0° C. to about 10° C., the basic amine is a trialkylamine, and the organic solvent (step (1)(c) is anhydrous dichloromethane, and the $R^{5A}S(O)_2R^{6A}$ moiety is

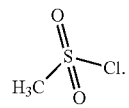

In another embodiment of Process 1, the mixture of (1)(a) and (1)(b) is reacted with (2)(a), the reaction is carried out at a temperature within the range of about −40° C. to about 40° C., the basic amine is TEA, and the organic solvent (step (1)(c) (preferably is anhydrous dichloromethane, and the $R^{5A}S(O)_2R^{6A}$ moiety is

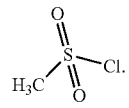

In another embodiment of Process 1, the mixture of (1)(a) and (1)(b) is reacted with (2)(a), the reaction is carried out at a temperature within the range of about 0° C. to about 30° C., the basic amine is TEA, and the organic solvent (step (1)(c) is anhydrous dichloromethane, and the $R^{5A}S(O)_2R^{6A}$ moiety is

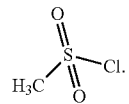

In another embodiment of Process 1, the mixture of (1)(a) and (1)(b) is reacted with (2)(a), the reaction is carried out at a temperature within the range of about 0° C. to about 10° C., the basic amine is TEA, and the organic solvent (step (1)(c) is anhydrous dichloromethane, and the $R^{5A}S(O)_2R^{6A}$ moiety is:

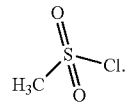

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, and the organic solvent (step (1)(c) is anhydrous dichloromethane, and the $R^{5A}S(O)_2R^{6A}$ moiety is

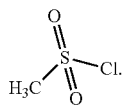

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, and the organic solvent (step (1)(c) is anhydrous dichloromethane, and the $R^{5A}S(O)_2R^{6A}$ moiety is

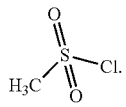

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, and the organic solvent (step (1)(c) is anhydrous dichloromethane, and the $R^{5A}S(O)_2R^{6A}$ moiety is

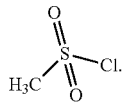

Another embodiment of Process 1 is directed to any one of the process embodiments described above wherein one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H.

Another embodiment of Process 1 is directed to any one of the process embodiments described above wherein one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, wherein said substituted aryl is substituted with one or more (e.g., 1 to 3, 1 to 2 or 1) substitutent independently selected from the group consisting of: —$NO_2$ and halo (e.g., Cl and F).

Another embodiment of Process 1 is directed to any one of the process embodiments described above wherein

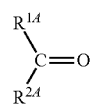

is selected from the group consisting of:

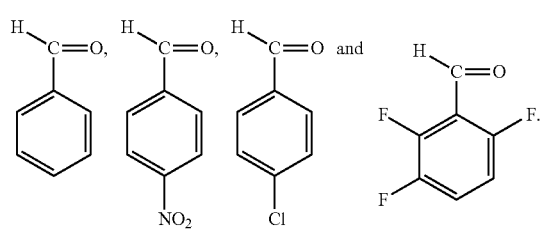

Another embodiment of Process 1 is directed to any one of the process embodiments described above wherein

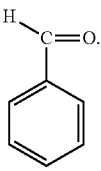

is

Another embodiment of Process 1 is directed to any one of the process embodiments described above wherein

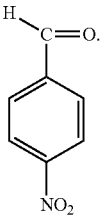

is

Another embodiment of Process 1 is directed to any one of the process embodiments described above wherein

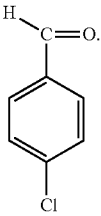

Another embodiment of Process 1 is directed to any one of the process embodiments described above wherein

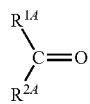

is

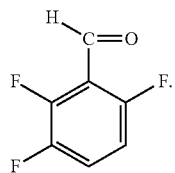

Another embodiment of Process 1 is directed to any one of the above process embodiments wherein $R^{3A}$ and $R^{4A}$ are each independently selected from the group consisting of: —C(O)OR$^{12A}$.

Another embodiment of Process 1 is directed to any one of the above process embodiments wherein $R^{3A}$ and $R^{4A}$ are the same —C(O)OR$^{12A}$ moiety.

Another embodiment of Process 1 is directed to any one of the above process embodiments wherein $R^{3A}$ and $R^{4A}$ are the same —C(O)OR$^{12A}$ moiety, and wherein $R^{12A}$ is a $C_1$ to $C_4$ alkyl.

Another embodiment of Process 1 is directed to any one of the above process embodiments wherein $R^{3A}$ and $R^{4A}$ are the same —C(O)OR$^{12A}$ moiety, and wherein $R^{12A}$ is methyl or ethyl.

Another embodiment of Process 1 is directed to any one of the above process embodiments wherein

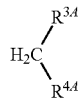

is:

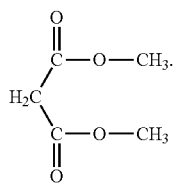

Thus, in another embodiment of Process 1, the mixture of (1)(a) and (1)(b) is reacted with (2)(a), the reaction is carried out at a temperature within the range of about −40° C. to about 40° C., the basic amine is a trialkylamine, the organic solvent (step (1)(c) is anhydrous dichloromethane, the $R^{5A}S(O)_2R^{6A}$ moiety is

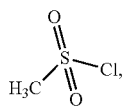

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 30° C., the basic amine is a trialkylamine, the organic solvent (step (1)(c) is anhydrous dichloromethane, the $R^{5A}S(O)_2R^{6A}$ moiety is

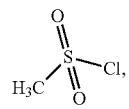

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 10° C., the basic amine is a trialkylamine, the organic solvent (step (1)(c) is anhydrous dichloromethane, the $R^{5A}S(O)_2R^{6A}$ moiety is

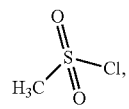

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about −40° C. to about 40° C., the basic amine is TEA, the organic solvent (step (1)(c) is anhydrous dichloromethane, the $R^{5A}S(O)_2R^{6A}$ moiety is

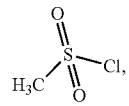

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 30° C., the basic amine is TEA, the organic solvent (step (1)(c) is anhydrous dichloromethane, the $R^{5A}S(O)_2R^{6A}$ moiety is

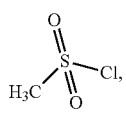

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 10° C., the basic amine is TEA, the organic solvent (step (1)(c) is anhydrous dichloromethane, the $R^{5A}S(O)_2R^{6A}$ moiety is:

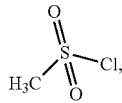

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, the organic solvent (step (1)(c) is anhydrous dichloromethane, the $R^{5A}S(O)_2R^{6A}$ moiety is

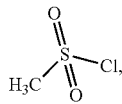

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, the organic solvent (step (1)(c) is anhydrous dichloromethane, the $R^{5A}S(O)_2R^{6A}$ moiety is

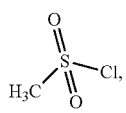

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, the organic solvent (step (1)(c) is anhydrous dichloromethane, the $R^{5A}S(O)_2R^{6A}$ moiety is

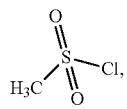

one of $R^{1A}$ and $R^{2A}$ is selected from the group consisting of: aryl (e.g., phenyl), and substituted aryl (e.g., substituted phenyl), and the other one of $R^{1A}$ and $R^{2A}$ is H, and $R^{3A}$ and $R^{4A}$ are the same —C(O)OR$^{12A}$ moiety, and wherein $R^{12A}$ is a $C_1$ to $C_4$ alkyl.

Thus, in another embodiment of Process 1, the mixture of (1)(a) and (1)(b) is reacted with (2)(a), the reaction is carried out at a temperature within the range of about −40° C. to about 40° C., the basic amine is a trialkylamine, the organic solvent (step (1)(c) is anhydrous dichloromethane, the $R^{5A}S(O)_2R^{6A}$ moiety is

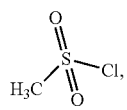

the moiety

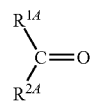

is selected from the group consisting of:

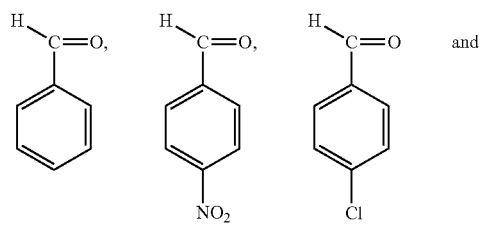

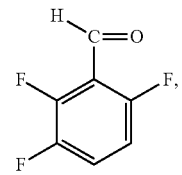

and the moiety

is

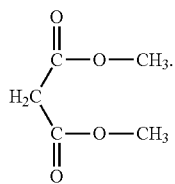

In another embodiment of Process 1, the mixture of (1)(a) and (1)(b) is reacted with (2)(a), the reaction is carried out at a temperature within the range of about 0° C. to about 30° C., the basic amine is a trialkylamine, the organic solvent (step (1)(c) is anhydrous dichloromethane, the $R^{5A}S(O)_2R^{6A}$ moiety is

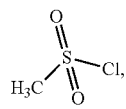

the moiety

is selected from the group consisting of:

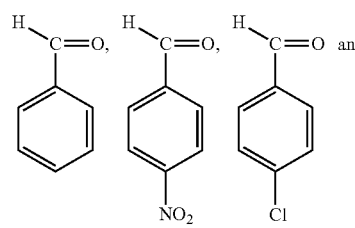

and the moiety

is

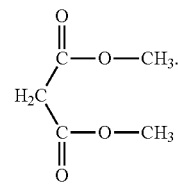

In another embodiment of Process 1, the mixture of (1)(a) and (1)(b) is reacted with (2)(a), the reaction is carried out at a temperature within the range of about 0° C. to about 10° C., the basic amine is a trialkylamine, the organic solvent (step (1)(c) is anhydrous dichloromethane, the $R^{5A}S(O)_2R^{6A}$ moiety is

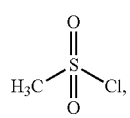

the moiety

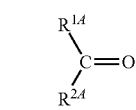

is selected from the group consisting of:

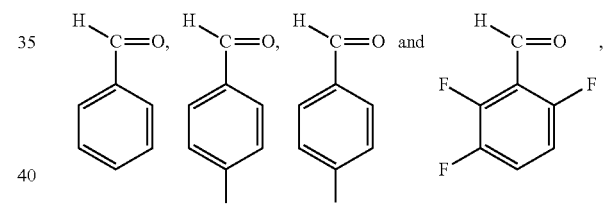

and the moiety

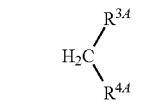

is

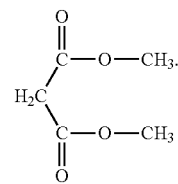

In another embodiment of Process 1, the mixture of (1)(a) and (1)(b) is reacted with (2)(a), the reaction is carried out at a temperature within the range of about −40° C. to about 40° C., the basic amine is TEA, the organic solvent (step (1)(c) is anhydrous dichloromethane, the $R^{5A}S(O)_2R^{6A}$ moiety is

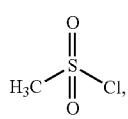

the moiety

is selected from the group consisting of:

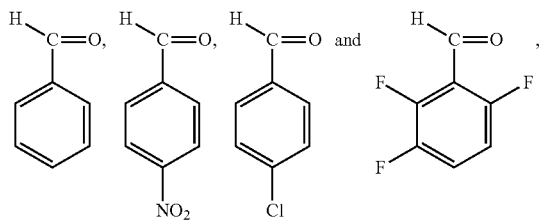

and the moiety

is

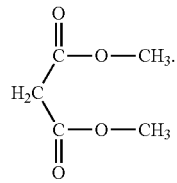

In another embodiment of Process 1, the mixture of (1)(a) and (1)(b) is reacted with (2)(a), the reaction is carried out at a temperature within the range of about 0° C. to about 30° C., the basic amine is TEA, the organic solvent (step (1)(c) is anhydrous dichloromethane, the $R^{5A}S(O)_2R^{6A}$ moiety is

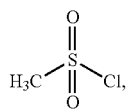

the moiety

is selected from the group consisting of:

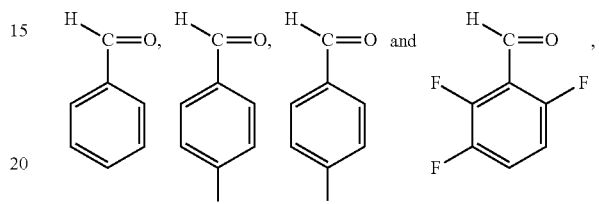

and the moiety

is

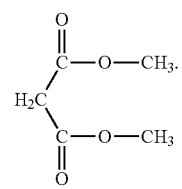

In another embodiment of Process 1, the mixture of (1)(a) and (1)(b) is reacted with (2)(a), the reaction is carried out at a temperature within the range of about 0° C. to about 10° C., the basic amine is TEA, the organic solvent (step (1)(c) is anhydrous dichloromethane, the $R^{5A}S(O)_2R^{6A}$ moiety is:

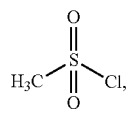

the moiety

is selected from the group consisting of:

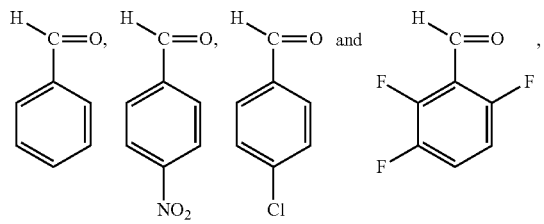

and the moiety is

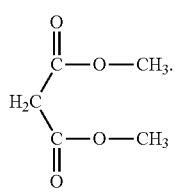

In another embodiment of Process 1, the mixture of (1)(a) and (1)(b) is reacted with (2)(a), the reaction is carried out at a temperature within the range of about −40° C. to about 40° C., the basic amine is diisopropyl ethyl amine, the organic solvent (step (1)(c) is anhydrous dichloromethane, the $R^{5A}S(O)_2R^{6A}$ moiety is

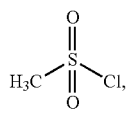

the moiety

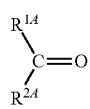

is selected from the group consisting of:

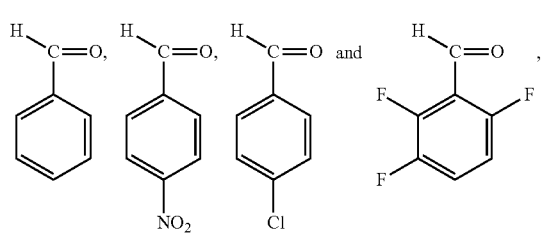

and the moiety

is

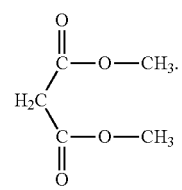

In another embodiment of Process 1, the mixture of (1)(a) and (1)(b) is reacted with (2)(a), the reaction is carried out at a temperature within the range of about 0° C. to about 30° C., the basic amine is diisopropyl ethyl amine, the organic solvent (step (1)(c) is anhydrous dichloromethane, the $R^{5A}S(O)_2R^{6A}$ moiety is

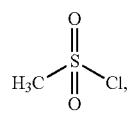

the moiety

is selected from the group consisting of:

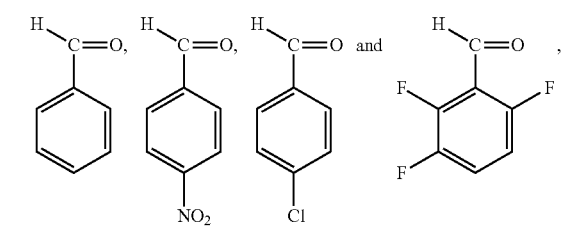

and the moiety

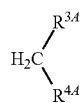

is

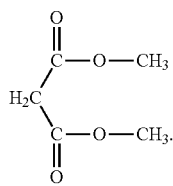

In another embodiment of Process 1, the mixture of (1)(a) and (1)(b) is reacted with (2)(a), the reaction is carried out at a temperature within the range of about 0° C. to about 10° C., the basic amine is diisopropyl ethyl amine, the organic solvent (step (1)(c) is anhydrous dichloromethane, the $R^{5A}S(O)_2R^{6A}$ moiety is

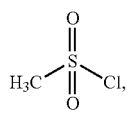

the moiety

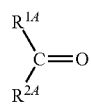

is selected from the group consisting of:

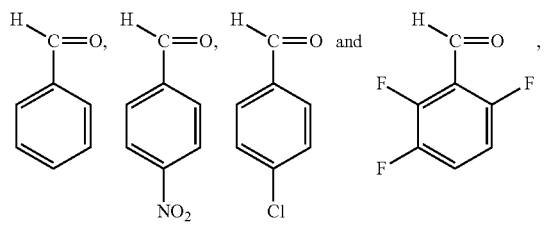

and the moiety

is

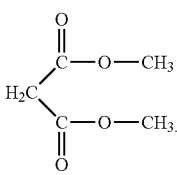

In another embodiment of Process 1, the mixture of (1)(a) and (1)(b) is reacted with a basic amine (e.g., a trialkylamine as defined above) and the compound $R^{7A}C(O)R^{8A}$.

In another embodiment of Process 1, the mixture of (1)(a) and (1)(b) is reacted with a basic amine (e.g., a trialkylamine as defined above) and the compound $R^{7A}C(O)R^{8A}$, wherein the reaction is carried out at a temperature within the range of about −40° C. to about 40° C., and preferably about 0° C. to about 30° C., and more preferably about 0° C. to about 10° C.

In another embodiment of Process 1, the mixture of (1)(a) and (1)(b) is reacted with a basic amine (e.g., a trialkylamine as defined above) and the compound $R^{7A}C(O)R^{8A}$, wherein the reaction is carried out at a temperature within the range of about −40° C. to about 40° C., and preferably about 0° C. to about 30° C., and more preferably about 0° C. to about 10° C., and wherein the (1)(c) organic solvent (preferably anhydrous) is selected from the group consisting of (i) haloalkanes (such as, for example, dichloromethane, dichloroethane (e.g., $CH_2Cl—CH_2Cl$), trichloromethane, and tetrachloromethane), (ii) arylhalides (such as, for example, chlorobenzene), (iii) DMSO, (iv) DMF, (v) THF, (vi) ethers (such as, for example, diethyl ether), and (vii) mixtures thereof, and preferably a haloalkane, and more preferably anhydrous dichloromethane.

In Process 1 and the embodiments of Process 1 described above, the molar ratio of $R^{1A}C(O)R^{2A}$ to $R^{3A}CH_2R^{4A}$ is usually about 1:0.8 to about 1:1.2, and preferably about 1:1.

In Process 1 and the embodiments of Process 1 described above, the molar ratio of $R^{1A}C(O)R^{2A}$ to $R^{5A}S(O)_2R^{6A}$ is usually about 1:1 to about 1:4, and preferably about 1:1.

In Process 1 and the embodiments of Process 1 described above, the molar ratio of $R^{1A}C(O)R^{2A}$ to $R^{7A}C(O)R^{8A}$ is usually about 1:1 to about 1:4, and preferably about 1:1.

In Process 1 and the embodiments of Process 1 described above, the molar ratio of $R^{5A}S(O)_2R^{6A}$ to the basic amine (e.g., $NR^{9A}R^{10A}R^{11A}$, such as, for example, a trialkylamine, such as, for example, triethylamine or diisopropyl ethyl amine) is usually about 1:2 to about 1:3, and preferably about 1:2.

In Process 1 and the embodiments of Process 1 described above, the molar ratio of $R^{7A}C(O)R^{8A}$ to the basic amine (e.g., $NR_9AR_{10}AR_{11}A$, such as, for example, a trialkylamine, such as, for example, triethylamine or diisopropyl ethyl amine) is usually about 1:2 to about 1:3, and preferably about 1:2.

Examples of the compound of the formula:

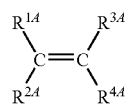

produced by the processes of this invention include, but are not limited to:

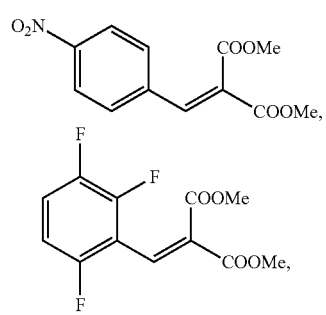

-continued

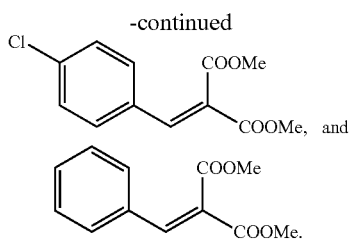

Thus, another embodiment of the processes of this invention is directed to a process for preparing a compound of the formula:

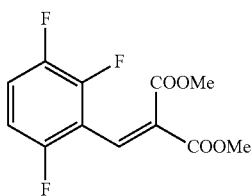 [SMILES: COC(=O)C(=Cc1c(F)ccc(F)c1F)C(=O)OC]

said process comprising reacting:
(1) a mixture comprising:
(a) 2,3,5-triflorobenzaldehyde, and
(b) $CH_2(C(O)OCH_3)_2$; and
(c) dichloromethane (preferably anhydrous); with
(2) mesyl chloride, i.e.,

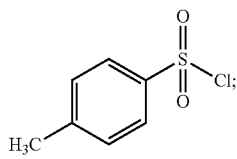

wherein:
said process is carried out at a temperature within the range of about −40° C. to about 40° C., and preferably about 0° C. to about 30° C., and more preferably about 0° C. to about 10° C.;
the molar ratio of 2,3,5-triflorobenzaldehyde to $CH_2(C(O)OCH_3)_2$ is about 1:0.8 to about 1:1.2, and preferably 1:1;
the molar ratio of 2,3,5-triflorobenzaldehyde to mesyl chloride is about 1:1 to about 1:4, and preferably 1:1; and
the molar ratio of mesyl chloride to TEA is about 1:2 to about 1:3, and preferably about 1:2.

Another embodiment of the processes of this invention is directed to a process for preparing a compound of the formula:

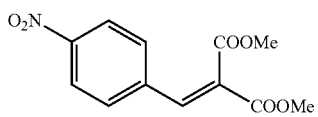 [SMILES: COC(=O)C(=Cc1ccc([N+](=O)[O-])cc1)C(=O)OC]

said process comprising reacting:
(1) a mixture comprising:
(a) 4-nitrobenzaldehyde, and
(b) $CH_2(C(O)OCH_3)_2$; and
(c) dichloromethane (preferably anhydrous); with
(2) mesyl chloride, i.e.,

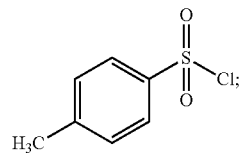

wherein:
said process is carried out at a temperature within the range of about −40° C. to about 40° C., and preferably about 0° C. to about 30° C., and more preferably about 0° C. to about 10° C.;
the molar ratio of 4-nitrobenzaldehyde to $CH_2(C(O)OCH_3)_2$ is about 1:0.8 to about 1:1.2, and preferably 1:1;
the molar ratio of 4-nitrobenzaldehyde to mesyl chloride is about 1:1 to about 1:4, and preferably 1:1; and
the molar ratio of mesyl chloride to TEA is about 1:2 to about 1:3, and preferably about 1:2.

Another embodiment of the processes of this invention is directed to a process for preparing a compound of the formula:

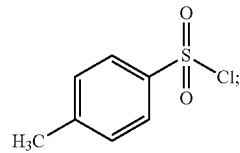

said process comprising reacting:
(1) a mixture comprising:
(a) 4-chlorobenzaldehyde, and
(b) $CH_2(C(O)OCH_3)_2$; and
(c) dichloromethane (preferably anhydrous); with
(2) mesyl chloride, i.e.,

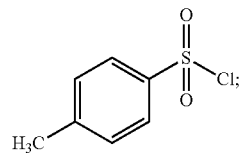

wherein: said process is carried out at a temperature within the range of about −40° C. to about 40° C., and preferably about 0° C. to about 30° C., and more preferably about 0° C. to about 10° C.;
the molar ratio of 4-chlorobenzaldehyde to $CH_2(C(O)OCH_3)_2$ is about 1:0.8 to about 1:1.2, and preferably 1:1;
the molar ratio of 4-chlorobenzaldehyde to mesyl chloride is about 1:1 to about 1:4, and preferably 1:1; and
the molar ratio of mesyl chloride to TEA is about 1:2 to about 1:3, and preferably about 1:2.

Another embodiment of the processes of this invention is directed to a process for preparing a compound of the formula:

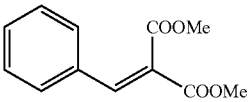 [SMILES: COC(=O)C(=Cc1ccccc1)C(=O)OC]

said process comprising reacting:
(1) a mixture comprising:
(a) benzaldehyde, and
(b) CH$_2$(C(O)OCH$_3$)$_2$; and
(c) dichloromethane (preferably anhydrous); with
(2) mesyl chloride, i.e.,

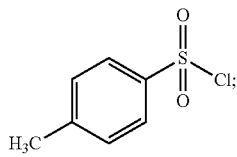

wherein:
said process is carried out at a temperature within the range of about −40° C. to about 40° C., and preferably about 0° C. to about 30° C., and more preferably about 0° C. to about 10° C.;
the molar ratio of benzaldehyde to CH$_2$(C(O)OCH$_3$)$_2$ is about 1:0.8 to about 1:1.2, and preferably 1:1;
the molar ratio of benzaldehyde to mesyl chloride is about 1:1 to about 1:4, and preferably 1:1; and
the molar ratio of mesyl chloride to TEA is about 1:2 to about 1:3, and preferably about 1:2.

The processes of this invention described above are generally carried out under an inert atmosphere, such as, for example N$_2$. Thus, for example the mixture of the compound R$^{1,4}$C(O)R$^{2,4}$, the the compound R$^{3,4}$CH$_2$R$^{4,4}$ (e.g., malonic acid dimethyl ether) and the organic solvent (preferably anhydrous, e.g., anhydrous dichloromethane) are under N$_2$, and then the basic amine (e.g., TEA) is added, and then the compound R$^{5,4}$S(O)$_2$R$^{6,4}$ (e.g., mesyl chloride, i.e., methanesulfonyl chloride) is added. The mixture of R$^{1,4}$C(O)R$^{2,4}$ and R$^{3,4}$CH$_2$R$^{4,4}$ is usually at a low temperature, such as, for example, the temperature resulting from the mixture being in an ice bath (e.g., 5° C.). Thus, another embodiment of Process 1 is directed to any of the embodiments described above wherein the reaction is carried out under an inert atmosphere, preferably N$_2$.

The desired compound of the processes of this invention can be isolated by techniques well known in the art. For example, water can be added creating an organic and an aqueous layer. The layers can be extracted with a suitable organic solvent, preferably the organic solvent used in the process itself (e.g., dichloromethane). The organic layer can be washed with water, and then the resulting organic layer can be dried over a suitable drying agent, such as, for example, anhydrous sodium sulfate. The dried organic layer can then be concentrated to produce the desired product (usually as a solid).

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me4Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min −10% CH$_3$CN, 5 min −95% CH$_3$CN, 7 min −95% CH$_3$CN, 7.5 min −10% CH$_3$CN, 9 min−stop. The retention time and observed parent ion are given.

The following solvents, reagents, and conditions may be referred to by their abbreviations in parenthesis:
Acetyl (Ac), i.e., CH$_3$C(O)—
Butyl (Bu)
Cyclopropyl (Pr-c)
Dichloroethane (DCE)
Dichloromethane (DCM)
Diethyl ether (Et$_2$O)
Diisobutylaluminum hydride (DIBAL-H)
Dimethyl formamide (DMF)
Ethanol (EtOH)
Ethyl (Et)
Ethyl acetate (EtOAc)
High resolution mass spectrometry (HRMS)
Lithium Aluminum Hydride (LAH)
Lithium diisopropyl amide (LDA)
Liquid chromatography/mass spectrometry (LCMS)
m-Chloroperoxybenzoic acid (mCPBA)
Mesyl (Ms), i.e., —S(O)$_2$CH$_3$
Methanol (MeOH)
Methyl (Me)
Nuclear magnetic resonance spectroscopy (NMR)
Preparative thin-layer chromatography (PTLC)
Pyridine (Pyr)
Room temperature (RT)
Tert-butyldimethylsilyl (TBS)
Tetrabutyl ammonium fluoride (TBAF)
Tetrahydrofuran (THF)
Trifluoroacetic acid (TFA)
Trimethylsilyl (TMS)
Trimethylsilyl chloride (TMSCI)
Triethylamine (NEt$_3$ or Et$_3$N or TEA)

Compounds of Formula (I) can be prepared by various methods well known to those skilled in the art, and by the methods described below.

Compounds of Formula (I) can be prepared according to the procedures described in Schemes 1 and 2.

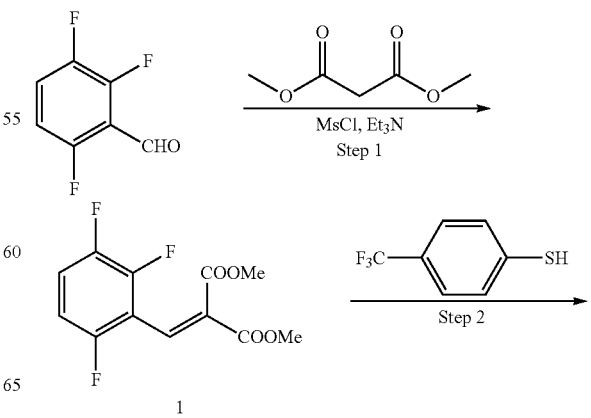

Scheme 1

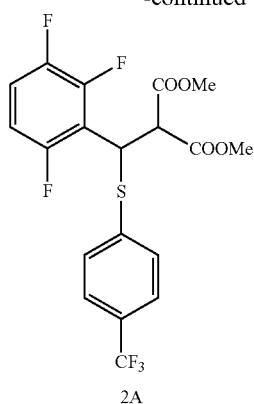
2A
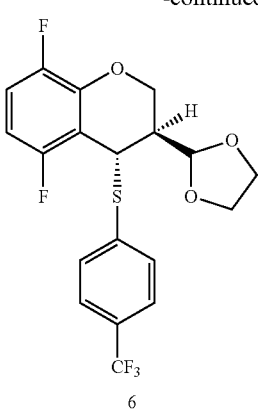
6
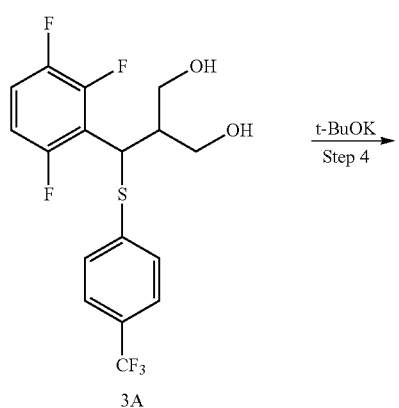
3A
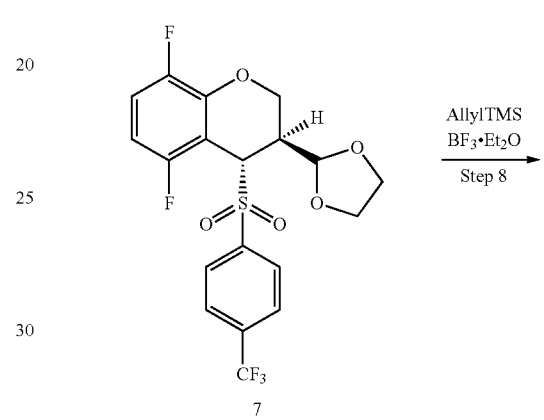
7
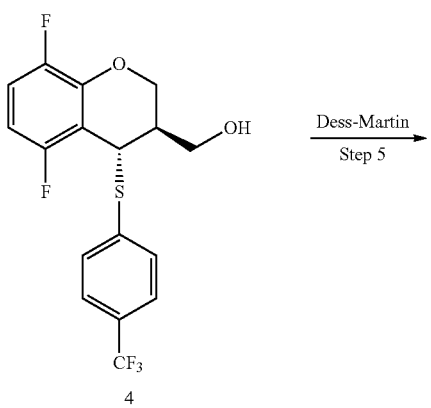
4
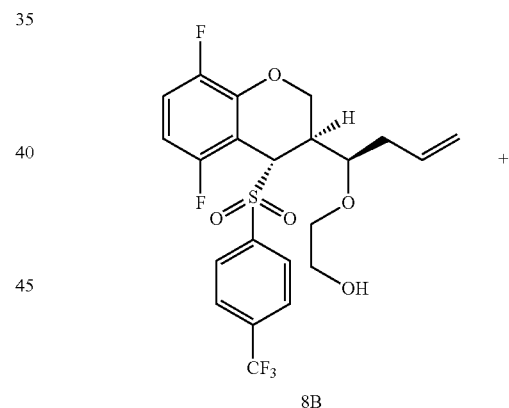
8B
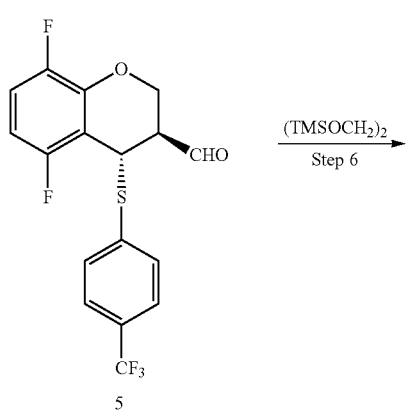
5
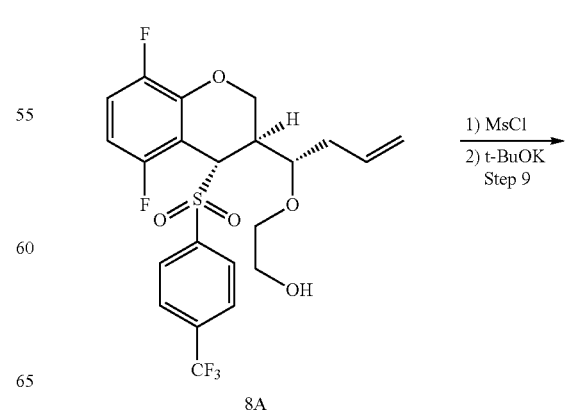
8A

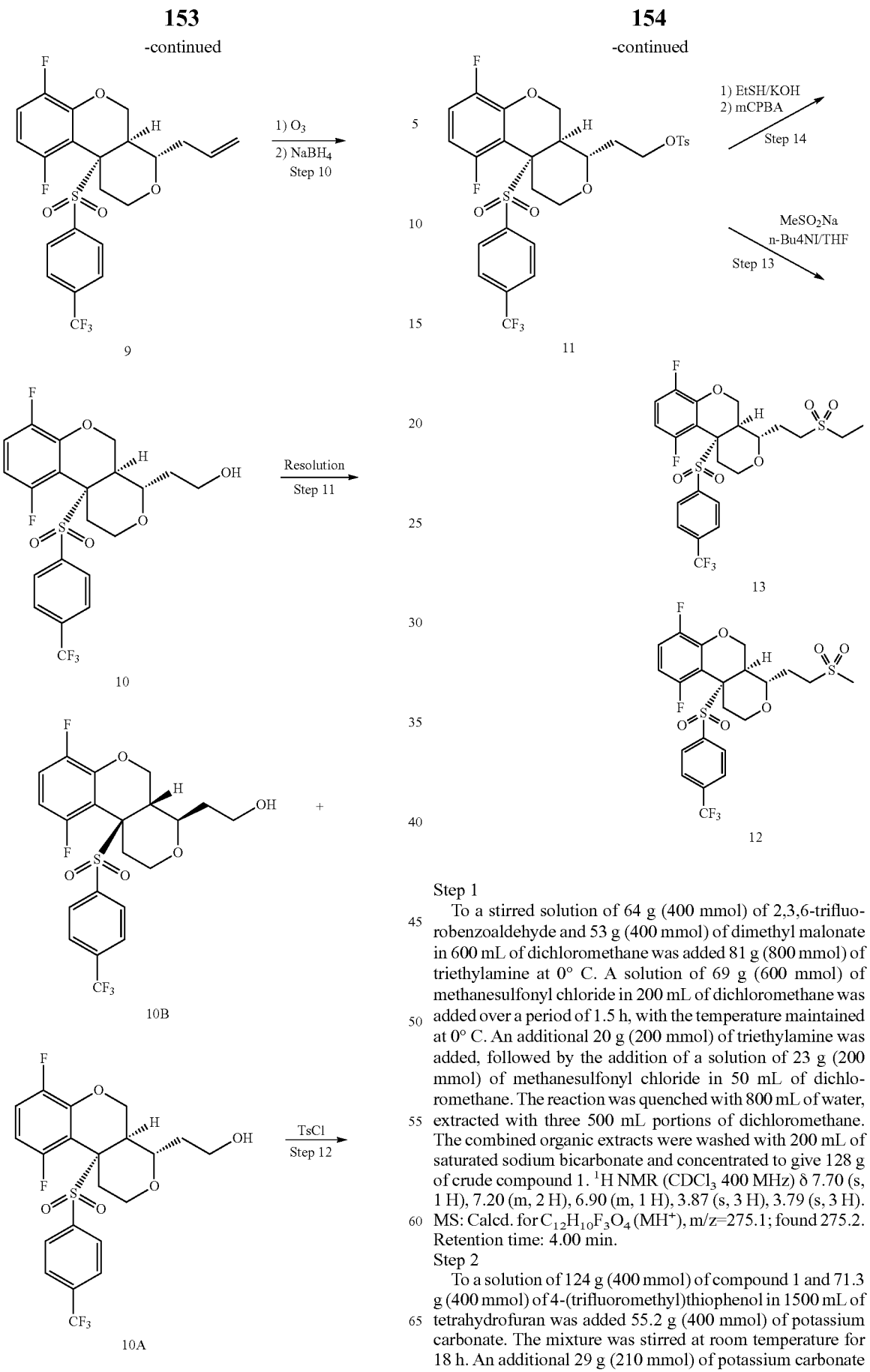

Step 1

To a stirred solution of 64 g (400 mmol) of 2,3,6-trifluorobenzoaldehyde and 53 g (400 mmol) of dimethyl malonate in 600 mL of dichloromethane was added 81 g (800 mmol) of triethylamine at 0° C. A solution of 69 g (600 mmol) of methanesulfonyl chloride in 200 mL of dichloromethane was added over a period of 1.5 h, with the temperature maintained at 0° C. An additional 20 g (200 mmol) of triethylamine was added, followed by the addition of a solution of 23 g (200 mmol) of methanesulfonyl chloride in 50 mL of dichloromethane. The reaction was quenched with 800 mL of water, extracted with three 500 mL portions of dichloromethane. The combined organic extracts were washed with 200 mL of saturated sodium bicarbonate and concentrated to give 128 g of crude compound 1. $^1$H NMR (CDCl$_3$ 400 MHz) δ 7.70 (s, 1 H), 7.20 (m, 2 H), 6.90 (m, 1 H), 3.87 (s, 3 H), 3.79 (s, 3 H). MS: Calcd. for C$_{12}$H$_{10}$F$_3$O$_4$ (MH$^+$), m/z=275.1; found 275.2. Retention time: 4.00 min.

Step 2

To a solution of 124 g (400 mmol) of compound 1 and 71.3 g (400 mmol) of 4-(trifluoromethyl)thiophenol in 1500 mL of tetrahydrofuran was added 55.2 g (400 mmol) of potassium carbonate. The mixture was stirred at room temperature for 18 h. An additional 29 g (210 mmol) of potassium carbonate and 12 g (67 mmol) of 4-trifluoromethyl thiophenol were added. After 2 h, it was quenched with 800 mL of water, extracted with three 600 mL portions of ethyl acetate. The combined organic extracts were concentrated and filtered. The filtrate was concentrated to give 205 g of crude compound 2A. $^1$H NMR (CDCl$_3$ 400 MHz) δ 7.50 (m, 4 H), 7.04 (m, 1 H), 6.78 (s, 1 H), 5.22 (d, J=12 Hz, 1 H), 4.36 (d, J=12 Hz, 1 H), 3.81 (s, 3 H), 3.66 (s, 1 H). MS: Calcd. for $C_{19}H_{15}F_6O_4S$ (MH$^+$), m/z=453.1; found 453.2. Retention time: 5.11 min.

Step 3

To a stirred suspension of 32 g (842 mmol) of lithium aluminum hydride in 1000 mL of tetrahydrofuran was added at 0° C. a solution of 200 g (400 mmol) of compound 2A in 500 mL of tetrahydrofuran over a period of 2 h. It was stirred at room temperature for 2 h and quenched with 100 mL of water (cooled with ice-water bath). After addition of 1500 mL of 6 N HCl, it was extracted with five 600 mL portions of dichloromethane. The combined organic extracts were concentrated, and the residue was purified by chromatography eluting with a gradient of 10% to 50% of ethyl acetate in hexanes to give 55 g of compound 3A. $^1$H NMR (CDCl$_3$ 400 MHz) δ 7.50 (m, 4 H), 7.03 (m, 1H), 6.78 (m, 1 H), 5.03 (d, J=12 Hz, 1 H), 4.35 (m, 1 H), 4.20 (dd, J=11, 2.4 Hz, 1 H), 3.87 (dd, J=11, 2.4 Hz, 1 H), 3.50 (dd, J=11, 4.8 Hz, 1 H), 2.46 (m, 1 H), 2.20 (br, 2 H). MS: Calcd. for $C_{17}H_{15}F_6O_2S$ (MH+), m/z=397.1; found 397.2. Retention time: 4.31 min.

Step 4

To a stirred solution of 55 g (139 mmol) of compound 3A in 600 mL of tetrahydrofuran cooled to 10° C. was added dropwise a solution of 20 g (179 mmol) of potassium tert-butoxide in 200 mL of tetrahydrofuran over a period of 1 h. It was stirred at room temperature for additional 1 h and quenched with 500 mL of water and 80 mL of 1 N HCl. It was separated, the aqueous layer was extracted with three 400 mL portions of dichloromethane. The combined organic extracts were concentrated, and the residue was purified by chromatography eluting with a gradient of 15% to 20% of ethyl acetate in hexanes to give 41 g of compound 4. $^1$H NMR (CDCl$_3$ 400 MHz) δ 7.58 (s, 4 H), 6.98 (m, 1H), 6.60 (m, 1 H), 4.75 (s, 1 H), 4.63 (dd, J=12, 2.4 Hz, 1 H), 4.10 (dd, J=10, 2.4 Hz, 1 H), 3.75 (m, 1 H), 3.55 (m, 1 H), 2.33 (m, 1 H). MS: Calcd. for $C_{17}H_{14}F_5O_2S$ (MH$^+$), m/z=377.1; found 377.2. Retention time: 4.81 min.

Step 5

To a stirred solution of 10 g (26.6 mmol) of compound 4 in 250 mL of dichloromethane was added 14.2 g (33.5 mmol) of Dess-Martin periodinane. The mixture was stirred at room temperature for 2 h and diluted with 400 mL of dichloromethane. It was stirred with 400 mL of saturated sodium bicarbonate and 200 mL of 10% sodium thiosulfate solution and separated. This procedure was repeated twice with 200 mL of saturated sodium bicarbonate and 200 mL of 10% sodium thiosulfate solution. The organic layer was dried over sodium sulfate and filtered. The filtrate was concentrated to give 10.1 g of crude aldehyde 5. $^1$H NMR (CDCl$_3$ 400 MHz) δ 9.74 (s, 1 H), 7.60 (m, 4 H), 6.97 (m, 1 H), 6.64 (m, 1 H), 5.08 (s, 1 H), 4.95 (d, J=12 Hz, 1 H), 4.75 (dd, J=12, 2.4 Hz, 1 H), 2.87 (s, 1 H). MS: Calcd. for $C_{17}H_{12}F_5O_2S$ (MH$^+$), m/z=375.1; found 375.2. Retention time: 5.00 min.

Step 6

To a stirred solution of 10 g (26.5 mmol) of compound 5 in 150 mL of dichloromethane was added 7.14 g (33.5 mmol) of 1,2-bis(trimethylsiloxy)ethane and 0.69 g (3.1 mmol) of trimethylsilyl trifluoromethanesulfonate at −78° C. After 30 min, it was warmed to room temperature and stirred for 30 min. The reaction was quenched with 200 mL of saturated sodium bicarbonate and extracted with three 200 mL portions of dichloromethane. The combined organic extracts were concentrated and the residue was purified by chromatography eluting with a gradient of 2% to 30% of ethyl acetate in hexanes to give 9.4 g of compound 6. $^1$H NMR (CDCl$_3$ 400 MHz) δ 7.60 (m, 4 H), 7.00 (m, 1 H), 6.57 (m, 1 H), 4.90 (s, 1H), 4.79 (d, J=7.6 Hz, 1 H), 4.60 (m, 1 H), 3.80-4.0 (m, 5 H), 2.18 (m, 1 H). MS: Calcd. for $C_{19}H_{16}F_5O_2S$ (MH$^+$), m/z=419.1; found 419.2. Retention time: 5.20 min.

Step 7

To a stirred solution of 9.8 g (23.4 mmol) of compound 6 in 250 mL of dichloromethane was added 14.4 g (58.5 mmol) of 3-chloroperoxybenzoic acid at 0° C. The mixture was stirred at room temperature overnight. It was diluted with 400 mL of dichloromethane and quenched at 0° C. with 200 mL of saturated sodium bicarbonate and 200 mL of 10% sodium thiosulfate. The dichloromethane layer was washed with 100 mL of 1 N NaOH, and dried over sodium sulfate. It was filtered, concentrated and the residue was purified by chromatography eluting with a gradient of 5% to 45% of ethyl acetate in hexanes to give 10.1 g of compound 7. $^1$H NMR (CDCl$_3$ 400 MHz) δ 7.96 (d, J=8.0 Hz, 2 H), 7.81 (d, J=8.0 Hz, 2 H), 7.03 (m, 1 H), 6.39 (m, 1 H), 4.89 (dd, J=12, 4 Hz, 1 H), 4.67 (m, 2 H), 4.64 (dd, J=6.4, 1.6 Hz, 1H), 3.8-4.0 (m, 4 H), 2.92 (m, 1 H). MS: Calcd. for $C_{19}H_{16}F_5O_5S$ (MH$^+$), m/z=451.1; found 451.2. Retention time: 4.43 min.

Step 8

A solution of 10.0 g (22.2 mmol) of compound 7, 12.7 g (111 mmol) of allyltrimethylsilane and 15.8 g (111 mmol) of boron trifluoride etherate in 120 mL of dichloromethane was stirred at reflux for 1 day. Additional 5.0 g (44 mmol) of allyltrimethylsilane and 6.2 g (44 mmol) of boron trifluoride etherate were added, and the mixture was stirred at reflux for another day. The reaction was quenched with 200 mL of saturated sodium bicarbonate, and extracted with three 150 mL potions of dichloromethane. The combined organic extracts were concentrated and the residue was purified by chromatography eluting with a gradient of 10% to 60% of ethyl acetate in hexanes to give 2.70 g of compound 8A and 5.3 g of 8B. 8A: $^1$H NMR (CDCl$_3$ 400 MHz) δ 7.97 (d, J=8.4 Hz, 2 H), 7.82 (d, J=8.4 Hz, 2 H), 7.03 (m, 1 H), 6.41 (m, 1 H), 5.80 (m, 1 H), 5.18 (d, J=12.4 Hz, 1 H), 4.97 (s, 1 H), 4.92 (d, J=9.6 Hz, 1 H), 4.67 (m, 1 H), 4.43 (d, J=12.4 Hz, 1 H), 3.56 (m, 3 H), 3.24 (m, 1 H), 2.97 (m, 1 H), 2.57 (m, 1 H), 2.36 (m, 1 H). MS: Calcd. for $C_{22}H_{22}F_5O_5S$ (MH$^+$), m/z=493.1; found 493.3. Retention time: 4.33 min. 8B: $^1$H NMR (CDCl$_3$ 400 MHz) δ 7.95 (d, J=8.0 Hz, 2 H), 7.82 (d, J=8.0 Hz, 2 H), 7.05 (m, 1 H), 6.45 (m, 1 H), 5.70 (m, 1 H), 5.0 (m, 2 H), 4.86 (d, J=5.6 Hz, 1 H), 4.67 (d, J=11.6 Hz, 1 H), 4.53 (s, 1 H), 3.61 (m, 3 H), 3.47 (m, 1 H), 3.29 (m, 1 H), 2.94 (m, 1 H), 2.37 (m, 1 H), 2.06 (m, 1 H). MS: Calcd. for $C_{22}H_{22}F_5O_5S$ (MH$^+$), m/z=493.1; found 493.3. Retention time: 4.21 min.

Step 9

To a solution of 2.68 g (5.44 mmol) of compound 8A in 40 mL of dichloromethane were added 1.0 g (10 mmol) of triethylamine and 1.0 g (8.7 mmol) of methanesulfonyl chloride. The mixture was stirred at room temperature for 1 h. It was quenched with 80 mL of saturated sodium bicarbonate and extracted with two 80 mL portions of dichloromethane. The combined organic extracts were concentrated and the residue was dissolved in 100 mL of tetrahydrofuran. To this solution was added 10 mL (10 mmol) of 1 N potassium tert-butoxide in THF. The mixture was stirred at room temperature for 15 min., quenched with 100 mL of water and extracted with two 150 mL portions of dichloromethane. The combined organic extracts were concentrated and the residue was purified by chromatography eluting with a gradient of 2% to 30% of ethyl acetate in hexanes to give 2.46 g of compound 9. $^1$H NMR (CDCl$_3$ 400 MHz) δ 7.85 (d, J=8.4 Hz, 2 H), 7.80 (d, J=8.4 Hz, 2 H), 7.10 (m, 1 H), 6.46 (m, 1 H), 5.60 (m, 1 H), 5.15 (m, 3 H), 4.47 (d, J=12.4 Hz, 1 H), 3.93 (m, 1 H), 3.37 (m, 1 H), 3.16 (t, J=11.6 Hz, 1 H), 2.60 (m, 2 H), 2.40 (m, 3 H). MS: Calcd. for C$_{22}$H$_{20}$F$_5$O$_4$S (MH$^+$), m/z=475.1; found 475.3. Retention time: 4.85 min.

Step 10

To a stirred solution of 6.01 g (12.7 mmol) of compound 9 in 125 mL of dichloromethane at −78° C. was bubbled with O$_3$ until blue color sustained. It was bubbled with N$_2$ to remove excess O$_3$. To this solution were added 3.0 g (75 mmol) of sodium borohydride and 25 mL of methanol. The mixture was stirred at room temperature overnight. After addition of 0.7 g (2.67 mmol) of triphenylphosphine, the reaction was stirred for 1 day and diluted with 200 mL of water. It was extracted with three 150 mL portions of dichloromethane and the combined extracts were dried over sodium sulfate. The extracts were filtered, concentrated, and the residue was purified by chromatography eluting with a gradient of 5% to 50% of ethyl acetate in hexanes to give 5.5 g of compound 10. $^1$H NMR (CDCl$_3$ 400 MHz) δ 7.86 (d, J=8.4 Hz, 2 H), 7.81 (d, J=8.4 Hz, 2 H), 7.10 (m, 1 H), 6.40 (m, 1 H), 5.16 (d, J=12.4 Hz, 1 H), 4.46 (d, J=12.8 Hz, 1 H), 3.94 (m, 1 H), 3.80 (m, 2 H), 3.50 (m, 1 H), 3.19 (t, J=12 Hz, 1 H), 2.70 (d, J=10 Hz, 1 H), 2.50 (d, J=13.6 Hz, 1 H), 2.1-2.40 (m, 3 H), 1.86 (m, 1 H). MS: Calcd. for C$_{21}$H$_{20}$F$_5$O$_5$S (MH$^+$) m/z=479.1; found 479.3. Retention time: 4.20 min.

Step 11

Compound 10 (2.1 g) was resolved on Chiral AS column eluting with 65% isopropanol in hexanes and 35 mL /min flow rate to give two enantiomers 10B (0.95 g, retention time 33.5-39.1 min, [α]$_D^{20}$ +98.4° and 10A (0.98 g, retention time 41.3-49.3 min., [α]$_D^2$ −91.4°.

Step 12

A solution of 0.98 g (2.05 mmol) of compound 10A, 0.82 g (4.3 mmol) of p-toluenesulfonyl chloride and 0.6 g (6.0 mmol) of triethylamine in 20 mL of dichloromethane was stirred at room temperature for 18 h. It was quenched with 80 mL of saturated sodium bicarbonate, and extracted with three 80 mL portions of dichloromethane. The combined organic extracts were concentrated and the residue was purified by chromatography eluting with a gradient of 2% to 45% of ethyl acetate in hexanes to give 1.33 g of compound 11. $^1$H NMR (CDCl$_3$ 400 MHz) δ 7.84 (d, J=8.4 Hz, 2 H), 7.80 (d, J=8.4 Hz, 2 H), 7.74 (d, J=8.4 Hz, 2 H), 7.30 (d, J=8.4 Hz, 2 H), 7.14 (m, 1 H), 6.48 (m, 1 H), 5.11 (d, J=10 Hz, 1 H), 4.32 (d, J=12.4 Hz, 1 H), 4.16 (m, 2 H), 3.76 (m, 1 H), 3.27 (m, 1 H), 2.96 (t, J=12 Hz, 1 H), 2.54 (m, 1 H), 2.46 (m, 1 H), 2.42 (s, 3 H), 2.20 (m, 2 H), 1.80 (m, 1 H). MS: Calcd. for C$_{28}$H$_{26}$F$_5$O$_7$S$_2$(MH$^+$), m/z=633.1; found 633.3. Retention time: 4.85 min.

Step 13

A mixture of 0.90 g (1.42 mmol) of compound 11 and 1.59 g (4.3 mmol) of tetrabutylammonium iodide in 50 mL of tetrahydrofuran was stirred at reflux for 3 h. After addition of 0.56 g (5.5 mmol) of sodium methanesulfinate, the mixture was stirred at reflux for 18 h and diluted with 80 mL of water. It was extracted with three 80 mL portions of dichloromethane. The combined organic extracts were concentrated and the residue was purified by chromatography eluting with a gradient of 10% to 75% of ethyl acetate in hexanes to give 0.52 g of compound 12. $^1$H NMR (CDCl$_3$ 400 MHz) δ 7.86 (d, J=8.4 Hz, 2 H), 7.81 (d, J=8.4 Hz, 2 H), 7.12 (m, 1 H), 6.48 (m, 1 H), 5.18 (d, J=10 Hz, 1 H), 4.48 (d, J=12.8 Hz, 1 H), 3.88 (m, 1 H), 3.0-3.40 (m, 4 H), 2.98 (s, 3 H), 2.61 (d, J=10 Hz, 1 H), 2.3-2.53 (m, 3 H), 2.05 (m, 1 H). MS: Calcd. for C$_{22}$H$_{22}$F$_5$O$_6$S$_2$(MH$^+$), m/z=541.1; found 541.3. Retention time: 4.32 min.

Step 14

A mixture of 0.43 g (0.68 mmol) of compound 11, 0.09 g (1.45 mmol) of 2-ethanethiol and 1 mL (1 mmol) of potassium hydroxide in ethanol in 50 mL of ethanol was stirred at 70° C. for 40 min. and concentrated. The residue was dissolved in 40 mL of water and extracted with two 50 mL portions of dichloromethane. The combined organic extracts were concentrated and the crude sulfide product was dissolved in 30 mL of dichloromethane. To this solution was added 0.42 g (1.7 mmol) of 70% 3-chloroperoxybenzoic acid. After stirring at room temperature for 1.5 h, it was diluted with 50 mL of dichloromethane, 40 mL of 10% sodium thiosulfate and 40 mL of saturated sodium bicarbonate. It was stirred for 8 min and separated. The organic layer was washed with 20 mL of 1N sodium hydroxide and concentrated. The residue was purified by chromatography eluting with a gradient of 10% to 60% of ethyl acetate in hexanes to give 0.35 g of compound 13. $^1$H NMR (CDCl$_3$ 400 MHz) δ 7.86 (d, J=8.4 Hz, 2 H), 7.81 (d, J=8.4 Hz, 2 H), 7.13 (m, 1 H), 6.48 (m, 1 H), 5.17 (d, J=10 Hz, 1 H), 4.48 (d, J=12.8 Hz, 1 H), 3.90 (m, 1 H), 3.36 (m, 1 H), 3.20 (m, 2 H), 2.95 (m, 3 H), 2.60 (d, J=9.6 Hz, 1 H), 2.3-2.58 (m, 3 H), 2.05 (m, 1 H), 1.40 (t, J=7.6 Hz, 3H). MS: Calcd. for C$_{23}$H$_{24}$F$_5$O$_6$S$_2$(MH$^+$), m/z=555.1; found 555.3. Retention time: 4.21 min.

The following compounds were prepared analogously:

Compound 22K

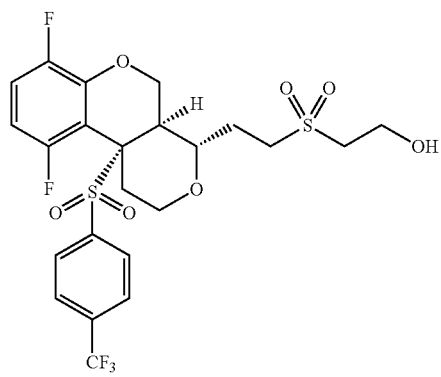

Compound 22K MS: Calcd. for C$_{23}$H$_{24}$F$_5$O$_7$S$_2$(M+1)$^+$, m/z=571.1; found 571.3. Retention time: 3.97 min.

Compound 22N

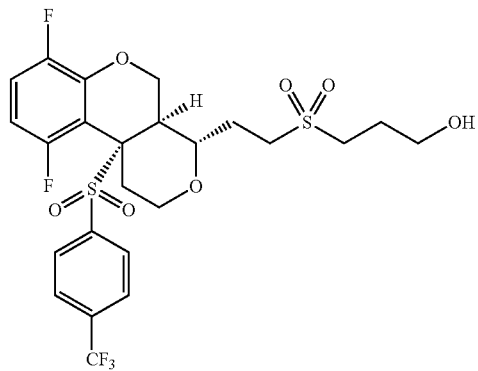

Compound 22N MS: Calcd. for C$_{24}$H$_{26}$F$_5$O$_7$S$_2$ (M+1)$^+$, m/z=585.1; found 585.3. Retention time: 3.96 min.

Scheme 2:
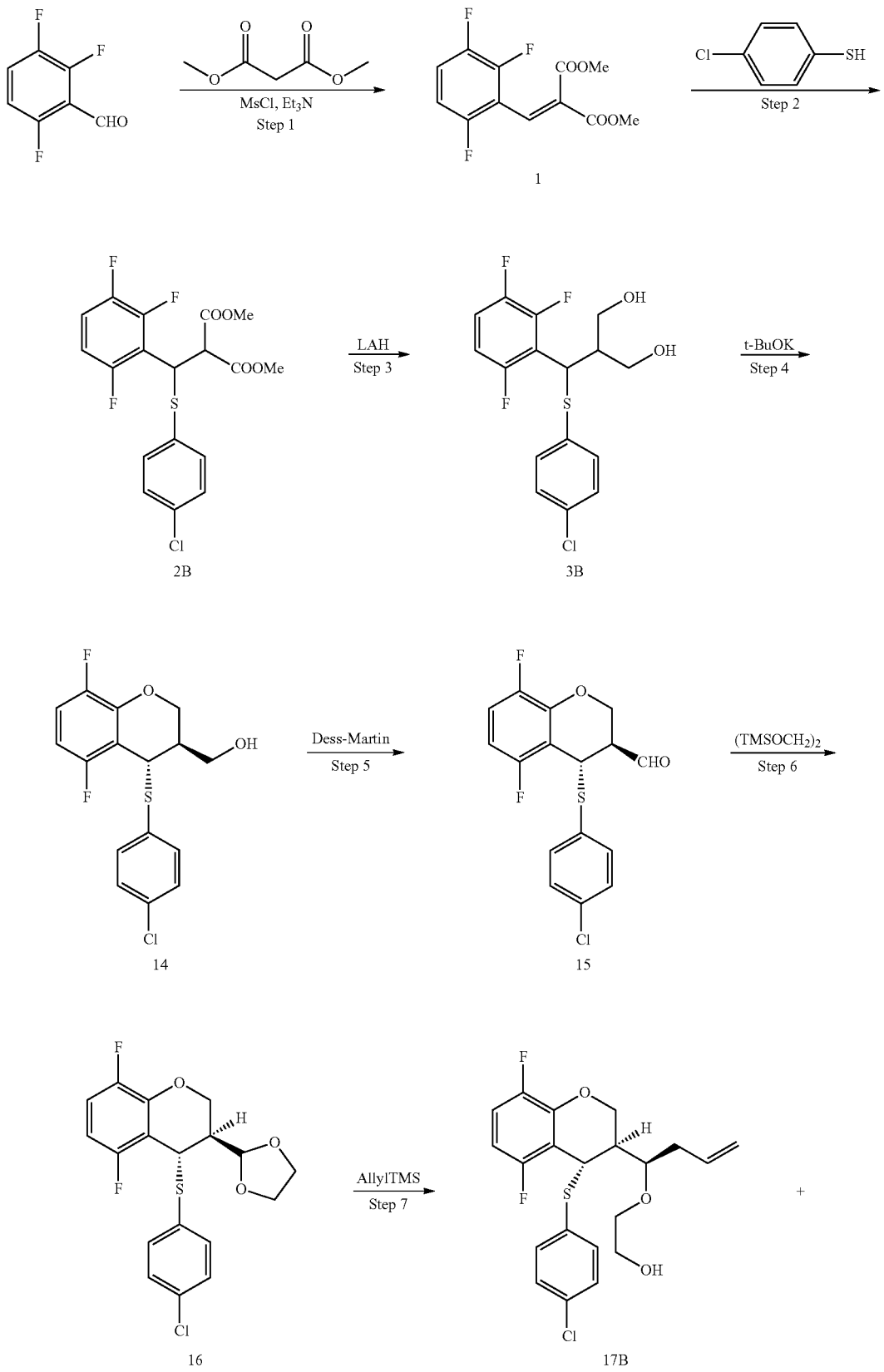

-continued
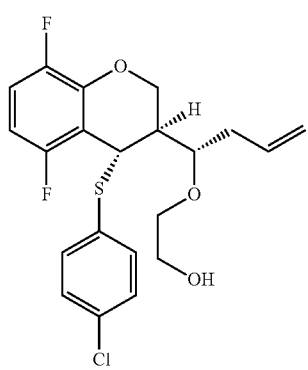
17A
Oxone
Step 8
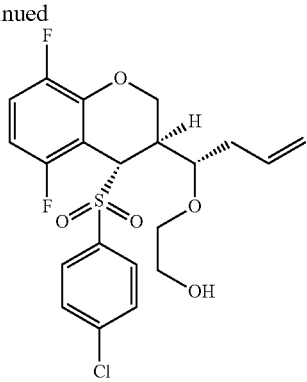
18
1) MsCl
2) t-BuOK
Step 9
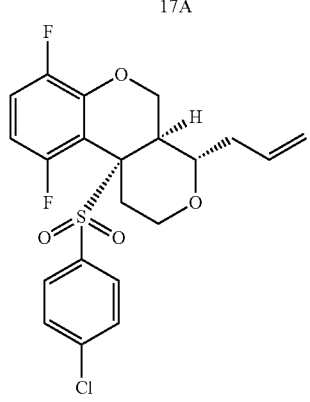
19
1) O₃
2) NaBH₄
Step 10
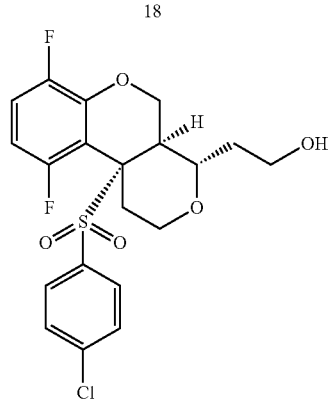
20
Chiral OJ
Step 11
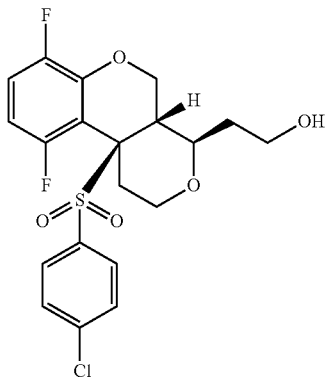
20B            20A
TsCl
Step 12
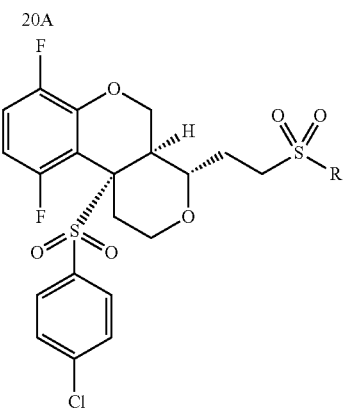
21
Step 13 Bu₄NI
MeSO₂Na
THF
or KI
CF₃SO₂Na
DMF
Step 14
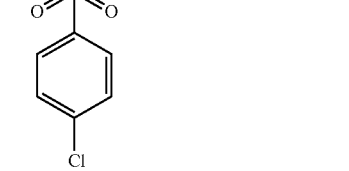
22A R = Me
22B R = CF₃
1) RSH/KOH
2) mCPBA    Step 15

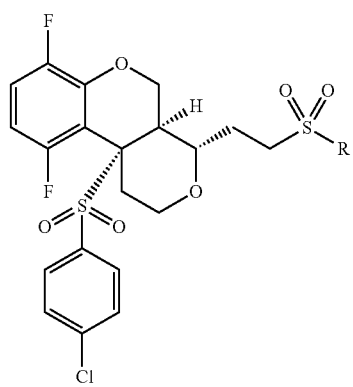
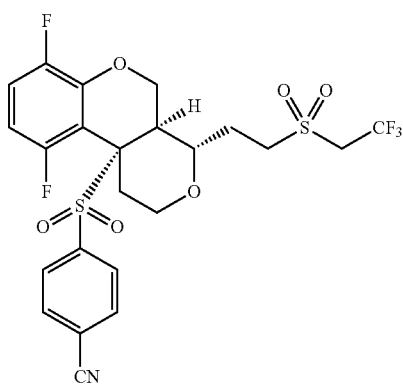

22C R = Et
22D R = CH$_2$CF$_3$
22E R = Pr
22F R = i-Pr
22L R = CH$_2$CH$_2$OH

Step 1

To a stirred cold (0° C.) solution of 2,3,5-triflouro-benzaldehyde (400 g, 2.5 mol) and dimethylmalonate (280.5 g, 2.875 mol) in dichloromethane (7 L) was added triethylamine (455 g, 4.5 mol). The mixture was stirred at 0 to 5° C. for 40 min. Methanesulfonyl chloride (430 g, 3.75 mol) was added over 2.5 h maintaining reaction temperature below 6° C. The reaction stirred for 30 min. at 0° C. Additional triethylamine (126 g, 1.25 mol) was added. The reaction was stirred for 1 hr at 0° C. NMR indicated 91% product. Additional triethylamine (126 g, 1.25 mol) and methanesulfonyl chloride (86 g, 0.75 mol) were added. It was stirred at 0° C. for 1 h. The reaction was stirred with cold water (3 L) and separated. The aqueous layer was extracted with dichloromethane (2.5 L). The combined dichloromethane layers were washed with water (4 L), 1N HCl (2.5 L) and brine (2 L), dried over sodium sulfate and filtered. The filtrate was concentrated to give 771 g of the desired product 1 as a crude oil. $^1$H NMR (CDCl$_3$): δ 3.78 (s, 3H), 3.82 (s, 3H), 6.83 (m, 1H), 7.18 (m, 1H), 7.62 (s, 1H).

Step 2

To a solution of the above crude oil (771 g, 2.5 mol) and 4-chlorothiophenol (366 g, 2.53 mol) in THF (10 L) was added potassium carbonate (345 g, 2.5 mol) at room temperature. The mixture was stirred overnight. Additional 4-chlorothiophenol (37 g, 0.25 mol) and potassium carbonate (355 g, 0.25 mol) were added. The reaction was stirred 1 h at room temperature. The reaction was stirred with ethyl acetate (4 L) and water (4 L) and separated. The aqueous layer was extracted with ethyl acetate (2 L). The combined organic layers were washed with brine (2 L), dried over sodium sulfate and filtered. The filtrate was concentrated to give 1152 g of the desired product 2B as crude oil. $^1$H NMR (CDCl$_3$): δ 3.58 (s, 3H), 3.80 (s, 3H), 4.35 (d, 2H), 5.08 (d, 2H), 6.75 (m, 1H), 7.00 (m, 1H), 7.22 (m, 4H)

Step 3

LAH pellets (100 g, 2.62 mol) were suspended and stirred in THF (5 L). To this cold suspension was added a solution of above crude oil 2B (split into two batches, 560 g, 1.25 mol) in THF (800 ml) over 1 h below 7° C. The reaction was stirred at 0° C. for 3 h. Water (200 ml) was dripped in slowly and the reaction was stirred for 30 min. 6N HCl (1 L) and hexane (4 L) were added and the reaction was stirred for 1 h. The organic layer was decanted. Residual solid was stirred with hexane (3 L) and ethyl ether (2 L) and decanted. The combined organic layer was washed with water (2×3 L). The combined aqueous layers were extracted with hexane (2 L) and ethyl ether (1 L). The combined organic layers were washed with brine (1.5 L), dried over sodium sulfate and filtered. The filtrate was concentrated to give 430 g crude oil. This crude product was combined with the other batch prepared in the same scale. The combined crude products were purified by silica gel chromatography (5 Kg) eluting with a gradient from 10% to 50% of ethyl acetate in hexanes to give 505 g of the diol product 3B. $^1$H NMR (CDCl$_3$): δ 2.21 (m, 1H), 2.39 (m, 1H), 2.42 (m, 1H), 3.47 (m, 1H), 3.81 (m, 1H), 4.20 (m, 1H), 4.25 (m, 1H), 4.81 (d, 1H), 6.75 (m, 1H), 6.88 (m, 1H), 7.18 (m, 2H), 7.23 (m, 2H)

Step 4

To a solution of above diol 3B (530 g, 1.19 mol) in THF was added 1M potassium tert-butoxide (1550 ml, 1.55 mol) in THF over 1 h keeping the temperature below 8° C. The reaction was stirred at room temperature for 105 min. Additional 1M potassium tert-butoxide (160 ml, 0.16 mol) was added. The reaction was stirred at room temperature for 1 h. Water (2 L) and hexane (4 L) were added to the reaction mixture in a ice bath and the layers were separated. The aqueous layer was extracted with ethyl acetate (1 L) and hexane (1 L). The combined organic layers were washed with brine (1 L), dried over sodium sulfate, filtered and concentrated. The residue was purified by silica gel chromatography (3 Kg) eluting with a gradient from 15% to 50% of ethyl acetate in hexanes to give 376 g of the desired bicyclic product 14. $^1$H NMR (CDCl$_3$): δ 2.22 (t, 1H), 3.45 (m, 1H), 3.63 (m, 1H), 4.40 (m, 1H), 4.48 (s, 1H), 4.60 (m, 1H), 6.58 (m, 1H), 6.95 (m, 1H), 7.29 (dd, 2H), 7.42 (dd, 2H).

Step 5

To a stirred solution of 9.1 g (26.5 mmol) of compound 14 in 200 mL of dichloromethane was added 14.6 g (34.5 mmol) of Dess-Martin periodinane. The mixture was stirred at room temperature for 2 h and diluted with 400 mL of dichloromethane. It was stirred with 400 mL of saturated sodium bicarbonate and 200 mL of 10% sodium thiosulfate solution and separated. This procedure was repeated twice with 200 mL of saturated sodium bicarbonate and 200 mL of 10% sodium thiosulfate solution. The organic layer was dried over sodium sulfate and filtered. The filtrate was concentrated to give 9.0 g of crude aldehyde 15. $^1$H NMR (CDCl$_3$ 400 MHz)

δ 9.69 (s, 1 H), 7.45 (d, J=8.6 Hz, 2 H), 7.34 (d, J=8.8 Hz, 2 H), 6.95 (m, 1 H), 6.62 (m, 1 H), 4.91 (m, 2 H), 4.74 (dd, J=12.5 Hz, 1 H), 2.83 (s, 1 H).

Step 6

To a stirred solution of 9.0 g (26.5 mmol) of compound 15 in 100 mL of dichloromethane were added 7.12 g (34.5 mmol) of 1,2-bis(trimethylsiloxy)ethane and 0.36 (1.6 mmol) of trimethylsilyl trifluoromethanesulfonate at −78° C. After 30 min., it was warmed to room temperature and stirred for 30 min. It was diluted with 150 mL of dichloromethane and washed with three 200 mL portions of saturated sodium bicarbonate. The organic layer was dried over sodium sulfate, concentrated, and the residue was purified by chromatography eluting with a gradient of 2% to 30% of ethyl acetate in hexanes to give 8.8 g of compound 16. $^1$H NMR (CDCl$_3$ 400 MHz) δ 7.42 (d, J=9.0 Hz, 2 H), 7.31 (d, J=8.6 Hz, 2 H), 6.95 (m, 1 H), 6.57 (m, 1 H), 4.74 (d, J=7.4 Hz, 1 H), 4.70 (s, 1 H), 4.59 (s, 2 H), 3.80-3.92 (m, 4 H), 2.10 (m, 1 H). MS: Calcd. for C$_{18}$H$_{16}$ClF$_2$O$_3$S(MH$^+$), m/z=385.1; found 385.2. Retention time: 5.28 min.

Step 7

A solution of 2.9 (7.5 mmol) of compound 16, 3.45 g (30.2 mmol) of allyltrimethylsilane and 4.3 g (30.2 mmol) of boron trifluoride diethyl etherate in 50 mL of dichloromethane was stirred at reflux for 1 day. It was quenched with 50 mL of water, and 50 mL of dichloromethane. The organic layer was washed with two 50 mL portions of saturated sodium bicarbonate, concentrated, and the residue was purified by chromatography eluting with a gradient of 1% to 30% of ethyl acetate in hexanes to give 1.1 g of compound 17A and 0.63 g of 17B. 17A: $^1$H NMR (CDCl$_3$ 400 MHz) δ 7.45 (d, J=8.9 Hz, 2 H), 7.31 (d, J=8.9 Hz, 2 H), 6.95 (m, 1 H), 6.60 (m, 1 H), 5.75 (m, 1 H), 5.10 (d, J=5.7 Hz, 1 H), 5.07 (s, 1 H), 4.80(m, 1 H), 4.61 (d, J=12.3 Hz, 1H), 4.39 (d, J=11.4 Hz, 1 H), 3.58 (m, 3 H), 3.24 (m, 2 H), 2.52 (m, 1 H), 2.34 (m, 1H), 2.15 (m, 1 H), 1.60 (m, 1 H). MS: Calcd. for C$_{21}$H$_{22}$ClF$_2$O$_3$S(MH$^+$), m/z=427.1; found 427.1. Retention time: 5.04 min. 17B: $^1$H NMR (CDCl$_3$ 400 MHz) δ 7.48 (d, J=8.1 Hz, 2 H), 7.33 (d, J=8.6 Hz, 2 H), 6.97 (m, 1 H), 6.59 (m, 1 H), 5.50 (m, 1 H), 4.90 (d, J=10.1 Hz, 1 H), 4.82(d, J=16.9 Hz, 1 H), 4.63 (m, 2 H), 4.29 (s, 1H), 3.64 (m, 3 H), 3.43 (m, 1 H), 3.20 (m, 1 H), 2.36 (m, 1 H), 1.90-2.18 (m, 3 H). MS: Calcd. for C$_{21}$H$_{22}$ClF$_2$O$_3$S(MH$^+$), m/z=427.1; found. Retention time: 4.32 min.

Step 8

A mixture of 3.6 g (8.4mmol) of compound 17A and 20.7 g (33.6 mmol) of potassium peroxomonosulfate in 110 mL of acetone and 35 mL of water was stirred at 50° C. for 3 h. It was concentrated, and the residue was dissolved in 200 mL of water. It was extracted with three 150 mL portions of ethyl acetate. The combined organic extracts were concentrated and the residue was purified by chromatography eluting with a gradient of 1% to 10% of ethyl acetate in dichloromethane to give 2.35 g of compound 18. $^1$H NMR (CDCl$_3$ 400 MHz) δ 7.75 (d, J=8.6 Hz, 2 H), 7.52 (d, J=8.1 Hz, 2 H), 7.05 (m, 1 H), 6.45 (m, 1 H), 5.83 (m, 1 H), 5.18 (d, J=13.5 Hz, 2 H), 4.93 (m, 2 H), 4.40 (d, J=12.4 Hz, 1 H), 3.55 (m, 3 H), 3.20 (m, 2 H), 2.93 (m, 1 H), 2.54 (m, 1 H), 2.38(m, 1 H), 1.64 (m, 1 H). MS: Calcd. for C$_{21}$H$_{22}$ClF$_2$O$_5$S(MH$^+$), m/z=459.1; found 459.3. Retention time: 4.39 min.

Step 9

To a solution of 2.33 g (5.1 mmol) of compound 18 in 100 mL of dichloromethane were added 0.7 g (7.0 mmol) of triethylamine and 0.87 g (7.6 mmol) of methanesulfonyl chloride. The mixture was stirred at room temperature for 1.5 h. It was diluted with 100 mL of dichloromethane and washed with two 80 mL portions of water, and 80 mL of saturated sodium bicarbonate. The organic layer was concentrated and the residue was dissolved in 100 mL of tetrahydrofuran. To this solution was added 12.7 mL (12.7 mmol) of 1 N potassium tert-butoxide in tetrahydrofuran. The mixture was stirred at room temperature for 30 min., quenched with 50 mL of water, and extracted with 250 mL portions of dichloromethane. The organic extract was concentrated and the residue was purified by chromatography eluting with a gradient of 1% to 30% of ethyl acetate in hexanes to give 1.59 g of compound 19. $^1$H NMR (CDCl$_3$ 400 MHz) δ 7.63 (d, J=8.0 Hz, 2 H), 7.50 (d, J=7.3 Hz, 2 H), 7.08 (m, 1 H), 6.46 (m, 1 H), 5.85 (m, 1 H), 5.15 (m, 3 H), 4.45 (d, J=12.4 Hz, 1 H), 3.91 (m, 1 H), 3.37 (m, 1 H), 3.17 (t, J=11.6 Hz, 1 H), 2.61 (m, 2 H), 2.25-2.54 (m, 3 H). MS: Calcd. for C$_{21}$H$_{20}$ClF$_2$O$_4$S(MH$^+$), m/z=441.1; found 441.1. Retention time: 4.20 min.

Step 10

To a stirred solution of 5.0 g (11.4 mmol) of compound 19 in 150 mL of dichloromethane at −78° C. was bubbled with O$_3$ until blue color sustained. It was bubbled with N$_2$ until the solution becomes colorless. To this solution were added 1.3 g (34.2 mmol) of sodium borohydride and 15 mL of methanol. The mixture was stirred at room temperature overnight. After addition of 3.0 g (11.4 mmol) of triphenylphosphine, it was stirred for 1 h and diluted with 200 mL of water. The mixture was extracted with three 150 mL portions of dichloromethane, and the combined extracts were dried over sodium sulfate. The combined organic extracts were filtered, concentrated, and the residue was purified by chromatography eluting with a gradient of 5% to 60% of ethyl acetate in hexanes to give 4.6 g of compound 20. $^1$H NMR (CDCl$_3$ 400 MHz) δ 7.64 (d, J=8.5 Hz, 2 H), 7.51 (d, J=8.9 Hz, 2 H), 7.12 (m, 1 H), 6.45 (m, 1 H), 5.16 (d, J=10.0 Hz, 1 H), 4.43 (d, J=13.5 Hz, 1H), 3.92 (m, 1 H), 3.79 (m, 2 H), 3.51 (m, 1 H), 3.20 (t, J=11.6 Hz, 1 H), 2.65 (d, J=11.0 Hz, 1 H), 2.53 (d, J=12.9 Hz, 1 H), 2.34 (m, 2 H), 2.15 (m, 1 H), 1.85 (m, 1 H). MS: Calcd. for C$_{20}$H$_{20}$ClF$_2$O$_5$S(MH$^+$) m/z=445.1; found 445.2 Retention time: 3.40 min.

Step 11

Compound 20 (1.8 g) was resolved on Chiral OJ column eluting with 70% isopropanol in hexanes and 28 mL/min flow rate to give two enantiomers 20A (0.67 g, retention time 41 min, [α]$_D^{20}$ −136.6°) and 20B (0.70 g, retention time 50 min., [α]$_D^{20}$ +132.5°).

Step 12

A solution of 1.5 g (3.37 mmol) of compound 20A, 1.27 g (6.7 mmol) of p-toluenesulfonyl chloride and 0.68 g (6.7 mmol) of triethylamine in 30 mL of dichloromethane was stirred at room temperature for 65 h. It was quenched with 80 mL of saturated sodium bicarbonate, and extracted with three 100 mL portions of dichloromethane. The combined organic extracts were concentrated and the residue was purified by chromatography eluting with a gradient of 2% to 40% of ethyl acetate in hexanes to give 1.95 g of compound 21. $^1$H NMR (CDCl$_3$ 400 MHz) δ 7.74 (d, J=8.4 Hz, 2 H), 7.61 (d, J=8.4 Hz, 2 H), 7.51 (d, J=8.8 Hz, 2 H), 7.30 (d, J=8.4 Hz, 2H), 7.12 (m, 1 H), 6.48 (m, 1 H), 5.10 (d, J=12.8 Hz, 1 H), 4.29 (d, J=12.8 Hz, 1 H), 4.19 (m, 2 H), 3.76 (m, 1 H), 3.24 (m, 1 H), 2.96 (t, J=11.6 Hz, 1 H), 2.51 (m, 2 H), 2.42 (s, 3 H), 2.20 (m, 2 H), 1.80 (m, 1 H). MS: Calcd. for C$_{27}$H$_{26}$ClF$_2$O$_7$S$_2$(MH$^+$), m/z=599.1; found 599.3. Retention time: 4.82 min.

Step 13

A mixture of 3.15 g (5.26 mmol) of compound 21 and 5.83 g (15.8 mmol) of tetrabutylammonium iodide in 80 mL of tetrahydrofuran was stirred at reflux for 2 h. After addition of 2.15 g (21.0 mmol) of sodium methanesulfinate, the mixture was stirred at reflux overnight and diluted with 100 mL of water. It was extracted with three 100 mL portions of ethyl acetate. The combined organic extracts were concentrated and the residue was purified by chromatography eluting with a gradient of 5% to 75% of ethyl acetate in hexanes to give 2.44 g of compound 22A. $^1$H NMR (CDCl$_3$ 400 MHz) δ 7.64 (d, J=8.8 Hz, 2 H), 7.52 (d, J=8.8 Hz, 2 H), 7.10 (m, 1 H), 6.48 (m, 1 H), 5.18 (d, J=13.2 Hz, 1 H), 4.45 (d, J=12.4 Hz, 1 H), 3.90 (m, 1H), 3.0-3.40 (m, 4 H), 2.92 (s, 3 H), 2.2-2.60 (m, 4 H), 2.05 (m, 1 H). MS: Calcd. for C$_{21}$H$_{22}$ClF$_2$O$_6$S$_2$ (MH$^+$), m/z=507.1.; found 507.3. Retention time: 4.22 min.

Starting with racemic alcohol 20, and proceeding through Scheme 2, steps 12 and 13 provided racemic compound 22A-rac: MS: Calcd. for C$_{21}$H$_{22}$ClF$_2$O$_6$S$_2$ (MH$^+$), m/z=507.0; found 507.3. Retention time: 4.20 min.

or Step 14

A mixture of 0.12 g (0.2 mmol) of compound 21, 0.10 g (0.6 mmol) of potassium iodide and 0.10 g (0.6 mmol) of sodium trifluoromethylsulfinate in 6 mL of DMF was stirred at 120° C. for 6 h. It was diluted with 25 mL of water and extracted with three 40 mL portions of dichloromethane. The combined organic extracts were concentrated and the residue was purified by preparative TLC eluting with 30% of ethyl acetate in hexanes to give 0.045 g of compound 22B. $^1$H NMR (CDCl$_3$ 400 MHz) δ 7.63 (d, J=8.8 Hz, 2 H), 7.52 (d, J=8.8 Hz, 2 H), 7.12 (m, 1 H), 6.48 (m, 1 H), 5.19 (d, J=12.8 Hz, 1 H), 4.42 (d, J=12.4 Hz, 1 H), 3.92 (m, 1 H), 3.1-3.54 (m, 4H), 2.50 (m, 2 H), 2.30 (m, 2 H), 2.10 (m, 1 H). MS: Calcd. for C$_{21}$H$_{19}$ClF$_5$O$_6$S$_2$ (MH$^+$), m/z=561.0; found 561.3. Retention time: 4.80 min.

The following compounds were prepared analogously:
Compound 22H

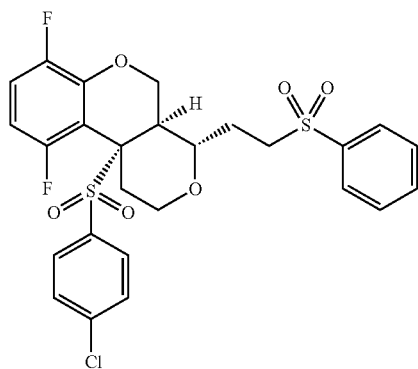

22H

Compound 22H: MS: Calcd. for C$_{26}$H$_{24}$ClF$_2$O$_6$S$_2$(MH$^+$), m/z=569.1; found 569.3. Retention time: 4.71 min.
Compound 22B-rac

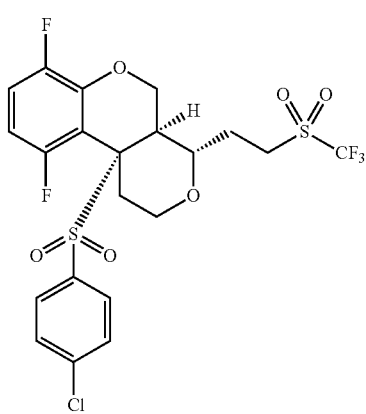

22B-rac

Starting with racemic alcohol 20, and proceeding through Scheme 2, steps 12 and 14 provided racemic compound 22B-rac: MS: Calcd. for C$_{21}$H$_{19}$ClF$_5$O$_6$S$_2$ (MH$^+$), m/z=561.0; found 561.3. Retention time: 4.89 min.

The following compounds were prepared analogously starting from compound 11 (Scheme 1) substituting Bu$_4$NI for KI:
Compound 22I

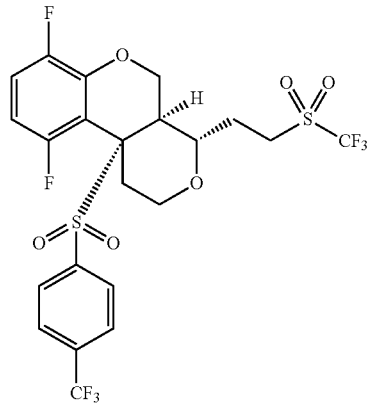

22I

Compound 22I: MS: Calcd. for C$_{22}$H$_{19}$ClF$_8$O$_6$S$_2$(M+H)$^+$, m/z=595.0 found 595.3. Retention time: 5.06 min.

Step 15

A mixture of 0.2 g (0.33 mmol) of compound 21, 0.04 g (0.67 mmol) of 2-ethanethiol 0.5 mL (1 mmol) of potassium hydroxide in ethanol in 5.5 mL of ethanol was stirred at 70° C. for 25 min. and concentrated The residue was dissolved in 15 mL of water and extracted with 30 mL of dichloromethane. The organic extract was concentrated and the crude sulfide product was dissolved in 10 mL of dichloromethane. To this solution was added 0.17 g (1.0 mmol) of 70% 3-chloroperoxybenzoic acid. After stirring at room temperature for 1 h, it was diluted with 30 mL of dichloromethane. It was washed with three 20 mL portions of saturated sodium bicarbonate. The organic layer was concentrated, the residue was purified by chromatography eluting with a gradient of 5% to 80% of ethyl acetate in hexanes to give 0.14 g of compound 22C. $^1$H NMR (CDCl$_3$ 400 MHz) δ 7.63 (d, J=7.8 Hz, 2 H), 7.51 (d, J=8.9 Hz, 2 H), 7.13 (m, 1 H), 6.47 (m, 1 H), 5.16 (d, J=15.3 Hz, 1H). 4.45 (d, J=12.2 Hz, 1 H), 3.89 (d, J=10.2, 1 H), 3.36 (m, 1 H), 3.20 (m, 2 H), 2.96 (m, 3H), 2.5 (m, 2 H), 2.40 (m, 1 H), 2.29 (m, 1 H), 2.02 (m, 1 H), 1.40 (t, J=7.4 Hz, 3 ). MS: Calcd. for C$_{22}$H$_{24}$ClF$_2$O$_6$S$_2$(MH$^+$), m/z=521.1; found 521.3 Retention time: 4.35 min.

The following compounds were prepared analogously:
Compound 22D

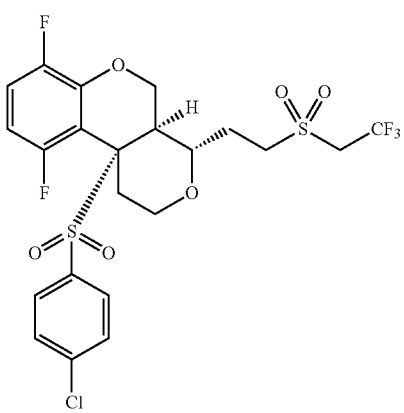 [SMILES: O=S(=O)(CC[C@@H]1OCC[C@@]2(S(=O)(=O)c3ccc(Cl)cc3)c3c(F)ccc(F)c3OC[C@@H]12)CC(F)(F)F]

Compound 22D: 7.62 (d, J=8.0 Hz, 2 H), 7.54 (d, J=8.4 Hz, 2 H), 7.13 (m, 1 H), 6.45 (m, 1 H), 5.19 (d, J=15 Hz, 1 H), 4.42 (d, J=12 Hz, 1 H), 3.92 (d, J=10 Hz, 1H), 3.79 (m, 2 H), 3.40 (m, 2 H), 3.19 (m, 2 H), 2.56 (m, 3 H), 2.34 (m, 1 H), 2.10 (m, 1 H). MS: Calcd. for $C_{22}H_{21}ClF_5O_6S_2(MH^+)$, m/z=575.0; found 575.3. Retention time: 4.76 min.

Compound 22E

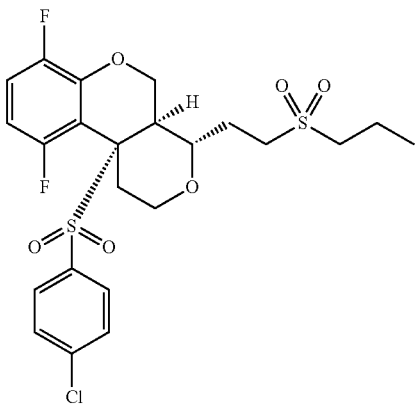 [SMILES: CCCS(=O)(=O)CC[C@@H]1OCC[C@@]2(S(=O)(=O)c3ccc(Cl)cc3)c3c(F)ccc(F)c3OC[C@@H]12]

Compound 22E: $^1$ H NMR (CDCl$_3$ 400 MHz) δ 7.62 (d, J=8.0 Hz, 2 H), 7.52 (d, J=8.4 Hz, 2 H), 7.10 (m, 1 H), 6.44 (m, 1 H), 5.18 (d, J=15 Hz, 1 H), 4.42 (d, J=12 Hz, 1 H), 3.88 (m, 1 H), 3.37 (m, 1 H), 3.18 (m, 2 H), 2.95 (m, 3 H), 2.55 (m, 1 H), 2.42 (m, 1 H), 2.28 (m, 1 H), 2.02 (m, 1 H), 1.88 (m, 2 H), 1.08 (t, J=7.4 Hz, 3 H). MS: Calcd. for $C_{23}H_{26}ClF_2O_6S_2$ (MH$^+$), m/z=535.1; found 535.3. Retention time: 4.53 min.

Compound 22F

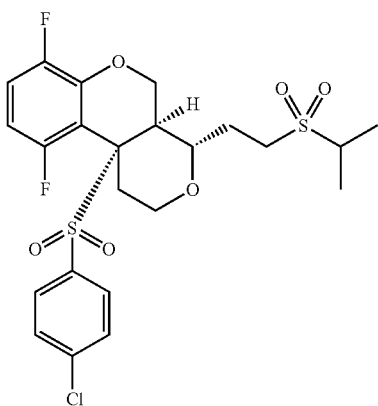 [SMILES: CC(C)S(=O)(=O)CC[C@@H]1OCC[C@@]2(S(=O)(=O)c3ccc(Cl)cc3)c3c(F)ccc(F)c3OC[C@@H]12]

Compound 22F: $^1$ H NMR (CDCl$_3$ 400 MHz) δ 7.64 (d, J=8.8 Hz, 2 H), 7.52 (d, J=8.6 Hz, 2 H), 7.13 (m, 1 H), 6.48 (m, 1 H), 5.17 (d, J=15.3 Hz, 1 H), 4.47 (d, J=8.5 Hz, 1 H), 3.89 (d, J=10.2 Hz, 1 H), 3.36 (m, 1 H), 3.17 (m, 3 H), 2.92 (m, 1 H), 2.56 (d, J=12.6 Hz, 2 H), 2.46 (m, 1 H), 2.29 (m, 1 H), 2.01 (m, 1 H), 1.40 (t, J=8.0 Hz, 6 H). MS: Calcd. for $C_{23}H_{26}ClF_2O_6S_2(MH^+)$, m/z=535.1; found 535.3. Retention time: 4.23 min.

Compound 22L

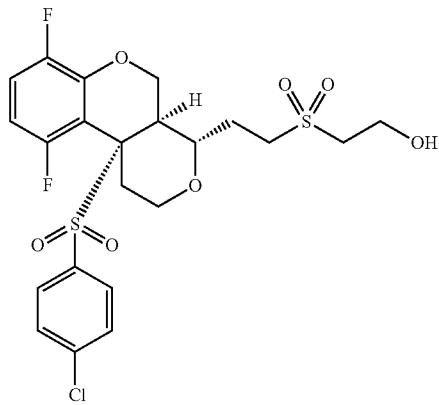 [SMILES: O=S(=O)(CCO)CC[C@@H]1OCC[C@@]2(S(=O)(=O)c3ccc(Cl)cc3)c3c(F)ccc(F)c3OC[C@@H]12]

Compound 22L: MS: Calcd. for $C_{22}H_{24}ClF_2O_7S_2(M+1)^+$, m/z=537.1, found 537.3. Retention time: 3.86 min.

Compound 22M

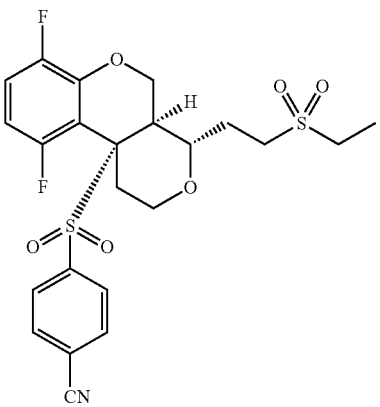

22M

Compound 22M was prepared analogously starting with tosylate 30 (see Scheme 6): MS: Calcd. for $C_{23}H_{24}F_2NO_6S_2$ (M+1)$^+$, m/z=512.1, found 512.3. Retention time: 3.73 min.

Step 16

A mixture of 0.049 g (0.085 mmol) of compound 22D, 0.007 g (0.009 mmol) of bis(dibenzylideneacetone) palladium (Pd$_2$(dba)$_3$), 0.008 g (0.013 mmol) of 1,1'-bis(diphenylphosphino)ferrocene (dppf), 0.010 g (0.085 mmol) of zinc cyanide and 0.002 g (0.03 mmol) of zinc power in 3 mL of N,N-dimethylacetamide in a sealed tube was heated at 150° C. for 1 h in microwave (Biotage). It was diluted with 20 mL of water, and extracted with 20 mL of dichloromethane. The organic extract was concentrated, the residue was purified by preparative TLC eluting with 30% ethyl acetate in hexanes to give 0.006 g of compound 22G. $^1$ H NMR (CDCl$_3$ 400 MHz) δ 7.82 (s, 4 H), 7.12 (m, 1 H), 6.46 (m, 1 H), 5.16 (d, J=10 Hz, 1 H), 4.46 (d, J=12 Hz, 1 H), 3.92 (m, 1 H), 3.80 (m, 3 H), 3.40 (m, 2 H), 3.16 (m, 2 H), 2.63 (m, 1 H), 2.46 (m, 1 H), 2.32 (m, 1 H), 2.08 (m, 1 H). MS: Calcd. for $C_{23}H_{21}F_5NO_6S_2(MH^+)$, m/z=566.1; found 566.3 Retention time: 4.66 min.

Scheme 3:

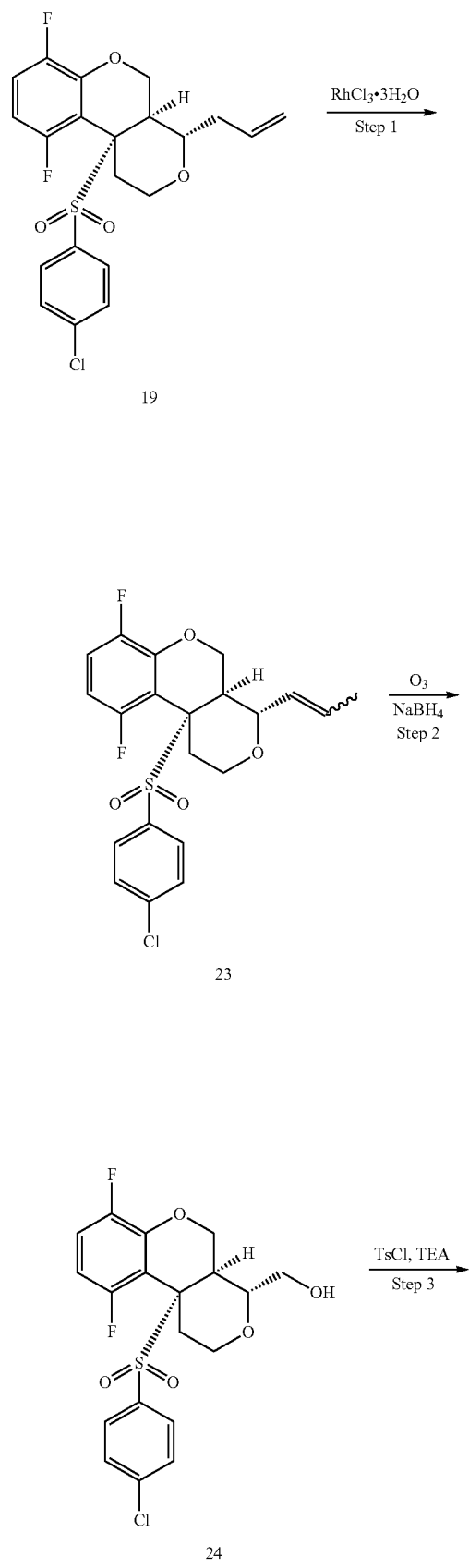

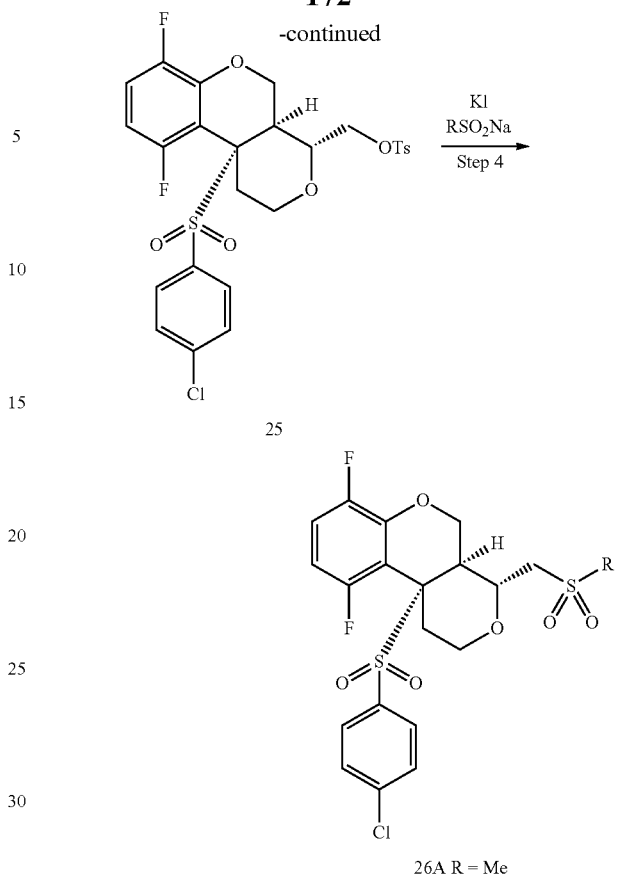

26A R = Me
26B R = CF$_3$

Step 1

A mixture of 2.2 g (5 mmol) of compound 19 and 0.052 (0.25 mmol) of RhCl$_3$.3H$_2$O in 80 mL of ethanol was stirred at reflux for 3 h, then concentrated. The residue was purified by chromatography eluting with 10-40% ethyl acetate in hexanes to give 2.1 g (95%) of olefin 23. MS: Calcd for C$_{21}$H$_{20}$ClF$_2$O$_4$S (M+1)$^+$ m/z=441.1, found 441.2, Rt=4.94 min.

Step 2

The ozonolysis of the olefin and subsequent reduction was accomplished using a procedure analogous to that shown in Step 10 of Scheme 2 to give alcohol 24: MS: Calcd for C$_{19}$H$_{18}$ClF$_2$O$_5$S (M+1)$^+$ m/z=431.1, found 431.2, Rt =3.93 min.

Step 3

The tosylation of the alcohol was accomplished using a procedure analogous to that shown in Step 12 of Scheme 2 to give tosylate 25: MS: Calcd for C$_{26}$H$_{24}$ClF$_2$O$_7$S$_2$ (M+1)$^+$ m/z=585.1, found 585.3, Rt=4.93 min.

Step 4

The displacement of the tosylate was accomplished using a procedure analogous to that shown in Step 13 of Scheme 2 using sodium methylsulfinate to give sulfone 26A (R=Me): MS: Calcd for C$_{20}$H$_{20}$ClF$_2$O$_6$S$_2$ (M+1)$^+$ m/z=493.0, found 493.3, Rt=4.14 min.

The displacement of the tosylate was also accomplished using a procedure analogous to that shown in Step 14 of Scheme 2 using sodium trifluoromethylsulfinate to give sulfone 26B (R=CF$_3$): MS: Calcd for C$_{20}$H$_{17}$ClF$_5$O$_6$S$_2$ (M+1)$^+$ m/z=547.1, found 371.2 (M-ClPhSO$_2$—)$^+$, Rt=4.90 min.

Scheme 4:

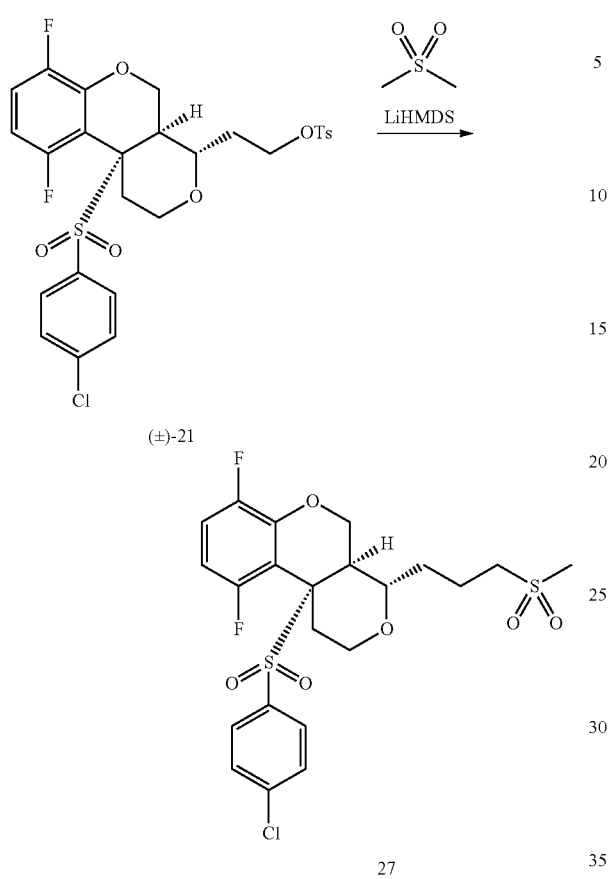

Step 1

To a solution of dimethylsulfone in 20 mL of THF was added LiHMDS in THF (1.0M) at −78° C. After 30 min., a solution of 0.12 g (0.2 mmol) of compound 21 in 5 mL of THF was added. The mixture was warmed to room temperature overnight. It was diluted with 50 mL of 1N HCl, extracted with three 50 mL portions of methylene chloride. the combined organic extracts were concentrated, the residue was purified by preparative TLC eluting with 50% ethyl acetate in hexanes to give 0.032 g of compound 27. MS: Calcd for $C_{22}H_{23}ClF_2O_6S_2$ (M+1)$^+$ m/z=521.1, found 521.3, Rt=4.03 min.

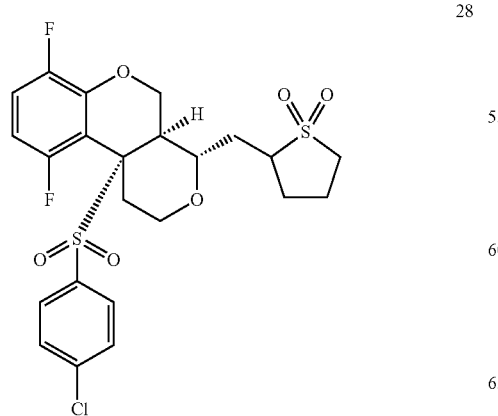

Using a similar procedure as Scheme 4, step 1 starting with compound 25 and sulfolane provided compound 28: MS: Calcd for $C_{23}H_{24}ClF_2O_6S_2$ (M+1)$^+$ m/z=533.1, found 533.3, Rt=4.36 min.

Using a similar procedure as Scheme 4, step 1 starting with compound 30 and sulfolane provided compound 31: MS: Calcd for $C_{24}H_{26}ClF_2O_6S_2$ (M+1)$^+$ M/z=547.1, found 547.3, Rt=4.23 min.

Scheme 5:

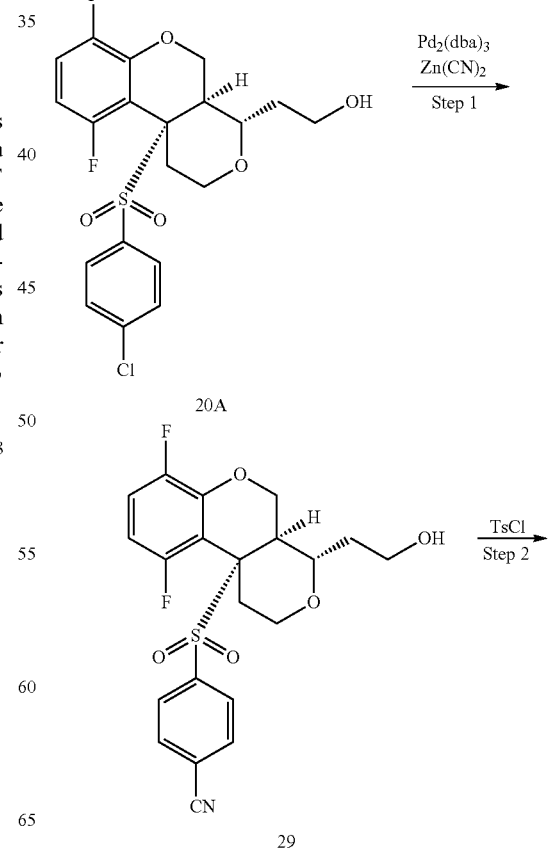

-continued

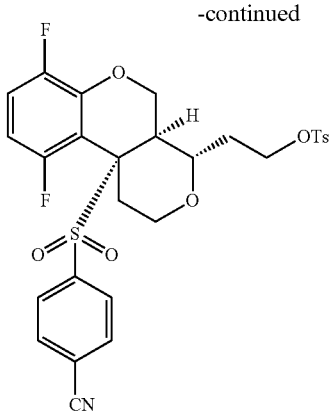

30

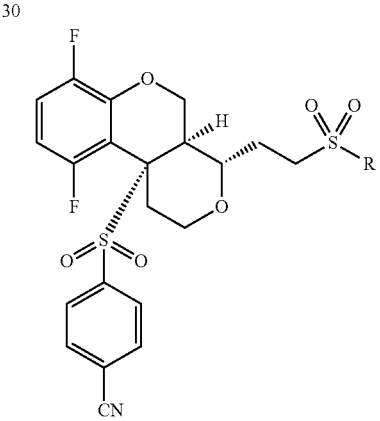

22J R = Me

Step 1

Chlorophenylsulfone 20A was converted to the cyanophenyl analog 29 using an anologous procedure to that used in Scheme 2, Step 16. MS: Calcd for $C_{21}H_{20}F_2NO_5S$ $(M+1)^+$ m/z=436.1, found 436.3, Rt=3.36 min.

Step 2

Alcohol 29 was converted to the tosylate 30 using an anologous procedure to that used in Scheme 2, Step 12. MS: Calcd for $C_{28}H_{26}F_2NO_7S_2$ $(M+1)^+$ m/z=590.1, found 590.3, Rt=4.43 min.

Step 3

Tosylate 30 was converted to the methyl sulfone 22J using an anologous procedure to that used in Scheme 2, Step 13. MS: Calcd for $C_{22}H_{22}ClF_2NO_6S_2$ $(M+1)^+$ m/z=498.1, found 498.3, Rt=3.85 min.

Scheme 6:

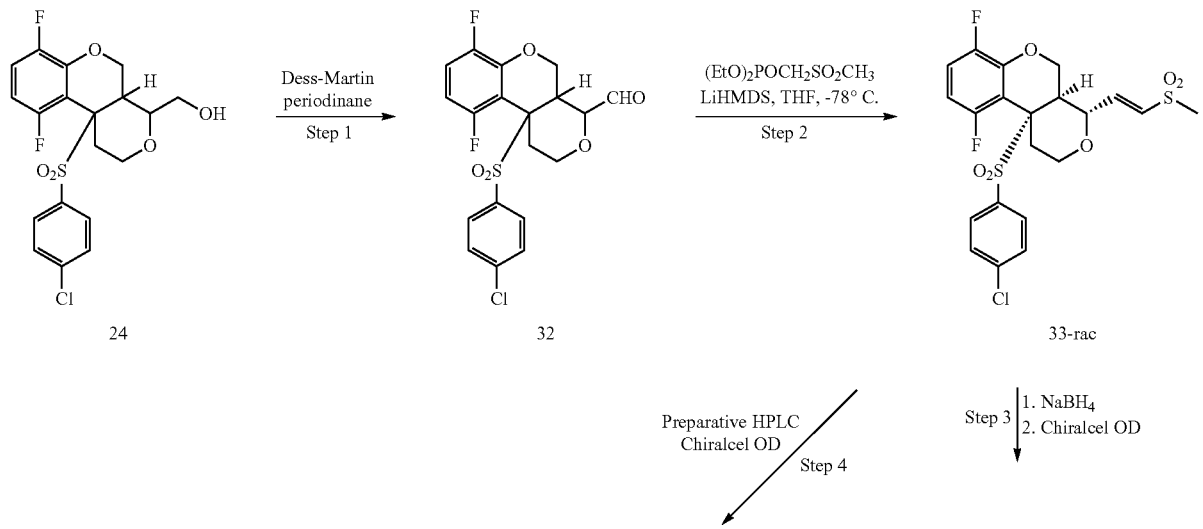

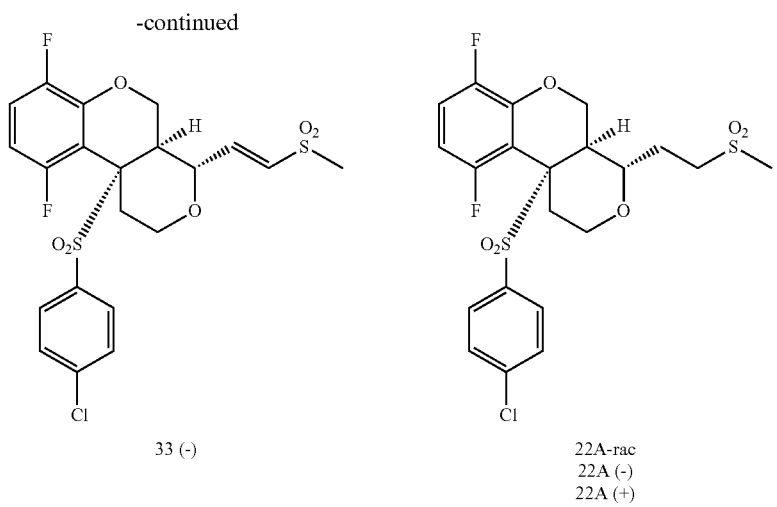

33 (−)

22A-rac
22A (−)
22A (+)

Step 1

The Dess-Martin periodinane (0.895 g, 2.11 mmol) was added in portions to a stirring solution of the hydroxymethyl compound 24 (0.700 g, 1.62 mmol) in dichloromethane (35 mL) at room temperature. The reaction was complete after 2.5 hrs (tlc: 30% EtOAc/hexane). The reaction was diluted with 100 mL of dichloromethane partitioned with 10% sodium thiosulfate/sat. sodium bicarbonate (380 mL portions of a 1:1 mixture). The dichloromethane was dried over anhydrous sodium sulfate and was concentrated in vacuo to yield compound 32 (0.680 g, 97%). MS: Calcd for $C_{19}H_{16}ClF_2O_5S$ $(M+1)^+$ m/z=429.0, found 429, Rt=4.10 min.

Step 2

To a solution of 34.5 g (150 mmol) of diethyl methylsulfonomethyl-phosphonate [ref:G. H. Posner and D. J. Brunelle *J. Org. Chem.* 1972, 37, 3547] in 500 mL of THF was added 145 mL (145 mmol) of LiHMDS in THF at −78° C. After 40 min., a solution of 31.5 g (73.5 mmol) of the aldehyde 32 in 60 mL of THF was added, and the mixture was stirred at −78° C. for 5 h. It was quenched with 200 mL of saturated aqueous $NH_4Cl$ and 500 mL of water, and extracted with four 500 mL portions of ethyl acetate. The combined organic extracts were dried over $Na_2SO_4$, filtered, and concentrated to give crude vinyl sulfone 33-rac. MS: Calcd for $C_{21}H_{20}ClF_2O_6S_2$ (M+1) $^{30}$ m/z=505.0, found 505, Rt=4.20 min.

Step 3

To a solution of the above racemic intermediate 33-rac in 400 mL of THF were added 5.0 g (132 mmol) of $NaBH_4$ and 100 mL of ethanol. The mixture was stirred at room temperature for 4 h. It was quenched with 200 mL of water, and the organic solvents were evaporated. To this residue were added 300 mL of water and 50 mL of 1N HCl. It was then extracted with four 500 mL portions of ethyl acetate. The organic extracts were dried over $NaSO_4$, filtered, and concentrated. The residue was stirred with 300 mL of ethyl acetate and filtered to give 17.1 g of compound 22A-rac. MS: Calcd for $C_{21}H_{22}ClF_2O_6S_2$ $(M+1)^+$ m/z=507.1, found 507.3, Rt=4.23 min.

Racemate 22A-rac could be resolved on a Chiralcel OD column eluting with 75% isopropyl alcohol in hexanes to give 22A (−) (peak 1, retention time =40.2 min, $[\alpha]_D^{20}$ −144.2°, conc =1.000 M in dichloromethane) and 22A (+) (peak 2, retention time=47.4 min, $[\alpha]_D^{20}$ −139.3°, conc=1.000 M in dichloromethane).

Step 4

The enantiomers of the vinyl sulfone were separated by preparative HPLC on a Chiralcel OD column eluting with 60% isopropanol/hexane at 40 mL/min to give 33 (−) (0.139 g). The desired isomer had a retention time of 56.6 min. MS: Calcd for $C_{21}H_{20}ClF_2O_6S_2$ $(M+1)^+$ m/z=505.0, found 505.3, Rt=4.33 min.

Scheme 7:

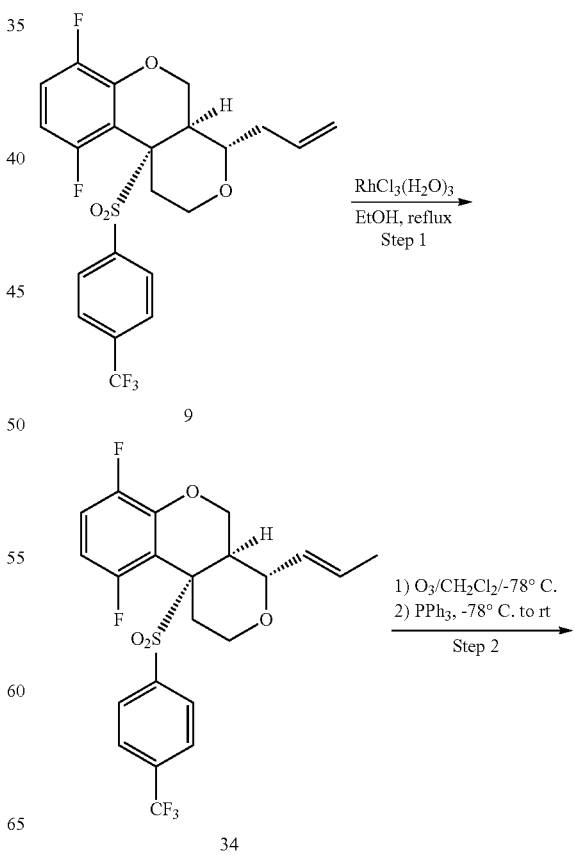

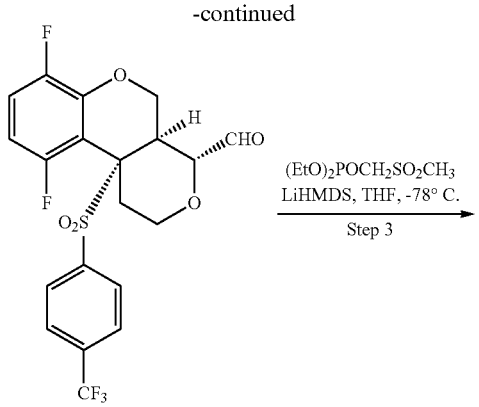

35

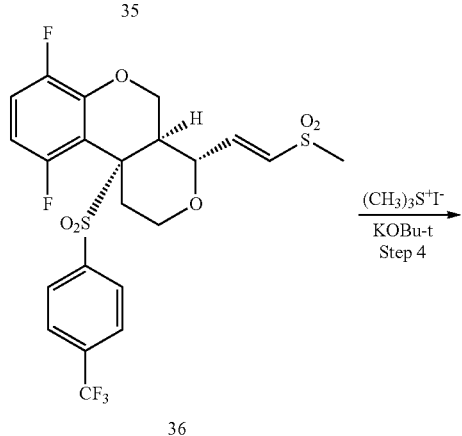

36

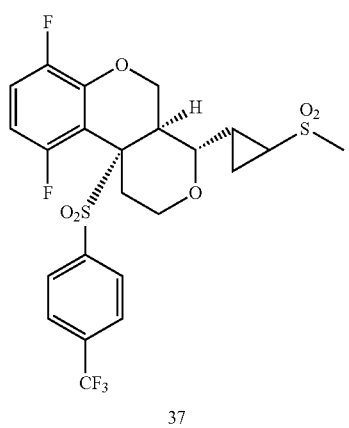 [SMILES: CS(=O)(=O)C1CC1[C@@H]1OCC[C@@]2(S(=O)(=O)c3ccc(C(F)(F)F)cc3)c3c(F)ccc(F)c3OC[C@@H]12]

37

Step 1

The allyl derivative 9 was isomerized using RhCl₃ as per Scheme 3, step 1 to give the olefin 34. Thus, a stirring mixture of the 9 (0.413 g, 0.87 mmol) and rhodium (III) chloride hydrate (0.020 g, 0.096 mmol) in 10 mL of ethanol was heated to reflux for 1 hr (tlc: 20% EtOAc/hexane). The EtOH was evaporated under vacuum to give 0.442 g crude product. This material was purified by flash column chromatography on silica gel, eluting with a solvent gradient from 1% EtOAc/hexane to 40% EtOAc/hexane over 30 min to yield 34 (0.343 g, 85%). MS: Calcd for $C_{22}H_{20}F_5O_4S$ (M+1)⁺ m/z=475.1, found 475.3, Rt=5.05 min.

Step 2

A stirring solution of 34 (0.322 g, 0.678 mmol) in 50 mL of dichloromethane was cooled to −78° C. A stream of O₃ was bubbled through the solution until a blue color of excess O₃ persisted. The mixture was stirred for an additional 5-10 min. A stream of N₂ was bubbled through the solution until it became colorless. Triphenylphosphine (0.268 g, 1.02 mmol) was added in one portion, and the reaction was stirred at −78° C. for 10 min and at room temperature for 16 hrs (tlc: 20% EtOAc/hexane). The solvent was evaporated to give an 0.730 g of an oil. The oil was purified by flash column chromatography on silica gel, eluting with a solvent gradient from 1% EtOAc/hexane to 40% EtOAc/hexane over 20 min to give aldehyde 35 (0.277 g, 88%). MS: Calcd for $C_{20}H_{16}F_5O_5S$ (M+1)⁺ m/z=463.1, found 463.3, Rt=4.05 min.

Step 3

The aldehyde 35 was converted to the vinyl sulfone 36 using an analogous procedure as that described in Scheme 6, step 2 (74% yield). MS: Calcd for $C_{22}H_{20}F_5O_6S_2$ (M+1)⁺ m/z=539.1, found 539.3, Rt=4.36 min.

Step 4

To a stirring mixture of the KOtBu (0.014 g, 0.121 mmol) in 1.5 mL of DMSO was added the trimethyl sulfonium iodide (0.027 g, 0.121 mmol). The solution was stirred at room temperature under argon for 1 hr. A solution of the 36 (0.050 g, 0.093 mmol) in 0.75 mL of DMSO was added dropwise. Stirring was continued overnight at room temperature (tlc: 40% EtOAc/hexane). The reaction was added to stirring water (40-50 mL) and was extracted with 2 40-mL portions of EtOAc. The combined EtOAc layers were washed with 20 mL of water and 20 mL of brine. The EtOAc layer was dried over anhydrous sodium sulfate and evaporated to give 0.050 g of the desired product. The product was purified by flash column chromatography on silica gel, eluting with a solvent gradient from 10% EtOAc/hexane to 80% EtOAc/hexane over 30 min to give 0.037 g of cyclopropylsulfone 37 (73%). MS: Calcd for $C_{23}H_{22}F_5O_6S_2$ (M+1)⁺ m/z=553.1, found 553.3, Rt=4.28 min Scheme 8:

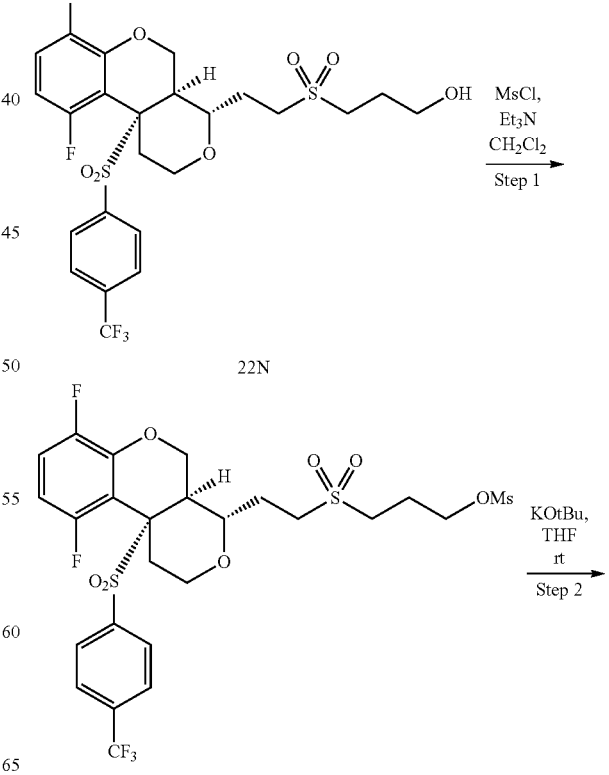

38

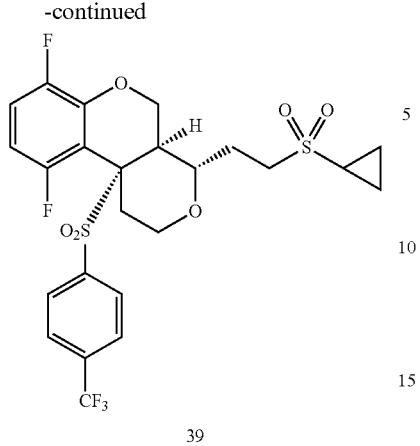

39

Step 1

Triethylamine (0.012 g, 0.123 mmol) was added to a stirring solution of the 22N (0.048 g, 0.082 mmol) and MsCl (0.014 g, 0.123 mmol) in 1 mL of dichloromethane at room temperature. After 1 hr the reaction was complete (tlc: 50%EtOAc/hexane). The reaction was diluted with 15 mL of dichloromethane and was washed with sat sodium bicarbonate (10 mL), water (10 mL) and brine (10 mL). The dichloromethane layer was dried with anhydrous sodium sulfate and evaporated to give 38 (0.048 g, 90%). This material was used directly in the next reaction.

Step 2

1M KOtBu in THF (0.054 mLs, 0.054 mmol) was added dropwise to a stirring solution of the 38 (0.024 g, 0.036 mmol) in 50 mL of THF at room temperature. The reaction was complete after 30 min (tlc: 30% EtOAc/hexane). The reaction was quenched with the dropwise addition of water (1 mL). The mixture was diluted with dichloromethane (20 mL) and partitioned with water (10 mL). The dichloromethane layer was dried over anhydrous sodium sulfate and evaporated to 0.020 g of the desired cyclopropyl compound. Purification by preparative tlc on silica gel (50% EtOAc/hexane) gave 0.018 g of desired compound 39 (85%). MS: Calcd for $C_{24}H_{24}F_5O_6S_2$ $(M+1)^+$ m/z=567.1, found 567.3, Rt=4.60 min Scheme 9:

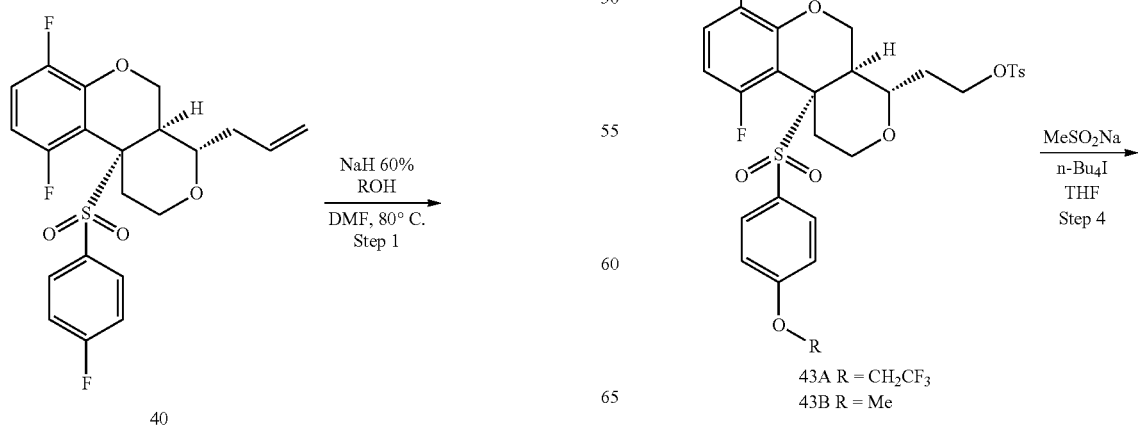

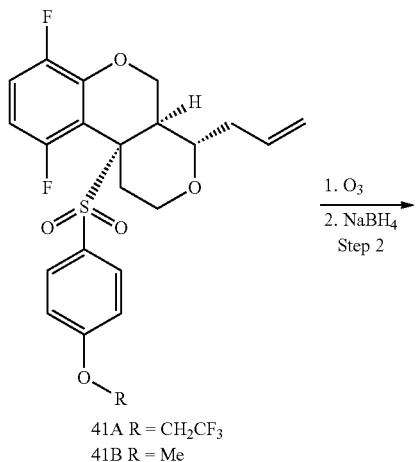

41A R = CH$_2$CF$_3$
41B R = Me

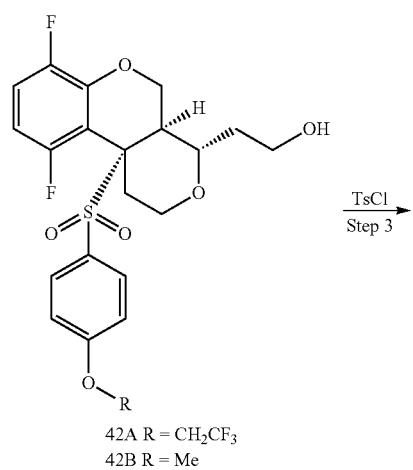

42A R = CH$_2$CF$_3$
42B R = Me

43A R = CH$_2$CF$_3$
43B R = Me

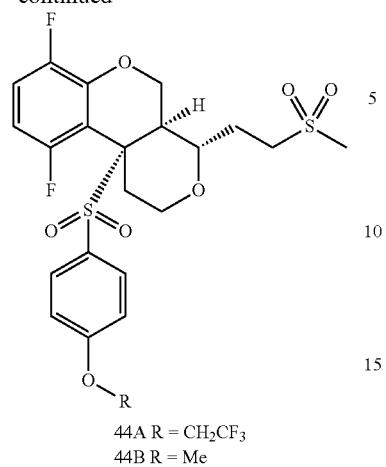

44A R = CH₂CF₃
44B R = Me

Step 1

A solution of trifluoroethanol (34 μL, 0.47 mmol) in 3 mL of DMF was treated with 60% NaH (5.0 mg, 0.23 mmol) and stirred for 20 min. 4-Allyl-7,10-difluoro-10-b-(4 fluoro-benzene sulfonyl)-1,4a,5,10b-tetrahydro-2H,4H-pyran[3,4-c] chromene 40 (100 mg, 0.23 mmol, prepared analogously to compound 19 from Scheme 2 using 4-fluorophenylsulfide in Step 2) 2 mL of DMF was added and the reaction was heated at 80° C. for 18 h. The reaction mixture was diluted with saturated aqueous NH₄Cl and extracted with dichloromethane (3×). The combined organic extracts were washed with H₂O, dried over MgSO₄, and concentrated in vacuo. The residue was purified by flash chromatography eluting with 15% EtOAc/hexanes to afford the desired compound 41A (80%) [1] H NMR (CDCl₃ 400 MHz) δ 7.67 (d, J=8.7 Hz, 2 H), 7.13-6.98 (m, 3 H), 6.44 (m, 1 H), 5.86 (m, 1 H), 5.21-5.03 (m, 3 H), 4.51-4.38 (m, 3 H), 3.91 (m, 1 H), 3.36 (m, 1 H), 3.15 (t, J=11.7 Hz, 1 H), 2.66-2.47 (m, 3 H), 2.45-2.24 (m, 2 H).

The following compound (41B) was prepared analogously using methanol as the alcohol:

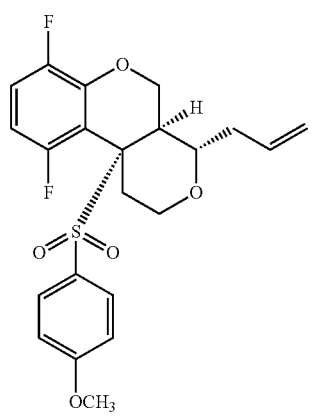

41B

[1] H NMR (CDCl₃ 400 MHz) δ 7.60(d, J=8.7 Hz, 2 H), 7.06 (m, 1 H), 6.97 (d, J=8.05 Hz, 2 H), 6.44 (m, 1 H), 5.85 (m, 1 H), 5.20-5.08 (m, 3 H), 4.42 (d, J=12.4 Hz, 1 H), 3.88 (s, 4 H), 3.35 (m, 1 H), 3.15 (t, J=11.7 Hz, 1 H), 2.66-2.50 (m, 3 H), 2.39 (m, 1 H), 2.27 (m, 1 H).

Step 2

Alcohol 42A was prepared analogously to Scheme 1, Step 10:

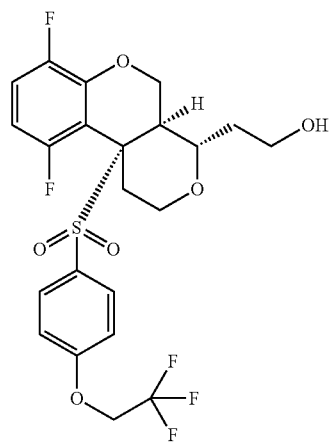

42A

[1] H NMR (CDCl₃ 400 MHz) δ 7.67 (d, J=8.7 Hz, 2 H), 7.16-6.98 (m, 3 H), 6.44 (m, 1 H), 5.86 (d, J=12.44 Hz, 1 H), 4.50-4.36 (m, 3 H), 3.91 (m, 1 H), 3.81-3.74 (m, 2 H), 3.49 (m, 1 H), 3.19 (t, J=11.7 Hz, 1 H), 2.65-2.49 (m, 3 H), 2.37-2.23 (m, 1H), 2.11 (m, 1 H), 1.78 (m, 1 H).

Analogously, alcohol 42B was prepared analogously to Scheme 1, Step 10:

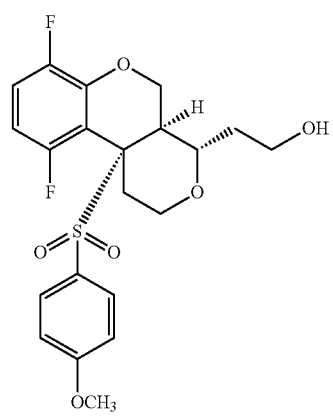

42B

[1] H NMR (CDCl₃ 400 MHz) δ 7.60(d, J=8.7 Hz, 2 H), 7.06 (m, 1 H), 6.97 (d, J=8.05 Hz, 2 H), 6.44 (m, 1 H), 5.17 (d, J=12.4 Hz, 1 H), 4.40 (d, J=12.4 Hz, 1 H), 3.88 (s, 4 H), 3.81-3.73 (m, 2 H), 3.49 (m, 1 H), 3.19 (t, J=11.7 Hz, 1 H), 2.58 (d, J=12.4 Hz, 2 H), 2.37-2.24 (m, 2 H), 2.10 (m, 1 H), 1.81 (m, 1 H).

Step 3

Tosylate 43A was prepared analogously to the method described in Scheme 1, Step 12.

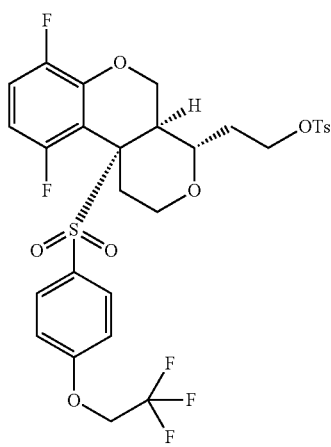

43A

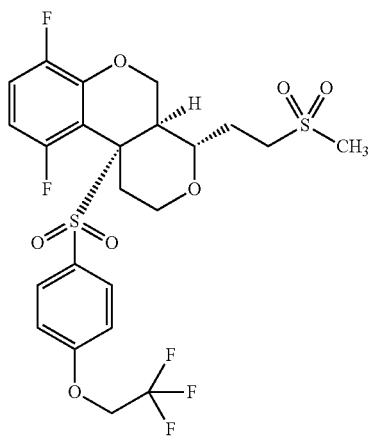

44A

¹H NMR (CDCl₃ 400 MHz) δ 7.72 (d, J=8.7 Hz, 2 H), 7.64 (d, J=8.7 Hz, 2 H), 7.29 (d, J=8.05 Hz, 2 H), 7.15-7.06 (m, 1 H), 7.03 (d, J=9.5 Hz, 2 H), 6.45 (m, 1 H), 5.10 (d, J=10.2 Hz, 1 H), 4.50-4.38 (m, 2 H), 4.27 (d, J=13.2 Hz, 1 H), 4.22-4.07 (m, 2 H), 3.75 (m, 1 H), 3.23 (m, 1 H), 2.97 (t, J=12.4 Hz, 1 H), 2.54-2.43 (m, 2 H), 2.42 (s, 3 H), 2.26-2.10 (m, 2 H), 1.78 (m, 1 H).

Compound 43B was prepared analogously to the method described in Scheme 1, Step 12.

Step 4

Sulfone 44A was prepared analogously to the method described in Scheme 1, Step 13.

¹H NMR (CDCl₃ 400 MHz) δ 7.64 (d, J=8.7 Hz, 2 H), 7.08 (m, 1 H), 7.04 (d, J=9.5 Hz, 2 H), 6.45 (m, 1 H), 5.19 (d, J=10.25 Hz, 1 H), 4.49-4.38 (m, 3 H), 3.89 (m, 1 H), 3.38-3.21 (m, 2 H), 3.19 (t, J=11.7 Hz, 1 H), 3.00 (m, 1 H), 2.90 (s, 3H), 2.62-2.50 (m, 2 H), 2.43 (m, 1 H), 2.28 (m, 1 H), 2.02 (m, 1 H). MS: Calcd. for $C_{23}H_{23}F_5O_7S_2$ (M+1)⁺, m/z=571.3; found 571.3. Retention time 4.26 min.

Sulfone 44B was also prepared analogously to the method described in Scheme 1, Step 13.

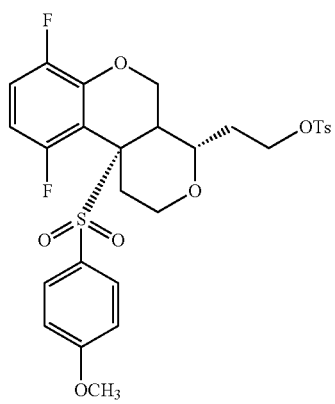

43B

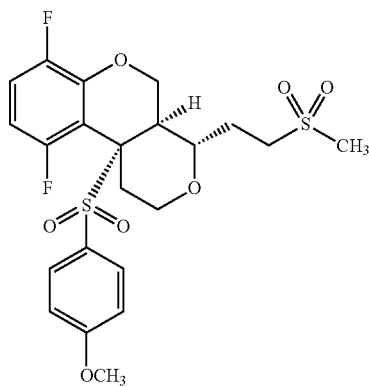

44B

¹H NMR (CDCl₃ 400 MHz) δ 7.72 (d, J=8.7 Hz, 2 H), 7.64 (d, J=8.7 Hz, 2 H), 7.29 (d, J=8.05 Hz, 2 H), 7.15-7.06 (m, 1 H), 7.03 (d, J=9.5 Hz, 2 H), 6.45 (m, 1 H), 5.10 (d, J=9.50 Hz, 1 H), 4.25 (d, J=13.2 Hz, 1 H), 4.21-4.07 (m, 3 H), 3.88 (s, 3 H), 3.74 (m, 1 H), 3.22 (m, 1 H), 2.94 (t, J=12.4 Hz, 1 H), 2.53 (d, J=13.9 Hz, 1 H), 2.47-2.37 (m, 2 H), 2.26-2.09 (m, 2 H), 1.78 (m, 1 H).

¹H NMR (CDCl₃ 400 MHz) δ 7.61 (d, J=8.7 Hz, 2 H), 7.08 (m, 1 H), 6.98 (d, J=8.7 Hz, 2 H), 6.46 (m, 1 H), 5.20 (d, J=10.25 Hz, 1 H), 4.41 (d, J=12.4 Hz, 1 H), 3.90 (s, 4 H), 3.47 (m, 1 H), 3.37-3.22 (m, 2 H), 3.14 (t, J=11.7 Hz, 1 H), 2.99 (m, 1H), 2.89(s, 3 H), 2.60 (m, 1 H), 2.49 (m, 1 H), 2.27 (m, 1 H), 2.01(m, 1 H). MS: Calcd. for $C_{22}H_{24}F_2O_7S_2$ (M+1)⁺, m/z=503.3; found 503.3. Retention time 3.92 min.

Scheme 10:

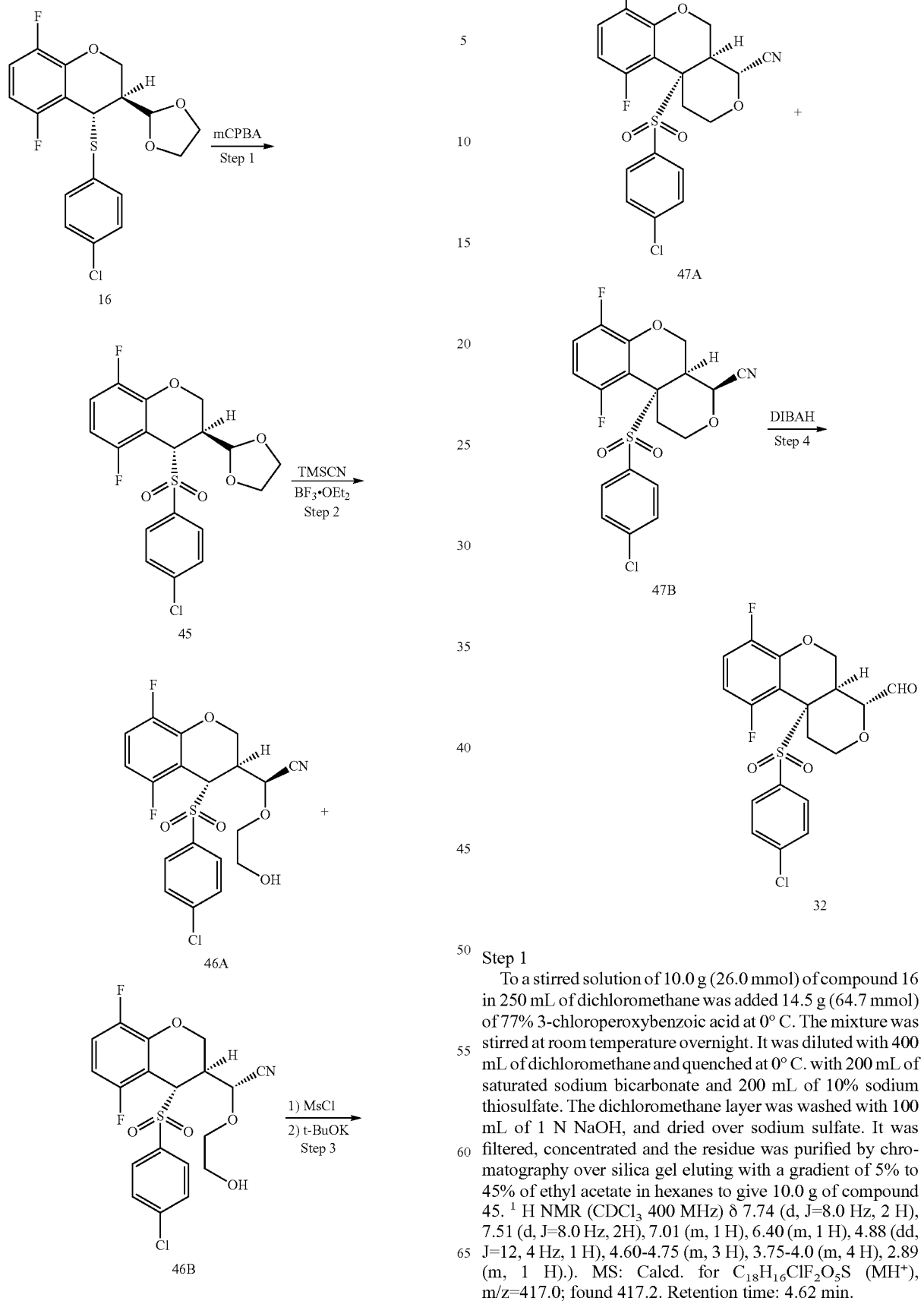

Step 1

To a stirred solution of 10.0 g (26.0 mmol) of compound 16 in 250 mL of dichloromethane was added 14.5 g (64.7 mmol) of 77% 3-chloroperoxybenzoic acid at 0° C. The mixture was stirred at room temperature overnight. It was diluted with 400 mL of dichloromethane and quenched at 0° C. with 200 mL of saturated sodium bicarbonate and 200 mL of 10% sodium thiosulfate. The dichloromethane layer was washed with 100 mL of 1 N NaOH, and dried over sodium sulfate. It was filtered, concentrated and the residue was purified by chromatography over silica gel eluting with a gradient of 5% to 45% of ethyl acetate in hexanes to give 10.0 g of compound 45. $^1$H NMR (CDCl$_3$ 400 MHz) δ 7.74 (d, J=8.0 Hz, 2 H), 7.51 (d, J=8.0 Hz, 2H), 7.01 (m, 1 H), 6.40 (m, 1 H), 4.88 (dd, J=12, 4 Hz, 1 H), 4.60-4.75 (m, 3 H), 3.75-4.0 (m, 4 H), 2.89 (m, 1 H).). MS: Calcd. for C$_{18}$H$_{16}$ClF$_2$O$_5$S (MH$^+$), m/z=417.0; found 417.2. Retention time: 4.62 min.

Step 2

To a solution of 3.99 g (9.58 mmol) of compound 45 in 60 mL of dichloromethane at 0° C. were added 2.40 mL (17.95 mmol) of trimethylsilyl cyanide followed by 1.60 mL (12.5 mmol) of boron trifluoride etherate and the reaction was allowed to warm to room temperature and stirred 90 min. The final mixture was quenched with water, and extracted with three 50 mL portions of dichloromethane. The combined organic extracts were dried over sodium sulfate and concentrated and the residue was purified by chromatography over silica gel eluting with a gradient of 20% to 100% of ethyl acetate in hexanes to provide 3.80 g of 46A and 46B as a ~1:1 mixture. These compounds were used directly in the next reaction. MS: Calcd. for $C_{19}H_{17}ClF_2NO_5S$ (MH+), m/z=444.0; found 444.2. Retention time: 3.93 min.

Step 3

To a solution of 3.80 g (8.56 mmol) of ~1:1 mixture of compounds 46A and 46B in 20 mL of dichloromethane at 0° C. was added 0.76 mL (9.84 mmol) of methane sulfonyl chloride followed by 1.40 mL (10.0 mmol) of triethyl amine and the reaction was allowed to warm to room temperature overnight. The final mixture was concentrated and the residue was purified by chromatography over silica gel eluting with a gradient of 1% to 100% of ethyl acetate in hexanes to provide 4.14 g of methane sulfonyl intermediate as a ~1:1 mixture. A solution of 2.45 g (4.70 mmol) of this methane sulfonyl intermediate in 50 mL of tetrahydrofuran at 0° C. was treated with 5.0 mL (5.0 mmol) of a 1 N solution of potassium tert-butoxide in tetrahydrofuran. The mixture was slowly allowed to warm to room temperature and stirred at this temperature for 2.5 h then quenched with 100 mL of water and extracted with three 50 mL portions of dichloromethane. The combined organic extracts were dried over sodium sulfate and concentrated and the residue was purified by chromatography over silica gel eluting with a gradient of 0% to 15% of ethyl acetate in dichloromethane to give 1.62 g of compound 47A and 0.30 g of compound 47B. 47A: [1] H NMR (CDCl$_3$ 400 MHz) δ 7.63 (d, J=8 Hz, 2 H), 7.53 (d, J=8 Hz, 2 H), 7.15 (m, 1 H), 6.51 (m, 1H), 5.25 (dd, J=13, 3 Hz, 1 H), 4.60 (d, J=12 Hz, 1 H), 4.15 (d, J=11 Hz, 1 H), 4.00 (m, 1 H), 3.21 (t, J=12 Hz, 1 H), 3.04 (br d, J=12 Hz, 1 H), 2.58 (d, J=14 Hz, 1 H), 2.38 (m, 1 H), MS: Calcd. for $C_{19}H_{15}ClF_2NO_4S$ (MH+), m/z=426.0; found 426.2. Retention time: 4.61 min. 47B: [1] H NMR (CDCl$_3$ 400 MHz) δ 7.55 (d, J=8 Hz, 2 H), 7.50 (d, J=8 Hz, 2 H), 7.15 (m, 1 H), 6.46 (m, 1 H), 5.22 (dd, J=12, 4 Hz, 1 H), 4.93 (d, J=6 Hz, 1 H), 4.35 (d, J=13 Hz, 1 H), 3.95 (m, 1 H), 3.61 (t, J=12 Hz, 1H), 3.20 (t, J=5 Hz, 1 H), 2.63 (d, J=14 Hz, 1 H), 2.44 (m, 1 H), MS: Calcd. for $C_{19}H_{15}ClF_2NO_4S$ (MH+), m/z=426.0; found 426.2. Retention time: 4.43

Step 4

To a solution of 0.75 g (1.76 mmol) of compound 47A in 15 mL of dichloromethane at −78° C. was added 1.85 mL (1.85 mmol) of a 1 N solution of diisobutyl aluminum hydride in hexanes and the reaction was stirred 2 h at this temperature, then allowed to warm to room temperature over 1 h. The mixture was quenched with 0.3 mL of methanol then poured into 1 N hydrochloric acid and stirred 25 min. The mixture was then extracted with dichloromethane. The combined organic extracts were dried over sodium sulfate and concentrated to give 0.63 g of aldehyde 32. [1] H NMR (CDCl$_3$ 400 MHz) δ 9.62 (s, 1 H), 7.63 (d, J=8 Hz, 2 H), 7.51 (d, J=8 Hz, 2 H), 7.11 (m, 1 H), 6.47 (m, 1 H), 5.07 (dd, J=13, 2 Hz, 1 H), 4.67 (d, J=12 Hz, 1 H), 4.02 (m, 1 H), 3.71 (d, J=11 Hz, 1 H), 3.25 (t, J=12 Hz, 1 H), 2.87 (d, J=11 Hz, 1 H), 2.61 (d, J=13 Hz, 1 H), 2.33 (m, 1 H). MS: Calcd. for $C_{19}H_{16}ClF_2O_5S$ (MH+), m/z=429.0; found 429.2. Retention time: 3.95 min.

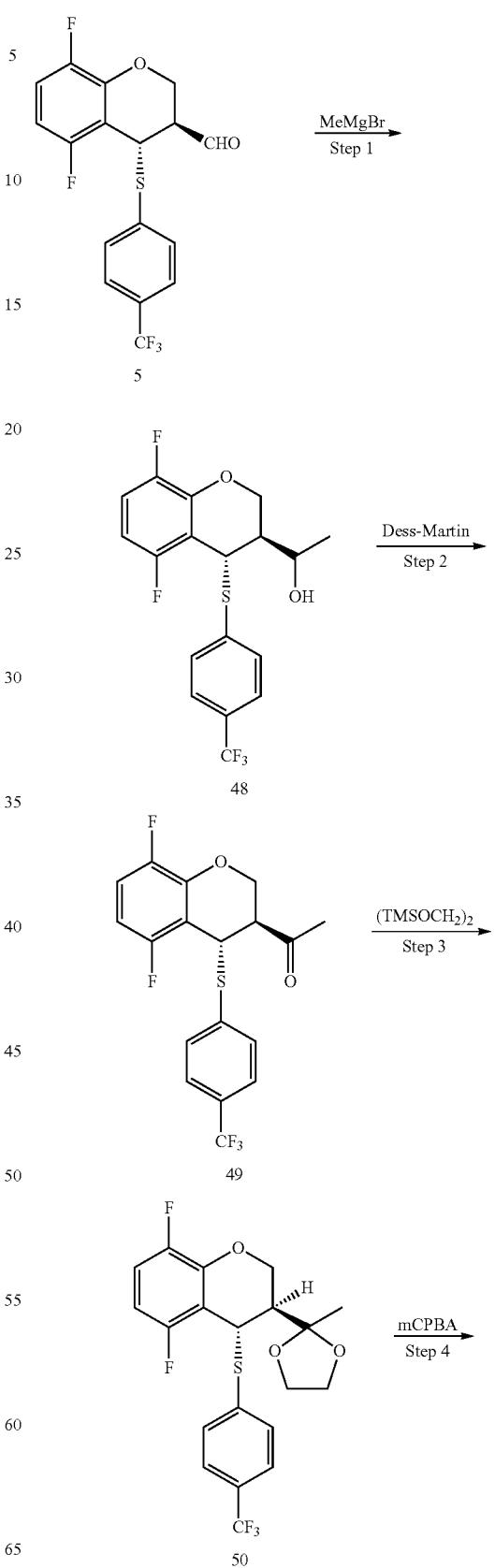

Scheme 11:

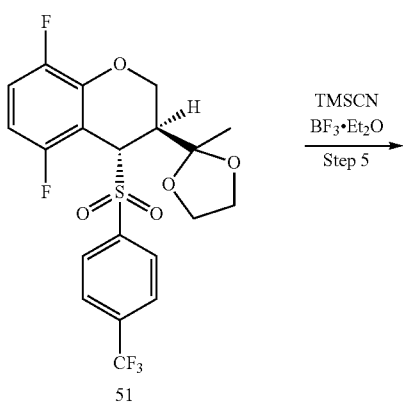
51
TMSCN
BF₃·Et₂O
Step 5
→
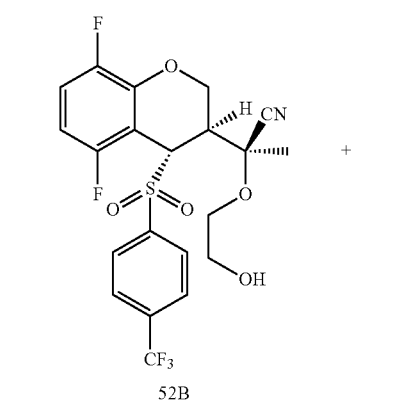
52B
+
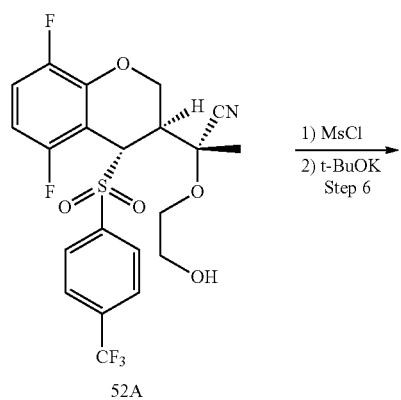
52A
1) MsCl
2) t-BuOK
Step 6
→
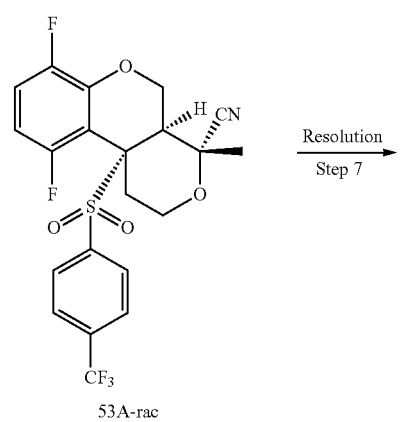
53A-rac
Resolution
Step 7
→
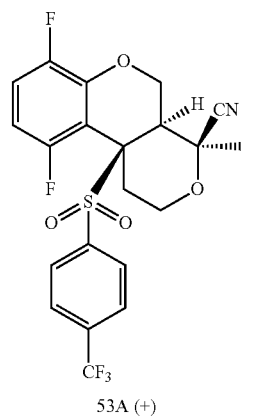
53A (+)
+
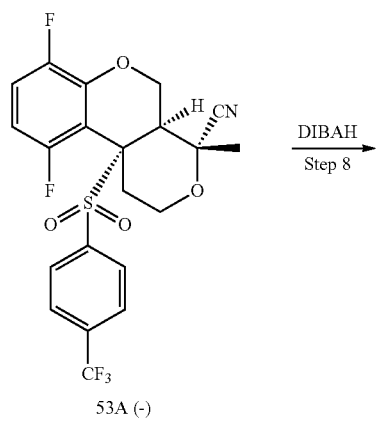
53A (−)
DIBAH
Step 8
→
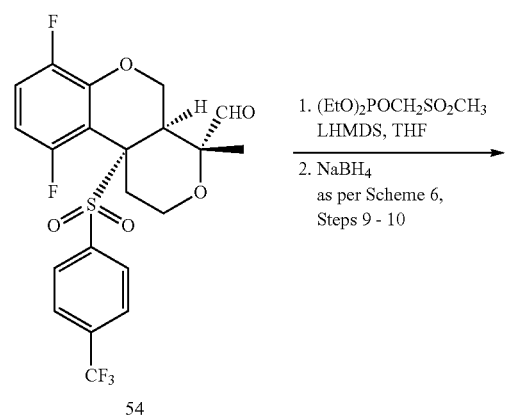
54
1. (EtO)₂POCH₂SO₂CH₃
   LHMDS, THF
2. NaBH₄
   as per Scheme 6,
   Steps 9 - 10
→
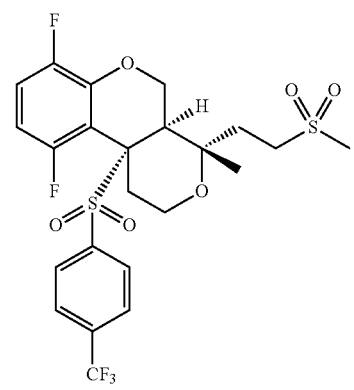
55

Step 1

To a suspension of 29.6 g (120 mmol) of cerium (III) chloride in 120 mL of tetrahydrofuran at 0° C. for 90 min was added 40 mL (120 mmol) of methylmagnesium bromide 3 N in diethylether and the reaction was stirred 1 h at 0° C. A solution of 15.0 g (40.1 mmol) of compound 5 in 60 mL of tetrahydrofuran was added and the reaction was stirred 1 h at 10° C. The final mixture was poured into saturated ammonium chloride, extracted with ethyl acetate, dried over sodium sulfate and concentrated. The residue was purified by chromatography over silica gel eluting with a gradient of 1% to 40% of ethyl acetate in hexanes to give 12.1 g of compound 48. $^1$H NMR (CDCl$_3$ 400 MHz) δ 7.59 (m, 4 H), 6.98 (m, 1 H), 6.61 (m, 1 H), 5.15 (s, 1 H), 4.35-4.75 (m, 2 H), 3.74 (m, 1 H), 1.95 (m, 1 H), 1.36 and 1.16 (t, J=7 Hz, 3 H), MS: Calcd. for C$_{18}$H$_{15}$F$_5$O$_2$S (MH$^+$), m/z=391.1; found 391.2. Retention time: 4.98 min.

Step 2

To a stirred solution of 12.1 g (30.9 mmol) of compound 48 in 150 mL of dichloromethane was added 15.7 g (37.0 mmol) of Dess-Martin periodinane. The mixture was stirred at room temperature for 1 h then filtered. The filtrate was concentrated and purified by chromatography over silica gel eluting with a gradient of 1% to 40% of ethyl acetate in hexanes to give 9.96 g of compound 49. $^1$H NMR (CDCl$_3$ 400 MHz) δ 7.59 (d, J=8 Hz, 2 H), 7.54 (d, J=8 Hz, 2 H), 6.98 (m, 1H), 6.62 (m, 1 H), 5.12 (s, 1 H), 4.86 (d, J=12 Hz, 1 H), 4.75 (d, J=12 Hz, 1 H), 2.89 (s, 1 H), 2.28 (s, 3 H), MS: Calcd. for C$_{18}$H$_{14}$F$_5$O$_2$S (MH$^+$), m/z=389.1; found 389.2. Retention time: 5.14 min.

Step 3

To a solution of 6.98 g (18.0 mmol) of compound 49 in 60 mL of dichloromethane were added 7.90 mL (32.5 mmol) of 1,2-bis(trimethylsiloxy)ethane and 0.25 mL (1.50 mmol) of trimethylsilyl trifluoromethanesulfonate at −78° C. After 30 min, the solution was warmed to room temperature and stirred for 48 h. The reaction was quenched with saturated sodium bicarbonate and extracted with dichloromethane. The combined organic extracts were dried over sodium sulfate and concentrated, and the residue was purified by chromatography over silica gel eluting with a gradient of 1% to 100% of dichloromethane in hexanes to give 7.37 g of compound 50. $^1$H NMR (CDCl$_3$ 400 MHz) δ 7.60 (m, 4 H), 6.98 (m, 1 H), 6.58 (m, 1H), 4.86 (s, 1 H), 4.60 (m, 2 H), 3.80-3.95 (m, 3 H), 3.59 (m, 1 H), 2.17 (s, 1H), 1.20 (s, 3 H), MS: Calcd. for C$_{20}$H$_{18}$F$_5$O$_3$S (MH$^+$), m/z=433.1; found 433.3. Retention time: 5.48 min.

Step 4

To a solution of 8.92 g (20.6 mmol) of compound 50 in 130 mL of dichloromethane was added 13.4 g (60.0 mmol) of 77% 3-chloroperoxybenzoic acid at 0° C. The mixture was stirred at room temperature overnight then filtered, concentrated and the residue was purified by chromatography over silica gel eluting with a gradient of 1% to 100% of dichloromethane in hexanes to give 9.13 g of compound 51. $^1$H NMR (CDCl$_3$ 400 MHz) δ 7.95 (d, J=8.0 Hz, 2 H), 7.80 (d, J=8.0 Hz, 2 H), 7.01 (m, 1 H), 6.38 (m, 1 H), 4.81 (dd, J=12, 5 Hz, 1 H), 4.74 (s, 1 H), 4.66 (d, J=12 Hz, 1 H), 2.93 (d, J=4 Hz, 1 H), 1.13 (s, 3 H), MS: Calcd. for C$_{20}$H$_{18}$F$_5$O$_5$S (MH$^+$), m/z=465.1; found 465.3. Retention time: 4.74 min.

Step 5

To a solution of 9.13 g (19.6 mmol) of compound 51 in 100 mL of dichloromethane at 0° C. was added 4.10 mL of trimethylsilyl cyanide (30.8 mmol) followed by 2.55 mL (20.3 mmol) of boron trifluoride etherate dropwise and the reaction was allowed to warm to room temperature and stirred 2 h. The mixture was quenched with water and extracted with dichloromethane. The combined organic extracts were dried over sodium sulfate and concentrated and the residue was purified by chromatography over silica gel eluting with a gradient of 1% to 50% of ethyl acetate in hexanes to provide 4.27 g of compound 52A and 3.50 g of compound 52B. 52A: $^1$H NMR (CDCl$_3$ 400 MHz) δ 7.96 (d, J=8 Hz, 2 H), 7.82 (d, J=8 Hz, 2H), 7.05 (m, 1 H), 6.42 (m, 1 H), 4.93 (dd, J=13, 4 Hz, 1 H), 4.82 (s, 1 H), 4.74 (d, J=13 Hz, 1 H), 3.71 (m, 2 H), 3.65 (m, 2 H), 3.37 (m, 1 H), 1.56 (m, 1 H), 1.42 (s, 3 H), MS: Calcd. for C$_{21}$H$_{19}$F$_5$NO$_5$S (MH$^+$), m/z=492.1; found 492.3. Retention time: 4.23 min. 52B: $^1$H NMR (CDCl$_3$ 400 MHz) δ 7.95 (d, J=8 Hz, 2 H), 7.82 (d, J=8 Hz, 2H), 7.07 (m, 1 H), 6.46 (m, 1 H), 4.86 (dd, J=13, 5 Hz, 1 H), 4.82 (s, 1 H), 4.67 (d, J=13 Hz, 1 H), 3.68 (m, 4 H), 3.22 (m, 1 H), 1.64 (br s, 1 H), 1.56 (s, 3 H), MS: Calcd. for C$_{21}$H$_{19}$F$_5$NO$_5$S (MH$^+$), m/z=492.1; found 492.3. Retention time: 4.22 min.

Step 6

To a solution of 4.27 g (8.69 mmol) of compound 52A in 40 mL of dichloromethane were added 1.40 mL (10.0 mmol) of triethylamine and 0.78 mL (10.0 mmol) of methanesulfonyl chloride. The mixture was stirred at room temperature overnight then concentrated and the residue was purified by chromatography over silica gel eluting with a gradient of 1% to 50% of ethyl acetate in hexanes to provide 4.91 g of methanesulfonyl intermediate. A solution of 4.91 g (8.73 mmol) of this methane sulfonyl intermediate in 70 mL of tetrahydrofuran at 0° C. was treated with 10.5 mL (10.5 mmol) of a solution of potassium tert-butoxide 1 N in tetrahydrofuran. The mixture was slowly allowed to warm to room temperature and stirred at this temperature for 30 min then quenched with 100 mL of water and extracted with two 150 mL portions of dichloromethane. The combined organic extracts were dried over sodium sulfate and concentrated and the residue was purified by chromatography over silica gel eluting with a gradient of 1% to 50% of ethyl acetate in hexanes to provide 1.77 g of compound 53A-rac and 0.42 g of recovered methanesulfonyl intermediate. 53A-rac: $^1$H NMR (CDCl$_3$ 400 MHz) δ 7.80 (m, 4 H), 7.13 (m, 1 H), 6.44 (m, 1 H), 5.20 (dd, J=13, 4 Hz, 1 H), 4.64 (d, J=13 Hz, 1 H), 3.95 (m, 1 H), 3.44 (m, 1 H), 3.36 (d, J=4 Hz, 1 H), 2.60 (m, 2 H), 1.52 (s, 3 H), MS: Calcd. for C$_{21}$H$_{17}$F$_5$NO$_4$S (MH$^+$), m/z=474.1; found 474.3. Retention time: 4.78 min.

Step 7

Compound 53A-rac (1.7 g) was resolved on Chiral OD column eluting with 60% isopropanol in hexanes and 35 mL/min flow rate to give two enantiomers 53A (−)(0.82 g, [α]$_D^{20}$ −94.4°) and 53A (+) (0.88 g, [α]$_D^{20}$ +90.3°).

Step 8

To a solution of 200 mg (0.42 mmol) of compound 53A (−) in 8 mL of dichloromethane at −78° C. was added 0.89 mL (0.89 mmol) of a 1 N solution of diisobutyl aluminum hydride in hexanes and the reaction was stirred 1 h at this temperature. The mixture was quenched with 0.2 mL of methanol then diluted with dichloromethane and brine. Celite was added and the slurry was stirred at room temperature for 15 min. The mixture was filtered over Celite then extracted with dichloromethane. The combined organic extracts were dried over sodium sulfate and concentrated and the residue was purified by chromatography over silica gel eluting with a gradient of 1% to 50% of ethyl acetate in hexanes to provide 92 mg of compound 54 (−). $^1$H NMR (CDCl$_3$ 400 MHz) δ 9.43 (s, 1 H), 7.78 (m, 4 H), 7.12 (m, 1H), 6.42 (m, 1 H), 5.06 (dd, J=12, 5 Hz, 1 H), 4.49 (d, J=12 Hz, 1 H), 3.90 (m, 1 H), 3.49(m, 1 H), 3.04 (d, J=4 Hz, 1 H), 2.58 (m, 1 H), 2.42 (m, 1 H), 1.13 (s, 3H), MS: Calcd. for C$_{21}$H$_{18}$F$_5$O$_5$S (MH$^+$), m/z=477.1; found 477.3. Retention time: 4.46 min.

Steps 9-10

Compound 54 (−) was subjected to conditions analogous to the ones described in Scheme 6, Steps 2 to 3, with the exclusion of the final chiral HPLC purification, to provide compound 55. $^1$H NMR (CDCl$_3$ 400 MHz) δ 7.76 (m, 4 H), 7.11 (m, 1 H), 6.40 (m, 1 H), 5.17 (dd, J=13, 5 Hz, 1 H), 4.45 (d, J=13 Hz, 1 H), 3.74 (m, 1 H), 3.37 (t, J=12 Hz, 1 H), 3.23 (m, 1 H), 3.14 (m, 1 H), 2.95 (s, 3 H), 2.74 (d, J=4 Hz, 1H), 2.54 (d, J=14 Hz, 1 H), 2.34 (m, 1 H), 2.24 (m, 1 H), 2.16 (m, 1 H), 1.01 (s, 3 H). MS: Calcd. for C$_{23}$H$_{24}$F$_5$O$_6$S$_2$ (MH$^+$), m/z=555.1; found 555.3. Retention time: 4.50 min.

Scheme 12:

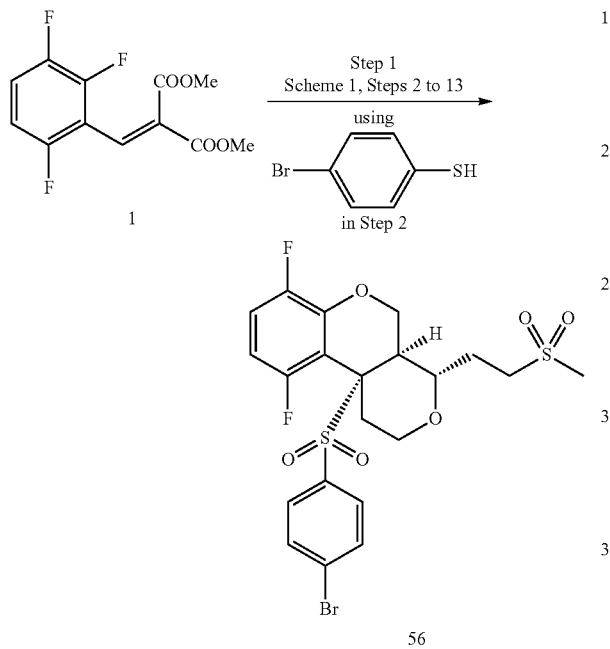

56

Step 1

Compound 1 was subjected to conditions analogous to the ones described in Scheme 1, Steps 2 to 13, and using 4-bromothiophenol instead of 4-chlorothiophenol in Step 2, to provide compound 56. $^1$H NMR (CDCl$_3$ 400 MHz) δ 7.68 (d, J=8 Hz, 2H), 7.55 (d, J=8 Hz, 2 H), 7.10 (m, 1 H), 6.48 (m, 1 H), 5.17 (dd, J=12, 2.4 Hz, 1 H), 4.44 (d, J=12 Hz, 1 H), 3.90 (br d, J=12 Hz, 1 H), 3.34 (m, 1 H), 3.27 (m, 1 H), 3.14 (m, 1 H), 3.02 (m, 1 H), 2.91 (s, 3 H), 2.50-2.60 (m, 2 H), 2.44 (m, 1 H), 2.29 (m, 1 H), 2.03 (m, 1 H). MS: Calcd. for C$_{21}$H$_{22}$BrF$_2$O$_6$S$_2$ (MH+), m/z=551.0; found 551.3. Retention time: 4.34 min.

Scheme 13:

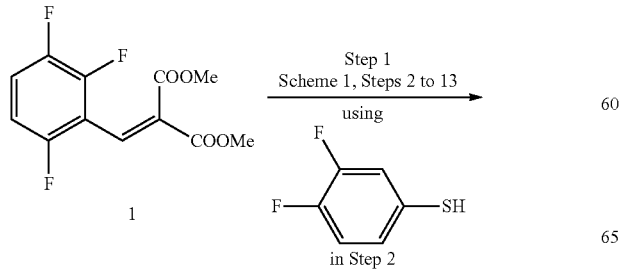

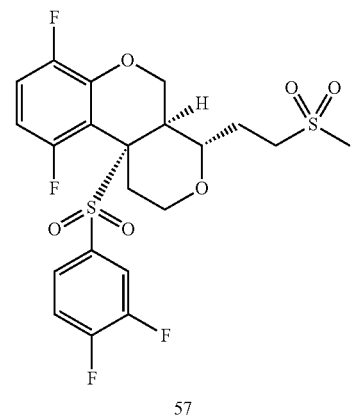

57

Step 1

Compound 1 was subjected to conditions analogous to the ones described in Scheme 1, Steps 2 to 13, and using 3,4-difluorothiophenol instead of 4-chlorothiophenol in Step 2, to provide compound 57. $^1$H NMR (CDCl$_3$ 400 MHz) δ 7.54 (m, 1 H), 7.48 (m, 1 H), 7.33 (m, 1 H), 7.11 (m, 1 H), 6.47 (m, 1 H), 5.15 (dd, J=13, 3 Hz, 1 H), 4.45 (d, J=12 Hz, 1 H), 3.91 (m, 1 H), 3.35 (m, 1 H), 3.27 (m, 1 H), 3.14 (t, J=12 Hz, 1 H), 3.01 (m, 1 H), 2.91 (s, 3 H), 2.50-2.60 (m, 2 H), 2.44 (m, 1 H), 2.31 (m, 1 H), 2.04 (m, 1 H). MS: Calcd. for C$_{21}$H$_{21}$F$_4$O$_6$S$_2$ (MH+), m/z=509.1; found 509.3. Retention time: 4.13 min.

Scheme 14:

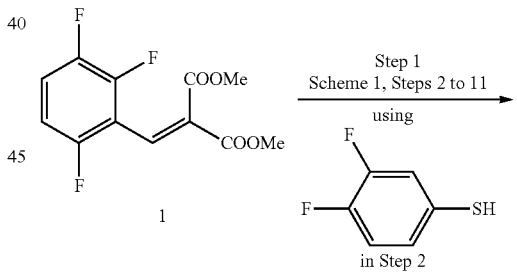

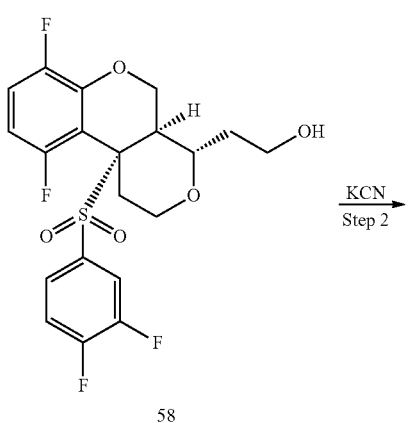

58

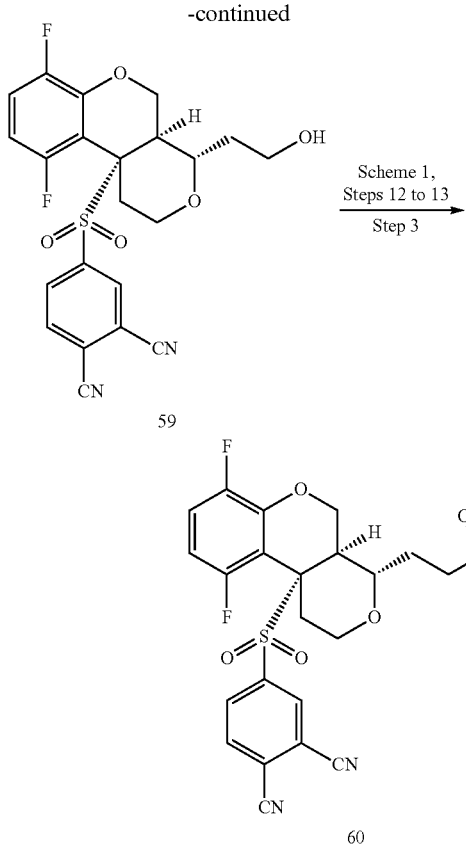

59

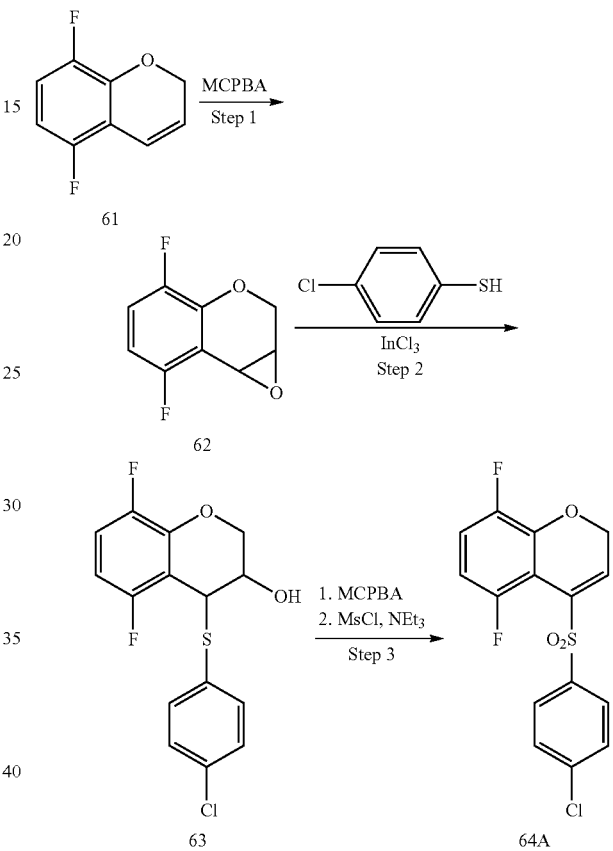

60

Step 1

Compound 1 was subjected to conditions similar to the ones described in Scheme 1 Steps 2 to 11, and using 3,4-difluorothiophenol instead of 4-chlorothiophenol in Step 2, to provide compound 58. [1] H NMR (CDCl$_3$ 400 MHz) δ 7.40-7.60 (m, 2 H), 7.34 (m, 1 H), 7.12 (m, 1 H), 6.47 (m, 1 H), 5.15 (dd, J=12, 3 Hz, 1 H), 4.44 (d, J=12 Hz, 1 H), 3.93 (m, 1 H), 3.80 (m, 2 H), 3.50 (m, 1 H), 3.20 (t, J=12 Hz, 1 H), 2.67 (m, 1 H), 2.52 (d, J=10 Hz, 1 H), 2.35 (m, 1 H), 2.26 (m, 1 H), 2.12 (m, 1 H), 1.85 (m, 1 H), 1.55 (s, 1 H), MS: Calcd. for $C_{20}H_{19}F_4O_5S$ (MH+), m/z=447.1; found 447.2. Retention time: 3.93 min.

Step 2

A solution of 100 mg (0.22 mmol) of compound 58 in 2 mL of acetonitrile was treated with 30 mg (0.44 mmol) of potassium cyanide and heated at reflux overnight. The mixture was diluted with water and dichloromethane and extracted with dichloromethane. The combined organic extracts were dried over sodium sulfate and concentrated and the residue was purified by chromatography over silica gel eluting with a gradient of 1% to 50% of ethyl acetate in hexanes to provide 25 mg of compound 59 and 25 mg of starting 58. 59: [1] H NMR (CDCl$_3$ 400 MHz) δ 8.10 (s, 1H), 8.05 (d, J=8 Hz, 1 H), 7.99 (d, J=8 Hz, 1 H), 7.16 (m, 1 H), 6.49 (m, 1 H), 5.08 (dd, J=12, 3 Hz, 1 H), 4.48 (d, J=13 Hz, 1 H), 3.93 (m, 1 H), 3.80 (m, 2 H), 3.52 (m, 1 H), 3.18 (m, 1 H), 2.74 (d, J=10 Hz, 1 H), 2.68 (m, 1 H), 2.38 (m, 1 H), 2.24 (m, 1H), 2.12 (m, 1 H), 1.86 (m, 1 H), 1.05 (s, 1 H), MS: Calcd. for $C_{22}H_{19}F_2N_2O_5S$ (MH+), m/z=461.1; found 461.3. Retention time: 3.78 min.

Step 3

Compound 59 was subjected to conditions similar to the ones described in Scheme 1, Steps 12 to 13 to provide compound 60. [1] H NMR (CDCl$_3$ 400 MHz) δ 8.10 (s, 1 H), 8.04 (d, J=9 Hz, 1 H), 7.99 (d, J=9 Hz, 1 H), 7.17 (m, 1 H), 6.50 (m, 1H), 5.11 (dd, J=12, 2.2 Hz, 1 H), 4.50 (d, J=12 Hz, 1 H), 3.93 (br d, J=12 Hz, 1 H), 3.38 (m, 1 H), 3.29 (m, 1 H), 3.14 (m, 1 H), 3.03 (m, 1 H), 2.93 (s, 3 H), 2.67 (d, J=9 Hz, 1 H), 2.45-2.55 (m, 2 H), 2.08 (m, 1 H); MS Calcd. for $C_{23}H_{21}F_2N_2O_6S_2$ (MH+), m/z=523.1; found 523.3. Retention time: 3.92 min.

Scheme 15:

Step 1: 5,8-Difluoro-2H-chromene oxide 5,8-Difluoro-2H-chromene 61 (35 g, 0.21 mol) was dissolved in 500 mL of dichloromethane and 93 g of MCPBA (77%, 0.42 mol) was added. The reaction was stirred at room temperature for 30 minutes. The reaction was quenched with a solution of 50 g Na$_2$S$_2$O$_3$ in 500 mL water. The organic layer was washed with two 500-mL portions of 2N NaOH solution, 200 mL of brine, dried over Na$_2$SO$_4$ and concentrated. The residue was recrystalized from EtOAc/Hexane solution to give rise to 21.6 g pure product 62. The residue from mother liquor was purified by column chromatography eluting with a gradient from hexanes to 25% EtOAc/hexanes over 55 minute to obtain an additional 1.4 g of 62. Total Yield: 23 g, 60%. [1] H NMR (CDCl$_3$ 400 MHz δ 7.00 (m, 1 H), 6.63 (m, 1 H), 4.67 (d, J=12.4 Hz, 1 H), 4.27 (m, 2 H), 3.84 (d, J=4.4Hz, 1 H).

Step 2: 4-(4-Chloro-phenylsulfanyl)-5,8-difluoro-chroman-3-ol 5,8-Difluoro-2H-chromene oxide 62 (23 g, 0.125 mol) and 4-chloro-benzenethiol (18.1 g, 0.125 mmol) were dissolved in 500 mL of dichloromethane and 2.9 g of InCl₃ (0.013 mol) was added. The reaction was stirred at room temperature overnight. The reaction was partitioned between 200 mL of dichloromethane and 200 mL of water. The organic layer was washed with brine, dried over Na₂SO₄ and concentrated. The product was purified by column chromatography eluting with a gradient from hexanes to 50% EtOAc/hexane over 55 minute to give 23.2 g of alcohol 63 (57%). ¹ H NMR (CDCl₃ 400 MHz δ 7.48 (d, J=8.8 Hz, 2 H), 7.34 (d, J=8.8 Hz, 2 H), 7.01 (m, 1 H), 6.64 (m, 1 H), 4.63 (d, J=11.7 Hz, 1 H), 4.32-4.41 (m, 2 H), 4.12 (m, 1 H).

Step 3: 4-(4-Chloro-benzenesulfonyl)-5,8-difluoro-2H-chromene 4-(4-Chloro-phenylsulfanyl)-5,8-difluoro-chroman-3-ol 63 (23.2 g, 71 mmol) was dissolved in 200 mL of dichloromethane and 31.7 g (77%, 142 mmol) of MCPBA was added. The reaction was stirred at room temperature for 3 hours, then quenched with a solution of 10 g of Na₂S₂O₃ in 50 mL water. The organic layer was washed with 2 100-mL portions of 1N NaOH solution, 100 mL of brine, dried over Na₂SO₄ and concentrated. The residue was dissolved in 200 mL of dichloromethane, 16.1 g of mesyl chloride (142 mmol) and 14.3 g of triethylamine (142 mmol) were added. The reaction was stirred at room temperature for one hour. The reaction solution was washed with 100 mL of brine, dried over Na₂SO₄ and concentrated. The residue was recrystalized from EtOAc/Hexane solution to give 8.4 g pure vinyl sulfone product 64. The residue from mother liquor was purified by column chromatography eluting with a gradient from hexanes to 25% EtOAc/hexane over 55 minute to give an additional 7.1 g vinyl sulfone 64A. Total yield: 15.5 g, 64%. ¹ H NMR (CDCl₃ 400 MHz δ 7.84 (dd, J=8.8 and 2.2 Hz, 2 H), 7.51 (d, J=8.1 Hz, 2 H), 7.30 (t, J=4.4Hz, 1 H), 7.00 (m, 1 H), 6.54 (m, 1 H), 4.99 (d, J=4.4 Hz, 2 H).

The following compound (64B) was prepared via an analogous three step route using 4-trifluoromethylphenylsulfide in Step 2:

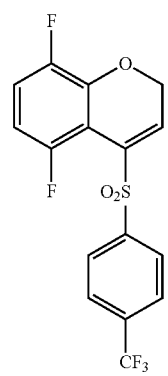

64B

¹ HNMR (CDCl3)δ: 8.03 (d, 2 H), 7.81 (d, 2 H), 7.38 (m, 1 H), 7.01 (m, 1 H), 6.54 (m, 1 H), 5.01 (d, 2 H)

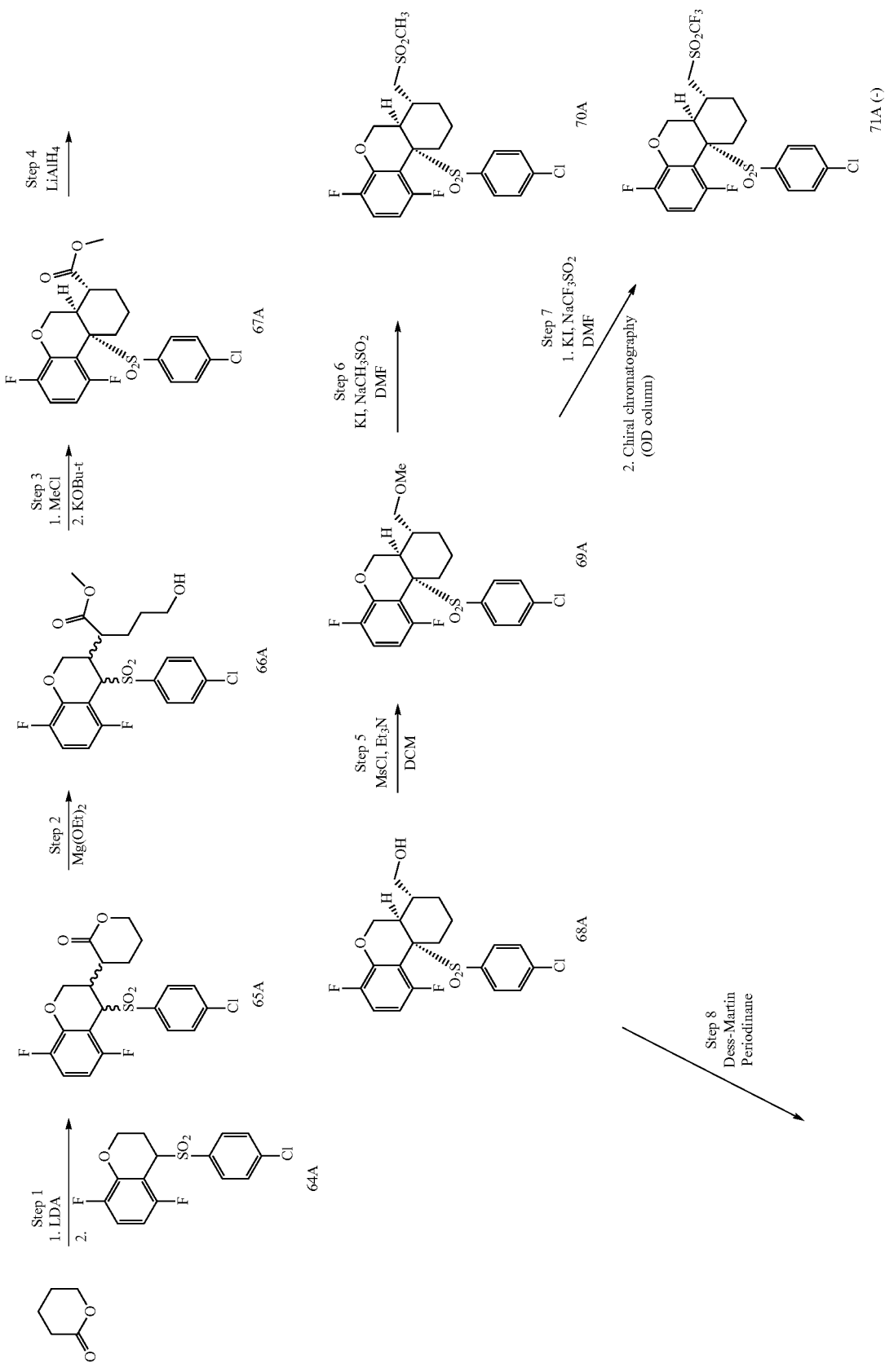

-continued
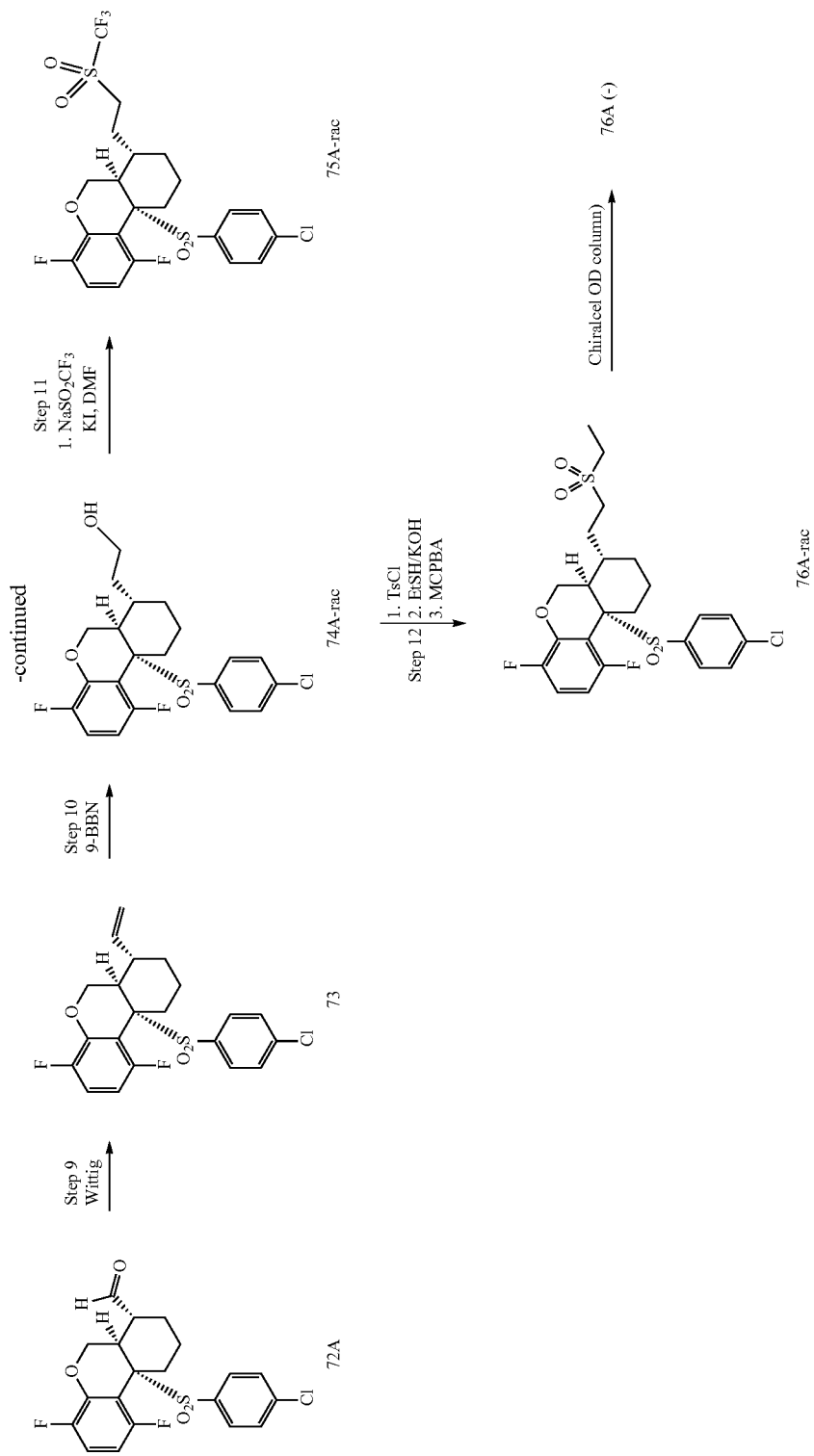

Step 1

To a solution of 8.25 mL (58.3 mmol) of diisopropylamine in 100 mL of THF at −40° C. was added 23.3 mL (58.3 mmol) of 2.5 M solution of n-butyl lithium in hexanes. The mixture was stirred for 20 min and cooled to −78° C. A solution of 5.84 g (58.35 mmol) of delta-valerolactone in 10 mL of THF was added dropwise. The resulting viscous mixture was stirred at −78° C. over a period of 45 min, followed by the dropwise addition of a solution of 10:0 g (29.177 mmol) of alkene 64A in 40 mL of THF. The mixture was stirred in the cold for 15 min, quenched with 50% saturated NH$_4$Cl, extracted with EtOAc, washed with brine, dried over MgSO$_4$, and concentrated. The crude product was passed through a 120 g silica gel column using gradient of 0% to 40% of ethyl acetate in hexanes to furnish 11.53 g of product 65A as a mixture of diastereomers. [1] H NMR (CDCl$_3$ 400 MHz) δ 7.91 (d, J=8.8 Hz, 1 H), 7.78 (d, J=8.8 Hz, 1 H), 7.75 (d, J=8.8 Hz, 1 H), 7.53 (d, J=8.8 Hz, 1 H), 7.10-7.01 (ser. m., 1 H), 6.59-6.47 (ser. m., 1 H), 5.09 (s, 0.5 H), 4.95 (dd, J=12.3, 8.6 Hz, 0.5 H), 4.81 (dd, J=12.6, 2.6 Hz, 0.5 H), 4.60 (dt, J=12.3, 1.8 Hz, 0.5 H), 4.47 (dt, J=12.6, 1.8 Hz, 0.5 H), 4.46 (s, 0.5 H), 4.29-4.14 (ser. m., 2 H), 3.34 (m, 0.5 H), 3.08 (dm, J=9.8 Hz, 0.5 H), 2.64-2.52 (ser. m, 0.5 H), 2.39-2.29 (m, 0.5 H), 2.28-2.19 (m, 0.5 H), 1.96-1.87 (ser m, 1.5 H), 1.70-1.62 (ser. m., 1.5 H), 1.39-1.28 (m, 0.5 H).

Step 2

To a mixture of 11.00 g (24.88 mmol) of compound 65A in 120 mL of methanol was added 3.20 g (29.86 mmol) of magnesium ethoxide. The resulting mixture was stirred overnight and taken into 1200 mL of ethyl acetate. The mixture washed sequentially with 600 mL of 1M NaOH, twice with 1 L of water, and 600 mL of brine. The organic phase was dried over MgSO$_4$ and concentrated in vacuo to furnish 11.0 g of alcohol 66A. [1] H NMR (CDCl$_3$ 400 MHz) δ 7.77 (d, J=8.8 Hz, 1 H), 7.74 (d, J=8.8 Hz, 1 H), 7.54 (d, J=8.8 Hz, 1 H), 7.52 (d, J=8.8 Hz, 1 H), 7.10-7.00 (m, 1 H), 6.53-6.40 (ser. m, 1 H), 4.90 (td, J=12.5, 3.1 Hz, 1 H), 4.56-4.46 (ser. m., 1 H), 4.31-4.24 (ser. m., 1 H), 3.65 (s, 1.5 H), 3.67-3.48 (ser. m., 2 H), 3.51 (s, 1.5 H), 3.12 (d, J=11.5 Hz, 0.5 H), 2.96 (d, J=9.7 Hz, 0.5 H), 2.43-2.28 (ser. m., 1 H), 1.97-1.29 (ser. m, 5 H).

Step 3

A mixture of alcohol 66A obtained in the previous step and triethylamine (10.49 mL, 74.65 mmol) in 120 mL of dichloromethane was chilled with ice/water and treated dropwise with 2.89 mL (37.23 mmol) of methanesulfonyl chloride. The reaction mixture was stirred for 1 h, washed with equal volume of 1M HCl, dried over Na$_2$SO$_4$, concentrated and pumped on a high vacuum overnight to furnish 12.16 g of crude mesylate which was used without further purification. To a solution of 11.16 g (20.18 mmol) of this material in 200 mL of THF was added in portions 2.94 g (20.18 mmol) of potassium tert-butoxide. The reaction mixture was stirred for 40 min and quenched with equal volumes of 50% sat. NH$_4$Cl and ethyl acetate. The organic phase was separated, dried over MgSO$_4$, and concentrated. The product was purified by column chromatography over silica gel using a gradient from 0-30% of ethyl acetate in hexanes as solvent to furnish 6.0 g of ester 67A. [1] H NMR (CDCl$_3$ 400 MHz) δ 7.61 (d, J=8.7 Hz, 2 H), 7.50 (d, J=8.7 Hz, 2 H), 7.12-7.04 (m, 1 H), 6.47-6.40 (m, 1 H), 5.19 (dd, J=12.5, 2.7 Hz, 1 H), 4.20 (d, J=12.2 Hz, 1 H), 3.72 (s, 3 H), 2.98 (d, J=9.9 Hz, 1 H), 2.64 (d, J=11.2 Hz, 1 H), 2.46 (td, J=11.9, 4.2 Hz, 1 H), 1.98-1.87 (m, 2H), 1.81-1.74 (m, 1 H), 1.58-1.49 (m, 2 H), 1.17-1.06 (m, 1 H).

Step 4

To a solution of 2.70 g (5.91 mmol) of ester 67A in 59 mL of THF at 0° C. was added 6.50 mL (6.50 mmol) of 1M lithium aluminum hydride solution in THF. The reaction mixture was stirred over 15 min and quenced by careful dropwise addition of 1M HCl, until no more gas was evolving. The mixture was partitioned between 1M HCl and ethyl acetate. The aqueous phase was separated and extracted with ethyl acetate. The combined organic phase was washed with brine, dried over MgSO$_4$, and concentrated to furnish 2.40 g of alcohol 68A which was used without further purification. δ 7.62 (d, J=8.6 Hz, 2 H), 7.49 (d, J=8.6 Hz, 2 H), 7.09-7.02 (m, 1 H), 6.46-6.39 (m, 1 H), 5.17 (dd, J=12.1, 2.5 Hz, 1 H), 4.63 (d, J=12.6 Hz, 1 H), 3.88 (dd, J=11.0, 4.4 Hz, 1 H), 3.71 (dd, J=11.2, 2.9 Hz, 1 H), 2.70 (d, J=11.0 Hz, 1 H), 2.57 (d, J=14.6 Hz, 1 H), 1.94-1.83 (m, 1 H), 1.78-1.66 (m, 2 H), 1.57-1.41 (m, 3 H), 1.17-1.04 (m, 1 H).

Step 5

To alcohol 68A (1.794 g, 4.18 mmol) in dichloromethane (50 mL) was added Et$_3$N (1.17 mL, 0.846 g, 8.36 mmol,) and MsCl (0.48 mL, 0.719 g, 6.27 mmol,) respectively, the mixture was stirred at 0° C. for 30 mins, and quenched with water. It was washed with 1N HCl, and extracted with dichloromethane. The combined organic layers were washed with saturated NaHCO$_3$ and brine, dried over MgSO$_4$, filtered, and evaporated under vacuum. The crude 69A (2.257 g, quantitative) was used for the next step directly. [1] H-NMR (CDCl3 400 MHz) δ: 7.61 (d, J=9.0 Hz, 2 H), 7.50 (d, J=8.7 Hz, 2 H), 7.12-7.03 (m, 1 H), 6.50-6.40 (m, 1 H), 5.21 (d, J=13.0 Hz, 1H), 4.55-4.46 (m, 2 H), 4.20 (dd, J=2.4, 10.4 Hz, 1 H), 3.06 (s, 3 H), 2.68 (d, J=11.6 Hz, 1 H), 2.57 (d, J=13.2 Hz, 1 H), 1.96-1.84 (m, 1 H), 1.82-1.66 (m, 3 H), 1.58-1.46 (m, 1 H), 1.18-1.04 (m, 1 H).

Step 6:

To compound 69A (0.131 g, 0.26 mmol) in DMF was added 0.129 g of KI (0.78 mmol) and 0.079 g of sodium methanesulfinate (0.78 mmol), the mixture was at 120° C. for 1 hr., and quenched with water. It was extracted with dichloromethane, dried over MgSO$_4$, filtered, and evaporated under vacuum. The crude 70A was purified by prep-TLC, followed by reverse phase HPLC. [1] H-NMR (CDCl3 400 MHz) δ: 7.62 (d, J=8.5 Hz, 2 H), 7.50 (d, J=8.7 Hz, 2 H), 7.15-7.03 (m, 1 H), 6.54-6.41 (m, 1H), 5.27 (d, J=12.4 Hz, 1 H), 4.44 (d, J=12.2 Hz, 1 H), 3.36 (d, J=14.7 Hz, 1 H), 3.02-2.88 (m, 1 H), 2.95 (s, 3 H), 2.57 (d, J=11.6 Hz, 2 H), 2.27 (d, J=12.4 Hz, 1 H), 2.10-1.95 (m, 1 H), 1.96-1.81 (m, 1 H), 1.79-1.66 (m, 1 H), 1.48-1.33 (m, 1 H), 1.17-1.02 (m, 1 H). LCMS [M+H]$^+$: 491.3 (4.44 min)

Step 7: Sulfone 71A was obtained by an analogous procedure to that described in the general procedure from preparation of sulfone 70A (Step 6 above, using sodium trifluoromethylsulfinate). The racemic form of 71A was separated by preparative Chiracel OD column chromatography to give two enantiomers:71A (−) [α]$_D$=−122.6° (c=1.00, dichloromethane) and 71A (+) [α]$_D$=+132.5 (c=1.00, dichloromethane). [1] H-NMR (CDCl3 400 MHz) δ: 7.62 (d, J=9.2 Hz, 2 H), 7.51 (d, J=8.8 Hz, 2 H), 7.15-7.05 (m, 1 H), 6.53-6.44 (m, 1 H), 5.27 (d, J=13.2 Hz, 1H), 4.44-4.40 (d, J=13.0 Hz, 1 H), 3.50 (d, J=14.0 Hz, 1 H), 3.23 (dd, J=8.2, 14.4 Hz, 1 H), 2.72-2.52 (m, 2 H), 2.28-2.10 (m, 2 H), 1.98-1.85 (m, 1 H), 1.78 (d, J=14.8 Hz, 1 H), 1.60-1.48 (m, 1 H), 1.20-1.04 (m, 1 H). LCMS [M+H]$^+$: 545.3 (5.08 min).

Step 8

Alcohol 68A was dissolved in 60 mL of dichloromethane and treated at with 2.50 g (5.91 mmol) of Dess-Martin reagent. After 30 min, completion of reaction was confirmed by TLC (30% ethyl acetate in hexanes was used as solvent) The reaction was quenched with a solution of 1 g sodium thiosulfate in 10 mL of water, followed by 10 mL of sat NaHCO$_3$. The bi-phasic mixture was stirred vigorously for 30 min, and extracted with dichloromethane. The organic phase was dried over Na$_2$SO$_4$, concentrated, and the residue chromatographed over silica gel eluting with 0-20% ethyl acetate in hexanes as solvent to furnish 2.356 g of aldehyde 72A. [1] H-NMR (CDCl3 400 MHz) δ 9.67 (s, 1 H), 7.62 (d, J=8.6 Hz, 2 H), 7.50 (d, J=8.6 Hz, 2H), 7.12-7.05 (m, 1 H), 6.49-6.41 (m, 1 H), 5.17 (dd, J=12.3, 2.7 Hz, 1 H), 4.33 (d, J=12.1 Hz, 1 H), 3.02 (d, J=11.7 Hz, 1 H), 2.68 (d, 11.7 Hz, 1 H), 2.53 (m, 1 H), 1.96 (m, 1 H), 1.92-1.81 (m, 2 H), 1.33-1.09 (ser. m., 2 H).

Step 9

To a stirring suspension of 14.42 g (40.36 mmol) of methyl triphenylphosphonium bromide in 200 mL of THF at −40° C. was added dropwise 15.52 mL (38.8 mmol) of 2.5 M solution of n-butyl lithium in hexanes, after which the reaction was stirred in an ice bath for 45 min. To this yellow mixture of Wittig reagent was added a solution of the 6.62 g (15.52 mmol) of aldehyde 72A in 75.0 mL of THF. The mixture was stirred 1 hr at 0° C., then cooling was removed and stirring continued for additional 2 hrs. The reaction was quenched with water and extracted with ethyl acetate. The organic phase was washed with brine, dried over MgSO$_4$, and concentrated. The product was purified by column chromatography over silica gel eluting with a gradient of 0-20% ethyl acetate in hexanes as solvent to furnish 5.560 g of alkene 73A. $^1$H-NMR (CDCl3 400 MHz) δ 7.60 (d, J=8.6 Hz, 2 H), 7.48 (d, J=8.6 Hz, 2 H), 7.10-7.03 (m, 1 H), 6.44-6.37 (m, 1 H), 5.62 (dt, J=18.0, 8.9 Hz, 1 H), 5.18 (s, 1 H), 5.15 (d, J=5.8 Hz, 1 H), 5.06 (dd, J=11.8, 2.8 Hz, 1 H), 4.52 (d, J=11.7 Hz, 1 H), 2.59 (d, J=13.2 Hz, 1 H), 2.38 (d, J=12.2 Hz, 1 H), 2.09-1.97 (m, 1 H), 1.96-1.87 (m, 1 H), 1.75-1.64 (m, 2 H), 1.38-1.25 (m, 1 H), 1.17-1.04 (m, 1 H).

Step 10

To a solution of 1.90 g (4.47 mmol) of alkene 73A in 10 mL of THF under nitrogen was added 17.88 mL (8.94 mmol) of 0.5 M solution of 9-BBN-THF. The flask was equipped with a reflux condenser and placed in a pre-heated oil bath at 80° C. for 1 hr. The reaction mixture was cooled down to 0° C. and treated dropwise with 7.96 g of 35% aqueous solution of hydrogen peroxide and then dropwise with 13.4 mL of 2M NaOH. The milky mixture was stirred for 1 hr at ambient temperature. Water (50 mL) was added and the mixture was extracted 3×100 mL portions of ethyl acetate. The combined organic phase was washed with brine, dried over MgSO$_4$, and concentrated in vacuo, with bath temperature not exceeding 40° C. The residue was purified by column chromatography over silica gel eluting with a gradient of 0-40 ethyl acetate in hexanes to furnish 1.8 g of alcohol 74A-rac. $^1$H-NMR (CDCl3 400 MHz) δ 7.61 (d, J=8.4 Hz, 2 H), 7.48 (d, J=8.6 Hz, 2 H), 7.09-7.02 (m, 1 H), 6.45-6.38 (m, 1H), 5.17 (dd, J=12.5, 2.3 Hz, 1 H), 4.61 (d, J=12.5 Hz, 1 H), 3.80-3.71 (m, 1 H), 3.71-3.63 (m, 1 H), 2.56 (d, J=13.7 Hz, 1 H), 2.41 (d, J=10.0 Hz, 1 H), 2.04-1.67 (ser. m., 4H), 1.19-1.00 (ser. m., 5 H).

Step 11

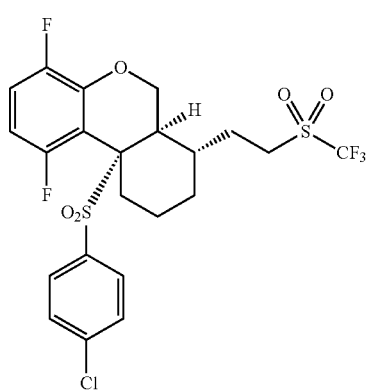

75A

Starting from alcohol 74A-rac and using an analogous procedure as described in Step 7 above, sulfone 75A-rac was obtained. MS: Calcd. for C$_{22}$H$_{21}$ClF$_5$O$_5$S$_2$ (MH$^+$), m/z=559.04.; found 559.3. Retention time: 5.08 min.

The following compounds were prepared analogously:

Compound 81A-rac

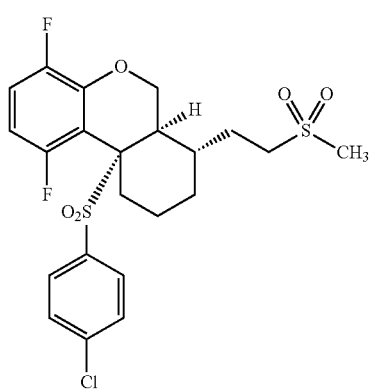

81A-rac

MS: Calcd. for C$_{22}$H$_{23}$ClF$_2$O$_5$S$_2$ (MH$^+$), m/z=505.1.; found 505.3. Retention time: 4.47 min. Resolution of this compound using Chiralcel OD chromatography gave:

Compound 81A(−)

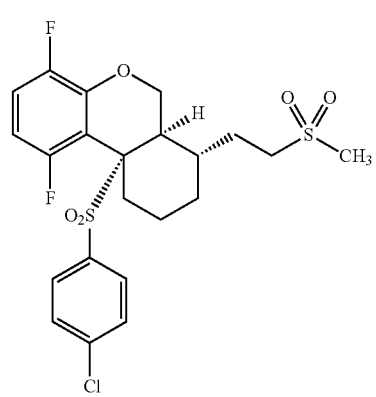

81A (−)

MS: Calcd. for C$_{22}$H$_{23}$ClF$_2$O$_5$S$_2$ (MH$^+$), m/z=505.1.; found 505.3. Retention time: 4.47 min.

Compound 81A(+)

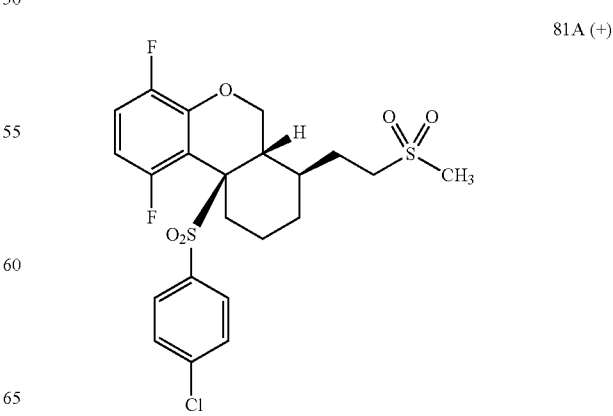

81A (+)

MS: Calcd. for $C_{22}H_{24}ClF_2O_5S_2$ (MH$^+$), m/z=505.1.; found 505.3. Retention time: 4.47 min.

Compound 75B(−)

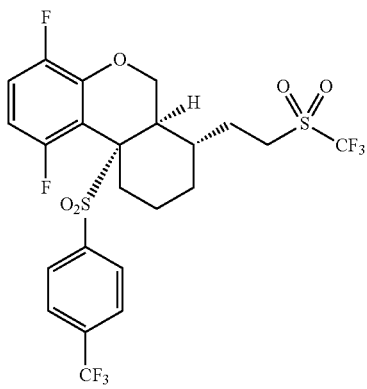

75B (−)

$^1$H NMR (CDCl$_3$) δ 7.83 (d, 2 H), 7.78 (d, 2 H), 7.06-7.12 (m, 1 H), 6.41-6.47 (m, 1 H), 5.17 (dd, 1 H), 4.58 (d, 1 H), 3.63 (m, 1 H), 3.47-3.54 (m, 1 H), 2.52 (d, 1 H), 2.44 (d, 1 H), 2.21-2.29 (m, 1 H), 1.92 (tt, 1 H), 1.67-1.84 (m, 3 H), 1.55-1.63 (m, 1 H), 1.02 (m, 2 H).

Step 12

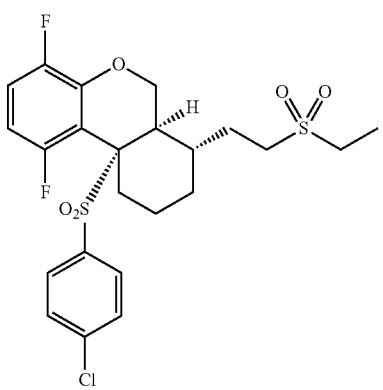

76A

Alcohol 74A-rac was tosylated using an analogous procedure to that described in Scheme 1, Step 12 and converted to sulfone 76A using an analogous procedure to that described in Scheme 1, Step 14. 76A-rac: MS: Calcd. for $C_{23}H_{26}ClF_2O_5S_2$ (M+1)$^+$, m/z=519.09; found 519.3. Retention time: 4.58 min. Using chiral chromatography on a Chiralcel OD column, 76A (−) was isolated [α]$_D^{20}$−163.18° (c=1, dichloromethane).

The following compounds were prepared analogously:

Compound 76A(+)

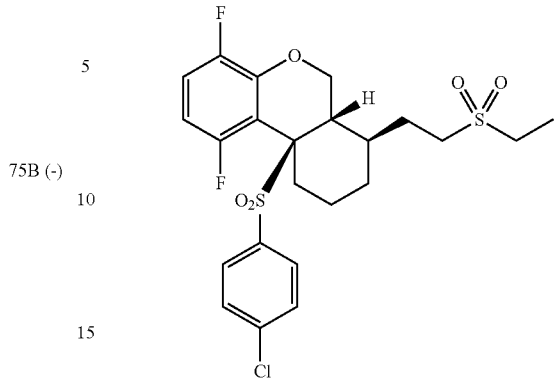

76A (+)

MS: Calcd. for $C_{23}H_{26}ClF_2O_5S_2$ (M+1)$^+$, m/z=519.09; found 519.3. Retention time: 4.58 min.

Compound 76B(−)

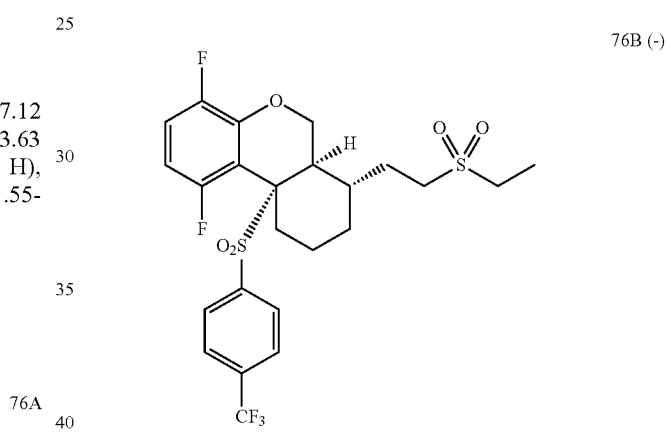

76B (−)

MS: Calcd. for $C_{24}H_{26}F_5O_5S_2$ (M+1)$^+$, m/z=553.1; found 553.3. Retention time 4.64 min.

Compound 82A

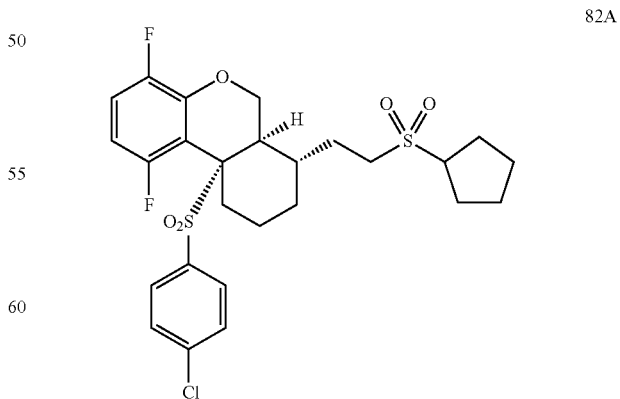

82A

MS: Calcd. for $C_{26}H_{30}ClF_2O_5S_2$ (M+1)$^+$, m/z=559.1; found 559.3. Retention time: 4.92 min.

Compound 83A

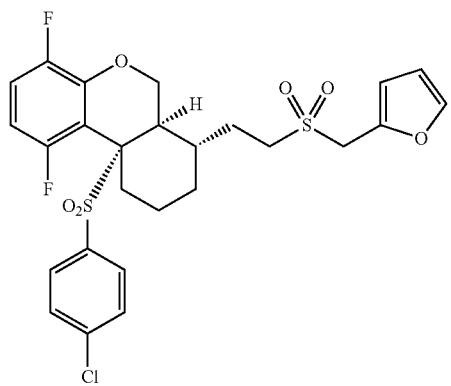

MS: Calcd. for $C_{26}H_{26}ClF_2O_6S_2$ $(M+1)^+$, m/z=571.1; found 571.3. Retention time: 4.81 min.

Compound 84A

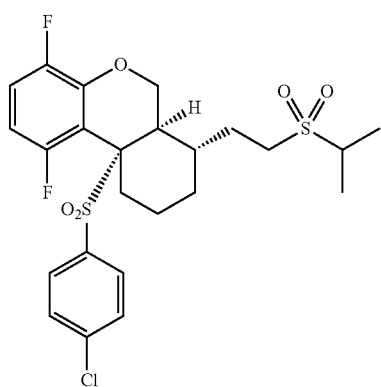

MS: Calcd. for $C_{24}H_{28}ClF_2O_5S_2$ $(M+1)^+$, m/z=533.1; found 533.1. Retention time: 4.70 min.

Compound 85A

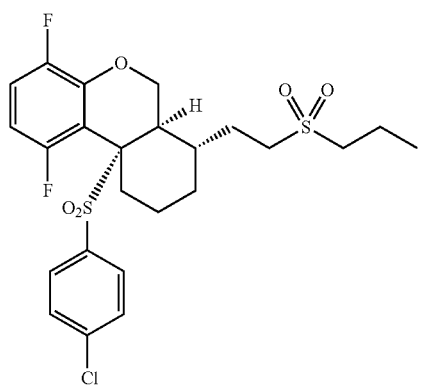

MS: Calcd. for $C_{24}H_{28}ClF_2O_5S_2$ $(M+1)^+$, m/z=533.1; found 533.3. Retention time: 4.76 min.

Compound 85B

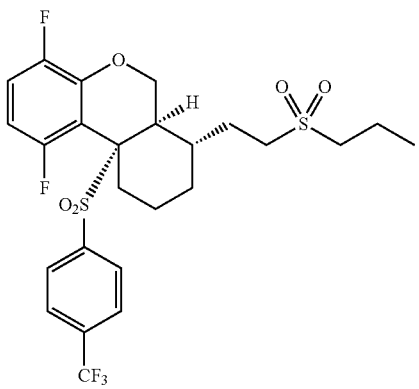

MS: Calcd. for $C_{25}H_{28}F_5O_5S_2$ $(M+1)^+$, m/z=567.1; found 567.3. Retention time: 4.79 min.

Compound 86A

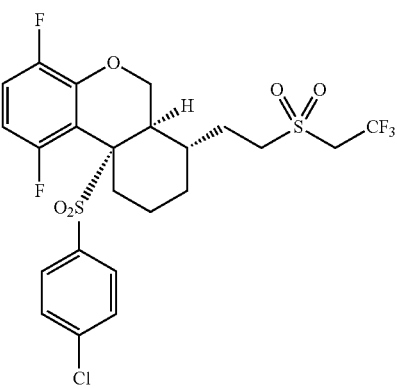

MS: Calcd. for $C_{23}H_{23}ClF_5O_5S_2$ $(M+1)^+$, m/z=573.1; found 573.3. Retention time: 4.86 min.

Compound 87B

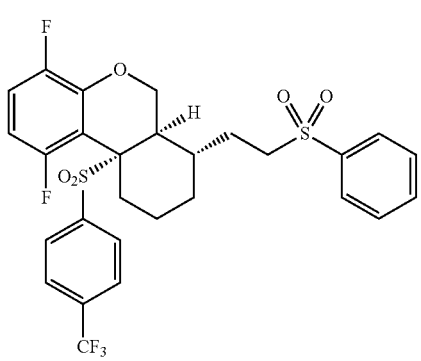

MS: Calcd. for $C_{28}H_{26}F_5O_5S_2$ $(M+1)^+$, m/z=601.1; found 601.3. Retention time: 4.95 min.

Scheme 17:

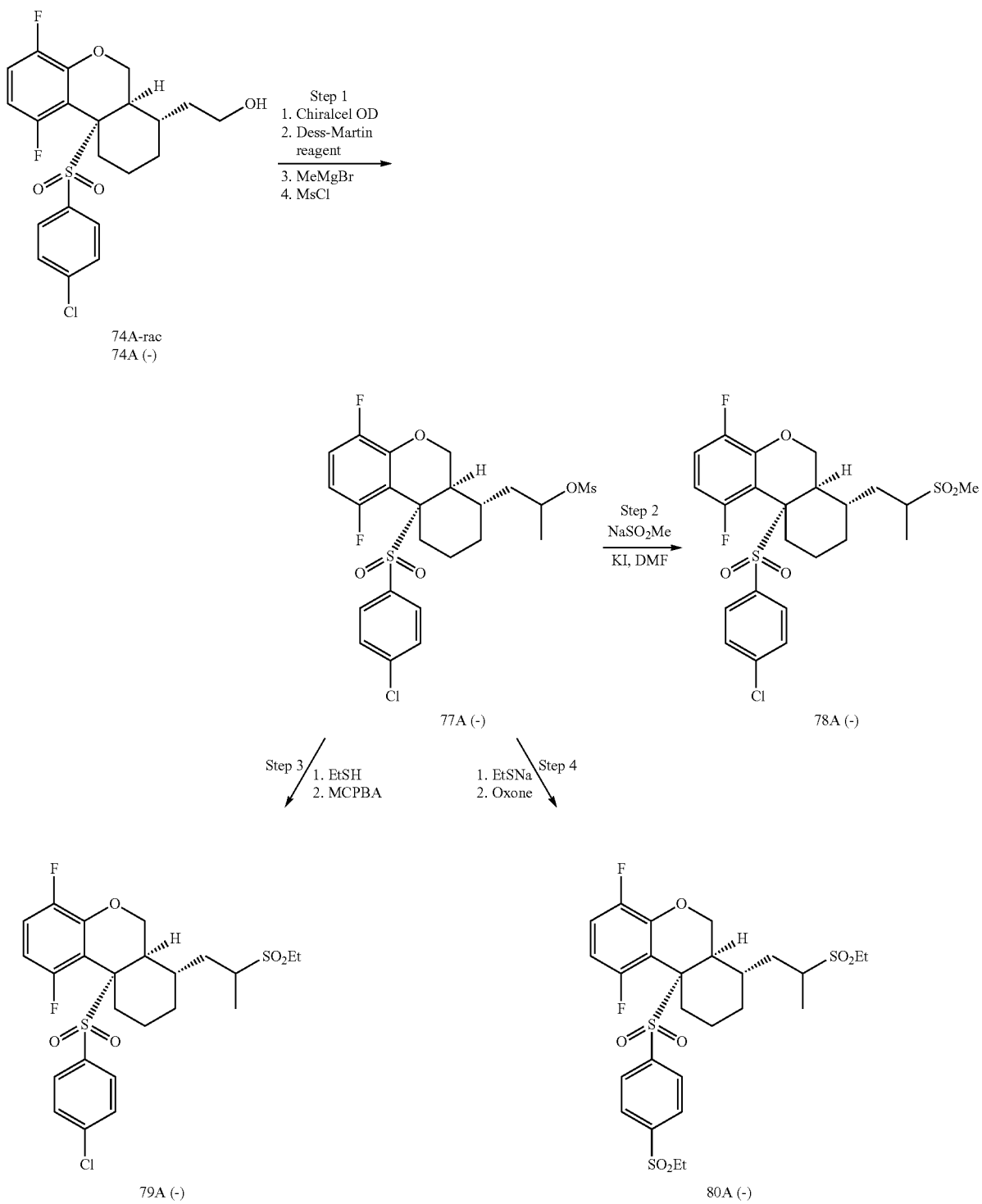

Step 1,
Alcohol 10 was resolved using a Chiracel OD column eluting with 30% isopropyl alcohol in hexanes. First eluting peak 74A (+) has positive optical rotation, $[\alpha]_D^{20}$ +1.71° (c=0.6, dichloromethane). Second eluting peak 74A (−) has negative optical rotation, $[\alpha]_D^{20}$ −1.69° (c=0.5, dichloromethane). For subsequent chemistry, 74 (−) was used.

Alcohol 74 (−) was oxidized to an aldehyde using a procedure analogous to that of Scheme 16, Step 8. $^1$H-NMR (CDCl3 400 MHz) δ 9.76 (dd, J=2.5, 1.1 Hz, 1 H), 7.61 (d, J=8.6 Hz, 2 H), 7.49 (d, J=8.6 Hz, 2 H), 7.13-7.05 (m, 1 H), 6.49-6.41 (m, 1H), 5.21 (dd, J=12.6, 2.5 Hz, 1 H), 4.43 (d, J=12.5 Hz, 1 H), 2.79 (dd, J=16.8, 2.5 Hz, 1 H), 2.57 (d, J=12.6 Hz, 1 H), 2.50 (d, J=11.5 Hz, 1 H), 2.40 (ddd, J=17.0, 8.8, 2.7 Hz, 1 H), 2.02-1.67 (ser. m., 4 H), 1.19-1.07 (m, 2 H).

The resulting aldehyde (100 mg, 0.227 mmol) was dissolved in 2.0 mL of THF, cooled to 0° C. and treated with 0.113 mL (0.34 mmol) of a 3 M solution of methylmagnesium bromide in ether. After 10 min of stirring, the mixture was quenched with water and extracted with ethyl acetate to furnish 40 mg of the secondary alcohol. $^1$H-NMR (CDCl3 400 MHz) δ 7.61 (d, J=8.6 Hz, 2 H), 7.49 (d, J=8.6 Hz, 2 H), 7.10-7.01 (m, 1 H), 6.46-6.39 (m, 1 H), 5.16 (dd, J=12.6, 2.5 Hz, 1 H), 4.61 (d, J=13.0 Hz, 1 H), 3.89 (m, 1 H), 2.57 (d, J=14.8 Hz, 1 H), 2.34 (d, J=12.8 Hz, 1 H), 1.94-1.68 (ser. m., 3 H), 1.30-1.19 (ser. M., 2 H), 1.23 (d, J=6.0 Hz, 3H), 1.14-1.05 (ser. m., 2 H).

The secondary alcohol was mesylated according to the procedure of Scheme 16, Step 5 to give intermediate mesylate 77A (−): $^1$H-NMR (CDCl3 400 MHz) δ 7.61 (d, J=8.6 Hz, 2 H), 7.49 (d, J=8.6 Hz, 2 H), 7.10-7.01 (m, 1 H), 6.46-6.39 (m, 1 H), 5.16 (dd, J=12.5, 2.5 Hz, 1 H), 4.87 (m, 1 H), 4.55 (d, J=12.1 Hz, 1 H), 2.97 (s, 3 H), 2.57 (d, J=13.3 Hz, 1 H), 2.34 (d, J=12.1 Hz, 1 H), 2.09 (m, 1 H), 2.00-1.83 (ser. m., 2H), 1.74-1.65 (m, 1 H), 1.46 (d, J=6.2 Hz, 3 H), 1.40-1.31 (ser. m., 2 H), 1.13-1.02 (m, 2 H).

Step 2

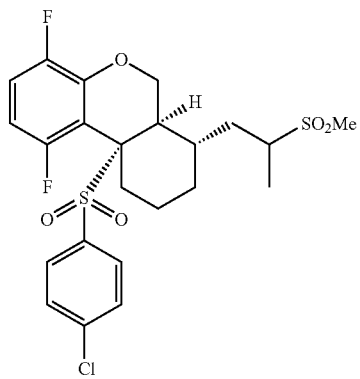

78A (−)

Mesylate 77A (−) was converted to sulfone 78A (−) using a procedure analogous to that used in Scheme 16, Step 6. MS: Calcd. for $C_{23}H_{26}ClF_2O_5S_2$ (M+1)$^+$, m/z=519.09.; found 519.3. Retention time: 4.38 min.

Step 3

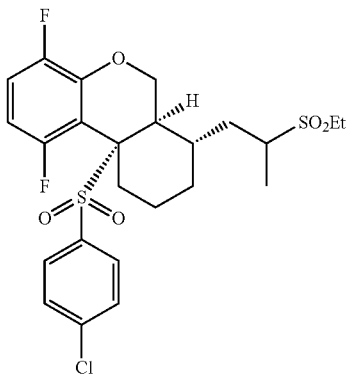

79A (−)

Mesylate 77A (−) was converted to sulfone 79A (−) using a procedure analogous to that used in Scheme 16, Step 12. MS: Calcd. for $C_{24}H_{28}ClF_2O_5S_2$ (M+1)$^+$, m/z=533.10; found 533.3. Retention time: 4.66 min.

Step 4

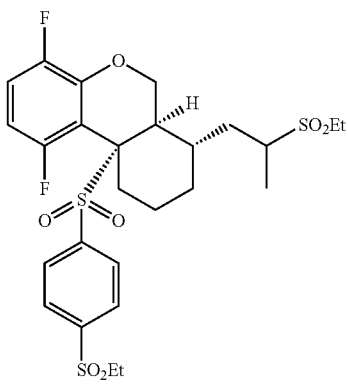

80A (−)

A solution of 0.088 mmol of mesylate 77A (−) in a mixture of 1.0 mL THF and 1.0 mL of DMF was treated with 100 mg (1.19 mmol) of sodium ethylthiolate. After 1 hr of stirring the reaction mixture was worked up using water and ethyl acetate. Organic phase was dried over MgSO$_4$ and concentrated. The product was re-dissolved in a mixture 0.88 mL of acetone and 0.22 mL of water and treated with 215 mg (0.35 mmol) of oxone. After 2 hrs of stirring the solids were filtered out and the product was placed on a preparative TLC plate and eluted with a mixture of 80% of ethyl acetate and 20% hexanes to furnish 9.0 mg of sulfone 80A (−). MS: Calcd. for $C_{26}H_{33}F_2O_7S_3$ (M+1)$^+$, m/z=591.14; found 591.3. Retention time: 4.11 min.

Scheme 18:

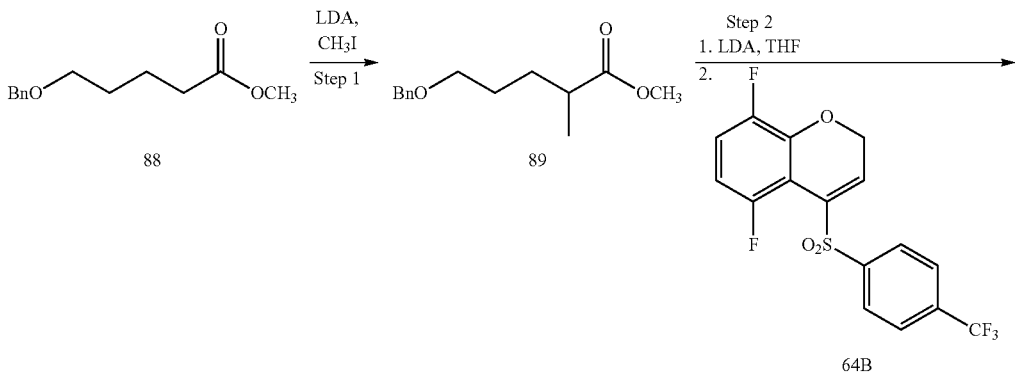

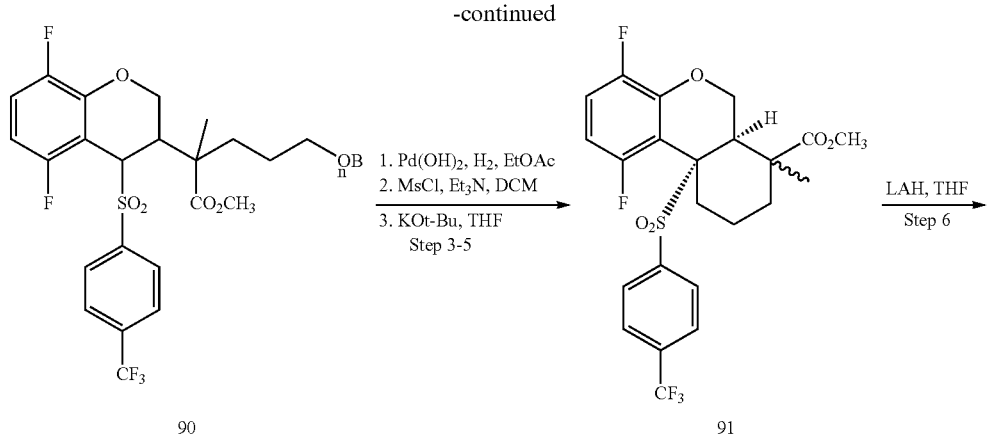

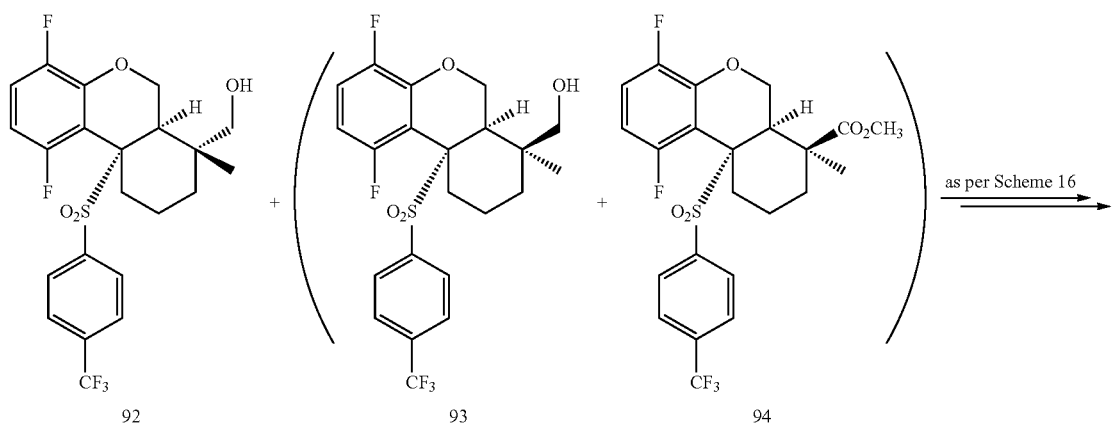

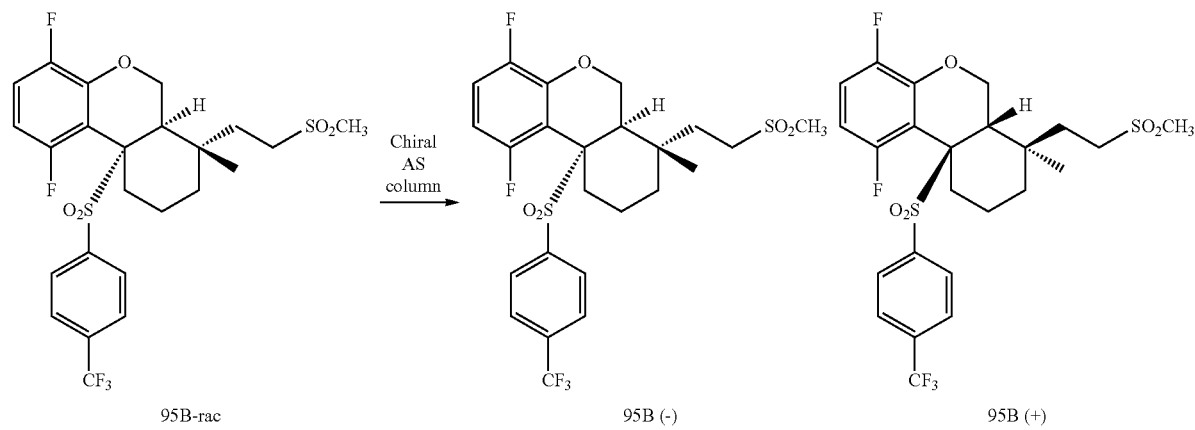

Step 1

At 0° C., to diisopropylamine (15 g, 1.1 equiv.) in 300 mL of THF was added 60 mL of n-BuLi (2.5 M in toluene, 0.15 mol, 1.1 equiv.) dropwise within 10 mins, and the reaction mixture was stirred for an additional 10 mins. The reaction was cooled to −78° C. and methyl ester 88 in 100 mL of THF was added within 20 minutes. The reaction was stirred for 30 minutes, followed by the addition of 21 g of iodomethane (0.15 mol, 1.1 equiv.) in 100 mL of THF dropwise over 30 mins. The reaction mixture was stirred for an hour with temperature slowly rising to r.t. The reaction was quenched with 500 mL of brine, and diluted with 1 L of EtOAc. The organic layer was separated, washed with 200 mL of brine, dried over $Na_2SO_4$ and concentrated. The crude reaction mixture was purified by the column chromatography over silica gel eluting with a gradient from 100% hexanes to 25% EtOAc/Hexane over 45 mins to give 20.0 g of compound 89 (63% yield). $^1$H-NMR (CDCl3 400 MHz) δ: 7.40-7.20 (m, 5 H), 4.49 (s, 2 H), 3.66 (s, 3 H), 3.46 (t, J=6.59, 2 H), 2.52-2.40 (m, 1 H), 1.78-1.46 (m, 4 H), 1.16 (d, J=6.4 Hz, 2 H).

Step 2

At 0° C., to diisopropylamine (6.1 g, 60 mmol, 3.0 equiv.) in 200 mL of THF was added dropwise 37.5 mL of 1.6 N n-BuLi in hexanes (60.0 mmol, 3.0 equiv.). The reaction was stirred for 10 mins, followed by the addition of 14.1 g of 89 (60 mmol, 3.0 equiv.) in 60 mL of anhydrous THF. The reaction was stirred at 0° C. for another 30 minutes before cooling to −78° C. Vinyl sulfone 64B (6.9 g, 20 mmol, 1.0 equiv.) in 70 mL of THF was cooled to −78° C., and added to the above reaction mixture. The cooling bath was removed and the mixture was stirred for 20 mins, quenched with 400 mL of water, and diluted with 300 mL of EtOAc. The organic layer was washed with 2 200-mL portions of 1N HCl solution, 100 mL of brine, dried over $Na_2SO_4$ and concentrated. The crude reaction mixture was purified by the column chromatography over silica gel eluting with a gradient from hexanes to 20% EtOAc/Hexane over 45 mins to give 9.7 g of compound 90 (78% yield) as a mixture of diastereomers. This material was used directly in the next reaction.

Steps 3-5

To 9.7 g of 90 (16 mmol, 1.0 equiv.) in 200 mL of EtOAc was added 1 g of $Pd(OH)_2$ and the mixture was stirred under 1 atm of $H_2$ at r.t. for 30 mins. The catalyst was filtered through a pad of celite, and solvent was removed in vacuo. The crude reaction mixture was dissolved in 200 mL of dichloromethane, followed by the addition of 8 mL $Et_3N$ and 5 mL of methanesulfonyl chloride. The reaction was stirred at r.t. for 10 mins, and quenched with 200 mL of water and diluted 100 mL of dichloromethane. The organic layer was separated, washed with 200 mL of 1N HCl solution, 200 mL of brine, dried over $Na_2SO_4$, and concentrated in vacuo. The residue was dissolved in 200 mL of anhydrous THF, followed by the addition of 40 mL of KOt-Bu (1M in t-BuOH). The mixture was stirred at r.t. for 10 mins and 300 mL of EtOAc was added. The organic layer was washed with 2 100-mL portions of brine, dried over $Na_2SO_4$ and concentrated. The crude reaction mixture was purified by column chromatography over silica gel eluting with a gradient from hexanes to 25% EtOAc/Hexane over 45 mins, to give 7.3 g of a mixture of two diastereomers 91 (14.4 mmol, 90% yield for three steps). MS: Calcd for $C_{23}H_{22}F_5O_5S$ [M-$HSO_2C_6H_4CF_3$+H]$^+$: m/z=295.2 (5.01 min), 295.2 (5.12 min).

Step 6

To 7.3 g of the mixture 91 (14.4 mmol, 1.0 equiv.) in 200 mL of THF was added 0.7 g LAH (18.4 mmol, 1.3 equiv.). The reaction was stirred at r.t. for 35 mins and the TLC showed starting material and two new spots. The reaction was quenched with 100 mL of 1N HCl and diluted with 300 mL of EtOAc. The organic layer was separated, washed with 200 mL of 1N HCl, 100 mL of brine, dried over $MgSO_4$ and concentrated. The crude reaction mixture was purified by column chromatography over silica gel three times eluting with a gradient from hexanes to 40% EtOAc/Hexane over 30 mins to give three different compounds: recovered trans-isomer 94, trans-isomer 93 and 3.5 g of alcohol 92 (7.3 mmol). Alcohol 92: [1] H-NMR (CDCl$_3$ 400 MHz) δ: 7.82-7.66 (m, 4 H), 7.10-7.03 (m, 1 H), 6.42-6.32 (m, 1 H), 5.14 (dd, J=4.8, 12.8 Hz, 1 H), 4.71 (d, J=12.4 Hz, 1 H), 3.68 (d, J=10.8 Hz, 1 H), 3.29 (d, J=12.0 Hz, 1 H), 3.00 (d, J=4.8 Hz, 1 H), 2.59 (d, J=13.2 Hz, 1 H), 2.01-1.90 (m, 1 H), 1.79-1.62 (m, 2 H), 1.39-1.18 (m, 2 H), 0.65 (s, 3 H). MS: Calcd for $C_{22}H_{22}F_5O_4S$ (M+1)$^+$ m/z=477.1, found 477.3, Rt=4.69 min Using procedures analogous to those in Scheme 16, compound 95B-rac was prepared. MS: Calcd for $C_{24}H_{26}F_5O_5S_2$ (M+1)$^+$ m/z=553.1, found 533.3, Rt=4.60 min. This compound was resolved on a Chiralpak AS column to give the following enantiomers:

Compound 95B(−)

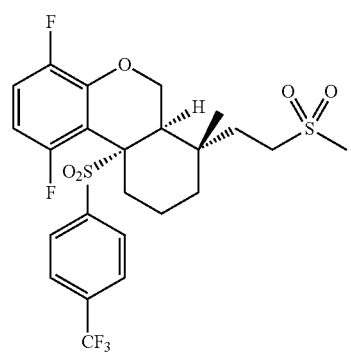

95B (−)

MS: Calcd for $C_{24}H_{26}F_5O_5S_2$ (M+1)$^+$ m/z=553.1, found 533.3, Rt=4.65 min.

Compound 95B(+)

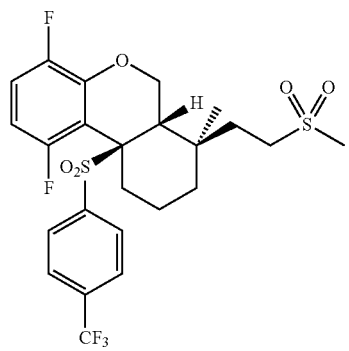

95B (+)

MS: Calcd for $C_{24}H_{26}F_5O_5S_2$ (M+1)$^+$ m/z=553.1, found 533.3, Rt=4.65 min.

Scheme 19:

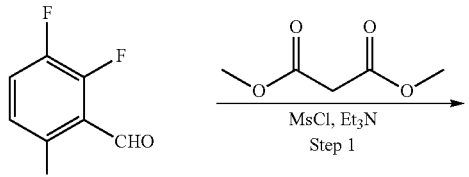

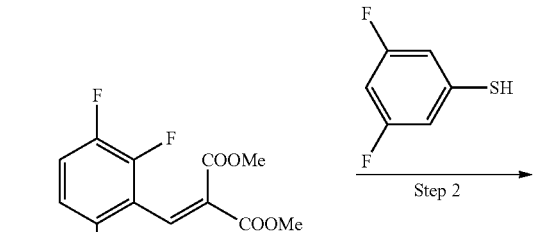

1

221
-continued
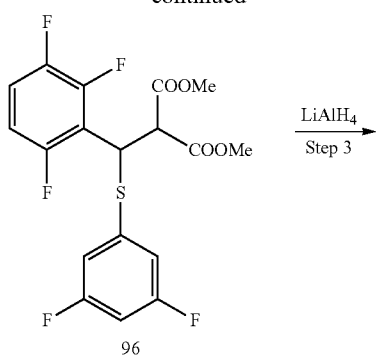
96
LiAlH₄
Step 3
→
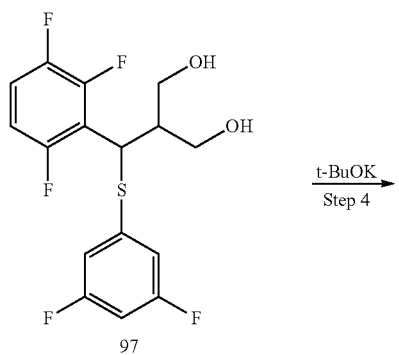
97
t-BuOK
Step 4
→
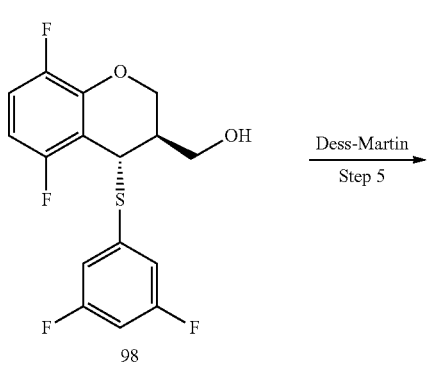
98
Dess-Martin
Step 5
→
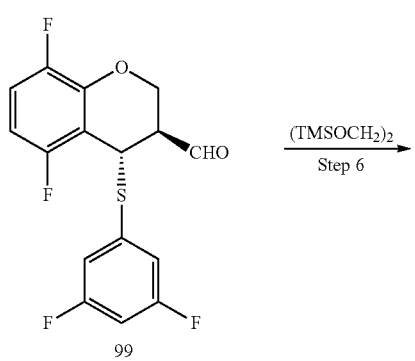
99
(TMSOCH₂)₂
Step 6
→
222
-continued
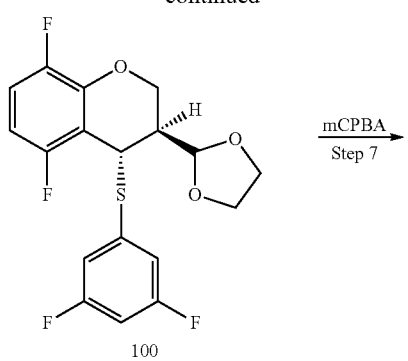
100
mCPBA
Step 7
→
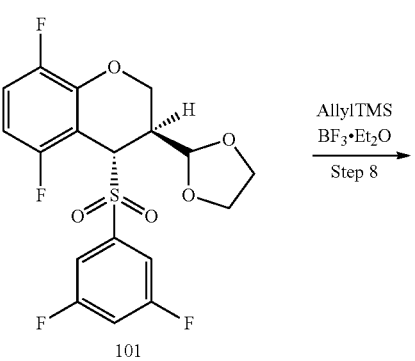
101
AllylTMS
BF₃·Et₂O
Step 8
→
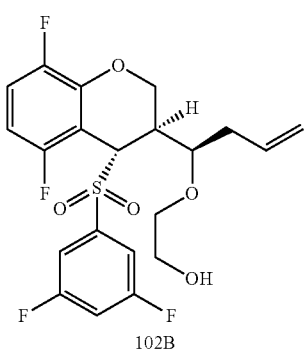
102B
+
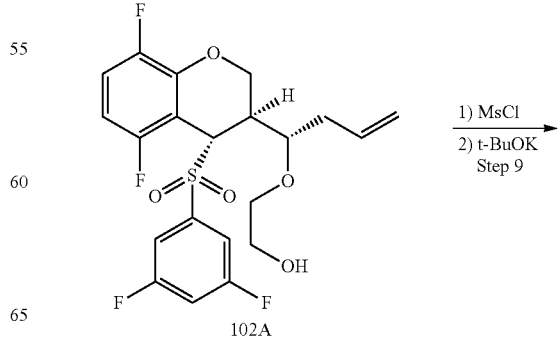
102A
1) MsCl
2) t-BuOK
Step 9
→

223

-continued

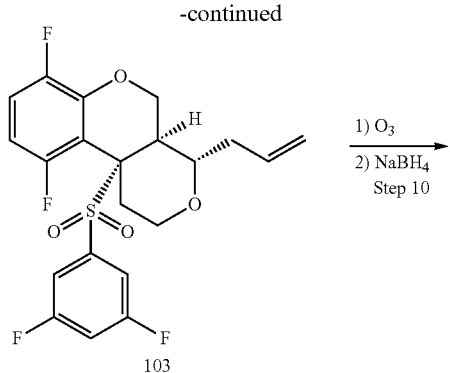
103

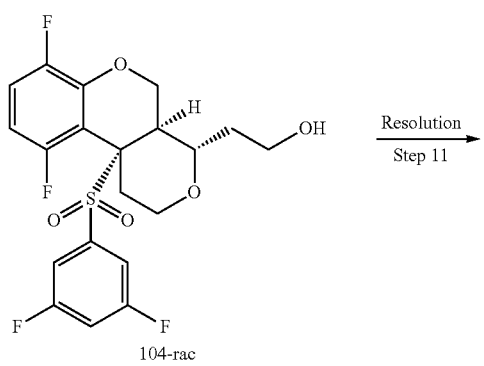
104-rac

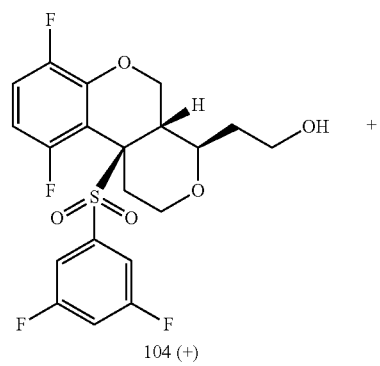
104 (+)

+

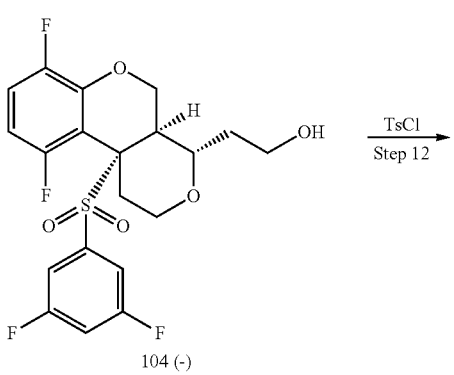
104 (−)

1) O₃
2) NaBH₄
Step 10
→

Resolution
Step 11
→

TsCl
Step 12
→

224

-continued

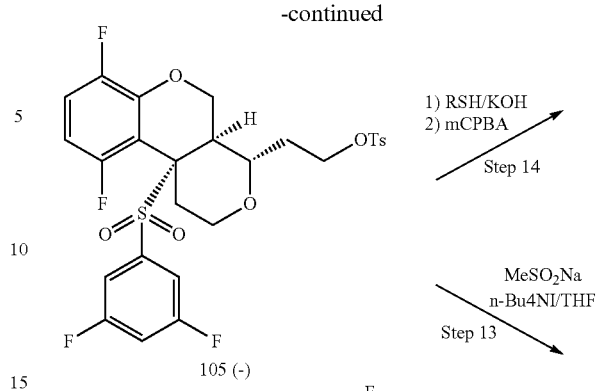
105 (−)

1) RSH/KOH
2) mCPBA
Step 14
→

MeSO₂Na
n-Bu4NI/THF
Step 13
→

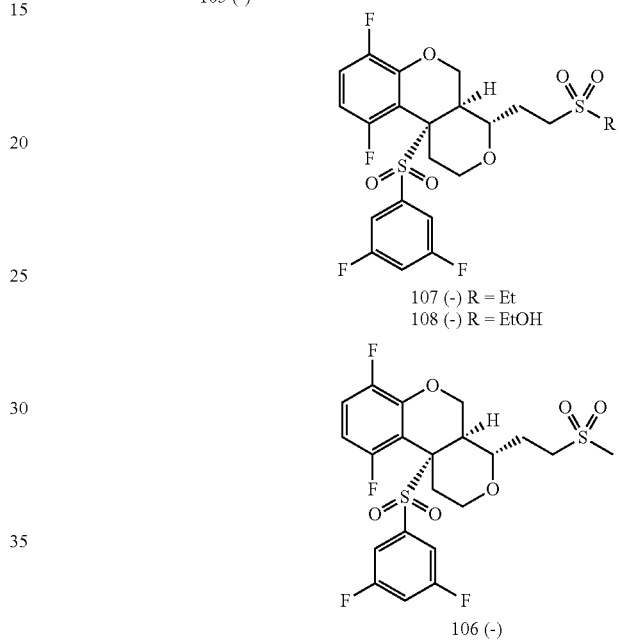

107 (−) R = Et
108 (−) R = EtOH 106 (−)

Step 1
  See Process Example 2 below.
Step 2
  To a solution of 20 g (72.9 mmol) of compound 1 and 10.7 g (72.9 mmol) of 3,5-difluorothiophenol in 500 mL of tetrahydrofuran was added 10.1 g (72.9 mmol) of potassium carbonate. After 5 h, it was quenched with 300 mL of water, extracted with two 300 mL portions of ethyl acetate. The combined organic extracts were washed with brine, concentrated and filtered. The filtrate was concentrated to give 31 g of crude compound 96. $^1$ H NMR (CDCl₃ 400 MHz) δ 7.03 (m, 1 H), 6.93 (m, 2 H), 6.79 (m, 2 H), 5.15 (d, J=12 Hz, 1 H), 4.35 (d, J=12 Hz, 1 H), 3.84 (s, 3 H), 3.57 (s, 3 H).
Step 3
  To a stirred suspension of 6.5 g (170 mmol) of lithium aluminum hydride in 600 mL of tetrahydrofuran was added at 0° C. a solution of 34 g (80.8 mmol) of compound 96 in 100 mL of tetrahydrofuran over a period of 1 h. It was stirred at room temperature for 2 h and quenched with 15 mL of water (cooled with ice-water bath). After addition of 500 mL of 6 N HCl, it was extracted with two 500 mL portions of ethyl ether followed by two 500 mL portions of ethyl acetate. The combined organic extracts were washed with brine, concentrated, and the residue was purified by chromatography eluting with a gradient of 8% to 90% of ethyl acetate in hexanes to give 9.1 g of compound 97. $^1$ H NMR (CDCl₃ 400 MHz) δ 7.05 (m, 1 H), 6.90 (m, 2 H), 6.80 (m, 1 H), 6.66 (m, 1 H), 4.99 (d, J=12

Hz, 1 H), 4.33 (m, 1 H), 4.21 (d, J=11 Hz, 1 H), 3.85 (dd, J=11, 2.4 Hz, 1 H), 3.50 (m, 1 H), 2.46 (m, 1 H), 2.20 (br s, 2 H).

Step 4

To a stirred solution of 9.1 g (25 mmol) of compound 97 in 50 mL of tetrahydrofuran cooled to 0° C. was added a solution of 27.5 mL (27.5 mmol) of potassium tert-butoxide (1.0M in THF). It was stirred at room temperature for 1.5 h and quenched with 100 mL of 1 N HCl. The reaction mixture was extracted with three 100 mL portions of dichloromethane. The combined organic extracts were concentrated, and the residue was purified by chromatography eluting with a gradient of 5% to 40% of ethyl acetate in hexanes to give 6.0 g of compound 98. $^1$H NMR (CDCl$_3$ 400 MHz) δ 7.04 (m, 3 H), 6.71 (m, 1 H), 6.59 (m, 1 H), 4.68 (s, 1 H), 4.57 (dd, J=11, 2.2 Hz, 1 H), 4.44 (d, J=11.7 Hz, 1 H), 3.76 (m, 1 H), 3.58 (m, 1 H), 2.32 (m, 1 H), 1.62 (s, 1 H).

Step 5

To a stirred solution of 6 g (17.4 mmol) of compound 98 in 100 mL of dichloromethane was added 8.9 g (21 mmol) of Dess-Martin periodinane. The mixture was stirred at room temperature for 2 h, concentrated in vacuo and diluted with 100 mL of ethyl ether. It was stirred with 100 mL of saturated sodium bicarbonate and 100 mL of 10% sodium thiosulfate solution and extracted twice with ethyl ether. The combined organic extracts were washed three times with saturated sodium bicarbonate, dried over magnesium sulfate and filtered. The filtrate was concentrated to give 6.0 g of aldehyde 99. $^1$H NMR (CDCl$_3$ 400 MHz) δ 9.74 (d, J=1.5 Hz, 1 H), 7.02 (m, 3 H), 6.78 (m, 1 H), 6.64 (m, 1 H), 5.00 (s, 1 H), 4.94 (d, J=11.7 Hz, 1 H), 4.74 (d, J=11.7 Hz, 1 H), 2.88 (s, 1 H).

Step 6

To a stirred solution of 6.0 g (17.4 mmol) of compound 99 in 90 mL of dichloromethane were added 4.31 g (20.9 mmol) of 1,2-bis(trimethylsiloxy)ethane and 0.39 g (1.75 mmol) of trimethylsilyl trifluoromethanesulfonate at −78° C. After 30 min, it was warmed to room temperature and stirred for 12 h. The reaction was diluted with dichloromethane and washed with three 100 mL portions of saturated sodium bicarbonate, and water. The organic phase was concentrated to give 6.1 g of compound 100. $^1$H NMR (CDCl$_3$ 400 MHz) δ 7.01 (m, 3 H), 6.68 (m, 1 H), 6.59 (m, 1H), 4.83 (s, 1 H), 4.81 (dd, J=7.3, 2.2 Hz, 1 H), 4.60 (dd, J=11.7, 2.2 Hz, 1 H), 4.56 (dd, J=11.7, 2.2 Hz, 1 H), 3.94 (m, 5 H), 2.18 (d, J=7.3 Hz, 1 H).

Step 7

To a stirred solution of 6.1 g (15.8 mmol) of compound 100 in 150 mL of dichloromethane was added 7.9 g (32 mmol) of 3-chloroperoxybenzoic acid. After 2 h, the reaction mixture was diluted with 200 mL of dichloromethane and washed with four 200 mL portions of saturated sodium bicarbonate. It was filtered, concentrated and the residue was purified by chromatography eluting with a gradient of 12% to. 100% of dichloromethane in hexanes to give 4.7 g of compound 101. $^1$H NMR (CDCl$_3$ 400 MHz) δ 7.39 (m, 2 H), 7.14 (m, 1 H), 7.02 (m, 1 H), 6.41 (m, 1 H), 4.86 (dd, J=11.7, 3.7 Hz, 1 H), 4.73 (m, 2 H), 4.66 (dd, J=11.7, 1.5 Hz, 1 H), 3.99-3.79 (m, 3 H), 2.89 (m, 1 H).

Step 8

A solution of 4.7 g (11.2 mmol) of compound 101, 6.4 g (56 mmol) of allyltrimethylsilane and 7.9 g (56 mmol) of boron trifluoride etherate in 75 mL of dichloromethane was stirred at room temperature for 1 day. Additional 3.2 g (28 mmol) of allyltrimethylsilane and 4.0 g (28 mmol) of boron trifluoride etherate were added, and the mixture was stirred at reflux for another day. An Additional 3.2 g (28 mmol) of allyltrimethylsilane and 4.0 g (28 mmol) of boron trifluoride etherate were added, and the mixture was stirred at reflux for another two days. The reaction was cooled (ice bath) and quenched dropwise with 50 mL of saturated sodium bicarbonate, and extracted with two 100 mL potions of dichloromethane followed by two 100 mL portions of ethyl acetate. The combined organic extracts were concentrated and the residue was purified by chromatography eluting with a gradient of 8% to 66% of ethyl acetate in hexanes to give 2.3 g of compound 102A and 1.3 g of 102B. 102A: $^1$H NMR (CDCl$_3$ 400 MHz) δ 7.39 (m, 2 H), 7.14 (m, 1 H), 7.07 (m, 1H), 6.49 (m, 1 H), 5.82 (m, 1 H), 5.20 (d, J=11.7 Hz, 1 H), 4.97 (s, 1 H), 4.86 (dd, J=12.4, 2.9 Hz, 1 H), 4.53 (s, 1 H), 4.43 (dd, J=12.4, 1.5 Hz, 1 H), 3.67 (m, 3 H), 3.22 (m, 1 H), 3.13 (m, 1 H), 2.90 (m, 1 H), 2.54 (m, 1 H), 1.57 (m, 1 H). 102B: $^1$H NMR (CDCl$_3$ 400 MHz) δ 7.35 (m, 2 H), 7.14 (m, 1 H), 7.06 (m, 1 H), 6.48 (m, 1 H), 5.72 (m, 1 H), 5.11 (d, J=10.3 Hz, 1 H), 5.07 (d, J=16.8 Hz, 1 H), 4.80 (dd, J=12.4, 2.9 Hz, 1 H), 4.67 (d, J=11.7 Hz, 1 H), 4.53 (s, 1 H), 3.67 (m, 3 H), 3.50 (m, 1 H), 3.30 (m, 1 H), 2.92 (m, 1 H), 2.35 (m, 1 H), 1.85 (m, 1 H).

Step 9

To a solution of 2.3 g (5.37 mmol) of compound 102A in 50 mL of dichloromethane were added 1.04 g (10.2 mmol) of triethylamine and 0.92 g (8.06 mmol) of methanesulfonyl chloride. The mixture was stirred at room temperature for 1 h. It was quenched with 80 mL of 1N HCl and extracted with two 100 mL portions of dichloromethane. The combined organic extracts were washed with saturated sodium bicarbonate, concentrated and the residue was dissolved in 50 mL of tetrahydrofuran and cooled to 0° C. To this solution was added 12 mL (12 mmol) of 1 N potassium tert-butoxide in THF. The mixture was stirred at room temperature for 15 min., quenched with 100 mL of saturated ammonium chloride and extracted with two 100 mL portions of ethyl acetate. The combined organic extracts were washed with brine, concentrated and the residue was purified by chromatography eluting with a gradient of 2% to 20% of ethyl acetate in hexanes to give 0.90 g of compound 103. $^1$H NMR (CDCl$_3$ 400 MHz) δ 7.24 (m, 2 H), 7.11 (m, 2 H), 6.47 (m, 1 H), 5.85 (m, 1 H), 5.11 (m, 3 H), 4.46 (d, J=13.2 Hz, 1 H), 3.93 (m, 1 H), 3.37 (m, 1 H), 3.15 (dd, J=11.6, 11.6 Hz, 1 H), 2.65 (m, 3 H), 2.40 (m, 1 H), 2.31 (m, 1 H).

Step 10

To a stirred solution of 900 mg (2.03 mmol) of compound 103 in 20 mL of 1:1 dichloromethane/methanol at −78° C. was bubbled with O$_3$ until blue color sustained. It was bubbled with N$_2$ to remove excess O$_3$. To this solution was added 230 mg (6.0 mmol) of sodium borohydride and warmed to 0° C. The mixture was stirred at room temperature. After 30 min, and additional 300 mg (7.94 mmol) of sodium borohydride was added. After 14 h, the reaction mixture was quenched with 20 mL saturated ammonium chloride and concentrated. The residue was extracted with two 100 mL portions of dichloromethane and the combined extracts were washed with saturated sodium bicarbonate and dried over magnesium sulfate to give 800 mg of compound 104-rac. $^1$H NMR (CDCl$_3$ 400 MHz) δ 7.25 (m, 2 H), 7.16 (m, 2 H), 6.49 (m, 1 H), 5.11 (dd, J=12.4, 2.2 Hz, 1 H), 4.46 (d, J=12.4 Hz, 1 H), 3.93 (m, 1 H), 3.79 (t, J=5.9 Hz, 2 H), 3.50 (ddd, J=12.4, 9.5, 2.9 Hz, 1 H), 3.20 (dd, J=11.7, 11.7 Hz, 1 H), 2.68 (d, J=11 Hz, 1 H), 2.55 (d, J=13.2 Hz, 1 H), 2.34 (m, 3 H), 2.11 (m, 1 H), 1.83 (m, 2 H).

Step 11

Compound 104-rac (800 mg) was resolved on Chiral OD column eluting with 20% isopropanol in hexanes and 40 mL/min flow rate to give two enantiomers 104 (+) (310 mg, retention time 49-68 min, [α]$_D^{20}$+95.5°) and 104 (−) (310 mg, retention time 71-88 min., [α]$_D^{20}$−89.9°).

Step 12

A solution of 305 mg (0.683 mmol) of compound 104 (−), 195 mg (1.02 mmol) of p-toluenesulfonyl chloride and 138 mg (1.4 mmol) of triethylamine in 7 mL of dichloromethane was stirred at room temperature for 6 h. Dimethylaminopyridine (10 mg) was added and the reaction stirred for 14 h. It was quenched with 80 mL of saturated ammonium chloride and extracted with two 80 mL portions of dichloromethane. The combined organic extracts were washed with saturated sodium bicarbonate, concentrated and the residue was purified by chromatography eluting with a gradient of 8% to 66% of ethyl acetate in hexanes to give 348 mg of compound 105 (−). $^1$H NMR (CDCl$_3$ 400 MHz) δ 7.73 (dd, J=8.8, 2.2 Hz, 2 H), 7.31 (dd, J=8.8, 1.5 Hz, 2 H), 7.23 (m, 2 H), 7.14 (m, 2 H), 6.51 (m, 1 H), 5.05 (dd, J=13.2, 2.9 Hz, 1H), 4.31 (d, J=12.4 Hz, 1 H), 4.18 (m, 2 H), 3.78 (m, 1 H), 3.27 (m, 1 H), 2.97 (dd, J=12.4, 11.7 Hz, 1 H), 2.51 (d, J=11.7 Hz, 1 H), 2.42 (s, 3 H), 2.26 (m, 1 H), 2.18 (m, 1 H), 1.79 (m, 1 H).

Step 13

A mixture of 75 mg (0.124 mmol) of compound 105 (−) and 138 mg (0.375 mmol) of tetrabutylammonium iodide in 4 mL of tetrahydrofuran was stirred at reflux for 1.5 h. After addition of 50 mg (0.50 mmol) of sodium methanesulfinate, the mixture was stirred at reflux for 18 h and diluted with 80 mL of saturated ammonium chloride. It was extracted with 80 mL of ethyl acetate, and the organic extract was washed with saturated sodium bicarbonate, brine, concentrated and the residue was purified by chromatography eluting with a gradient of 8% to 66% of ethyl acetate in hexanes to give 54 mg of compound 106 (−). $^1$H NMR (CDCl$_3$ 400 MHz) δ 7.24 (m, 2 H), 7.13 (m, 2 H), 6.50 (m, 1 H), 5.13 (dd, J=12.4, 2.9 Hz, 1 H), 4.48 (d, J=12.4 Hz, 1 H), 3.94 (m, 1 H), 3.36 (m, 1 H), 3.28 (m, 1 H), 3.15 (dd, J=12.4, 11.7 Hz, 1 H), 3.01 (m, 1 H), 2.91 (s, 3 H), 2.57 (m, 2 H), 2.44 (m, 1 H), 2.32 (m, 1 H), 2.04 (m, 1 H). MS: Calcd. for C$_{21}$H$_{21}$F$_4$O$_6$S$_2$ (MH$^+$), 509.6; found 509.3. Retention time: 4.20 min.

Step 14

A mixture of 50 mg (0.08 mmol) of compound 105 (4 and 10.6 mg (0.17 mmol) of ethanethiol and 8 mg (0.15 mmol) of potassium hydroxide was stirred at 50° C. for 1 h and diluted with saturated ammonium chloride. The reaction mixture was extracted with three 20 mL portions of dichloromethane. The combined organic extracts were concentrated and the crude sulfide product was dissolved in 1 mL of dichloromethane. To this solution was added 50 mg (0.29 mmol) of 70% 3-chloroperoxybenzoic acid. After stirring at room temperature for 14 h, it was diluted with 20 mL of saturated sodium carbonate and extracted with three 20 mL portions of ethyl acetate. The combined organic extracts were washed with brine and concentrated. The residue was purified by preparative thin layer chromatography eluting with 33% of ethyl acetate in hexanes to give 35.8 mg of compound 107 (−). $^1$H NMR (CDCl$_3$ 400 MHz) δ 7.26 (m, 2 H), 7.16 (m, 2 H), 6.50 (m, 1 H), 5.16 (d, J=13.2, Hz, 1 H), 4.48 (d, J=12.4 Hz, 1 H), 3.91 (m, 1 H), 3.36 (m, 1 H), 3.22 (m, 1 H), 3.15 (dd, J=12.4, 11.7 Hz, 1 H), 3.01 (m, 3 H), 2.59 (d, J=13.2 Hz, 2 H), 2.45 (m, 1H), 2.32 (m, 1 H), 2.02 (m, 1 H), 1.40 (t, J=7.3 Hz, 3 H). MS: Calcd. for C$_{22}$H$_{23}$F$_4$O$_6$S$_2$ (MH$^+$), 523.1; found 523.3. Retention time: 4.29 min.

Step 14 (alternate)

A mixture of 50 mg (0.08 mmol) of compound 105 (−) and 105 mg (0.280 mmol) of tetrabutylammonium iodide in 2 mL of tetrahydrofuran was stirred at reflux for 3.5 h. The reaction mixture was diluted with 50 mL of ethyl ether, washed with 1N HCl, saturated sodium bicarbonate, dried and concentrated. The residue was dissolved in 1 mL of ethanol and 26 μL (0.37 mmol) of β-mercaptoethanol and 10 mg (0.18 mmol) of potassium hydroxide was stirred at 50° C. for 1 h and diluted with saturated ammonium chloride. The reaction mixture was extracted with three 20 mL portions of dichloromethane. The combined organic extracts were concentrated and the crude sulfide product was dissolved in 1 mL of dichloromethane. To this solution was added 60 mg (0.35 mmol) of 70% 3-chloroperoxybenzoic acid. After stirring at room temperature for 14 h, it was diluted with 20 mL of saturated sodium carbonate and extracted with three 20 mL portions of dichloromethane. The combined organic extracts were concentrated. The residue was purified by preparative thin layer chromatography eluting with 67% of ethyl acetate in hexanes to give 39.4 mg of compound 108 (−). $^1$H NMR (CDCl$_3$ 400 MHz) δ 7.24 (m, 2 H), 7.14 (m, 2 H), 6.50 (m, 1 H), 5.11 (d, J=12.4, Hz, 1 H), 4.49 (d, J=12.4 Hz, 1 H), 4.11 (m, 2 H), 3.90 (d, J=11.7 Hz, 1 H), 3.36 (m, 2 H), 3.21 (m, 2 H), 3.14 (m, 2 H), 2.57 (m, 2 H), 2.45 (m, 1 H), 2.31 (m, 1 H), 2.06 (m, 1 H). MS: Calcd. for C$_{22}$H$_{23}$F$_4$O$_7$S$_2$(MH$^+$), 539.1; found 539.3. Retention time: 3.88 min.

Scheme 20:

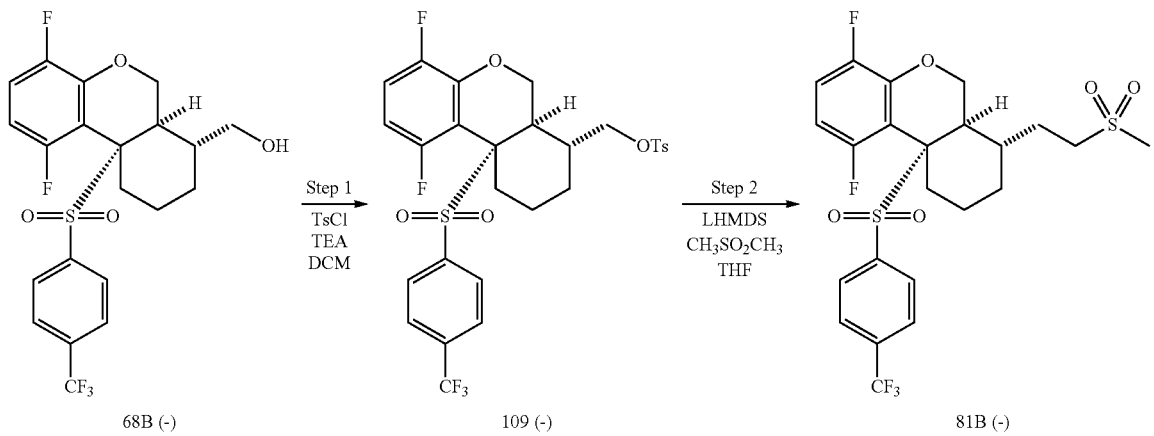

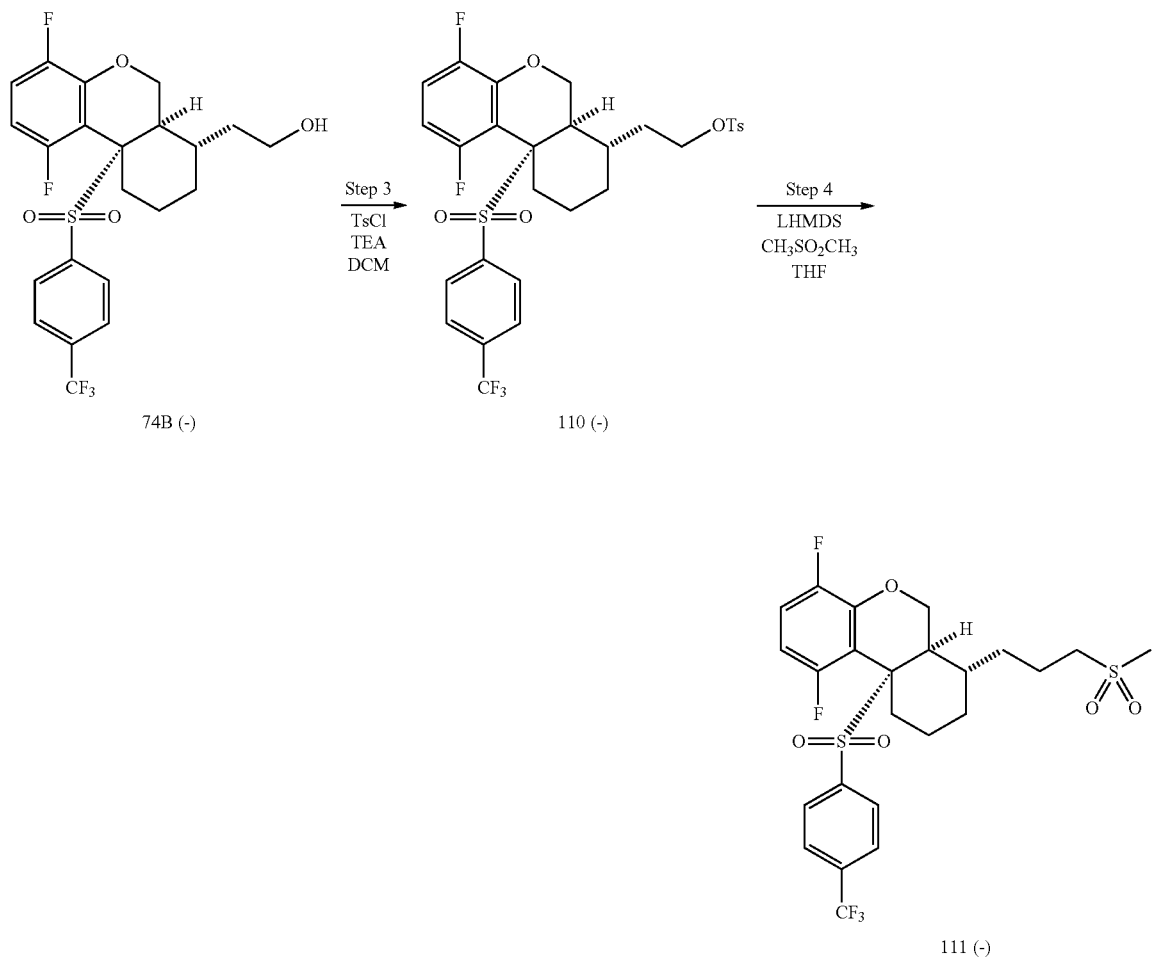

Compound 68B (−) was prepared similar to Scheme 16, Steps 1-4 starting with vinyl sulfone 64B and resolved on a Chiralcel OD column.

Step 1

To a solution of 0.165 g of alcohol 68B (−) (0.357 mmol) in dichloromethane (10 mL) was added 0.15 mL of Et$_3$N (0.1 mmol,) and 0.137 g of TsCl (0.718 mmol,) respectively. The mixture was stirred at room temperature overnight. Tosyl chloride (0.14 g) was added and stirred at room temperature overnight. The solvent was removed in vacuo and the product was isolated by silica gel chromatography eluting with a gradient from hexanes to 40% ethyl acetate/hexane to afford 0.21 g of compound 109 (−). $^1$H-NMR (CDCl$_3$ 400 MHz) δ 7.80 (m, 6 H), 7.39 (d, 2 H), 7.08 (m, 1 H), 6.42 (m, 1 H), 5.03 (d, 1 H), 4.24 (d, 1 H), 4.18 (d, 1 H), 4.01 (d, 1 H), 2.65 (d, 1 H), 2.47 (s, 3 H), 1.86 (m, 1 H), 1.71 (m, 1 H), 1.51 (m, 4 H), 1.05 (m, 1 H).

Step 2

To a solution of 0.18 g of dimethyl sulfone (1.9 mmol) in 20 mL of THF at −78° C. was added 1.9 mL of LHMDS (1M solution in THF, 1.9 mmol) and the reaction was stirred for 20 minutes. A solution of 0.12g of 109 (−) (0.19 mmol) in 5 mL of THF was added. The reaction mixture was slowly warmed to room temperature and stirred overnight. The reaction was quenched by the addition of 50 mL of 1N HCl solution and extracted with dichloromethane. The solvent was removed in vacuo and the product was isolated by silica gel chromatography eluting with a gradient from hexanes to 50% ethyl acetate/hexane to afford 0.029 g of compound 81B (−). $^1$H-NMR (CDCl$_3$ 400 MHz) δ 7.79 (m, 4 H), 7.07 (m, 1 H), 6.44 (m, 1 H), 5.20 (d, 1 H), 4.48 (d, 1 H), 3.07 (m, 1 H), 2.98 (m, 1 H), 2.96 (s, 3 H), 2.55 (d, 1 H), 2.44 (d, 1 H), 2.25 (m, 1 H), 1.89 (m, 3 H), 1.60 (m, 2 H), 1.16 (m, 2 H). MS: Calcd. for C$_{23}$H$_{24}$F$_5$O$_5$S$_2$ (MH$^+$), m/z=539.10; found 539.3. Retention time: 4.56 min.

The primary alcohol 74B (−) was prepared analogously to the reactions in Scheme 16, Steps 8-10 from compound 68B (−). It was tosylated according to the procedure Scheme 20 (this scheme), Step 1 to give tosylate 110 (−): $^1$H-NMR (CDCl$_3$ 400 MHz) δ 7.83 (m, 6 H), 7.40 (d, 2 H), 7.08 (m, 1 H), 6.46 (m, 1 H), 5.05 (d, 1 H), 4.34 (d, 1 H), 4.28 (d, 1 H), 4.11 (d, 1 H), 2.65 (d, 1 H), 2.48 (s, 3 H), 1.9 (m, 3 H), 1.71 (m, 1 H), 1.51 (m, 4 H), 1.15 (m, 1 H).

Tosylate 110 (−) was converted to sulfone 111 (−) according to the procedure in Step 2 (above). $^1$H-NMR (CDCl$_3$ 400 MHz) δ 7.79 (m, 4 H), 7.08 (m, 1 H), 6.43 (m, 1 H), 5.18 (d, 1 H), 4.58 (d, 1 H), 3.00 (m, 2 H), 2.98 (s, 3 H), 2.52 (d, 1 H), 2.43 (d, 1 H), 1.78 (m, 6 H), 1.45 (s, 1 H), 1.40 (m, 1 H), 1.05 (m, 2 H). MS: Calcd. for C$_{24}$H$_{26}$F$_5$O$_5$S$_2$ (MH$^+$), m/z=553.11; found 553.3. Retention time: 4.62 min.

The following examples illustrate the processes of this invention.

Process Example 1

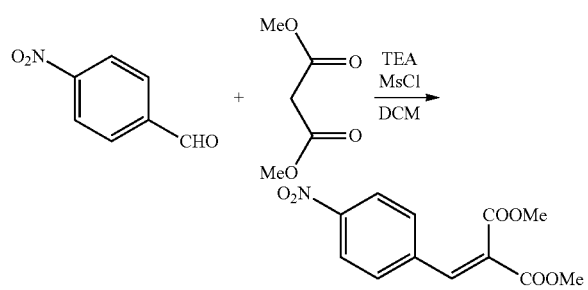

To a solution of 4-nitrobenzaldehyde (3.02 g, 20 mmol) and dimethylmalonate (2.77 g, 21 mmol) in anhydrous dichloromethane (30 ml) under $N_2$ at 5° C. in ice and water bath, was added triethylamine (4.86 g, 48 mmol) over 5 min. The reaction was stirred for 20 min. Methanesulfonyl chloride (2.75 g, 24 mmol) was added over 4 hrs at 5° C. The reaction was stirred for 30 min. Water (20 ml) was added, separated the layers. Aqueous layer was extracted with dichloromethane (20 ml). The Combined dichloromethane layer was washed with water and dried over anhydrous sodium sulfate. It was concentrated to solid (5.7 g) and identified as 2-(4-nitrobenzylidene)-malonic acid dimethyl ester. [1] H NMR ($CDCl_3$): δ 8.25 (d, 2 H), 7.80 (s, 1 H), 7.58 (d, 2 H), 3.88 (s, 3 H), 3.84 (s, 3 H). Mass: [M+1] 266.

Process Example 2

2-(2,3,5-triflorobenzylidene)-malonic acid dimethyl ester

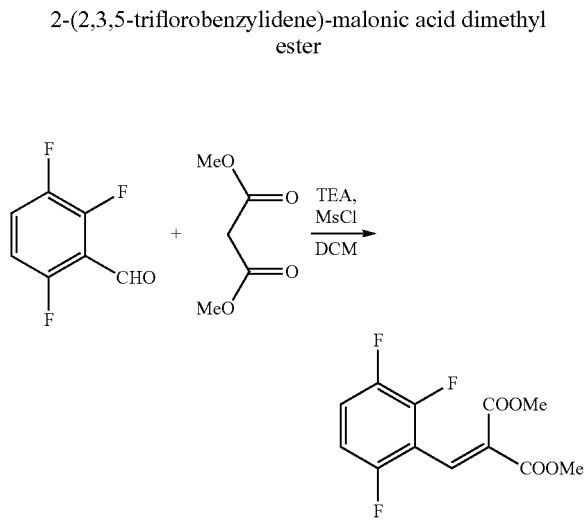

To a solution of 2,3,5-triflorobenzaldehyde (1.6 g, 10 mmol) and dimethylmalonate (1.2 ml, 10.5 mmol) in anhydrous dichloromethane (20 ml) under $N_2$ at room temperature in a water bath, was added triethylamine (2.1 ml, 15.4 mmol). Methanesulfonyl chloride (1.0 ml, 12.8 mmol) was added at room temperature. The reaction was stirred for 1 hr. Additional triethylamine (2.1 ml, 15.4 mmol) was added. After the mixture was stirred for 3 hr at room temperature, additional methanesulfonyl chloride (0.5 ml, 6.4 mmol) and triethylamine (1.5 ml, 10 mmol) were added. The mixture was stirred for 1 hr. Water (50 ml) and ethyl acetate (50 ml) were added, separated the layers. Aqueous layer was extracted with ethyl acetate (50 ml). The combined organic layer was washed with brine and dried over anhydrous sodium sulfate. It was concentrated to oil (3.5 g) and identified as 2-(2,3,5-triflorobenzylidene)-malonic acid dimethyl ester. [1] H NMR ($CDCl_3$): δ 7.20 (m, 1 H), 6.85 (m, 1 H), 3.88 (s, 3 H), 3.84 (s, 3 H). Mass: [M+1] 243.

Process Example 3

2-(4-chlorobenzylidene)-malonic acid dimethyl ester

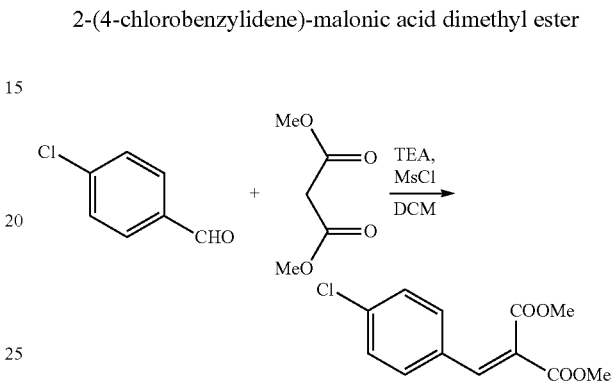

Following a process similar to that of Process Example 1, 4-chlorobenzaldehyde reacts with dimethylmalonate under triethylamine and methanesulfonyl chloride in anhydrous dichloromethane to yield 2-(4-chlorobenzylidene)-malonic acid dimethyl ester.

Process Example 4

2-(benzylidene)-malonic acid dimethyl ester

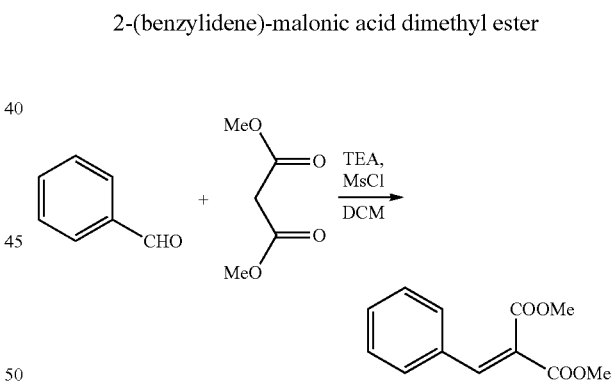

Following a process similar to that of Process Example 1, Benzaldehyde reacts with dimethylmalonate under triethylamine and methanesulfonyl chloride in anhydrous dichloromethane to yield 2-(benzylidene)-malonic acid dimethyl ester.

Assay

The pharmacological properties of the compounds of this invention may be evaluated by a number of pharmacological assays. Gamma secretase activity can be determined by the assay described below.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents.

Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction.

The construct SPC99-Ion, which contains the first 18 residues and the C-terminal 99 amino acids of APP carrying the London mutation, has been described (Zhang, L., Song, L., and Parker, E. (1999) J. Biol. Chem. 274, 8966-8972). Upon insertion into the membrane, the 17 amino acid signal peptide is processed, leaving an additional leucine at the N-terminus of Aβ. SPC99-Ion was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation.

C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37 C before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis.

To measure γ-secretase activity, membranes were incubated at 37° C. for 1 h in 50 µL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

Compounds 12, 13, 22A to 22N, 22B-RAC, 26A, 26B, 27, 28, 31, 33(−), 36, 37, 39, 44A, 44B, 55 to 57, 60, 70A, 71A(−), 75A-rac, 75B(−), 76A(−), 76A(+), 76B(−), 78A(−), 79A(−), 80A(+), 81A-rac, 81A(−), 81A(+), 81B(−), 82A, 83A, 84A, 85A, 85B(−), 86A, 87B, 95B-rac, 95B(−), 95B(+), 106(−), 107(−), 108(−), and 111(−) had a Aβ$_{40}$ IC$_{50}$ in the range of about 6 µM to about 1 nM.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

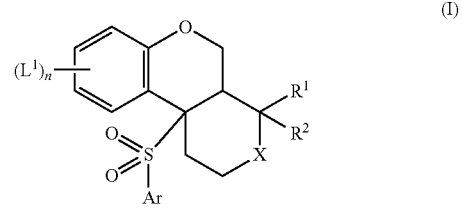

(I)

or a pharmaceutically acceptable salt thereof, wherein:
X is selected from the group consisting of O and CH$_2$;
R$^1$ is selected from the group consisting of: (1) -alkylene-S(O)$_2$—(C$_1$-C$_6$)alkyl, (2) -alkylene-S(O)$_2$—(C$_1$-C$_6$)haloalkyl; (3) -alkylene-S(O)$_2$—R$^6$, (4) -alkylene-S(O)$_2$—R$^8$, (5) -alkylene-S(O)$_2$-substituted(C$_1$-C$_6$)alkyl, (6) -alkylene-(tetrahydrothiophene1,1-dioxide), (7) -alkenyl-S(O)$_2$—(C$_1$-C$_6$)alkyl, and (8) -cycloalkyl-S(O)$_2$—(C$_1$-C$_6$)alkyl;
wherein said -alkylene-S(O)$_2$-substituted(C$_1$-C$_6$)alkyl R$^1$ group is substituted with one or more substituents independently selected from the group consisting of:
—OH, halo, —CN, —CF$_3$, —O—(C$_1$-C$_6$)alkyl, and —O-(halo(C$_1$-C$_6$)alkyl);
R$^2$ is selected from the group consisting of: H and alkyl;
R$^6$ is selected from the group consisting of: (1) unsubstituted (C$_6$-C$_{14}$)aryl, (2) (C$_6$-C$_{14}$)aryl substituted with one or more L$^{1.4}$ groups, (3) unsubstituted (C$_5$-C$_{14}$)heteroaryl, (4) (C$_5$-C$_{14}$)heteroaryl substituted with one or more L$^{1.4}$ groups, (5) unsubstituted (C$_5$-C$_{14}$)heteroarylalkyl-, and (5) (C$_5$-C$_{14}$)heteroarylalkyl- substituted with one or more L$^{1.4}$ groups;
R$^8$ is selected from the group consisting of unsubstituted (C$_3$-C$_{10}$) cycloalkyl and (C$_3$-C$_{10}$) cycloalkyl substituted with one or more L$^3$ groups;
each L$^3$ is independently selected from the group consisting of: (1) —CN, (2) =(O), (3) —CH$_2$OH, (4) amino, (5) halo, (6) —CH$_2$NH$_2$, (7) —CH$_2$NHalkyl, (8) —C(O)OH, (9) -alkylene-C(O)NH(C$_1$ to C$_6$)alkyl, (10) -alkylene-C(O)N((C$_1$ to C$_6$)alkyl)$_2$ wherein each alkyl is independently selected, (11) -alkylene-C(O)NH(C$_1$ to C$_6$)haloalkyl, and (12) -alkylene-C(O)N((C$_1$ to C$_6$)haloalkyl)$_2$ wherein each alkyl is independently selected);
Ar is selected from the group consisting of: (1) unsubstituted aryl, (2) aryl substituted with one or more L$^{1.4}$ groups, (3) unsubstituted heteroaryl, and (4) substituted heteroaryl substituted with one or more L$^{1.4}$ groups;

each L¹ is independently selected from the group consisting of: halogen, $(C_1-C_6)$ alkyl, —CN, —CF$_3$, —O—$(C_1-C_6)$alkyl, —O-(halo$(C_1-C_6)$alkyl), —C(O)—O—$(C_1-C_6)$alkyl, -alkylene-OH, halo$(C_1-C_6)$alkyl, hydroxyalkoxy-, alkoxyalkoxy-, and —S(O)$_2$(C$_1$-C$_6$) alkyl;

each L$^{1A}$ is independently selected from the group consisting of: halogen, alkyl, —CN, —CF$_3$, —O—$(C_1-C_6)$alkyl, —O-(halo$(C_1-C_6)$alkyl), —C(O)—O—$(C_1-C_6)$alkyl, -alkylene-OH, halo$(C_1-C_6)$alkyl, hydroxyalkoxy-, alkoxyalkoxy-, and —S(O)$_2$(C$_1$-C$_6$) alkyl; and n is 0, 1, 2 or 3.

2. The compound of claim 1 having the formula:

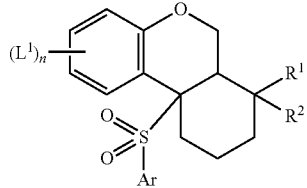
(I.A1)

or a pharmaceutically acceptable salt thereof.

3. The compound of claim 1 having the formula:

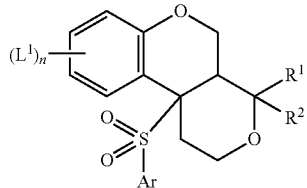
(I.A2)

or a pharmaceutically acceptable salt thereof.

4. The compound of claim 1 or a pharmaceutically acceptable salt thereof, wherein said compound is selected from the group consisting of the compounds of formulas

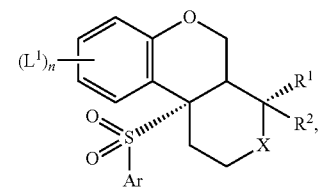
(Ii)

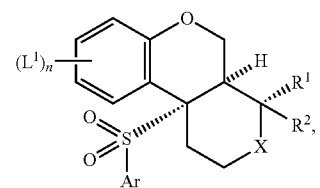
(Iii)

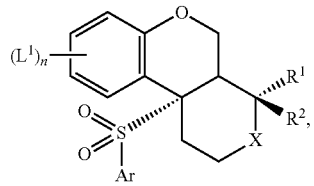
(Iiii)

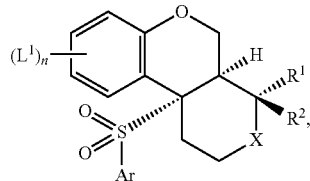
(Iiv)

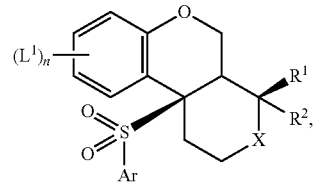
(Iv)

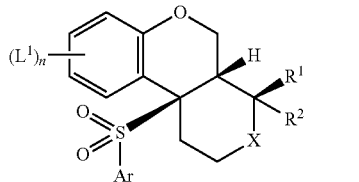
(Ivi)

and

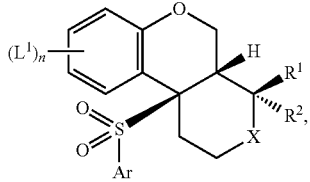
(Ivii)

wherein n is 2, and the L¹ groups are bound to the phenyl moiety as shown in (IIA)

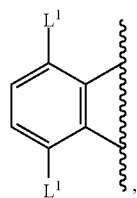
(IIA)

and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl, —CN, —CF$_3$, —O—$(C_1-C_6)$ alkyl, —O-(halo$(C_1-C_6)$alkyl), —C(O)—O—$(C_1-C_6)$alkyl, -alkylene-OH, halo$(C_1-C_6)$alkyl, hydroxyalkoxy-, and alkoxyalkoxy-.

5. The compound of claim 1 or a pharmaceutically acceptable salt thereof, wherein said compound is selected from the group consisting of the compounds of formulas

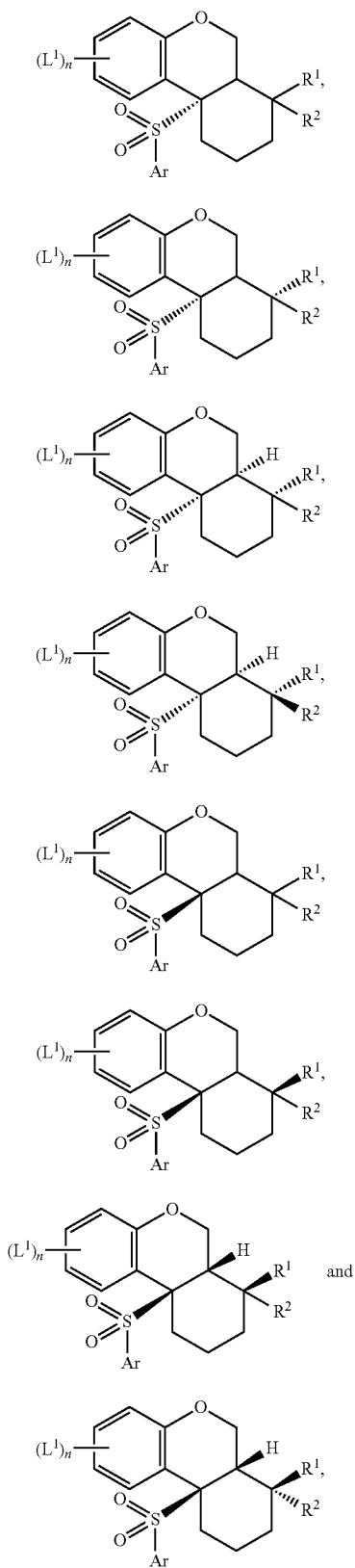

(I.A1a)
(I.A1b)
(I.A1c)
(I.A1d)
(I.A1e)
(I.A1f)
(I.A1g)
(I.A1h)

wherein n is 2, and the $L^1$ groups are bound to the phenyl moiety as shown in (IIA)

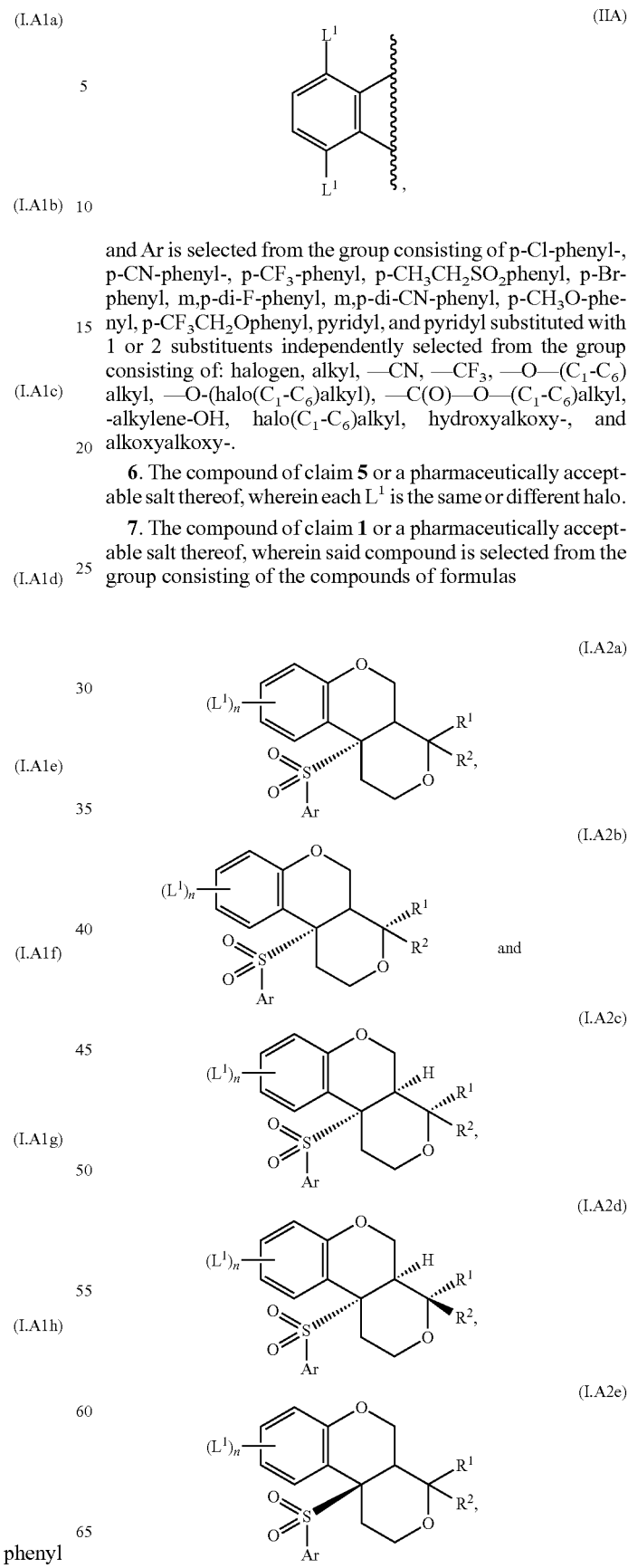

(IIA)

and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$)alkyl, -alkylene-OH, halo(C$_1$-C$_6$)alkyl, hydroxyalkoxy-, and alkoxyalkoxy-.

6. The compound of claim 5 or a pharmaceutically acceptable salt thereof, wherein each $L^1$ is the same or different halo.

7. The compound of claim 1 or a pharmaceutically acceptable salt thereof, wherein said compound is selected from the group consisting of the compounds of formulas (I.A2a)
(I.A2b)
(I.A2c)
(I.A2d)
(I.A2e)

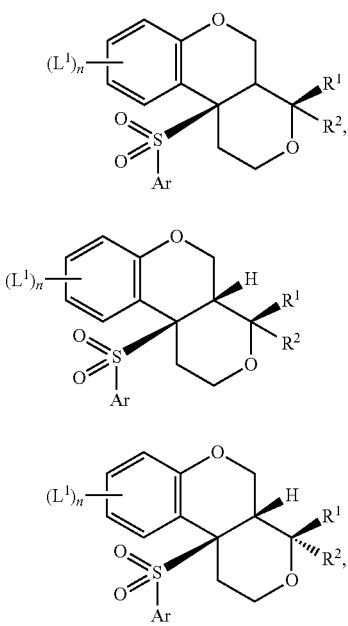

(I.A2f)

(I.A2g) and (I.A2h)

wherein n is 2, and the $L^1$ groups are bound to the phenyl moiety as shown in (IIA)

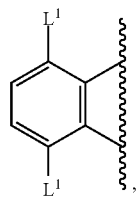

(IIA)

and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$)alkyl, -alkylene-OH, halo(C$_1$-C$_6$)alkyl, hydroxyalkoxy-, and alkoxyalkoxy-.

8. The compound of claim 1 or a pharmaceutically acceptable salt thereof, wherein $R^1$ is selected from the group consisting of:

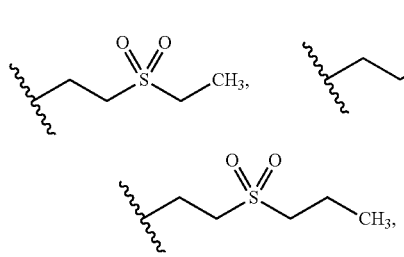

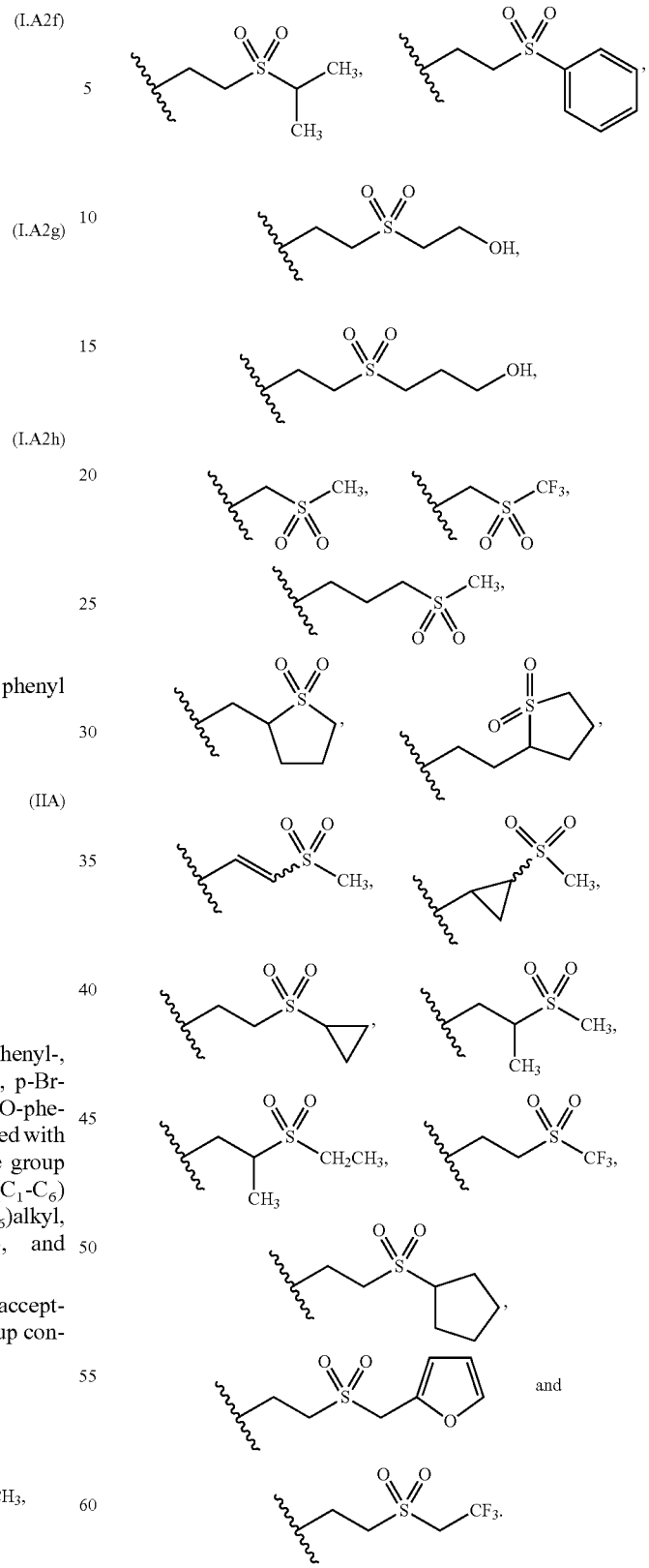

9. The compound of claim 1 or a pharmaceutically acceptable salt thereof, wherein $R^1$ is selected from the group consisting of:

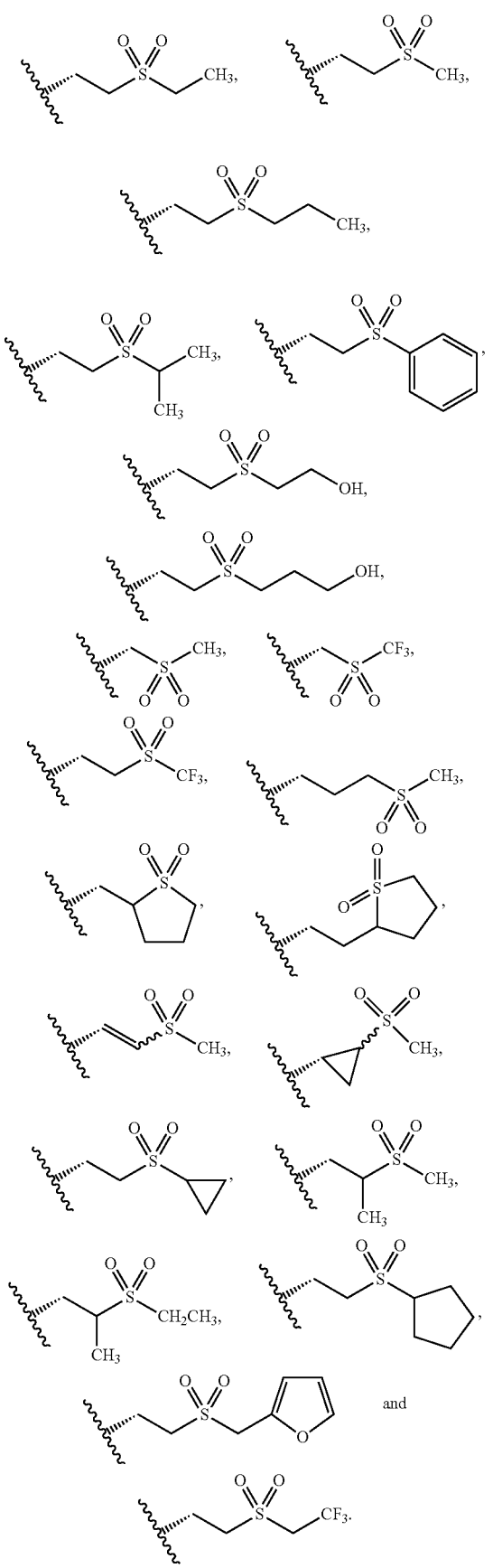
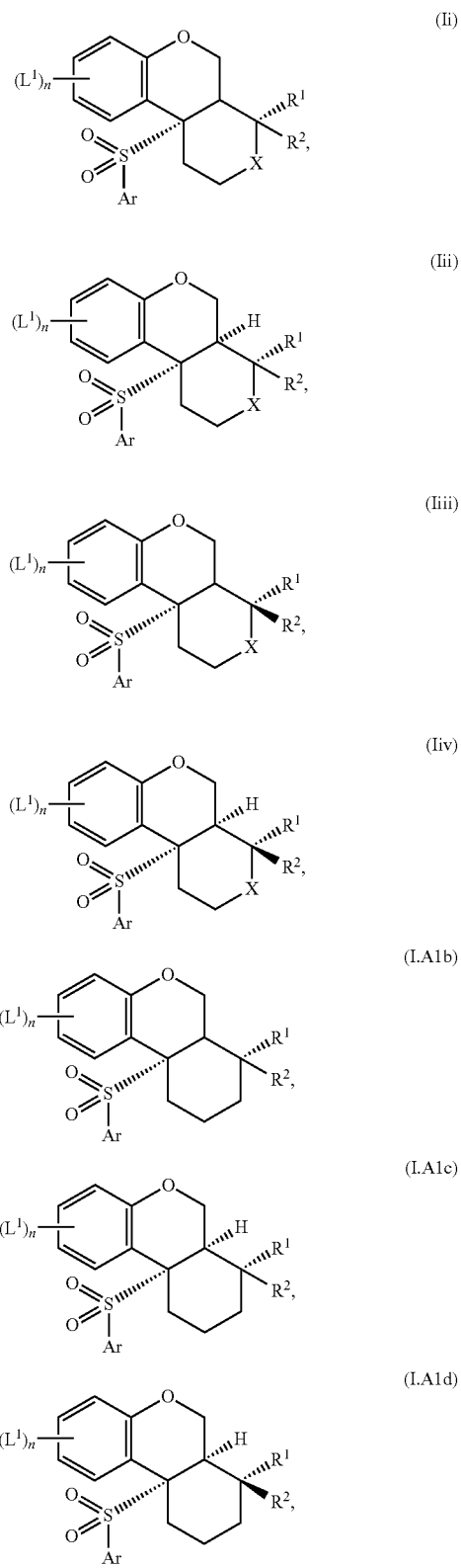
10. The compound of claim 9 or a pharmaceutically acceptable salt thereof, wherein the compound of formula (I) is a compound selected from the group consisting of the compounds of formulas

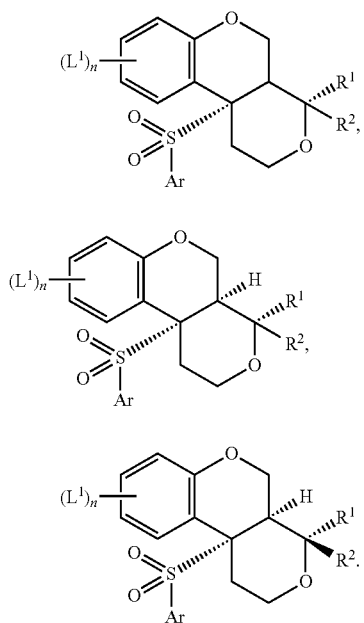

(I.A2b)

(I.A2c) and (I.A2d)

11. The compound of claim 10 or a pharmaceutically acceptable salt thereof, wherein n is 2, and the $L^1$ groups are bound to the phenyl moiety as shown in (IIA)

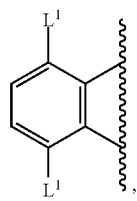

(IIA)

and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$)alkyl, -alkylene-OH, halo(C$_1$-C$_6$)alkyl, hydroxyalkoxy-, and alkoxyalkoxy-.

12. The compound of claim 11 or a pharmaceutically acceptable salt thereof, wherein each $L^1$ is the same or different halo.

13. The compound of claim 12 or a pharmaceutically acceptable salt thereof, wherein said $L^1$ groups are F.

14. The compound of claim 13 or a pharmaceutically acceptable salt thereof, wherein $R^2$ is selected from the group consisting of: H and methyl.

15. The compound of claim 13 or a pharmaceutically acceptable salt thereof, wherein $R^2$ is alkyl.

16. The compound of claim 1 or a pharmaceutically acceptable salt thereof, wherein $R^1$ is selected from the group consisting of:

17. The compound of claim 16 or a pharmaceutically acceptable salt thereof, wherein

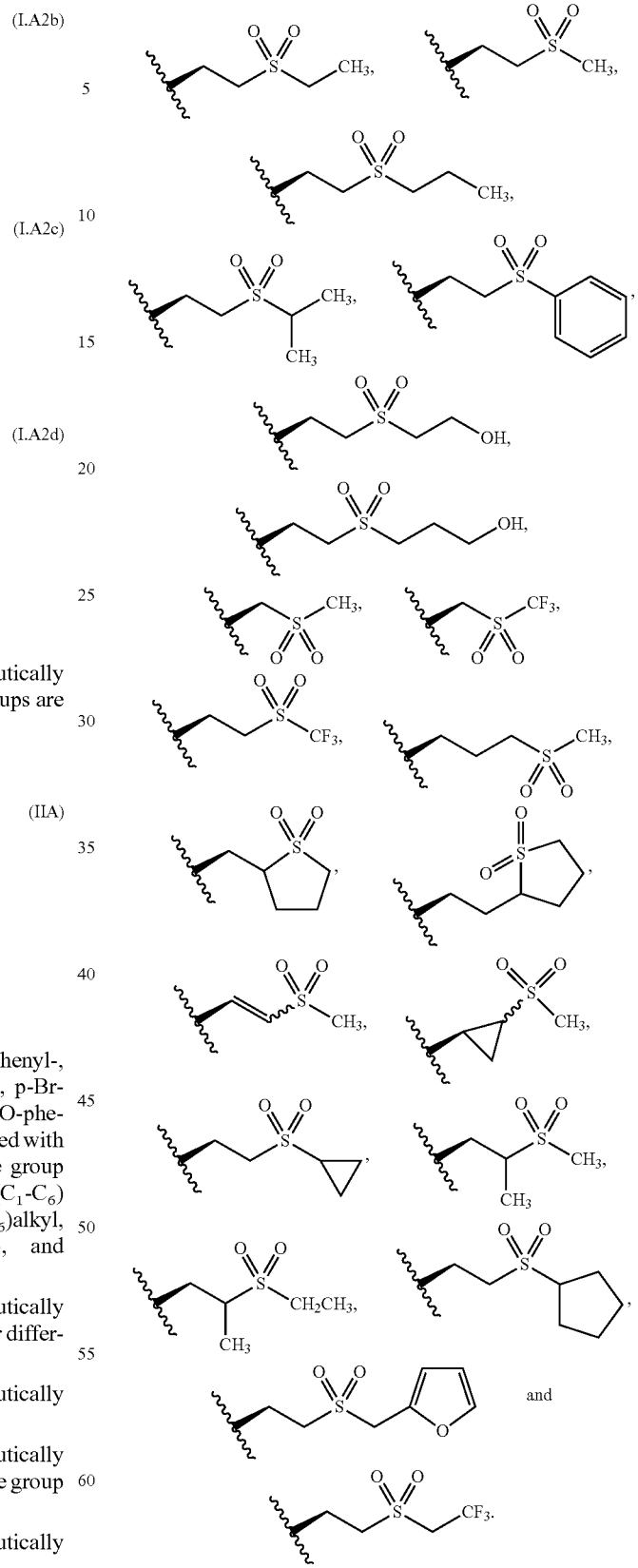

the compound of formula (I) is selected from the group consisting of the compounds of formulas

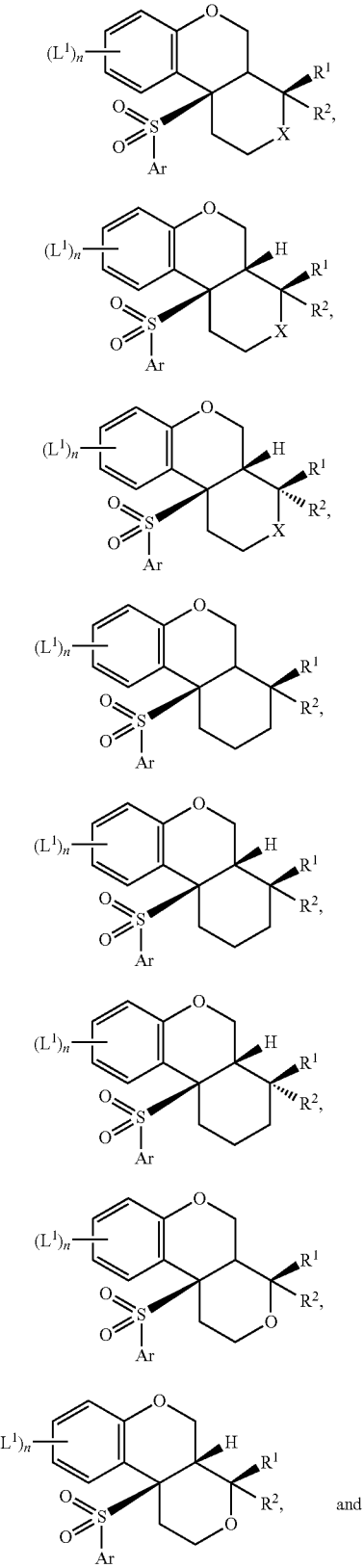

(Iv)

(Ivi)

(Ivii)

(I.A1f)

(I.A1g)

(I.A1h)

(I.A2f)

(I.A2g) and

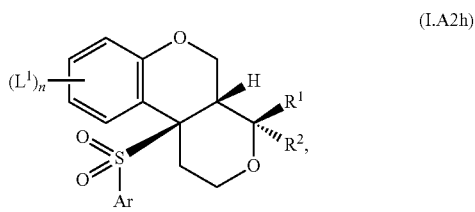

(I.A2h)

and n is 2, and the $L^1$ groups are bound to the phenyl moiety as shown in (IIA)

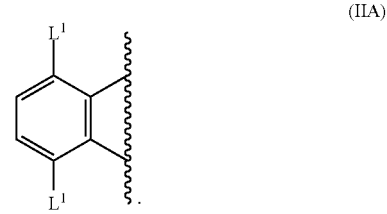

(IIA)

and Ar is selected from the group consisting of p-Cl-phenyl-, p-CN-phenyl-, p-CF$_3$-phenyl, p-CH$_3$CH$_2$SO$_2$phenyl, p-Br-phenyl, m,p-di-F-phenyl, m,p-di-CN-phenyl, p-CH$_3$O-phenyl, p-CF$_3$CH$_2$Ophenyl, pyridyl, and pyridyl substituted with 1 or 2 substituents independently selected from the group consisting of: halogen, alkyl, —CN, —CF$_3$, —O—(C$_1$-C$_6$) alkyl, —O-(halo(C$_1$-C$_6$)alkyl), —C(O)—O—(C$_1$-C$_6$)alkyl, -alkylene-OH, halo(C$_1$-C$_6$)alkyl, hydroxyalkoxy-, and alkoxyalkoxy-, and said $L^1$ groups are F.

18. The compound of claim 17 or a pharmaceutically acceptable salt thereof, wherein $R^2$ is selected from the group of: H and methyl.

19. The compound of claim 1 or a pharmaceutically acceptable salt thereof, selected from the group consisting of

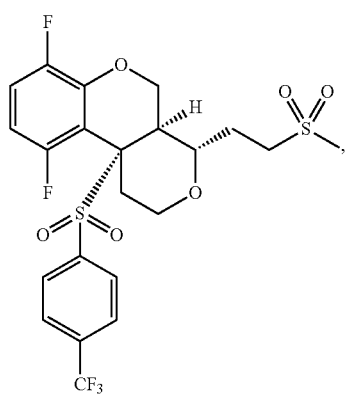

247
-continued
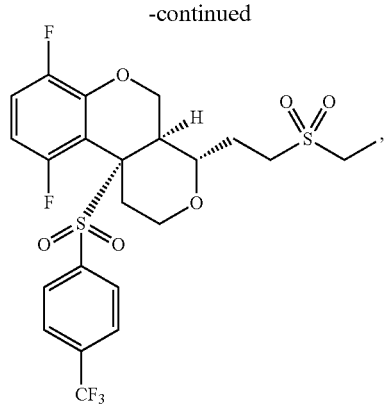
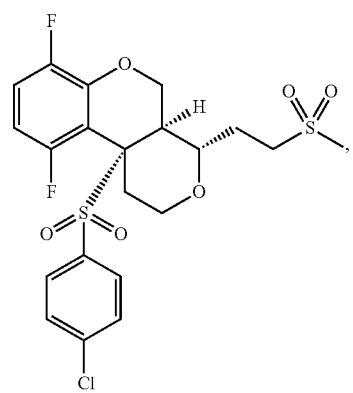
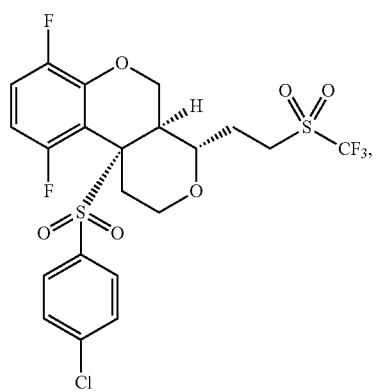
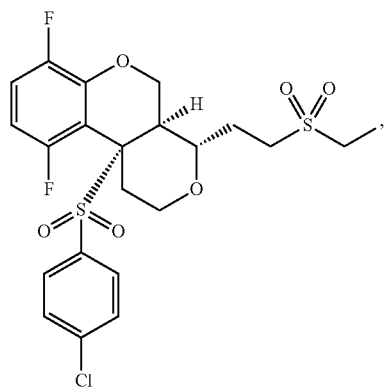
248
-continued
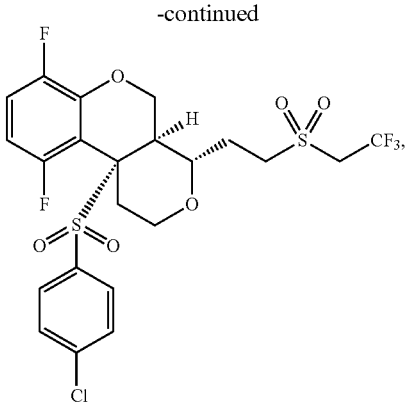
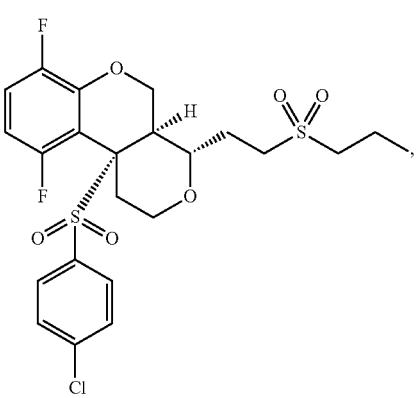
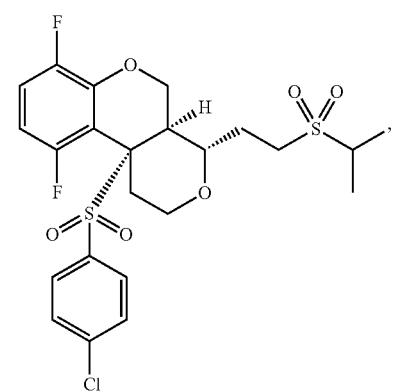
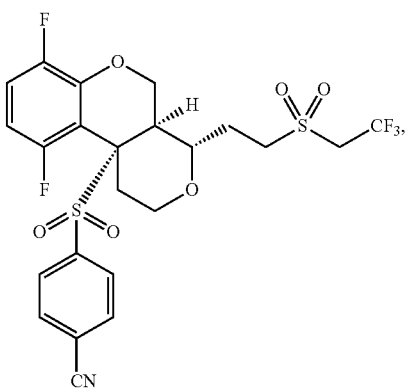

249
-continued
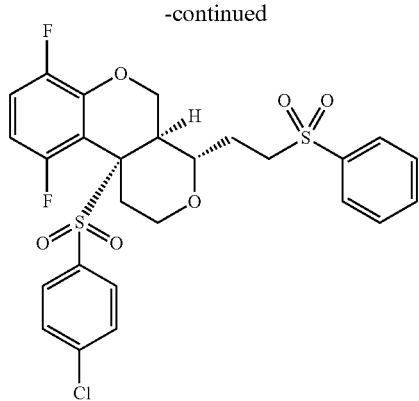
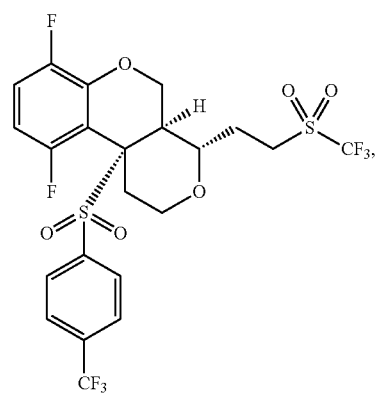
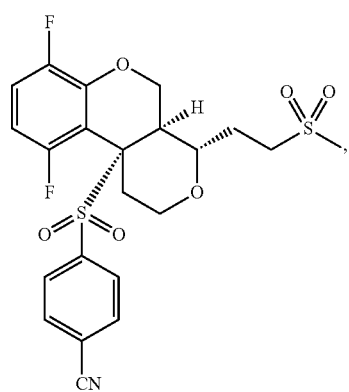
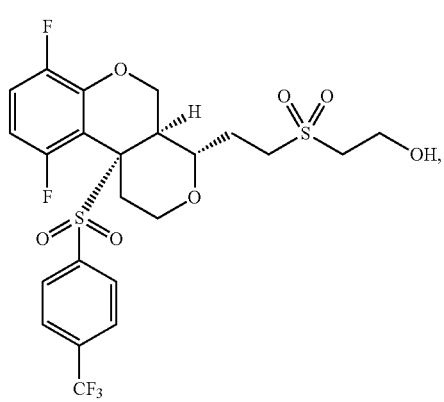
250
-continued
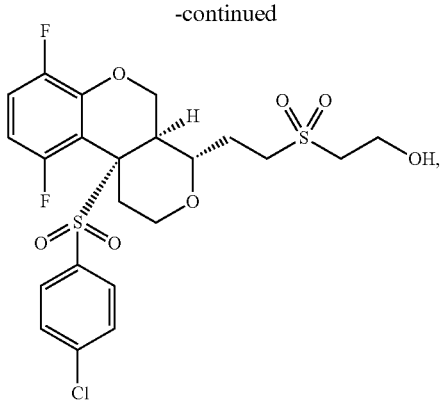
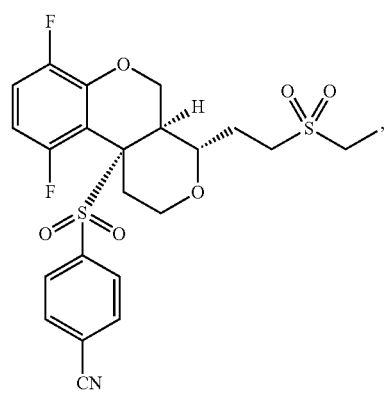
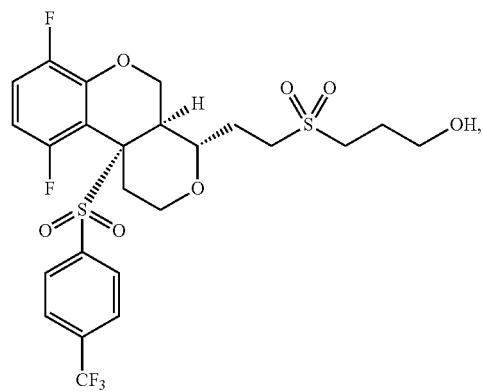
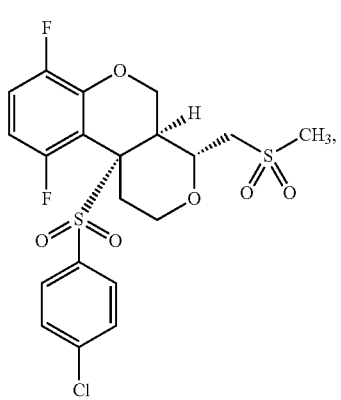

251
-continued
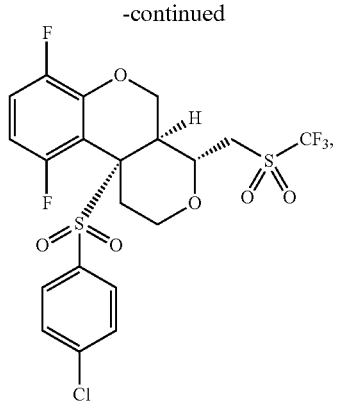
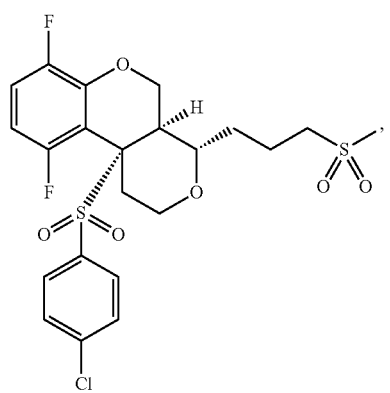
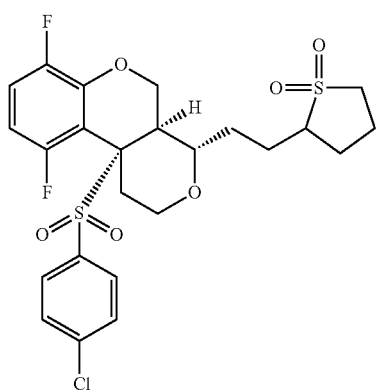
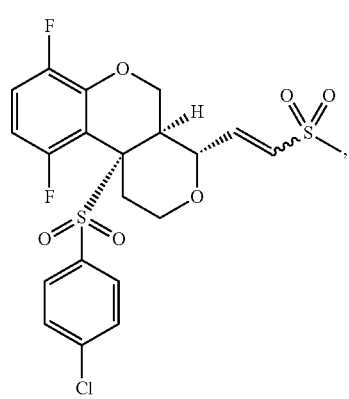
252
-continued
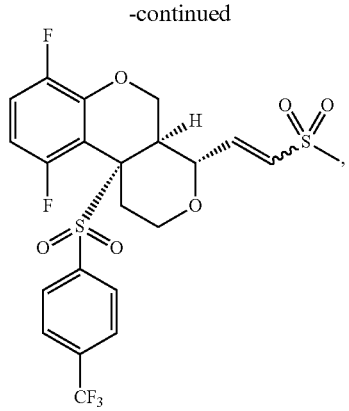
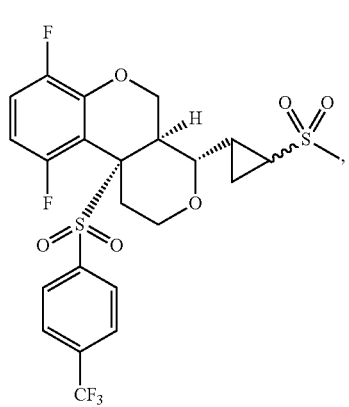
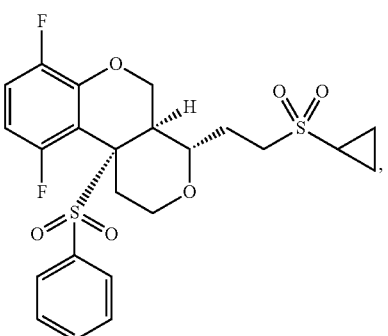
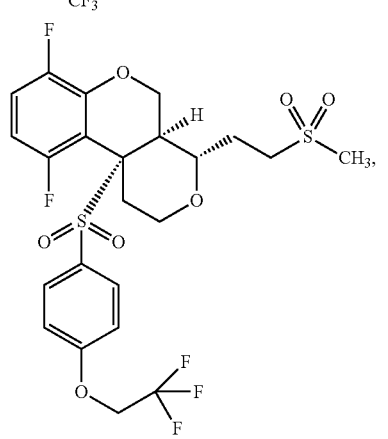

253
-continued
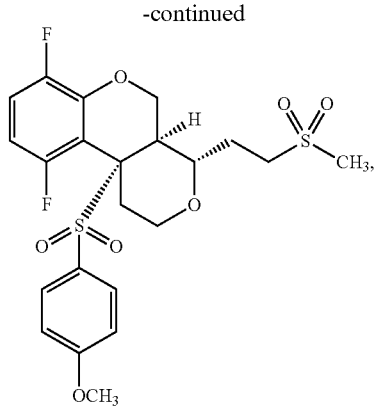
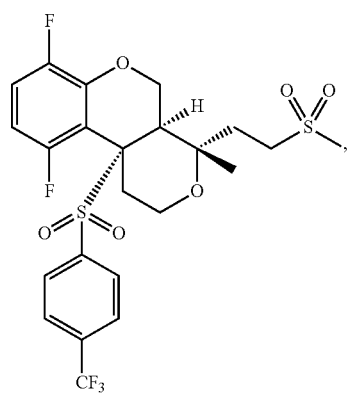
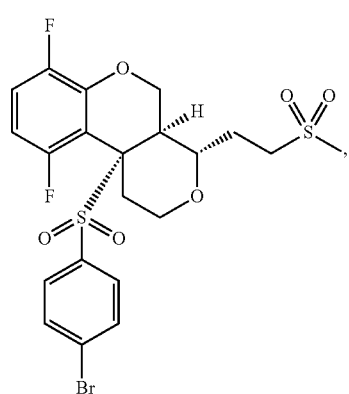
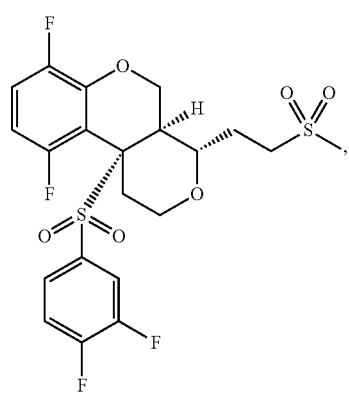
254
-continued
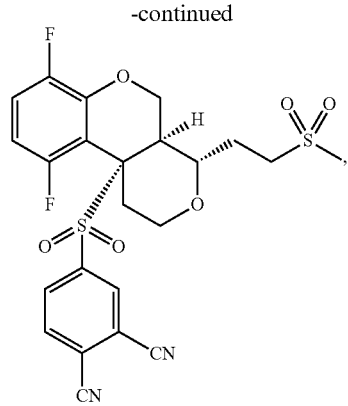
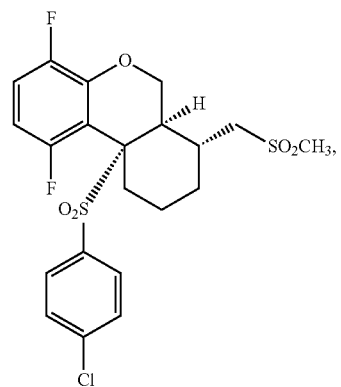
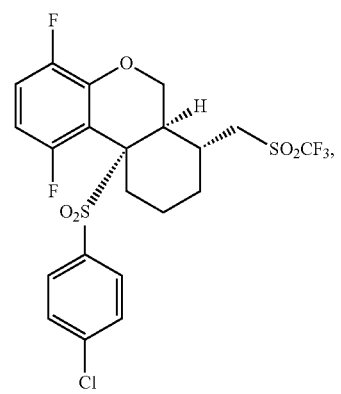
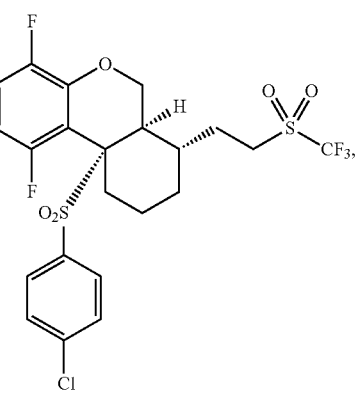

255
-continued
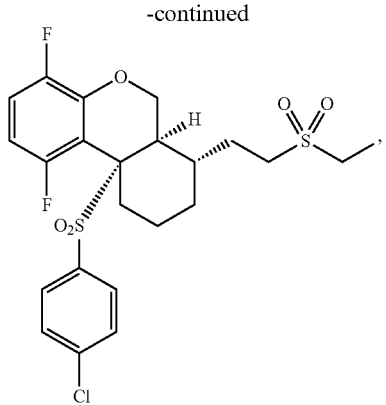
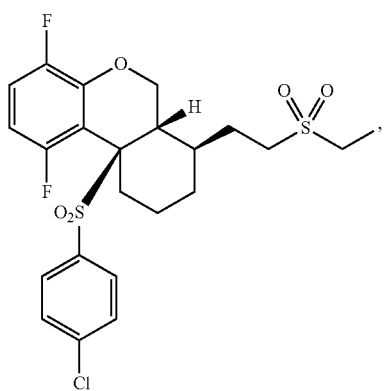
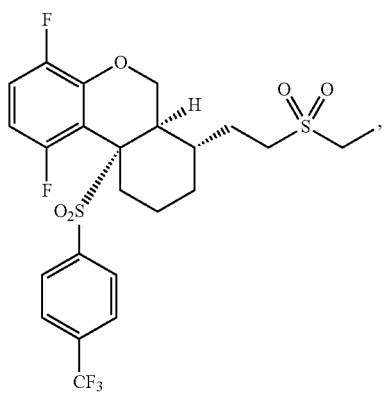
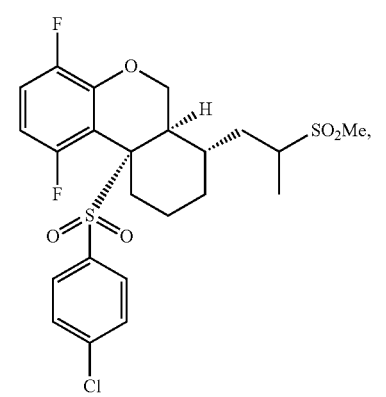
256
-continued
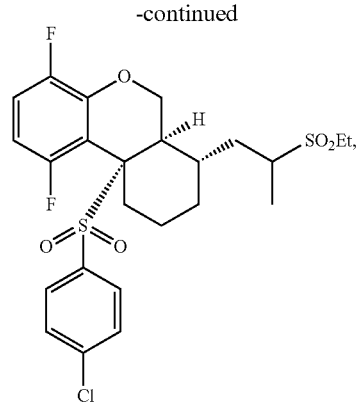
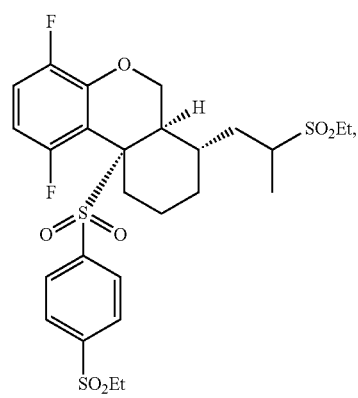
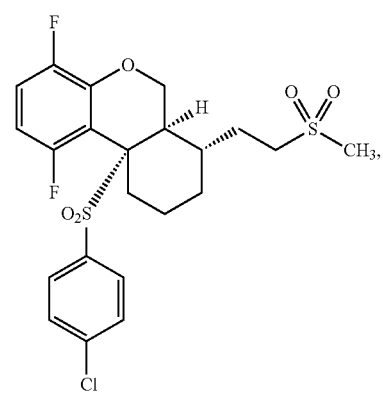
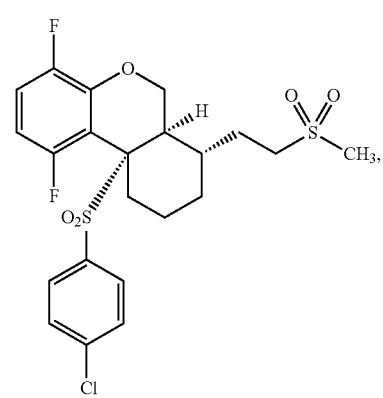

257
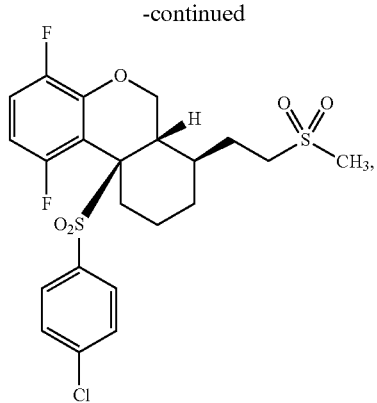
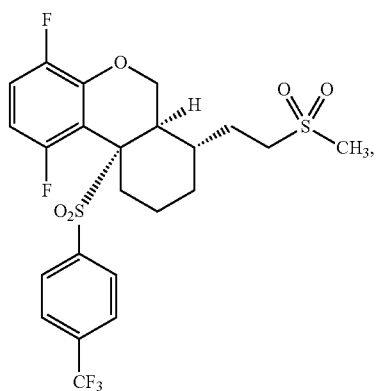
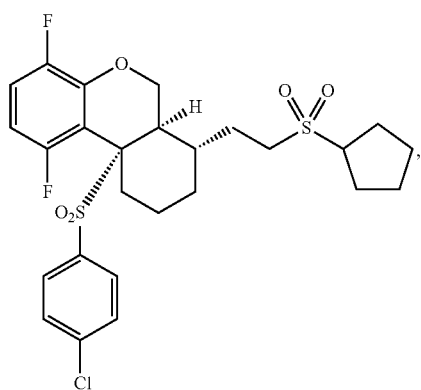
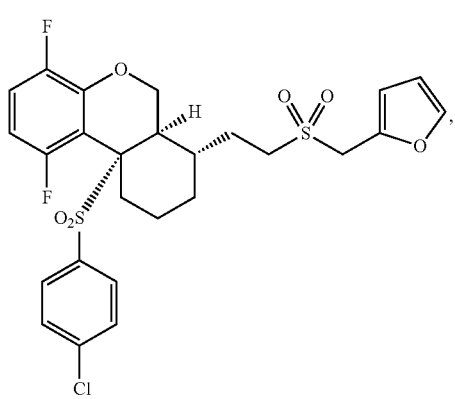
258
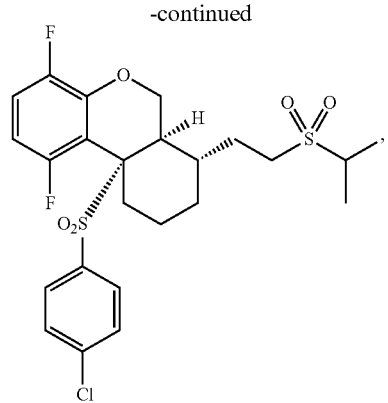
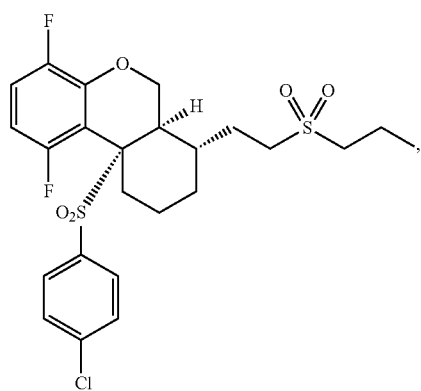
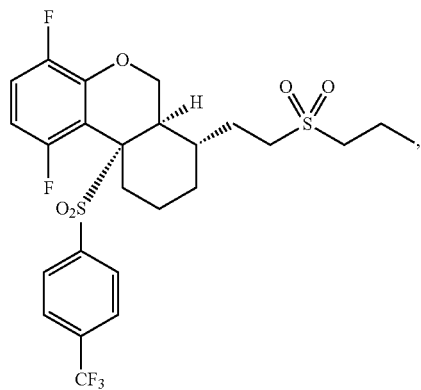
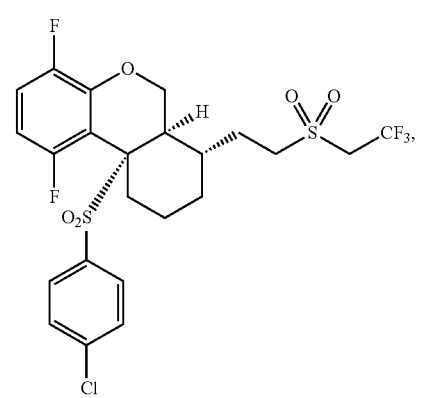

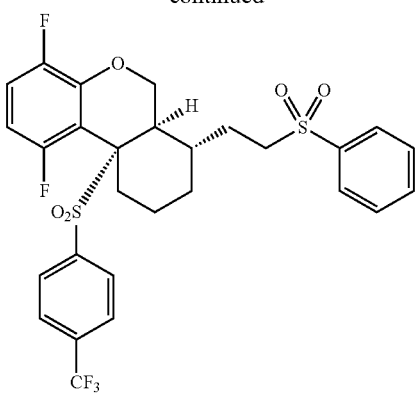
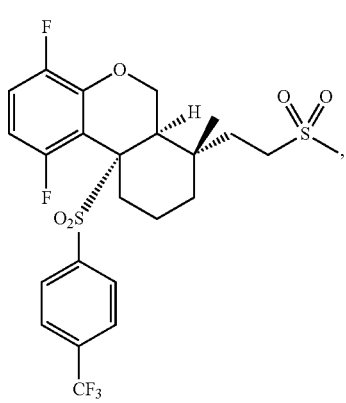
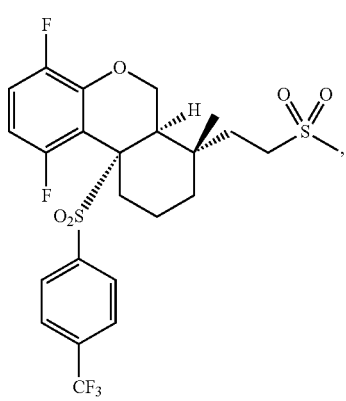
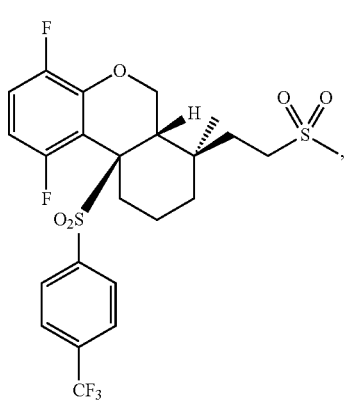
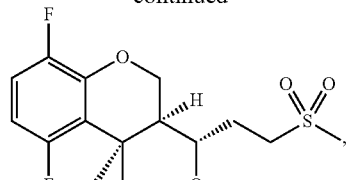

20. A pharmaceutical composition comprising an effective amount of a compound of claim 1 or a pharmaceutically acceptable salt thereof, and a pharmaceutically acceptable carrier.

21. A method of:
 (1) inhibiting gamma-secretase in a patient in need of such treatment comprising administering to said patient a therapeutically effective amount of one or more compounds of claim 1 or a pharmaceutically acceptable salt thereof; or
 (2) treating one or more neurodegenerative diseases in a patient in need of such treatment comprising administering to said patient a therapeutically effective amount of one or more compounds of claim 1 or a pharmaceutically acceptable salt thereof; or (3) inhibiting the deposition of beta amyloid protein in a patient in need of such treatment comprising administering to said patient a therapeutically effective amount of one or more compounds of claim 1 or a pharmaceutically acceptable salt thereof; or (4) inhibiting gamma secretase in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: (a) drugs for the treatment of Alzheimer's disease, (b) drugs for inhibiting the deposition of amyloid protein in, on or around neurological tissue, (c) drugs for treating neurodegenerative diseases, and (d) drugs for inhibiting gamma-secretase; or (5) inhibiting gamma secretase in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: BACE inhibitors, muscarinic antagonists, cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors; or (6) inhibiting gamma secretase in a patient in need of such treatment comprising administering to said patient a therapeutically effective amount of one or more compounds of claim 1 or a pharmaceutically acceptable salt thereof, and a therapeutically effective amount of one or more BACE inhibitors; or (7) treating one or more neurodegenerative diseases in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: (a) drugs for the treatment of Alzheimer's disease, (b) drugs for inhibiting the deposition of amyloid protein in, on or around neurological tissue, (c) drugs for treating neurodegenerative diseases, and (d) drugs for inhibiting gamma-secretase; or (8) treating one or more neurodegenerative diseases in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: BACE inhibitors, muscarinic antagonists, cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors; or (9) inhibiting the deposition of amyloid protein in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: (a) drugs for the treatment of Alzheimer's disease, (b) drugs for inhibiting the deposition of amyloid protein in, on or around neurological tissue, (c) drugs for treating neurodegenerative diseases, and (d) drugs for inhibiting gamma-secretase; or

(10) inhibiting the deposition of amyloid protein in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: BACE inhibitors, muscarinic antagonists, cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors; or

(11) inhibiting the deposition of amyloid protein in a patient in need of such treatment comprising administering to said patient a therapeutically effective amount of one or more compounds of claim 1 or a pharmaceutically acceptable salt thereof, and a therapeutically effective amount of one or more BACE inhibitors; or

(12) treating Alzheimer's disease in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: (a) drugs for the treatment of Alzheimer's disease, (b) drugs for inhibiting the deposition of amyloid protein in, on or around neurological tissue, (c) drugs for treating neurodegenerative diseases, and (d) drugs for inhibiting gamma-secretase; or

(13) treating Alzheimer's disease in a patient in need of such treatment comprising administering to said patient a therapeutically effective amount of one or more compounds of claim 1 or a pharmaceutically acceptable salt thereof, and a therapeutically effective amount of one or more other drugs selected from the group consisting of: BACE inhibitors, muscarinic antagonists, cholinesterase inhibitors; gamma secretase inhibitors; gamma secretase modulators; HMG-CoA reductase inhibitors;

non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors; or

(14) treating Alzheimer's disease in a patient in need of such treatment comprising administering to said patient a therapeutically effective amount of one or more compounds of claim 1 or a pharmaceutically acceptable salt thereof, and a therapeutically effective amount of one or more BACE inhibitors.

22. A method of treating Alzheimer's disease in a patient in need of such treatment comprising administering to said patient a therapeutically effective amount of one or more compounds of claim 1 or a pharmaceutically acceptable salt thereof.

23. The compound of claim 1 or a pharmaceutically acceptable salt thereof, wherein the compound is

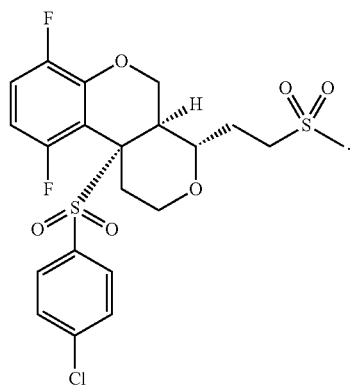 [SMILES: CS(=O)(=O)CC[C@@H]1OCC[C@@]2(S(=O)(=O)c3ccc(Cl)cc3)c3c(F)ccc(F)c3OC[C@@H]12]

* * * * *